US008637028B2

(12) United States Patent
Alexis et al.

(10) Patent No.: US 8,637,028 B2
(45) Date of Patent: *Jan. 28, 2014

(54) ADJUVANT INCORPORATION IN IMMUNONANOTHERAPEUTICS

(75) Inventors: Frank Alexis, Greenville, SC (US); Matteo Iannacone, Milan (IT); Jinjun Shi, Boston, MA (US); Pamela Basto, Boston, MA (US); Elliott Ashley Moseman, Jamaica Plain, MA (US); Ulrich von Andrian, Chestnut Hill, MA (US); Robert S. Langer, Newton, MA (US); Omid C. Farokhzad, Waban, MA (US); Elena Tonti, Riccione (IT)

(73) Assignees: President and Fellows of Harvard College, Cambridge, MA (US); Massachusetts Institute of Technology, Cambridge, MA (US); The Brigham and Women's Hospital, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/123,888

(22) PCT Filed: Oct. 9, 2009

(86) PCT No.: PCT/US2009/060242
§ 371 (c)(1),
(2), (4) Date: Jul. 20, 2011

(87) PCT Pub. No.: WO2010/042870
PCT Pub. Date: Apr. 15, 2010

(65) Prior Publication Data
US 2011/0268805 A1  Nov. 3, 2011

Related U.S. Application Data

(63) Continuation-in-part of application No. 12/428,395, filed on Apr. 22, 2009, now Pat. No. 8,343,498, and a continuation-in-part of application No. PCT/US2008/011932, filed on Oct. 12, 2008.

(51) Int. Cl.
*A61K 39/40* (2006.01)
*A61K 39/395* (2006.01)
*A61K 49/04* (2006.01)

(52) U.S. Cl.
USPC ............... 424/143.1; 424/9.321; 424/9.322; 424/9.34; 424/130.1; 424/134.1; 424/153.1; 424/154.1; 424/178.1; 424/185.1; 424/278.1

(58) Field of Classification Search
None
See application file for complete search history.

(56) References Cited

U.S. PATENT DOCUMENTS 3,766,774 A  10/1973  Clark
(Continued)

FOREIGN PATENT DOCUMENTS

CA  2453959  1/2003
(Continued)

OTHER PUBLICATIONS

McNeil (J. of Leukocyte Biology, 2005. vol. 78(585-594).*
(Continued)

*Primary Examiner* — Ja'na Hines
(74) *Attorney, Agent, or Firm* — Pabst Patent Group LLP

(57) ABSTRACT

The present invention provides compositions and systems for delivery of nanocarriers to cells of the immune system. The invention provides nanocarriers capable of stimulating an immune response in T cells and/or in B cells. The invention provides nanocarriers that comprise an immunofeature surface and an immunostimulatory moiety. In some embodiments, the immunostimulatory moiety is an adjuvant. The invention provides pharmaceutical compositions comprising inventive nanocarriers. The present invention provides methods of designing, manufacturing, and using inventive nanocarriers and pharmaceutical compositions thereof.

34 Claims, 52 Drawing Sheets

(56) References Cited

U.S. PATENT DOCUMENTS

| | | |
|---|---|---|
| 4,270,537 A | 6/1981 | Romaine |
| 4,446,122 A | 5/1984 | Chu |
| 4,596,556 A | 6/1986 | Morrow |
| 4,631,211 A | 12/1986 | Houghten |
| 4,638,045 A | 1/1987 | Kohn |
| 4,790,824 A | 12/1988 | Morrow |
| 4,806,621 A | 2/1989 | Kohn |
| 4,862,851 A | 9/1989 | Washino |
| 4,886,499 A | 12/1989 | Cirelli |
| 4,902,615 A | 2/1990 | Freeman |
| 4,940,460 A | 7/1990 | Casey |
| 4,941,880 A | 7/1990 | Burns |
| 4,946,929 A | 8/1990 | DAmore |
| RE33,405 E | 10/1990 | Chu |
| 4,970,299 A | 11/1990 | Bazinet |
| 5,010,167 A | 4/1991 | Ron |
| 5,015,235 A | 5/1991 | Crossman |
| 5,019,379 A | 5/1991 | Domb |
| 5,055,404 A | 10/1991 | Ueda |
| 5,064,413 A | 11/1991 | McKinnon |
| 5,093,246 A | 3/1992 | Cech |
| 5,118,528 A | 6/1992 | Fessi |
| 5,141,496 A | 8/1992 | Dalto |
| 5,162,504 A | 11/1992 | Horoszewicz |
| 5,175,296 A | 12/1992 | Gerster |
| 5,190,521 A | 3/1993 | Hubbard |
| 5,270,163 A | 12/1993 | Gold |
| 5,312,335 A | 5/1994 | McKinnon |
| 5,328,483 A | 7/1994 | Jacoby |
| 5,334,144 A | 8/1994 | Alchas |
| 5,334,497 A | 8/1994 | Inaba |
| 5,339,163 A | 8/1994 | Homma |
| 5,342,781 A | 8/1994 | Su |
| 5,383,851 A | 1/1995 | McKinnon |
| 5,389,640 A | 2/1995 | Gerster |
| 5,399,665 A | 3/1995 | Barrera |
| 5,417,662 A | 5/1995 | Hjertman |
| 5,466,220 A | 11/1995 | Brenneman |
| 5,472,704 A | 12/1995 | Santus |
| 5,480,381 A | 1/1996 | Weston |
| 5,500,161 A | 3/1996 | Andrianov |
| 5,503,627 A | 4/1996 | McKinnon |
| 5,512,600 A | 4/1996 | Mikos |
| 5,514,378 A | 5/1996 | Mikos |
| 5,520,639 A | 5/1996 | Peterson |
| 5,527,288 A | 6/1996 | Gross |
| 5,543,158 A | 8/1996 | Gref |
| 5,567,588 A | 10/1996 | Gold |
| 5,569,189 A | 10/1996 | Parsons |
| 5,578,325 A | 11/1996 | Domb |
| 5,595,877 A | 1/1997 | Gold |
| 5,599,302 A | 2/1997 | Lilley |
| 5,649,912 A | 7/1997 | Peterson |
| 5,660,985 A | 8/1997 | Pieken |
| 5,696,175 A | 12/1997 | Mikos |
| 5,696,249 A | 12/1997 | Gold |
| 5,704,911 A | 1/1998 | Parsons |
| 5,716,404 A | 2/1998 | Vacanti |
| 5,733,925 A | 3/1998 | Kunz |
| 5,736,372 A | 4/1998 | Vacanti |
| 5,763,177 A | 6/1998 | Gold |
| 5,766,635 A | 6/1998 | Spenleuhauer |
| 5,770,417 A | 6/1998 | Vacanti |
| 5,786,204 A | 7/1998 | He |
| 5,789,163 A | 8/1998 | Drolet |
| 5,804,178 A | 9/1998 | Vacanti |
| 5,817,785 A | 10/1998 | Gold |
| 5,820,879 A | 10/1998 | Fernandez |
| 5,837,752 A | 11/1998 | Shastri |
| 5,843,653 A | 12/1998 | Gold |
| 5,843,732 A | 12/1998 | Davis |
| 5,853,984 A | 12/1998 | Davis |
| 5,869,103 A | 2/1999 | Yeh |
| 5,871,747 A | 2/1999 | GengouxSedlik |
| 5,874,218 A | 2/1999 | Drolet |
| 5,876,727 A | 3/1999 | Swain |
| 5,893,397 A | 4/1999 | Peterson |
| 5,898,031 A | 4/1999 | Crooke |
| 5,902,599 A | 5/1999 | Anseth |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken |
| 5,977,089 A | 11/1999 | Arimilli |
| 5,993,412 A | 11/1999 | Deily |
| 6,001,577 A | 12/1999 | Gold |
| 6,005,087 A | 12/1999 | Cook |
| 6,007,845 A | 12/1999 | Domb |
| 6,030,613 A | 2/2000 | Blumberg |
| 6,031,086 A | 2/2000 | Switzer |
| 6,039,969 A | 3/2000 | Tomai |
| 6,043,224 A | 3/2000 | Lee |
| 6,083,505 A | 7/2000 | Miller |
| 6,095,148 A | 8/2000 | Shastri |
| 6,107,094 A | 8/2000 | Crooke |
| 6,110,462 A | 8/2000 | Barbas |
| 6,120,666 A | 9/2000 | Jacobson |
| 6,123,727 A | 9/2000 | Vacanti |
| 6,127,533 A | 10/2000 | Cook |
| 6,184,364 B1 | 2/2001 | Pieken |
| 6,190,913 B1 | 2/2001 | Singh |
| 6,225,460 B1 | 5/2001 | Jones |
| 6,232,082 B1 | 5/2001 | Ennifar |
| 6,238,705 B1 | 5/2001 | Liu |
| 6,242,246 B1 | 6/2001 | Gold |
| 6,245,776 B1 | 6/2001 | Skwierczynski |
| 6,254,890 B1 | 7/2001 | Hirosue |
| 6,288,040 B1 | 9/2001 | Muller |
| 6,344,318 B1 | 2/2002 | Gold |
| 6,348,462 B1 | 2/2002 | Gerster |
| 6,365,187 B2 | 4/2002 | Mathiowitz |
| 6,376,190 B1 | 4/2002 | Gold |
| 6,399,754 B1 | 6/2002 | Cook |
| 6,403,779 B1 | 6/2002 | Kawasaki |
| 6,429,200 B1 | 8/2002 | Monahan |
| 6,451,527 B1 | 9/2002 | Larocca |
| 6,458,539 B1 | 10/2002 | Gold |
| 6,458,543 B1 | 10/2002 | Gold |
| 6,482,594 B2 | 11/2002 | Gold |
| 6,492,554 B2 | 12/2002 | Dalton |
| 6,506,559 B1 | 1/2003 | Fire |
| 6,506,577 B1 | 1/2003 | Deming |
| 6,558,951 B1 | 5/2003 | Tomai |
| 6,569,896 B2 | 5/2003 | Dalton |
| 6,589,562 B1 | 7/2003 | Shefer |
| 6,589,563 B2 | 7/2003 | Prokop |
| 6,608,201 B2 | 8/2003 | Gerster |
| 6,610,319 B2 | 8/2003 | Tomai |
| 6,610,713 B2 | 8/2003 | Tracey |
| 6,632,922 B1 | 10/2003 | Deming |
| 6,656,469 B1 | 12/2003 | Svensson |
| 6,686,446 B2 | 2/2004 | Deming |
| 6,686,472 B2 | 2/2004 | Gerster |
| 6,696,076 B2 | 2/2004 | Tomai |
| 6,699,474 B1 | 3/2004 | Cerny |
| 6,716,583 B2 | 4/2004 | Gold |
| 6,723,429 B2 | 4/2004 | Bengs |
| 6,737,056 B1 | 5/2004 | Presta |
| 6,747,156 B2 | 6/2004 | Johansson |
| 6,767,702 B2 | 7/2004 | Mirkin |
| 6,818,732 B2 | 11/2004 | Deming |
| 6,838,484 B2 | 1/2005 | Steiner |
| 6,875,605 B1 | 4/2005 | Ma |
| 6,932,971 B2 | 8/2005 | Bachmann |
| 6,995,284 B2 | 2/2006 | Dalton |
| 6,998,500 B2 | 2/2006 | Dalton |
| 7,008,411 B1 | 3/2006 | Mandrusov |
| 7,022,870 B2 | 4/2006 | Dalton |
| 7,026,500 B2 | 4/2006 | Dalton |
| 7,029,859 B2 | 4/2006 | Thompson |
| 7,030,228 B1 * | 4/2006 | Schmitz et al. ............ 530/389.6 |
| 7,056,704 B2 | 6/2006 | Tuschl |
| 7,078,196 B2 | 7/2006 | Tuschl |
| 7,097,837 B2 | 8/2006 | Nielsen |

(56) References Cited

U.S. PATENT DOCUMENTS

| | | |
|---|---|---|
| 7,149,574 B2 | 12/2006 | Yun |
| 7,163,680 B2 | 1/2007 | Bander |
| 7,247,502 B2 | 7/2007 | Ennifar |
| 7,250,499 B2 | 7/2007 | Mirkin |
| 7,335,744 B2 | 2/2008 | Liu |
| 7,363,076 B2 | 4/2008 | Yun |
| 7,375,180 B2 | 5/2008 | Gorden |
| 7,387,271 B2 | 6/2008 | Noelle |
| 7,427,629 B2 | 9/2008 | Kedl |
| 7,488,792 B2 | 2/2009 | Ruoslahti |
| 7,550,441 B2 | 6/2009 | Farokhzad |
| 7,727,969 B2 | 6/2010 | Farokhzad |
| 7,767,803 B2 | 8/2010 | Diener |
| 2001/0012890 A1 | 8/2001 | Thompson |
| 2002/0009466 A1 | 1/2002 | Brayden |
| 2002/0064780 A1 | 5/2002 | Gold |
| 2002/0068091 A1 | 6/2002 | Davis |
| 2002/0086356 A1 | 7/2002 | Tuschl |
| 2002/0099036 A1 | 7/2002 | Dalton |
| 2002/0099096 A1 | 7/2002 | Dalton |
| 2002/0102613 A1 | 8/2002 | Hoogenboom |
| 2002/0106647 A1 | 8/2002 | Segal |
| 2002/0116054 A1 | 8/2002 | Lundell |
| 2002/0150578 A1 | 10/2002 | He |
| 2002/0151004 A1 | 10/2002 | Craig |
| 2002/0153251 A1 | 10/2002 | Sassi |
| 2002/0156125 A1 | 10/2002 | Broder |
| 2002/0173495 A1 | 11/2002 | Dalton |
| 2003/0003103 A1 | 1/2003 | Thompson |
| 2003/0009029 A1 | 1/2003 | Buchholz |
| 2003/0022868 A1 | 1/2003 | Dalton |
| 2003/0035804 A1 | 2/2003 | D'Amico |
| 2003/0054360 A1 | 3/2003 | Gold |
| 2003/0087301 A1 | 5/2003 | Smith |
| 2003/0099668 A1 | 5/2003 | Bachmann |
| 2003/0108611 A1 | 6/2003 | Bosch |
| 2003/0108923 A1 | 6/2003 | Tuschl |
| 2003/0133988 A1 | 7/2003 | Fearon |
| 2003/0134810 A1 | 7/2003 | Springate |
| 2003/0138557 A1 | 7/2003 | Allison |
| 2003/0162761 A1 | 8/2003 | Steiner |
| 2003/0165478 A1 | 9/2003 | Sokoll |
| 2003/0175950 A1 | 9/2003 | McSwiggen |
| 2003/0219766 A1 | 11/2003 | Raitano |
| 2003/0225040 A1 | 12/2003 | Dalton |
| 2003/0232013 A1 | 12/2003 | Sieckman |
| 2003/0232792 A1 | 12/2003 | Dalton |
| 2003/0235619 A1 | 12/2003 | Allen |
| 2004/0014975 A1 | 1/2004 | Dalton |
| 2004/0022727 A1 | 2/2004 | Stanton |
| 2004/0022840 A1* | 2/2004 | Nagy et al. .................. 424/450 |
| 2004/0029913 A1 | 2/2004 | Dalton |
| 2004/0043923 A1 | 3/2004 | Parma |
| 2004/0052727 A1 | 3/2004 | Dalton |
| 2004/0059094 A1 | 3/2004 | Bachmann |
| 2004/0067196 A1 | 4/2004 | Brunke |
| 2004/0067503 A1 | 4/2004 | Tan |
| 2004/0067979 A1 | 4/2004 | Dalton |
| 2004/0072234 A1 | 4/2004 | Parma |
| 2004/0087810 A1 | 5/2004 | Dalton |
| 2004/0092470 A1 | 5/2004 | Leonard |
| 2004/0136961 A1 | 7/2004 | Prokop |
| 2004/0141958 A1 | 7/2004 | Steinaa |
| 2004/0147489 A1 | 7/2004 | Dalton |
| 2004/0147550 A1 | 7/2004 | Dalton |
| 2004/0156846 A1 | 8/2004 | Daum |
| 2004/0167103 A1 | 8/2004 | Dalton |
| 2004/0192626 A1 | 9/2004 | McSwiggen |
| 2004/0241790 A1 | 12/2004 | Eriksen |
| 2004/0247680 A1 | 12/2004 | Farokhzad |
| 2004/0248088 A1 | 12/2004 | Raitano |
| 2004/0260092 A1 | 12/2004 | Miller |
| 2004/0260108 A1 | 12/2004 | Dalton |
| 2004/0266688 A1 | 12/2004 | Nayak |
| 2005/0017667 A1 | 1/2005 | Yamamoto |
| 2005/0019870 A1 | 1/2005 | Afar |
| 2005/0019872 A1 | 1/2005 | Afar |
| 2005/0020525 A1 | 1/2005 | McSwiggen |
| 2005/0032733 A1 | 2/2005 | McSwiggen |
| 2005/0033074 A1 | 2/2005 | Dalton |
| 2005/0037075 A1 | 2/2005 | Farokhzad |
| 2005/0048063 A1 | 3/2005 | Ruoslahti |
| 2005/0069910 A1 | 3/2005 | Turner |
| 2005/0079152 A1 | 4/2005 | Bot |
| 2005/0079533 A1 | 4/2005 | Samuelson |
| 2005/0079553 A1* | 4/2005 | Ayyoub et al. ................ 435/7.2 |
| 2005/0080128 A1 | 4/2005 | Tsukamoto |
| 2005/0100877 A1 | 5/2005 | Xu |
| 2005/0107322 A1 | 5/2005 | OHagan |
| 2005/0122550 A1 | 6/2005 | Plewa |
| 2005/0158390 A1 | 7/2005 | Rana |
| 2005/0191294 A1 | 9/2005 | Arap |
| 2005/0207940 A1 | 9/2005 | Butler |
| 2005/0214378 A1 | 9/2005 | Hoarau |
| 2005/0233948 A1 | 10/2005 | DAmico |
| 2005/0244863 A1 | 11/2005 | Mir |
| 2005/0249799 A1 | 11/2005 | Jacob |
| 2005/0260186 A1 | 11/2005 | Bookbinder |
| 2006/0002852 A1 | 1/2006 | Saltzman |
| 2006/0004042 A1 | 1/2006 | Dalton |
| 2006/0009529 A1 | 1/2006 | Dalton |
| 2006/0035966 A1 | 2/2006 | Dalton |
| 2006/0062787 A1 | 3/2006 | Hitraya |
| 2006/0083711 A1 | 4/2006 | Berry |
| 2006/0111271 A1 | 5/2006 | Cerny |
| 2006/0173170 A1 | 8/2006 | Chamberlain |
| 2006/0183931 A1 | 8/2006 | Dalton |
| 2006/0228371 A1 | 10/2006 | Raso |
| 2006/0239907 A1 | 10/2006 | Luzzi |
| 2006/0240093 A1 | 10/2006 | MacLachlan |
| 2006/0241180 A1 | 10/2006 | Dalton |
| 2006/0258628 A1 | 11/2006 | Steiner |
| 2006/0269557 A1 | 11/2006 | Sherman |
| 2006/0276540 A1 | 12/2006 | Dalton |
| 2006/0287547 A1 | 12/2006 | Dalton |
| 2007/0014807 A1 | 1/2007 | Maida |
| 2007/0116768 A1 | 5/2007 | Chorny |
| 2007/0184068 A1 | 8/2007 | Renner |
| 2007/0225213 A1 | 9/2007 | Kosak |
| 2008/0026000 A1 | 1/2008 | Ennifar |
| 2008/0031899 A1 | 2/2008 | Reddy |
| 2008/0081074 A1 | 4/2008 | Gu |
| 2008/0171059 A1 | 7/2008 | Howland |
| 2008/0213377 A1 | 9/2008 | Bhatia |
| 2008/0268063 A1 | 10/2008 | Jon |
| 2008/0299177 A1 | 12/2008 | Hardy |
| 2009/0004118 A1 | 1/2009 | Nie |
| 2009/0028910 A1 | 1/2009 | DeSimone |
| 2009/0117549 A1 | 5/2009 | Tan |
| 2009/0298710 A1 | 12/2009 | Farokhzad |
| 2010/0022680 A1 | 1/2010 | Karnik |
| 2010/0092425 A1 | 4/2010 | vonAndrian |
| 2010/0129439 A1 | 5/2010 | Alexis |
| 2010/0144845 A1 | 6/2010 | Farokhzad |
| 2010/0183727 A1 | 7/2010 | Iannacone |
| 2010/0196482 A1 | 8/2010 | Radovic-Moreno |
| 2010/0203142 A1 | 8/2010 | Zhang |
| 2010/0233251 A1 | 9/2010 | VonAndrian |

FOREIGN PATENT DOCUMENTS

| | | |
|---|---|---|
| CA | 2649149 A1 | 10/2007 |
| DK | 0418187 | 3/1991 |
| EP | 1279404 | 1/2003 |
| EP | 1752141 A1 | 2/2007 |
| EP | 1932538 | 6/2008 |
| WO | 8804300 | 6/1988 |
| WO | 9011364 | 3/1990 |
| WO | 9704747 | 2/1997 |
| WO | 9713537 A1 | 4/1997 |
| WO | 9737705 A1 | 10/1997 |
| WO | 9808856 | 3/1998 |
| WO | 98/14216 | 4/1998 |
| WO | 9851325 | 11/1998 |

(56) References Cited

FOREIGN PATENT DOCUMENTS

| | | |
|---|---|---|
| WO | 9901498 | 1/1999 |
| WO | 9934850 A1 | 7/1999 |
| WO | 99/61054 | 12/1999 |
| WO | 0021572 | 4/2000 |
| WO | 0027363 | 5/2000 |
| WO | 0032239 | 6/2000 |
| WO | 0044895 | 8/2000 |
| WO | 0175164 | 10/2001 |
| WO | 0218477 | 3/2002 |
| WO | 02076469 | 10/2002 |
| WO | 02076603 | 10/2002 |
| WO | 02100442 | 12/2002 |
| WO | 03004654 | 1/2003 |
| WO | 03028657 | 4/2003 |
| WO | 03030941 | 4/2003 |
| WO | 03051304 | 6/2003 |
| WO | 03072637 | 9/2003 |
| WO | 03074679 | 9/2003 |
| WO | 03102708 | 12/2003 |
| WO | 2004030608 | 4/2004 |
| WO | 2004071493 A1 | 8/2004 |
| WO | 2004096998 | 11/2004 |
| WO | 2004105782 | 12/2004 |
| WO | 03000777 | 1/2005 |
| WO | 2005012407 | 2/2005 |
| WO | 2005028539 | 3/2005 |
| WO | 2005042573 | 5/2005 |
| WO | 2005072710 | 8/2005 |
| WO | 2005111192 | 11/2005 |
| WO | 2005112885 | 12/2005 |
| WO | 2005121181 | 12/2005 |
| WO | 2006037979 | 4/2006 |
| WO | 2006042146 | 4/2006 |
| WO | 2006066158 | 6/2006 |
| WO | 2006078278 | 7/2006 |
| WO | 2006090924 | 8/2006 |
| WO | 2006096754 | 9/2006 |
| WO | 2006117217 | 11/2006 |
| WO | 2006133271 | 12/2006 |
| WO | 2006138463 | 12/2006 |
| WO | 2007001448 A2 | 1/2007 |
| WO | 2007021142 | 2/2007 |
| WO | 2007024026 | 3/2007 |
| WO | 2007070682 | 6/2007 |
| WO | 2007076371 | 7/2007 |
| WO | 2007084797 | 7/2007 |
| WO | 2007098254 | 8/2007 |
| WO | 2007098254 A2 | 8/2007 |
| WO | 2007109364 | 9/2007 |
| WO | 2007118653 | 10/2007 |
| WO | 2007150030 | 12/2007 |
| WO | 2008051291 | 5/2008 |
| WO | 2009051837 A2 | 4/2009 |
| WO | 2009109428 | 9/2009 |

OTHER PUBLICATIONS

Cerchia, et al. "Neutralizing aptamers from whole-cell SELEX inhibit the RET receptor tyrosine kinase", PLoS Biology, 3(4):849-60 (2005).

Foss, et al., "Radiolabeled small-molecule ligands for prostate-specific membrane antigen: in vivo imaging in experimental models of prostate cancer", Clin. Cancer Res., 11:4022-28 (2005).

Govender, at al., "Defining the drug incorporation properties of PLA-PEG nanoparticles", Intl J of Pharmaceutics, 1999:95-110(2000).

Mitra, et al., "Tumour targeted delivery of encapsulated dextran-doxorubicin conjugate using chitosan nanoparticles as carrier", J Controlled Release, 74:317-23 (2001).

Wu, et al., ng-circulation Poly(ethylene glycol)-poly(D,L-lactide) block copolymermicelles with modulated surace chane, J Conti Rel., 77:27-38 (2001).

Zhou, et al., "NAAG peptidase inhibitors and their potential for diagnosis and therapy", Nature Rev. Drug Disc., 4:1015-26 (2005).

U.S. Appl. No. 12/239,136, filed Sep. 26, 2008, Farokhzad, et al.
U.S. Appl. No. 12/301,225, filed Nov. 17, 2008, Farokhzad, et al.
U.S. Appl. No. 12/515,465, filed May 5, 2010, Farokhzad, et al.
U.S. Appl. No. 12/526,300, filed Aug. 11, 2010, Moretti, et al.

Abad, et al., "Comparison of a Monoclonal Antibody-Based Enzyme-Linked Immunosorbent Assay and Gas Chromatography for the Determination of Nicotine in Cigarette Smoke Condensates", Anal. Chem., 65:3227-3231 (1993).

Ackermand & Cresswell, "Cellular mechanisms governing cross-presentation presentation of exogenous antigens", Nat. Immunol., 5(7):678-684 (2004).

Aime, et al., "Lanthanide(III) chelates for NMR biomedical applications", Chemical Society Reviews, 27:19-29 (1998).

Akaishi, et al., "Targeting chemotherapy using antibody-combined liposome against human pancreatic cancer cell-line.", The Tohoku Journal of Experimental Medicine, 175(1):29-42 (1995).

Allen, et al., "Nano-engineering block copolymer aggregates for drug delivery.", Colloids Surfaces B-Biointerfaces, 16:3-27 (1999).

Allison, et al., "The mode of action of immunological adjuvants.", Dev. Biol. Stand., 92:3-11 (1998).

Altschul, et al., "Basic local alignment search tool.", J. Mol Biol., 215 (3):403-10 (1990).

Altschul, et al., "Gapped BLAST and PSI-BLAST: a new generation of protein database search programs.", Nucleic Acids Res., 25(17):3389-3402 (1997).

Angelucci, et al., "Neuroendocrine transdifferentiation induced by VPA is mediated by PPAR$^3$ activation and confers resistance to antiblastic therapy in prostate carcinoma", The Prostate, 68(6):588-598 (2008).

Astete and Sabliov, "Synthesis and characterization of PLGA nanoparticles", J. Biomat. Sci.,-Polymer Ed., 17:247-289 (2006).

Atkinson, et al., "Conjugation of folate via gelonin carbohydrate residues retains ribosomal-inactivating properties of the toxin and permits targeting to folate receptor positive cells.", J. Biol. Chem., 276(30):27930-27935 (2001).

Baba, et al., "Human neutralizing monoclonal antibodies of the IgG1 subtype protect against mucosal simian-human immunodeficiency virus infection.", Nat. Med., 6(2):200-206 (2000).

Babaian, et al., "Radioimmunological imaging of metastatic prostatic cancer with 111indium-labeled monoclonal antibody PAY 276.", J. Urol., 137(3):439-443 (1987).

Bachmann, et al., "T helper cell-independent neutralizing B cell response against vesicular stomatitis virus: role of antigen patterns in B cell induction?", Eur. J. Immunol., 25 (12):3445-3451 (1995).

Bagalkot, et al., "An Aptamer-Doxorubicin Physical Conjugate as a Novel Targeted Drug-Delivery Platform", Angew. Chem. Int. Ed., 45(48):8149-8152 (2006).

Bander, et al., "Targeting metastatic prostate cancer with radiolabeled monoclonal antibody J591 to the extracellular domain of prostate specific membrane antigen.", J. Urol., 170(5):1717-1721 (2003).

Barchet, et al., "Virus-induced interferon alpha production by a dendritic cell subset in the absence of feedback signaling in vivo.", J. Exp. Med., 195 (4):507-516 (2002).

Barrera, et al., "Synthesis and RGD peptide modification of a new biodegradable copolymer: poly(lactic acid-co-lysine)", J. Am. Chem. Soc., 115 (23):11010-11011 (1993).

Bauer, et al., "SMS 201-995: a veryotent and selective octapeptide analogue of somatostatin with prolonged action.", Life Sci., 31(11):1133-1140 (1982).

Beaureparie, et al., "Functionalized Fluorescent Oxide Nanoparticles: Artificial Toxins for Sodium Channel Targeting and Imaging at the Single-Molecule Level", Nano Letters, 4 (11):2079-2083 (2004).

Bennett, et al., "Inhibition of the Aminopeptidase from *Aeromonas Proteolytica* by I-Leucinephosphonic Acid, a Transition State Analogue of Peptide Hydrolysis", J. Am. Chem. Soc., 120(46):12139-12140 (1998).

Bies et al., Lectin-medicated drug targeting: history and applications\, Advanced Drug Delivery Reviews, 56:425-435 (2004).

Binetruy-Tournaire, et al., "Identification of a peptide blocking vascular endothelial growth factor (VEGF)-mediated angiogenesis.", EMBO J., 19 (7):1525-1533 (2000).

(56) References Cited

OTHER PUBLICATIONS

Bjerke, et al., "Comparison of monoclonal and polyclonal antibodies to continine in nonisotopic and isotopic immunoassays", J. Immunol. Meth., 96:239-246 (1987).
Bocca, et al., "Phagocytic uptake of fluorescent stealth solid lipid nanoparticles", Int. J. Pharmaceutics, 175:185-193 (1998).
Boes, et al., "T-cell engagement of dendritic cells rapidly rearranges MHC class II transport.", Nature, 418(6901):983-988 (2002).
Bonifaz, et al., "Efficient targeting of protein antigen to the dendritic cet receptor DEC-205 in the steady state leads to antigen presentation on major histocompatibility complex class I products and peripheral CD8+ T cell tolerance.", J. Exp. Med,, 196(12):1627-1638 (2002).
Bottausci, et al., "Mixing in the shear superposition micromixer: three-dimensional analysis", Philosophical Transactions of the Royal Society of London Series a—Mathematical Physical and Engineering Sciences, 362:1001-1018 (2004).
Boussif, et al., "A versatile vector for gene and oligonucleotide transfer into cells in culture and in vivo: polyethylenimine.", Proc. Nati. Acad. Sci., USA, 1995, 92:7297-7301 (1995).
Bozzacco, et al., "DEC-205 receptor on dendritic cells mediates presentation of HIV gag protein to CD8+ T cells in a spectrum of human MHC I haplotypes.", Proc. Natl. Acad. Sci., USA, 104(4):1289-1294 (2007).
Brito, et al., "Nanoparticulate carriers for the treatment of coronary restenosis.", Int J Nanomedicine, 2(2):143-161 (2007).
Brooking et al., "Transport of Nanoparticles Across the Rat Nasal Mucosa", Journal of Drug Targeting, 9(4):267-279 (2001).
Burmeister, et al., "Direct in vitro selection of a 2'-O-methyl aptamer to VEGF.", Chem Biol, 12(1):25-33 (2005).
Carino, et al., "Nanosphere based oral insulin delivery," J. Control. Release, 65 (1-2):261-9 (2000).
Casola, et al., "B cell receptor signal strength determines B cell fate.", Nat. Immunol., 5(3):317-327 (2004).
Castro, et al., "Nicotine Antibodies: Comparison of Ligand Specificities of Antibodies Produced against Two Nicotine Conjugates", Eur. J. Biochem., 104:331-340 (1980).
Castro & Prieto, "Nicotine Antibody Production: Comparison of two nicotine conjugates in different animal species", Biochem. Biophys. Res. Comm., 67 (2):583-589 (1975).
Chacon, et al., "Optimized preparation of poly D,L (lactic-glycolic) microspheres and nanoparticles for oral administration", Int'l J. Pharmaceutics, 141:81-91 (1996).
Chaires, et al., "Preferential binding of daunomycin to 5'ATCG and 5'ATGC sequences revealed by footprinting titration experiments.", Biochemistry, 29 (26):6145-6153 (1990).
Chandy, et al., "5-Fluorouracil-loaded chitosan coated polylactic acid pmicrospheres as biodegradable drug carriers for cerebral tumors", J. Microencapsulation, 17(5):625-638 (2000).
Chandy et al., "Development of Poly(Lactic Acid)/Chitosan Co-Matrix Microspheres: Controlled Release of Taxol-Heparin for Preventing Restenosis", Drug Delivery, 8:77-86 (2001).
Chang, et al., "Five Different Anti-Prostate-specific Membrane Antigen (PSMA) Antibodies Confirm PSMA Expression in Tumor-associated Neovasculature", Cancer Res., 59:3192-3198 (1999).
Cheng, et al., "Formulation of functionalized PLGA-PEG nanoparticles for in vivo targeted drug delivery.", Biomaterials, 28(5):869-876 (2007).
Christian, et al., "Nucleolin expressed at the cell surface is a marker of endothelial cells in angiogenic blood vessels.", J. Cell Biol., 163(4):871-878 (2003).
Chu, et al., "Aptamer mediated siRNA delivery", Nuc. Acid Res., 34:e73 (2006).
Chu, et al., "Labeling tumor cells with fluorescent nanocrystal-aptamer bioconjugates.", Biosens. Bioelectron., 21:1859-1866 (2006).
Clark, "The reticulum of lymph nodes in mice studied with the electron microscope.", Am. J. Anat., 110:217-257 (1962).
Connor, et al., "Ex vivo evaluation of anti-EpCAM immunocytokine huKS-IL2 in ovarian cancer.", J. Immunother., 27(3):211-219 (2004).

Coppi, et al., "Chitosan-Alginate Microparticles as a Protein Carrier", Drug Development and Industrial Pharmacy, 27(5):393-400 (2001).
Croy and Kwon, "Polymeric micells for drug delivery", Curr. Pharm. Design, 12:4669-4684 (2006).
Dang and Rock, "Stimulation of B lymphocytes through surface Ig receptors induces LFA-1 and ICAM-1-dependent adhesion.", J. Immunol., 146(10):3273-3279 (1991).
De Graaf, et al., "A fully human anti-Ep-CAM scFv-beta-glucuronidase fusion protein for selective chemotherapy with a glucuronide prodrug.", Br. J. Cancer, 86(5):811-818 (2002).
De Jaeghere, et al., "Freeze-drying and lyopreservation of diblock and triblock poly (lactic acid)-polyethylene oxide) (PLA-PEO) copolymer nanoparticles.", Pharm. Dev. Technol., 5(4):473-483 (2000).
Delemarre, et al., "Repopulation of macrophages in popliteal lymph nodes of mice after liposome-mediated depletion.", J. Leukoc. Biol., 47(3):251-257 (1990).
Demello, "Control and detection of chemical reactions in microfluidic systems.", Nature, 442(7101):394-402 (2006).
Demello and Demello, "Microscale reactors: nanoscale products.", Lab on a Chip, 4(2):11N-15N (2004).
Deming, et al., "Facile synthesis of block copolypeptides of defined architecture.", Nature, 390(6658):386-389 (1997).
Derfus, et al., "Intracellular Delivery of Quantum Dots for Live Cell Labeling and Organelle Tracking", Advanced Materials, 16:961-966 (2004).
Dimarco and Arcamone, "DNA complexing antibiotics: Daunomycin, adriamycin and their derivates.", Arzneim-Forsch. (Drug Res.), 25:368-375 (1975).
Ding, et al., "Syntheses of conformationally constricted molecules as potential NAALADase/PSMA inhibitors.", Org. Lett., 6(11):1805-1808 (2004).
Dinkla, et al., "Identification of a streptococcal octapeptide motif involved in acute rheumatic fever.",J. Biol. Chem., 282(26):18686-18693 (2007).
Dykxhoorn, et al., "Killing the messenger: short RNAs that silence gene expression.", Nat. Rev. Mol. Cell Biol., 4(6):457-467 (2003).
D\Antonio, et al., "Longitudinal analysis of androgen deprivation of prostate cancer cells identifies pathways to androgen independence", The Prostate, 68(7):698-714 (2008).
Eklund, et al., "Denileukin diftitox: a concise clinical review.", Expert Rev. Anticancer Ther., 5(1):33-38 (2005).
Elbashir, et al., "RNA interference is mediated by 21- and 22-nucleotide RNAs.", Genes Dev., 15(2):188-200 (2001).
Eldridge, et al., "Biodegradable microspheres as a vaccine delivery system," Mol. Immunol., 28(3):287-94 (1991).
Elsässer-Beile, et al., "A new generation of monoclonal and recombinant antibodies against cell-adherent prostate specific membrane antigen for diagnostic and therapeutic targeting of prostate cancer.", Prostate, 66(13):1359-1370 (2006).
Elvassore, et al., "Production iof Insulin-Loaded Poly(Ethylene Glycol)/Poly(I-Lactide) (PEG/PLA) Nanoparticles by Gas Antisolvent Techniques", Journal of Pharmacrutical Sciences, 90(10):1628-36 (2001).
Ermak and Giannasca, "Microparticle targeting to M cells", Advanced Drug Delivery Reviews, 34:261-283 (1998).
Farokhzad, et al., "Nanoparticle-Aptamer Bioconjugates: A New Approach for Targeting Prostate Cancer Cells," Cancer Research, 64:7668-7672 (2004).
Farokhzad, et al., "Nanoparticle-aptamer bioconjugates for cancer targeting", Expert Opin. Drug Delivery, 3(3):311-324 (2006).
Farokhzad, et al., "Targeted nanoparticle-aptamer bioconjugates for cancer chemotherapy in vivo.", Proc. Natl. Acad. ScL, USA, 103(16):6315-6320 (2006).
Farr, et al., "The structure of the sinus wall of the lymph node relative to its endocytic properties and transmural cell passage.", Am. J. Anat., 157(3):265-284 (1980).
Fire, et al., "Potent and specific genetic interference by double-stranded RNA in Caenorhabditis elegans.", Nature, 391(6669):806-811 (1998).

(56) References Cited

OTHER PUBLICATIONS

Fi Li Povic-Grcic et al., "Mucoadhesive chitosan-coated liposomes: characteristics and stability", J. Microencapsulation, 18 1 :3-12 (2001).
Fonseca, et al., "Paclitaxel-loaded PLGA nanoparticles: preparation, physicochemical characterization and in vitro anti-tumoral activity.", J. Control. Release, 83(2):273-286 (2002).
Fracasso, et al., "Anti-tumor effects of toxins targeted to the prostate specific membrane antigen.", Prostate, 53(1):9-23 (2002).
Francis, et al., "A phase I trial of antibody directed enzyme prodrug therapy (ADEPT) in patients with advanced colorectal carcinoma or other CEA producing tumours.", Br. J. Cancer, 87(6):600-607 (2002).
Frankel, et al., "Phase I trial of a novel diphtheria toxin/granulocyte macrophage colony-stimulating factor fusion protein (DT388GMCSF) for refractory or relapsed acute myeloid leukemia.", Clln. Cancer Res., 8(5):1004-1013 (2002).
Frederick, et al., "Structural comparison of anticancer drug-DNA complexes: adriamycin and daunomycin.", Biochemistry, 29(10):2538-2549 (1990).
Froidevaux, et al., "Somatostatin analogs and radiopeptides in cancer therapy.", Biopolymers, 66(3):161-183 (2002).
Fujita, et al., "Cytokine profiling of prostatic fluid from cancerous prostate glands identifies cytokines associated with extent of tumor and inflammation", The Prostate, 68(8):872-882 (2008).
Gao, et al., "A method for the generation of combinatorial antibody libraries using pIX phage display," Proc. Natl. Acad. Sci. U.S.A., 99(20): 12612-6 (2002).
Gao, et al., "In vivo cancer targeting and imaging with semiconductor quantum dots.", Nat. Biotechnol., 22(8):969-976 (2004).
Gao, et al., "In vivo molecular and cellular imaging with quantum dots.", Curr. Op. Biotechnol., 16:63-72 (2005).
Gaserod et al., "The enhancement of the bioadhesive properties of calcium alginate gel beads by coating with chitosan", Intl. J. of Pharmaceutics, 175:237-246 (1998).
Gershlick, "Treating atherosclerosis: local drug delivery from laboratory studies to clinical trials," Atherosclerosis, 160(2): 259-71 (2002).
Gillies, et al., "An anti-CD20-IL-2 immunocytokine is highly efficacious in a SCID mouse model of established human B lymphoma.", Blood, 105(10):3972-3978 (2005).
Grauer, et al., "Identification, purification, and subcellular localization of prostate-specific membrane antigen PSM' protein in the LNCaP prostatic carcinoma cell line.", Cancer Res., 58(21):4787-4789 (1998).
Gref, et al., "Biodegradable long-circulating polymeric nanospheres.", Science, 263(5153):1600-1603 (1994).
Haensler, et al., "Polyamidoamine cascade polymers mediate efficient transfection of cells in culture", Bioconjugate Chem., 4(5):372-379 (1993).
Haj, et al., "New findings in the study on the intercalation of bisdaunorubicin and its monomeric analogues with naked and nucleus DNA.", Chem. Biol. Interact., 145(3):349-358 (2003).
Hanes, et al., "Polymer microspheres for vaccine delivery.", Pharm. Biotechnol., 6:389-412 (1995).
Hangartner, et al., "Antiviral immune responses in gene-targeted mice expressing the immunoglobulin heavy chain of virus-neutralizing antibodies." , Proc. Natl. Acad. Sci., USA, 100:12883-12888 (2003).
Hannon, et al., "Unlocking the potential of the human genome with RNA interference", Nature, 431(7006):371-378 (2004).
Harada and Kataoka, "Supramolecular assemblies of block copolymers in aqueous media as nanocontainers relevant to biological applications", Progress Polymer Sci., 31(11):949-982 (2006).
Harper, et al., "Efficacy of a bivalent L1 virus-like particle vaccine in prevention of infection with human papillomavirus types 16 and 18 in young women: a randomised controlled trial.", Lancet, 364(9447):1757-1766 (2004).

Haseloff and Gerlach, "Simple RNA enzymes with new and highly specific endoribonuclease activities.", Nature, 334(6183):585-591 (1988).
Hawiger, et al., "Dendritic cells induce peripheral T cell unresponsiveness under steady state conditions in vivo.", J. Exp. Med. 194(6):769-779 (2001).
He, et al., "A microRNA polycistron as a potential human oncogene," Nature, 435(7043): 828-833 (2005).
Heald, et al., "Poly(lactic acid)-poly(ethylene oxide) (PLA-PEG) nanoparticles: NMR studies of the central solidlike PLA core and the liquid PEG corona", Langmuir, 18:3669-3675 (2002).
Hejazi et al ., "Stomach-specific anti-H. pylon therapy. I: preparation and characterization of tetracyline-loaded chitosan microshpheres", Intl. J. of Pharmaceutics, 235:87-94 (2002).
Helene, et al., "Control of gene expression by triple helix-forming oligonucleotides. The antigene strategy.", Ann, N.Y. Acad. Sci. 660:27-36 (1992).
Hermann and Patel, "Adaptive recognition by nucleic acid aptamers," Science, 287: 820-825 (2000).
Hieda, et al., "Active Immunization Alters the Plasma Nicotine Concentration in Rats", J. Pharmacol. Exp. Therapeutics, 283:1076-1081 (1997).
Hieda, et al., "Immunization of rats reduces nicotine distribution to brain", Psychopharmacology, 143:150-157 (1999).
Horoszewicz, et al., "Monoclonal antibodies to a new antigenic marker in epithelial prostatic cells and serum of prostatic cancer patients.", Anticancer Res., 7(5B):927-935 (1987).
Houghton, "General method for the rapid solid-phase synthesis of large numbers of peptides: Specificity of antigen-antibody interaction at the level of individual amino acids", Immunol., 82:5131-5135 (1985).
Huang et al., "Microencapsulation of Chlorpheniramine Maleate-Resin Particles with Crosslinked Chitosan for Sustained Release", Pharmaceutical Development and Technology, 4 1:107-115 (1999).
Hélène, "The anti-gene strategy: control of gene expression by triplex-forming-oligonucleotides.", Anticancer Drug Des. 6(6):569-584 (1991).
Jackson, et al., "Design and pharmacological activity of phosphinic acid based NAALADase inhibitors.", J. Med. Chem., 44(24):4170-4175 (2001).
Jackson, et al., "Design of NAALADase inhibitors: a novel neuroprotective strategy.", Curr. Med. Chem., 8(8):949-957 (2001).
Janes et al., "Chitosan nanoparticles as delivery systems for doxorubicin", Journal of Controlled Release, 73:255-267 (2001).
Jayasena, "Aptamers: An Emerging Class of Molecules That Rival Antibodies in Diagnostics", Clinical Chemistry, 45(9):1628-1650 (1999).
Johnson and Prud\Homme, "Mechanism for rapid self-assembly of block copolymer nanoparticles.", Phys. Rev. Lett., 91(11):118302 (2003).
Jones and Leroux, "Polymeric micelles a new generation of colloidal drug carriers" , Eur. J. Pharmaceutics Biopharmaceutics, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", Pharmaceutical Research, 18(3):352-360 (2001).
Junt, et al., "Subcapsular sinus macrophages in lymph nodes clear lymph-borne viruses and present them to antiviral B cells", Nature, 450:110-116 (2007).
Kabanov, et al., "DNA Complexes with Polycations for the Delivery of Genetic Material into Cells", Bioconjugate Chem., 6(1):7-20 (1995).
Kamentsky, "Laser scanning cytometry.", Methods Cell Biol., 63:51-87 (2001).
Kanashiro, et al., "Inhibition of mutant p53 expression and growth of DMS-153 small cell lung carcinoma by antagonists of growth hormone-releasing hormone and bombesin,", Proc. Natl. Acad. Sci., USA, 100(26):15836-15841 (2003).
Karlin and Altschul, "Applications and statistics for multiple high-scoring segments in molecular sequences.", Proc. Natl Acad. Sci. USA, 90(12):5873-5877 (1993).

(56) References Cited

OTHER PUBLICATIONS

Karlin and Altschul, "Methods for assessing the statistical significance of molecular sequence features by using general scoring schemes.", Proc. Natl Acad Sci. USA, 87:2264-2268 (1990).
Karrer, et al., "On the key role of secondary lymphoid organs in antiviral immune responses studied in alymphoplastic (aly/aly) and spleenless (Hox11(−)/−) mutant mice.", J. Exp. Med., 185(12):2157-2170 (1997).
Kawashima, et al., "Mucoadhesive DL-Lactide/Glycolide Copolymer Nanoshperes Coated with Chitosan to Improve Oral Delivery of Elcatonin", Pharmaceutical Development and Technology, 5(1):77-85 (2000).
Kelly, et al., "The Optical Properties of Metal Nanoparticles: The Influence of Size, Shape, and Dielectric Environment", J. Phys. Chem. B., 107(3):668-677 (2003).
Khademhosseini, et al., "Cell docking inside microwells within reversibly sealed microfluidic channels for fabricating multiphenotype cell arrays," Lab Chip, 5(12):1380-6 (2005).
Khandare, et al., "Polymer-drug conjugates: Progress in polymeric prodrugs," Progress in Polymer Science, 31(4): 359-397 (2006).
Kim, et al., "Target-specific cellular uptake of PLGA nanoparticles coated with poly(L-lysine)-poly(ethyleneglycol)-folate conjugate", Langmuir, 21(19): 8852-8857 (2005).
Knight, et al., "Hydrodynamic Focusing on a Silicon Chip: Mixing Nanoliters in Microseconds", Phys. Rev. Lett., 80:3863-3866 (1998).
Koivunen, et al., "Phage libraries displaying cyclic peptides with different ring sizes: ligand specificities of the RGD-directed integrins.", Biotechnology (NY), 13(3):265-270 (1995).
Koivunen, et al., "Tumor targeting with a selective gelatinase inhibitor", Nat. Biotechnol., 17:768-774 (1999).
Konan, et al., "Preparation and characterization of sterile sub-200 nm meso-tetra(4-hydroxylphenyl)porphyrin-loaded nanoparticles for photodynamic therapy", Eur. J. Pharmaceutics Biopharmaceutics, 55:115-124 (2003).
Kozikowski, et al., "Synthesis of urea-based inhibitors as active site probes of glutamate carboxypeptidase II: efficacy as analgesic agents.", J. Med. Chem., 47(7):1729-1738 (2004).
Kreitman, et al., "Efficacy of the anti-CD22 recombinant immunotoxin BL22 in chemotherapy-resistant hairy-cell leukemia.", N. Engl J. Med., 345(4):241-347 (2001).
Kreitman, et al., "Phase I trial of recombinant immunotoxin anti-Tac(Fv)-PE38 (LMB-2) in patients with hematologic malignancies.", J. Clin. Oncol., 18(8):1622-1636 (2000).
Krieg, et al., "CpG motifs in bacterial DNA trigger direct B-cell activation.", Nature, 374(6522):546-549 (1995).
Kukowska-Latallo, et al., "Efficient transfer of genetic material into mammalian cells using Starburst polyamidoamine dendrimers", Proc. Natl. Acad. Sci., USA, 93(10):4897-4902 (1996).
Kumar, et al., "Inhibition of angiogenesis and tumor growth by SCH221153, a dual alpha(v)beta3 and alpha(v)beta5 integrin receptor antagonist.", Cancer Res., 61(5):2232-2238 (2001).
Kwon, et al., "Pseudopoly(amino acids): A study of the synthesis and characterization of poly(acyl-hydroxyproline-esters)", Macromolecules, 22:3250-3255 (1989).
Köhrer, et al., "Complete set of orthogonal 21st aminoacyl-tRNA synthetase-amber, ochre and opal suppressor tRNA pairs: concomitant suppression of three different termination codons in an mRNA in mammalian cells.", Nucleic Acids Res., 32(21):6200-6211 (2044).
Köhrer, et al., "Import of amber and ochre suppressor tRNAs into mammalian cells: a general approach to site-specific insertion of amino acid analogues into proteins.", Proc. Nati. Acad. Sci., USA, 98(25):14310-14315 (2001).
Köhrer and Rajbhandary, "Proteins carrying one or more unnatural amino acids," In Ibba, et al., (eds.), Aminoacyl-tRNA Synthetases, Landes Bioscience, Chapter 31 (2005).
Laakkonen, et al., "Antitumor activity of a homing peptide that targets tumor lymphatics and tumor cells.", Proc. Natl. Acad. Sci., USA, 101(25):9381-9386 (2004).

Labhasetwar, et al., "Arterial uptake of biodegradable nanoparticies: Effect of surface modifications ," J. Pharm. Sci., 87(10): 1229-34 (1998).
Langer, "Biomaterials in drug delivery and tissue engineering: one laboratory's experience.", Acc. Chem. Res., 33(2):94-101 (2000).
Langer, "New methods of drug delivery," Science, 249(4976):1527-33 (1990).
Langer, "Selected advances in drug delivery and tissue engineering", J. Control. Release, 62:7-11 (1999).
Langone, et al., "Nicotine and its metabolites. Radioimmunoassays for nicotine and cotinine", Biochem., 12(24):5025-5030 (1973).
Langone & Van Vunakis, "Radioimmunoassay of Nicotine, Cotinine, and $^3$-(3-Pyridyl)-$^3$-oxo-N-methylbutyramide", Met. Enzymol., 84:628-640 (1982).
Leamon, et al., "Cytotoxicity of folate-*Pseudomonas* exotoxin conjugates toward tumor cells. Contribution of translocation domain.", J. Biol. Chem., 268 (33):24847-24854 (1993).
Leamon, et al., "Selective targeting of malignant cells with cytotoxin-folate conjugates.", J. Drug Target., 2(2):101-112 (1994).
Lee, et al. "Adaptations of Nanoscale Viruses and Other Protein Cages for Medical Applications" Nanomedicine-Nanotechnology Biology and Medicine. 2(3):137-149 (2006).
Lehr, "Lectin-mediated drug delivery: The second generation of bioadhesives", J. of Controlled Release, 65:19-29 (2000).
Leopold, et al., "Fluorescent virions: dynamic tracking of the pathway of adenoviral gene transfer vectors in living cells.", Human Gene Therapy, 9(3):367-378 (1998).
Leroy, et al., "Radioimmunodetection of lymph node invasion in prostatic cancer. The use of iodine 123 (123i)-labeled monoclonal anti-prostatic acid phosphatase (PAP) 227 A F(ab')2 antibody fragments in vivo.", Cancer, 64(1):1-5 (1989).
Leucuta, et al., "Albumin microspheres as a drug delivery system for epirubicin: pharmaceutical, pharmacokinetic and biological aspects," International Journal of Pharmaceutics, 41: 213-7 (1988).
Lim, et al., "A Self-Destroying Polycationic Polymer: Biodegradable Poly(4-hydroxy-l-proline ester)", J. Am. Chem. Soc., 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior,", J. Am. Chem. Soc, 123(10):2460-2461 (2001).
Lim et al., "Preparation and evaluation of the in vitro drug release properties and mucoadhesion of novel microspheres of hyaluronic acid and chitosan", J. of Controlled Release, 66:281-292 (2000).
Lin, et al., "A microRNA polycistron as a potential human oncogene p828", Nature, 435(7043):828-833 (2005).
Lin, et al., "Well-Ordered Mesoporous Silica Nanoparticles as Cell Markers", Chem. Mater., 17:4570-4573 (2005).
Liu, et al., "Cell-Surface labeling and internalization by a fluorescent inhibitor of prostate-specific membrane antigen", The Prostate, 68(9):955-964 (2008).
Liu, et al., "Constitutive and antibody-induced internalization of prostate-specific membrane antigen.", Cancer Res., 58(18):4055-4060 (1998).
Liu, et al, "Folate-targeted enzyme prodrug cancer therapy utilizing penicillin-V amidase and a doxorubicin prodrug.", J. Drug Target., 7:43-53 (1999).
Liu, et al., "Hypermethylation of MCAM gene is associated with advanced tumor stage in prostate cancer", The Prostate, 68(4):418-426 (2008).
Liu, et al., "Monoclonal antibodies to the extracellular domain of prostate-specific membrane antigen also react with tumor vascular endothelium.", Cancer Res., 57(17):3629-3634 (1997).
Low, et al., "Folate receptor-targeted drugs for cancer and inflammatory diseases.", Adv. Drug Deliv. Rev., 56(8):1055-1058 (2004).
Lu, et al., "MicroRNA expression profiles classify human cancers", Nature, 435(7043):834-838 (2005).
Ludewig, et al., "Induction of optimal anti-viral neutralizing B cell responses by dendritic cells requires transport and release of virus particles in secondary lymphoid organs.", Eur. J. Immunol., 30(1):185-196 (2000).

(56) References Cited

OTHER PUBLICATIONS

Lupold, et al., "Identification and characterization of nuclease-stabilized RNA molecules that bind human prostate cancer cells via the prostate-specific membrane antigen.", Cancer Res., 62(14):4029-4033 (2002).
Lyu, et al., "The immunocytokine scFv23/TNF sensitizes HER-2/neu-overexpressing SKBR-3 cells to tumor necrosis factor (TNF) via up-regulation of TNF receptor-1.", Mol. Cancer Ther., 4(8):1205-1213 (2005).
Maher, "DNA triple-helix formation: An approach to artificial gene repressors?", Bioassays 14:807-815 (1992).
Majer, et al., "Synthesis and biological evaluation of thiol-based inhibitors of glutamate carboxypeptidase II: discovery of an orally active GCP II inhibitor.", J. Med. Chem., 46 (10):1989-1996 (2003).
Manolova, et al., "Nanoparticles target distinct dendritic cell populations according to their size", Eur. J. Immunol., 38:1404-1413 (2008).
Manz, et al., "Capillary electrophoresis on a chip", J. Chromatography, 593:253-258 (1992).
Mathiowitz, et al., "Novel microcapsules for delivery systems", Reactive Polymers, 6:275-283 (1987).
Mathiowitz, et al., "Polyanhydride Microspheres as Drug Carriers. II.. Microencapsulation by Solvent Removal", J. Appl. Polymer Sci., 35:755-774 (1988).
Mathiowitz, et al., "Polyanhydride Microspheres as Drug Carriers I. Hot Melt Encapsulation", J. Control. Release, 5:13-22 (1987).
Mattheakis, et al., "Optical coding of mammalian cells using semiconductor quantum dots.", Analytical Biochemistry, 327(2):200-208 (2004).
Maung, et al., "Probing for a hydrophobic a binding register in prostate-specific membrane antigen with phenylalkylphosphonamidates.", Bioorg. Med. Chem., 12(18):4969-4979 (2004).
McDevitt, et al., "An alpha-particle emitting antibody ([213Bi]J591) for radioimmunotherapy of prostate cancer.", Cancer Res., 60(21):6095-6100 (2000).
McDevitt, et al., "Tumor therapy with targeted atomic nanogenerators.", Science, 294(5546):1537-1540 (2001).
Mead, et al., "Laboratory vector competence of black flies (Diptera:Simuliidae) for the Indiana serotype of vesicular stomatitis virus.", Ann. N.Y. Acad. Sci., 916:437-443 (2000).
Meister, et al., "Mechanisms of gene silencing by double-stranded RNA.", Nature, 431(7006):343-349 (2004).
Melani, et al., "Targeting of interleukin 2 to human ovarian carcinoma by fusion with a single-chain Fv of antifolate receptor antibody.", Cancer Res., 58 (18):4146-4154 (1998).
Mempel, et al., "T-cell priming by dendritic cells in lymph nodes occurs in three distinct phases.", Nature, 427(6970):154-159 (2004).
Metelitsa, et al., "Antidislatoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", Blood, 99(11):4166-4173 (2002).
Meyers, et al., "Development of monoclonal antibody imaging of metastatic prostatic carcinoma.", Prostate, 14(3):209-220 (1989).
Milligan and Uhlenbeck, "Synthesis of small RNAs using T7 RNA polymerase," Methods in Enzymology, 180: 51-62 (1989).
Mi, et al., "Release of Indomethacin from a Novel Chitosan Microsphere Prepared by a Natrually Occurring Crosslinker: Examination of Crosslinking and Polycation-Anionic Drug Interaction", J. of Applied Polymer Science, 81:1700-1711 (2001).
Moghimi, et al., "Long-circulating and target-specific nanoparticles: theory to practice," Pharmacol, Rev., 53(2): 283-318 (2001).
Mulligan, "The basic science of gene therapy," Science, 260(5110):926-32 (1993).
Murphy, et al., "Isolation and characterization of monoclonal antibodies specific for the extracellular domain of prostate specific membrane antigen.", J. Urol., 160(6 Pt 2):2396-2401 (1998).
Murray, et al., "Synthesis and characterization of monodisperse nanocrystals and close-packed nanocrystal assemblies", Ann. Rev. Mat. Sci., 30:545-610 (2000).
Myers and Miller, Optimal alignments in linear space, CABIOS, 4(1):11-17 (1988).
Nan, et al., "Dual function glutamate-related ligands: discovery of a novel, potent inhibitor of glutamate carboxypeptidase II possessing mGluR3 agonist activity.", J. Med. Chem., 43 (5):772-774 (2000).
Neidle, "The molecular basis for the action of some DNA-binding drugs.", Prog. Med. Chem., 16:151-221 (1979).
Nguyen and Wu, "Micromixers a review.", J. Micromechan. Microeng., 15:R1 (2005).
Notter, et al., "Targeting of a B7-1 (CD80) immunoglobulin G fusion protein to acute myeloid leukemia blasts increases their costimulatory activity for autologous remission T cells.", Blood, 97(10):3138-3145 (2001).
O'Donnell, et al., "c-Myc-regulated microRNAs modulate E2F1 expression," Nature, 435(7043): 839-843 (2005).
Ochsenbein, et al., "Control of early viral and bacterial distribution and disease by natural antibodies.", Science, 286(5447):2156-2159 (1999).
Ochsenbein, et al., "Protective T cell-independent antiviral antibody responses are dependent on complement.", J. Exp. Med., 190(8):1165-1174 (1999).
Okada, et al., "Antigen-engaged B cells undergo chemotaxis toward the T zone and form motile conjugates with helper T cells.", PLoS Biol., 3(6):e150 (2005).
Oliver, et al., "Conformational and SAR analysis of NAALADase and PSMA inhibitors.", Bioorg. Med. Chem., 11(20):4455-4461 (2003).
Olivier, et al., "Drug Transport to Brain with Targeted Nanoparticles", J. of the Am. Society of Experimental NeuroTherapeutics, 2:108-119 (2005).
Pape, et al., "The humoral immune response is initiated in lymph nodes by B cells that acquire soluble antigen directly in the follicles.", Immunity, 26(4):491-502 (2007).
Papisov, "Acyclic Polyacetals from Polysaccharides: Biomimetic Biomedical "Stealth" Polymers", ACS Symposium Series, 786:301-314 (2001).
Parekh, et al., "Biomarkers for Prostate Cancer Detection", The Journal of Urology, 178(6):2252-2259 (2007).
Pasqualini, et al., "Aminopeptidase N is a receptor for tumor-homing peptides and a target for inhibiting angiogenesis.", Cancer Res., 60(3):722-727 (2000).
Patri, et al., "Synthesis and in Vitro Testing of J591 Antibody Dendrimer Conjugates for Targeted Prostate Cancer Therapy", Bioconj. Chem., 15:1174-1181 (2004).
Pellegrino, et al., "On the development of colloidal nanoparticles towards multifunctional structures and their possible use for biological applications.", Small, 1(1):48-63 (2005).
Pfohl, et al., "Trends in microfluidics with complex fluids.", Chemphyschem, 4(12):1291-1298 (2003).
Phillips, et al., "Enhanced antibody response to liposome-associated protein antigens: preferential stimulation of IgG2a/b production.", Vaccine, 10(3):151-158 (1992).
Pimentel, et al., "Peptide nanoparticles as novel immunogens: design and analysis of a prototypic severe acute respiratory syndrome vaccine", Chemical Biology & Drug Design, 73(1):53-61 (2009).
Ponchel, et al., "Specific and non-specific bioadhesive particulate systems for oral delivery to the gastrointestinal tract", Advanced Drug Delivery Reviews, 34:191-219 (1998).
Porkka, et al., "A fragment of the HMGN2 protein homes to the nuclei of tumor cells and tumor endothelial cells in vivo.", Proc. Natl. Acad. Sci., USA, 99(11):7444-7449 (2002).
Putnam, et al., "Poly(4-hydroxy-l-proline ester): Low-Temperature Polycondensation and Plasmid DNA Complexation", Macromolecules, 32(11):3658-3662 (1999).
Qi, et al., "Extrafollicular activation of lymph node B cells by antigen-bearing dendritic cells", Science, 312(5780):1672-1676 (2006).
Quintanar-Guerrero, et al., "Preparation Techniques and Mechanisms of Formation of Biodegradable Nanoparticles from Preformed Polymers", Drug Dev. Industrial Pharmacy, 24(12):1113-1128 (1998).

(56) References Cited

OTHER PUBLICATIONS

Reddy, et al., "Exploiting lymphatic transport and complement activation in nanoparticle vaccines", Nat. Biotech., 25(10):1159-1164 (2007).
Reif, et al, "Balanced responsiveness to chemoattractants from adjacent zones determines B-cell position.", Nature, 416(6876):94-99 (2002).
Reiher, et al., "Inhibition of tumor growth by systemic treatment with thrombospondin-1 peptide mimetics.", Int. J. Cancer, 98(5):682-689 (2002).
Reubi, et al., "Peptide receptors as molecular targets for cancer diagnosis and therapy.", Endocr. Rev., 24(4):389-427 (2003).
Reynolds, et al., "Rational siRNA design for RNA interference.", Nat. Biotechnol., 22(3):326-330 (2004).
Robbins, et al., "Stable expression of shRNAs in human CD34+ progenitor cells can avoid induction of interferon responses to siRNAs in vitro", Nature Biotechnology, 24(5):566-571 (2006).
Robinson, et al, "LEAPT: lectin-directed enzyme-activated prodrug therapy.", Proc. Natl. Acad. Sci., USA, 101(40):14527-14532 (2004).
Roost, et al., "Mapping of the dominant neutralizing antigenic site of a virus using infected cells.", J. Immunol. Methods, 189(2):233-242 (1996).
Rossbacher and Shlomchik, "The B cell receptor itself can activate complement to provide the complement receptor 1/2 ligand required to enhance B cell immune responses in vivo.", J. Exp. Med., 198(4):591-602 (2003).
Sampson, et al., "Progress report of a Phase I study of the intracerebral microinfusion of a recombinant chimeric protein composed of transforming growth factor (TGF)-alpha and a mutated form of the *Pseudomonas* exotoxin termed PE-38 (TP-38) for the treatment of malignant brain tumors,", J. Neurooncol., 65(1):27-35 (2003).
Santoyo, et al., "Highly specific and accurate selection of siRNAs for high-throughput functional assays.", Bioinformatics, 21(8):1376-1382 (2005).
Sarkar, et al., "Ligand-DNA interaction in a nanocage of reverse micelle", Biopolymer., 83(6):675-86 (2006).
Sarver, et al., "Ribozymes as potential anti-HIV-1 therapeutic agents.", Science 247(4947):1222-1225 (1990).
Schally, et al., "Peptide analogs in the therapy of prostate cancer.", Prostate, 45(2):158-166 (2000).
Schultz, et al., "Single-target molecule detection with nonbleaching multicolor optical immunolabels.", Proc. Natl. Acad. Sci., USA, 97(3):996-1001(2000).
Schultz, "Plasmon resonant particles for biological detection", Curr. Op. Biotechnol., 14:13-22 (2003).
Shaida, et al., "Expression of BNIP3 correlates with hypoxia-inducible factor (HIF)-1±, HIF-2± and the androgen receptor in prostate cancer and is regulated directly by hypoxia but not androgens in cell lines", The Prostate, 68(3):336-343 (2008).
Shen, et al. 'Enhanced and Prolonged Cross-Presentation Following Endosomal Escape of Exogenus Antigens Encapsulated in Biodegradable Nanoparticles' Immunology. 117(1):78-88 (2006).
Shestopalov, et al., "Multi-step synthesis of nanoparticles performed on millisecond time scale in a microfluidic droplet-based system.", Lab on a Chip, 4(4):316-321 (2004).
Shimoda, et al., "Bioadhesive Characteristics of Chitosan Mircroshperes to the Mucosa of Rat Small Intestine", Drug Delvelopment and Inustrial Pharmacy, 27(6):567-576 (2001).
Shiow, et al., "CD69 acts downstream of interferon-alpha/beta to inhibit S1P1 and lymphocyte egress from lymphoid organs.", Nature, 440(7083):540-544 (2006).
Silver, et al., "Prostate-specific membrane antigen expression in normal and malignant human tissues.", Clin. Cancer Res., 3(1):81-85 (1997).
Simberg, et al., "Biomimetic amplification of nanoparticle homing to tumors", Nat\l. Acad. Sic. USA, 104(3):921-936 (2007).

Smith-Jones, et al., "In vitro characterization of radiolabeled monoclonal antibodies specific for the extracellular domain of prostate-specific membrane antigen.", Cancer Res., 60(18):5237-5243 (2000).
Sondel, et al., "Preclinical and clinical development of immunocytokines.", Curr. Opin. Investig. Drugs, 4(6):696-700 (2003).
Song, et al., "A Microfluidic System for Controlling Reaction Networks in Time", Angewandte Chemie-Int'l Ed., 42:768-772 (2003).
Spooner, et al., "A novel vascular endothelial growth factor-directed therapy that selectively activates cytotoxic prodrugs.", Br. J. Cancer, 88(10):1622-1630 (2003).
Stoermer, et al., "Synthesis and biological evaluation of hydroxamate-Based inhibitors of glutamate carboxypeptidase II.", Bioorg. Med. Chem. Lett., 13(13):2097-2100 (2003).
Storm, et al., "Surface Modification of Nanoparticles to Oppose Uptake by the Mononuclear Phagocyte System", Adv. Drug Deliv. Rev., 17:31-48 (1995).
Stroock, et al., "Chaotic mixer for microchannels,", Science, 295 (5555):647-651 (2002).
Sutcliffe, et al., "Antibodies that react with predetermined sites on proteins", Science, 219:660-666 (1983).
Takeuchi, et al., "Enteral Absorption of Insulin in Rats from Mucoadhesive Chitosan-Coated Liposomes", Pharmaceutical Research, 13(6):896-901 (1996).
Takeuchi, et al., "Spray-Dried Lactose Composite Particles Containing an Ion Complex of Alginate-Chitosan for Desinging a Dry-Coated Tablet Having a Time-Controlled Releasing Function", Pharmaceutical Research, 17 (1):94-99 (2000).
Takeuchi et al., "Mucoashesive Upsomes Coated with Chitosan or Carbopol for Oral Administration of Peptide Drugs", Proceed. Intl. Symp. Control. Rel. Bioact. Mater., 26:988-989 (1999).
Tang, et al., "In Vitro Gene Delivery by Degraded Polyamidoamine Dendrimers", Bioconjugate Chem., 7:703-714 (1996).
Tang, et al., "Prostate targeting ligands based on N-acetylated alpha-linked acidic dipeptidase.", Biochem. Biophys. Res. Commun., 307(1):8-14 (2003).
Tavitian, et al., "In vivo imaging with oligonucleotides for diagnosis and drug development", Gut, 52 Su, I IV :40-47 (2003).
Taylor, et al., "Macrophage receptors and immune recognition.", Annu. Rev. Immunol., 23:901-944 (2005).
Tindall, et al., "The Rationale for Inhibiting 5±-Reductase Isoenzymes in the Prevention and Treatment of Prostate Cancer", The Journal of Urology, 179 (4):1235-1242 (2008).
Tobio, et al,"Role of PEG on the stability in digestive fluids and in vivo fate of PEG-PLA nanoparticles following oral administration", Colloids and Surfaces B: Biointerferences, 18:315-323 (2000).
Tomai, et al., "Resiquimod and other immune response modifiers as vaccine adjuvants", Expert Rev Vaccines, 6:835-847 (2007) Abstract Only.
Trindade, et al., "Nanocrystalline Semiconductors: Synthesis, Properties, and Perspectives", Chem. Mat., 13(11):3843-3858 (2001).
Tsukamoto, et al., "Phosphonate and phosphinate analogues of N-acylated gamma-glutamylgluternate. potent inhibitors of glutamate carboxypeptidase II.", Bioorg. Med. Chem. Lett., 12(16):2189-2192 (2002).
Uhrich, et al., "Polymeric Systems for Controlled Drug Release", Chem. Rev., 99(11):3181-3198 (1999).
Unkeless, et al., "Structure and function of human and murine receptors for IgG.", Annu. Rev. Immunol., 6:251-281 (1998).
Uwatoku, et al., "Application of Nanoparticle Technology for the Prevention of Restenosis After Balloon Injury in Rats," Circ. Res., 92(7): e62-9 (2003).
Valentini, et al., "Association of anthracycline derivatives with DNA: a fluorescence study.", Farmaco [Sci], 40:377-390 (1985).
Vallabhajosula, et al., "Radioimmunotherapy of prostate cancer in human xenografts using monoclonal antibodies specific to prostate specific membrane antigen (PSMA): studies in nude mice.", Prostate, 58(2):145-155 (2004).
Vascotto, et al., "Antigen presentation by B lymphocytes: how receptor signaling directs membrane trafficking.", Curr., Opin., Immunol., 19(1):93-98 (2007).

(56) References Cited

OTHER PUBLICATIONS

Vihko, et al., "Radioimaging of Prostatic Carcinoma With Prostatic Acid Phosphatase—Specific Antibodies", Biotechnology in Diagnostics, 131-134 (1985).
Vila, et al., "Design of biodegradable particles for protein delivery", Journal of Controlled Release, 78:15-24 (2002).
Vila, et al., "PLA-PEG Nanospheres: New Carriers for Transmucosal Delivery of Proteins and Plasmid DNA", Poly. Adv. Technol., 13:851-858 (2002).
Villa, et al., "PLA-PEG particles as nasal protein carriers: the influence of the particle size", Int. J Pharmaceut., 292:43-52 (2005).
Von Allmen, et al., "V domain of RAGE interacts with AGEs on prostate carcinoma cells", The Prostate, 68(7):748-758 (2008).
Von Andrian and Mempel, "Homing and cellular traffic in lymph nodes.", Nat. Rev. Immunol., 3(11):867-878 (2003).
Wang, et al., "A novel biodegradable gene carrier based on polyphosphoester.", J. Am. Chem. Soc., 123(38):9480-9481 (2001).
Wang, et al., "Autoantibody signatures in prostate cancer.", N Engl J Med, 353 (12):1224-1235 (2005).
Wang, et al., "Identification of prostate specific membrane antigen (PSMA) as the target of monoclonal antibody 107-1A4 by proteinchip; array, surface-enhanced laser desorption/ionization (SELDI) technology.", Int. J. Cancer, 92(6):871-876 (2001).
Wang, et al., "Interactions between an anthracycline antibiotic and DNA: molecular structure of daunomycin complexed to d(CpGpTpApCpG) at 1.2-A resolution.", Biochemistry, 28(4):1152-1163 (1987).
Weaver, et al., "Transferrin receptor ligand-targeted toxin conjugate (Tf-CRM107) for therapy of malignant gliomas.", J. Neurooncol., 65(1):3-13 (2003).
Wessels, et al., "Studies of group B streptococcal infection in mice deficient in complement component C3 or C4 demonstrate an essential role for complement in both innate and acquired immunity.", Proc. Natl. Acad. Sci., USA, 92(25):11490-11494 (1995).
Whelan, et al., "Efficient recovery of infectious vesicular stomatitis virus entirely from cDNA clones.", Proc. Natl. Acad. Sci., USA, 92(18):8388-8392 (1995).
Wilson, et al., "The Structure of an Antigenic Determinant in a Protein", Cell, 37:767-778 (1984).
Wind, et al., "An integrated confocal and magnetic resonance microscope for cellular research.", J. Magn. Reson., 147(2):371-377 (2000).
Wlotzka, et al., "In vivo properties of an anti-GnRH Spiegelmer: an example of an oligonucleotide-based therapeutic substance class," Proc. Natl. Acad. Sci. U. S. A., 99 (13):8898-902 (2002).
Wright, et al., "Cyclophosphamide/granulocyte colony-stimulating factor causes selective mobilization of bone marrow hematopoietic stem cells into the blood after M phase of the cell cycle.", Blood, 97(8):2278-2285 (2001).
Wu, et al., "Immunofluorescent labeling of cancer marker Her2 and other cellular targets with semiconductor quantum dots.", Nat. Biotechnol., 21(1):41-46 (2003).
Wu, "Arming antibodies: prospects and challenges for immunoconjugates.", Nat. Biotechnol., 23(9):1137-1146 (2005).
Yamada, et al., "In Vitro and in Vivo Evaluation of Sustained Release Chitosan-Coat Ketoprofen Microparticles", Yakugaku Zasshi, 121(3):239-245 (2001).
Yang, et al., "Micelles formed by self-assmbling of polylactide(ethylene glycol) block copolymers in aqueous solutions", J Colloid Interfac Si., 314:470-77 (2007).
Yang, "Imaging of vascular gene therapy.", Radiology, 228:36-249 (2003).
Yoo, et al., "In vitro and in vivo anti-tumor activities of nanoparticles based on doxorubicin-PLGA conjugates.", J. Control. Release, 68(3):419-431 (2000).
Yourong, et al, "Preparation of DHAQ-loaded mPEG-PLGA-mPEG nanoparticles and evaluation of drug release behaviors in vitro/in vivo," J. Mat. Sci.: Mat. Med., 17(6): 509-16 (2006).

Yuan, et al. 'Intranasal immunization with Chitosan/pCETP Nanoparticles Inhibits Atherosclerosis in a Rabbit Model of Atherosclerosis' Vaccine. 26 (29-30):3727-3734 (2008).
Yuan, et al., "siRNA Selection Server: an automated siRNA oligonucleotide prediction server.", Nucl. Acids. Res., 32:W130-W134 (2004).
Zamore, et al., "RNAi: double-stranded RNA directs the ATP-dependent cleavage of mRNA at 21 to 23 nucleotide intervals.", Cell, 101(1):25-33 (2000).
Zauner, et al., "Polylysine-basedtransfection systems utilizing receptor-mediated delivery.", Adv. Drug Del. Rev., 30:97-113 (1998).
Zhang, et al., "The proliferative effect of estradiol on human prostate stromal cells is mediated through activation of ERK", The Prostate, 68(5):508-516 (2008).
Zheng, et al., "Highly fluorescent, water-soluble, size-tunable gold quantum dots.", Phys. Rev. Lett., 93(7):077402 (2004).
Zhou, et al., "Investigation on a novel core-coated microspheres protein delivery system.", J. Control. Release, 75(1-2):27-36 (2001).
Zhou, et al., "Preparation of poly(L-serine ester): a structural analog of conventional poly(L-serine)", Macromolecules, 23(14):3399-3406 (1990).
Zuker, "Mfold web server for nucleic acid folding and hybridization prediction", Nuc. Acid. Res., 31:3406-3415 (2003).
Akagi, et al., "Multifunctional conjugation of proteins on/into bionanoparticles prepared by amphiphilic poly(gamma-glutamic acid)", J Biomat Sci Polym Ed., 17 (8):875-92 (2006).
Akagi, et al., "Development of vaccine adjuvants using polymeric nanoparticles and their potential applications for anti-HIV vaccine", Yakugaku Zasshi, 127(2):307-17 (2007) English Abstract.
Argov-Argaman, et al., "Lactosomes: Structural and compositional classification of unique nanometer-sized protein lipid particles of human milk", J Agric Food Chem., 58:11234-42 (2010).
Avgoustakis, "Pegylated poly(lactide) and poly(lactide-co-glycolide) nanoparticles: preparation, properties and possible applications in drug delivery", Curr Drug Deliv., 1:321-33 (2004).
Chu, et al, "Aptamer:toxin conjugates that specifically target prostate tumor cells", Cancer Res., 66:5989-92 (2006).
Elamanchili, et al., "Pathogen-mimicking nanoparticles for vaccine delivery to dendritic cells", J Cont. Rel., 30(4):378-95 (2007).
Gorelik, et al., "Scanning surface confocal microscopy for simultaneous topographical and fluorescence imaging: application to single virus-like particle entry into a cell", PNAS, 99(25):16018-23 (2002).
Hallahanm, et al., "Integrin-mediated targeting of drug delivery to irradiated tumor blood vessels", Cancer Cell, 3:63-74 (2003).
Harris, et al., "Proteolytic actuation o nanoparticle self-assembly", Angewandte Chemie, 118:3233-7 (2006).
Hennenfent, et al., "Novel formulations of taxanes: a review. Old wine in a new bottle", Ann Oncol., 17:735-49 (2005).
Jayaprakash, et al., "Design and synthesis of a PSMA inhibitor-doxorubicin conjugate for targeted prostate cancer therapy", Chem Med Chem., 1:299-302 (2006).
Kawamura, et al., "Dendritic cells that endocytosed antigen-containing IgG-liposomes elicit effective antitumor immunity", J Immunother., 29(2):165-74 (2006).
Koenig, et al., "Immunologic factors in human milk: the effects of gestational age and pasteurization", J Human Lactation, 21:439-43 (2002).
Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).
Martin, et al., "Crystal structure at 2.8 A of an FcRn/heterodimeric Fc complex: mechanism of pH-dependent binding.", Mol Cell, 7:867-77 (2001).
Matsuo, et al., "Efficient generation of antigen-specific cellular immunity by vaccination with poly (gamma-glutamic acid) nanoparticles entrapping endoplasmic reticulum-targeted peptides", Biochem Biophys Res Commun., 362:1069-72 (2007).
Moon, et al., "Engineering Nano- and microparticles to tune immunity", Adv Mater., DOI:10.1002/adma.201200446 (2012).

(56) References Cited

OTHER PUBLICATIONS

Oyewumi, et al., "Comparison of cell uptake, biodistribution and tumor retention of folate-coated and PEG-coated gadolinium nanoparticles in tumor-bearing mice", J Control Rel., 93:613-26 (2004).

Oyewumi, et al., "Nano-microparticles as immune adjuvants: correlating particle sizes and the resultant immune responses", Exp Rev Vaccines, 9(9):1095-1107 (2010).

Riley, et al., "Colloidal stability and drug incorporation aspects of micellar-like PLA-PEG nanoparticles", Colloids Surfaces B Biointerfaces, 16:147-59 (1999).

Riley, et al., "Physicochemical evaluation of nanoparticles assembled from Poly(lactic acid)-Poly(ethylene glycol) (PLA_PEG) block copolymers as drug delivery vehicles", Langmuir, 17:3168-74 (2001).

Shields, et al., "High resolution mapping of the binding site on human IgG1 for Fc gamma RI, Fc gamma RII, Fc gamma RIII, and FcRn and design of IgG1 variants with improved binding to the Fc gamma R", J Biolo Chem., 276(9):6591-6604 (2001).

Shim, "One target different effects: a comparison of distinct therapeutic antibodies against the same targets", Exp Mole Med., 43(10):539-49 (2011).

Suzuki, et al., "Development of effective antigen delivery carrier to dendritic cells via Fc receptor in cancer immunotherapy",Yakugaku Zasshi, 127(2):301-6 (2007). English Abstract.

Taylor, et al., "Development of a specific system for targeting protein to metallophilic macrophages", PNAS, 101(7):1963-8 (2004).

Uto, et al., "Targeting of antigen to dendritic cells with poly(gamma-glutamic acid) nanoparticles induces antigen-specific humoral and cellular immunity", J Immunology, 178 (5):2979-86 (2007).

Wakita, et al., "An indispensable role of type-1 IFNs for inducing CTL-mediated complete eradication of established tumor tissue by CpG-liposome co-encapsulated with model tumor antigen", Int. Immunol., 18(3):425-34 (2006).

Yu, et al., "Engineered bio-nanocapsules, the selective vector for drug delivery system", IUBMB Like, 58(1):1-6 (2006).

* cited by examiner

Amine modified latex nanoparticles accumulate on SCS-Mph

Fluorescent micrographs of frozen sections from mouse popliteal lymph nodes 24h after footpad injection of Latex NPs surface modified with eitheramine (left and middle panel) or carboxy moieties (right panel). Sections on left and right were counterstained with anti-CD169.

Fig 28A

Vaccination with antigen-bearing targeted nanoparticles protects against lethal infection with VSV

Fig 28B

ADJUVANT INCORPORATION IN IMMUNONANOTHERAPEUTICS

RELATED APPLICATIONS

This application is a national phase filing under 35 U.S.C. §371 of PCT/US2009/060242 filed under the Patent Cooperation Treaty on Oct. 9, 2009, which is a continuation-in-part, and claims priority to, PCT Application Serial No. PCT/US2008/011932, filed under the Patent Cooperation Treaty on Oct. 12, 2008. This application also claims priority to U.S. Ser. No. 12/428,395, filed Apr. 22, 2009. The contents of the aforementioned applications are incorporated herein by reference in their entirety.

GOVERNMENT SUPPORT

This invention was made with government support under grant numbers RO1 AI069259, AI078897, EB003647 and RO1 AI072252 awarded by the National Institutes of Health. The government has certain rights in this invention.

REFERENCE TO SEQUENCE LISTING

The Sequence Listing submitted Jun. 4, 2013 as a text file named "MIT_13399_2_371_US.txt", created on Jun. 3, 2013, and having a size of 866 bytes is hereby incorporated by reference pursuant to 37 C.F.R. §1.52(e)(5).

BACKGROUND OF THE INVENTION

Many current vaccines against microbial pathogens comprise live attenuated or non-virulent strains of the causative microorganisms. Many vaccines comprise killed or otherwise inactivated microorganisms. Other vaccines utilize purified components of pathogen lysates, such as surface carbohydrates or recombinant pathogen-derived proteins. Vaccines that utilize live attenuated or inactivated pathogens typically yield a vigorous immune response, but their use has limitations. For example, live vaccine strains can sometimes cause infectious pathologies, especially when administered to immune-compromised recipients. Moreover, many pathogens, particularly viruses, undergo continuous rapid mutations in their genome, which allow them to escape immune responses to antigenically distinct vaccine strains.

Given the difficulty of vaccine development, many vaccines are in extremely short supply. For example, as of October 2007, there are influenza, varicella, and hepatitis A vaccine shortages in the United States. In some instances, vaccine shortages occur because not enough manufacturers devote their facilities to vaccine production to keep up with demand. In some cases, vaccine shortages are attributed to low potency of the vaccine, which means a large amount of vaccine product must be administered to each individual in order to achieve a prophylactic effect. For example, some vaccines cannot be administered as an intact organism (even if attenuated or killed) because they cause infectious pathologies. Instead, such vaccines usually comprise purified pathogen components, which typically leads to a much less potent immune response.

Thus, there is a need in the art for systems and methods for producing highly immunogenic, effective vaccines. There is also a need for improved vaccine compositions that can potently induce long-lasting immune responses. For the treatment and prevention of infectious diseases, there is a need for improved vaccine compositions that are highly immunogenic but do not cause disease.

SUMMARY OF THE INVENTION

The present invention provides synthetic nanocarriers for modulating the immune system. The synthetic nanocarriers comprise one or more surfaces. In some embodiments, at least one of the surfaces comprises an immunofeature surface. Optionally the synthetic nanocarriers of the invention contain one or more of an immunomodulatory agent, an immunostimulatory agent, and a targeting agent (also referred to herein as "targeting moiety"). The immunomudulatory agent induces an immune response in B and/or T cells. The immunostimulatory agent helps stimulate the immune system (in a manner that can ultimately enhance, suppress, direct, or redirect an immune response). The immunofeature surface recognizes one or more targets associated with antigen presenting cells. The optional targeting agent recognizes one or more targets associated with a particular organ, tissue, cell, and/or subcellular locale. In some embodiments, the synthetic nanocarriers comprise a surface comprising a plurality of moieties in an amount effective to provide a humoral response to the moieties. The humoral response is obtained, for example, when the synthetic nanocarriers are administered to a patient. The nanocarriers are useful in pharmaceutical preparations and kits for the prophylaxis and/or treatment of diseases, disorders, or conditions susceptible to treatment by immune system modulation. Such conditions include those diseases, disorders, or conditions modified by enhancing the immune response specifically or nonspecifically, suppressing the immune response specifically or nonspecifically, or directing/redirecting the immune response specifically or nonspecifically.

An immunofeature surface, as described in more detail herein, provides for specific targeting of the nanocarriers to antigen presenting cells (APCs). In particular, the immunofeature surface provides for high avidity binding of the nanocarriers to APC surfaces. Furthermore, the high avidity binding is specific to APC cells. For example, in some embodiments, nanocarriers of the invention are capable of specifically targeting subcapsular sinus macrophages (SCS-Mphs). Such nanocarriers accumulate in the subcapsular sinus region of lymph nodes when administered to a subject. In other embodiments, the nanocarriers of the invention are capable of specifically targeting dendritic cells and eliciting a T-cell response. In preferred embodiments, the immunofeature surface provides low affinity, high avidity binding of the nanocarriers to APC surfaces. In some embodiments, nanocarriers comprising an immunofeature surface exhibit specific low affinity high avidity binding to APCs, and do not provide such binding to other types of cells. Further details of immunofeature surfaces are provided herein.

The ability of the immunofeature surface to target APCs is a key feature that allows the nanocarriers of the invention to deliver immunostimulatory and immunomodulatory agents to B-cells and/or T-cells when administered to a subject. Such delivery allows the inventive nanocarriers to elicit an immune system response, or to enhance an immune system response. In some embodiments, the synthetic nanocarriers of the invention comprise a surface comprising a plurality of moieties in an amount effective to provide a humoral response to the moieties.

As will be recognized by those skilled in the art, immune system modulation is useful, among other things, in connection with medical treatments, such as, for example, for prophylaxis and/or treatment of infectious disease, cancer, autoimmune disease (including rheumatoid arthritis), immune suppression in connection with transplants to ameliorate transplant rejection, immunization against addictive substances, and immunization against biohazards and other toxic substances. Immune system modulation also is useful as a tool in industrial and academic research settings, such as, for example, to immunize an animal to produce antibodies.

One aspect of the invention is the provision of vaccines. A vaccine according to the invention typically contains an antigen. In one embodiment, the antigen is physically 'bound' to the nanocarrier by covalent or noncovalent means. Noncovalently bound includes, for example, ionic bonding, hydrophobic bonding, physical entrapment, and the like, all described in greater detail below. Such nanocarriers which themselves carry an antigen are included in the category referred to below as vaccine nanocarriers. In another embodiment, the nanocarrier has bound to it an immunostimulatory agent for enhancing, suppressing, directing, or redirecting an immune response, preferably to an antigen. In this case, the antigen may be mixed with the preparation of agent bound nanocarrier to which the immunostimulatory agent is bound form the vaccine. The antigen, of course may also be bound to a nanocarrier, including as discussed below, the same nanocarrier to which the immunostimulatory agent is bound. The antigen may also be a moiety of the immunofeature surface.

The preparations of the invention in many instances will include one or more nanocarriers. In some embodiments, the preparation includes a nanocarrier having an immunofeature surface where the nanocarrier is bound to one or more, but not all, of an immunomodulatory agent, an immunostimulatory agent, and a targeting agent. In some embodiments, the preparation is a mixture of nanocarriers with subpopulations carrying one or more, but not all, of an immunomodulatory agent, an immunostimulatory agent, and a targeting agent. In some embodiments, the preparation is a mixture of different nanocarriers, each nanocarrier carrying one or more, but not all, of an immunomodulatory agent, an immunostimulatory agent, and a targeting agent. The preparations likewise may be one of nanocarriers, wherein each nanocarrier has bound to it all of an immunomodulatory agent, an immunostimulatory agent, and a targeting agent. In this instance, the nanocarriers themselves, apart from the agents they deliver, may be the same or different. The targeting agents mentioned here (and as described in more detail herein) are, for example, B-cell targeting moieties or T-cell targeting moieties. It will be appreciated that, throughout this disclosure, such moieties are in addition to the plurality of moieties that are present on the immunofeature surface and that provide targeting of the nanocarriers to APCs.

Important is the discovery that the nanocarriers of the invention are powerful at stimulating the immune system. Important is the discovery that the nanocarriers can be fashioned to mimic, and from an immunological standpoint, improve on, what the immune system 'sees' when exposed to antigens in nature or in prior vaccine technology. In this respect, it has been discovered unexpectedly that the activity of adjuvants can be markedly enhanced if covalently bound to nanocarriers. It also has been discovered unexpectedly that the immunofeature surface of the nanocarriers can help target an immunomodulatory agent or immunostimulatory agent to appropriate immune cells even without a specific cell targeting agent.

The systems described herein permit the manipulation of the parameters affecting the immune system in a manner which results in improved immune modulation. One important aspect of the invention is that the nanocarriers can be controlled in terms of size, density of agent, degree and location of targeting, degradation, release of agent, etc. A variety of aspects of the invention achieve one or more of these benefits, described in more detail below. In particular, below are described immune modulating preparations, synthetic nanocarrier components of such preparations, specific and preferred nanocarriers, specific and preferred immunomodulatory, immunostimulatory, and targeting agents, component parts and building blocks of nanocarriers of the invention, as well as methods for manufacturing such nanocarriers, including a preferred method involving self-assembled nanocarriers. In addition, preparations and systems for generating robust immune modulation in connection with weak antigens and antigens not recognized by T cells (e.g., carbohydrate and small molecule antigens) are described. In some aspects, a composition comprising a nanocarrier (e.g., one that targets a specific organ, tissue, cell, or subcellular locale) is provided. In some embodiments, the nanocarrier targets one or more secondary lymphoid tissues or organs. In some embodiments, the secondary lymphoid tissue or organ is the lymph nodes, spleen, Peyer's patches, appendix, or tonsils.

The scaffold of the nanocarrier (and which the agents provided herein may be associated with or encapsulated by) can be composed of polymer and/or non-polymer molecules. Accordingly, the nanocarrier scaffold can be protein-based, nucleic acid based, or carbohydrate-based. The scaffold, in some embodiments, is macromolecular. In some embodiments, the scaffold is composed of amino acids or nucleic acids. In some embodiments, the scaffold is composed of crosslinking chains of molecules, such as nucleic acids. In some embodiments, the scaffold is composed of RNAi crosslinking chains. In some embodiments, the scaffold is polyamino-based. A nanocarrier can be, but is not limited to, one or a plurality of lipid-based nanoparticles, polymeric nanoparticles, metallic nanoparticles, surfactant-based emulsions, dendrimers, and/or nanoparticles that are developed using a combination of nanomaterials such as lipid-polymer nanoparticles.

In some embodiments, the nanocarrier is composed of one or more polymers. In some embodiments, the one or more polymers is a water soluble, non-adhesive polymer. In some embodiments, polymer is polyethylene glycol (PEG) or polyethylene oxide (PEO). In some embodiments, the polymer is polyalkylene glycol or polyalkylene oxide. In some embodiments, the one or more polymers is a biodegradable polymer. In some embodiments, the one or more polymers is a biocompatible polymer that is a conjugate of a water soluble, non-adhesive polymer and a biodegradable polymer. In some embodiments, the biodegradable polymer is polylactic acid (PLA), poly(glycolic acid) (PGA), or poly(lactic acid/glycolic acid) (PLGA). In some embodiments, the nanocarrier is composed of PEG-PLGA polymers.

In some embodiments, the nanocarrier is formed by self-assembly. Self-assembly refers to the process of the formation of a nanocarrier using components that will orient themselves in a predictable manner forming nanocarriers predictably and reproducibly. In some embodiments, the nanocarriers are formed using amphiphillic biomaterials which orient themselves with respect to one another to form nanocarriers of predictable dimension, constituents, and placement of constituents. According to the invention, the amphiphillic biomaterials may have attached to them immunomodulatory agents, immunostimulatory agents and/or targeting agents such that when the nanocarriers self assemble, there is a reproducible pattern of localization and density of the agents on/in the nanocarrier.

In some embodiments, the nanocarrier is a microparticle, nanoparticle, or picoparticle. In some embodiments, the microparticle, nanoparticle, or picoparticle is self-assembled.

In some embodiments, the nanocarrier has a positive zeta potential. In some embodiments, the nanocarrier has a net positive charge at neutral pH. In some embodiments, the nanocarrier comprises one or more amine moieties at its surface. In some embodiments, the amine moiety is a primary, secondary, tertiary, or quaternary amine. In some embodiments, the amine moiety is an aliphatic amine. In some embodiments, the nanocarrier comprises an amine-containing polymer. In some embodiments, the nanocarrier comprises an amine-containing lipid. In some embodiments, the nanocarrier comprises a protein or a peptide that is positively charged at neutral pH. In some embodiments, the nanocarrier is a latex particle. In some embodiments, the nanocarrier with the one or more amine moieties on its surface has a net positive charge at neutral pH.

The nanocarriers of the compositions provided herein, in some embodiments, have a mean geometric diameter that is less than 500 nm. In some embodiments, the nanocarriers have mean geometric diameter that is greater than 50 nm but less than 500 nm. In some embodiments, the mean geometric diameter of a population of nanocarriers is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75-250 nm. In some embodiments, 30%, 40%, 50%, 60%, 70%, 80%, 90%, or more of the nanocarriers of a population of nanocarriers have a diameter that is less than 500 n. In some embodiments, 10%, 20%, 30%, 40%, 50%, 60%, 70%, 80%, 90%, or more of the nanocarriers of a population of nanocarriers have a diameter that is greater than 50 nm but less than 500 nm. In some embodiments, 10%, 20%, 30%, 40%, 50%, 60%, 70%, 80%, 90%, or more of the nanocarriers of a population of nanocarriers have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the nanocarriers of a population of nanocarriers have a diameter that is between 100-400 nm, 100-300 nm, 100-250 nm, or 100-200 nm. In some embodiments, 10%, 20%, 30%, 40%, 50%, 60%, 70%, 80%, 90%, or more of the nanocarriers of a population of nanocarriers have a diameter that is between 60-400 nm, 60-350 nm, 60-300 nm, 60-250 nm, or 60-200 nm. In some of the foregoing embodiments, the nanocarriers are nanoparticles.

The nanocarrier provided herein can be used to modulate an immune response (e.g., enhance, suppress, direct, or redirect) and comprises an immunofeature surface. In some embodiments, such immune response is a humoral immune response. In other embodiments, such immune response is a cellular immune response. In some embodiments, such immune response is a combination of a cellular and humoral immune response. The nanocarriers may comprise at least one of an immunomodulatory agent, an immunostimulatory agent, and a targeting agent. In some embodiments, the nanocarrier comprises at least one of a B cell antigen, a T cell antigen, an immunostimulatory agent, and a targeting agent. In some embodiments, the nanocarrier comprises at least two of a B cell antigen, a T cell antigen, an immunostimulatory agent, and a targeting agent. In some embodiments, the nanocarrier comprises at least three of a B cell antigen, a T cell antigen, an immunostimulatory agent, and a targeting agent. In some embodiments, the nanocarrier comprises all of a B cell antigen, a T cell antigen, an immunostimulatory agent, and a targeting agent.

In some embodiments, the nanocarrier comprises a B cell antigen. The B cell antigen may be on the immunofeature surface of the nanocarrier, on a second surface of the nanocarrier, encapsulated within the nanocarrier, or combination thereof. In some embodiments, the B cell antigen is on the surface of the nanocarrier at a density which activates B cell receptors. In some embodiments, the B cell antigen is associated with the nanocarrier. In some embodiments, the B cell antigen is covalently associated with the nanocarrier. In some embodiments, the B cell antigen is non-covalently associated with the nanocarrier. In some embodiments, the nanocarrier further comprises a targeting moiety. In some embodiments, the B cell antigen is a poorly immunogenic antigen. In some embodiments, the B cell antigen is a small molecule. In some embodiments, the B cell antigen is an addictive substance. In some embodiments, the B cell antigen is a toxin. In some embodiments, the toxin for inclusion in a nanocarrier is the complete molecule or a portion thereof. In some embodiments the B cell antigen is not a T cell antigen. In some embodiments, the B cell antigen is a carbohydrate. In some embodiments, the B cell antigen is a degenerative disease antigen, an infectious disease antigen, a cancer antigen, an atopic disease antigen, an autoimmune disease antigen, an alloantigen, a xenoantigen, an addictive substance, or a metabolic disease enzyme or enzymatic product.

In some embodiments, the nanocarrier comprises a T cell antigen. In some embodiments, the T cell antigen is on the immunofeature surface of the nanocarrier, on a second surface of the nanocarrier, encapsulated within the nanocarrier, or combination thereof. In some embodiments, the T cell antigen is associated with the nanocarrier. In some embodiments, the T cell antigen is covalently associated with the nanocarrier. In some embodiments, the T cell antigen is non-covalently associated with the nanocarrier. In some embodiments, the antigen is a degenerative disease antigen, an infectious disease antigen, a cancer antigen, an atopic disease antigen, an autoimmune disease antigen, an alloantigen, a xenoantigen, an addictive substance, or a metabolic disease enzyme or enzymatic product. In some embodiments the T cell antigen is a 'universal' T cell antigen (i.e., one which can be used with an unrelated B cell antigen, including a carbohydrate, to stimulate T cell help). In some embodiments, the nanocarrier further comprises a targeting moiety. Again, the targeting moieties mentioned here (and as described in more detail herein) is in addition to the plurality of moieties that are present on the immunofeature surface and that provide targeting of the nanocarriers to APCs.

In some embodiments, the nanocarrier comprises both a B cell antigen and a T cell antigen. In some embodiments, the B cell antigen and the T cell antigen are different antigens. In some embodiments, the B cell antigen and the T cell antigen are the same antigen. In some embodiments, the B cell antigen is on the immunofeature surface of the nanocarrier, on a second surface of the nanocarrier (e.g., covalently or non-covalently associated) or is both on the surface of the nanocarrier (e.g., covalently or non-covalently associated) and encapsulated within the nanocarrier (e.g., covalently or non-covalently associated), while the T cell antigen is on the immunofeature surface of the nanocarrier, on a second surface of the nanocarrier (e.g., covalently or non-covalently associated), is encapsulated within the nanocarrier (e.g., covalently or non-covalently associated), or is both on the surface of the nanocarrier (e.g., covalently or non-covalently associated) and encapsulated within the nanocarrier (e.g., covalently or non-covalently associated).

In some embodiments, where a nanocarrier comprises both a B cell antigen and a T cell antigen, the nanocarrier further comprises an immunostimulatory agent. In some embodiments, the immunostimulatory agent is on the surface of the nanocarrier and/or is encapsulated within the nanocarrier. In some embodiments, the immunostimulatory agent is associated with the nanocarrier. In some embodiments, the immunostimulatory agent is covalently associated with the nanocarrier. In some embodiments, the immunostimulatory agent is non-covalently associated with the nanocarrier.

In some embodiments, where a nanocarrier comprises both a B cell antigen and a T cell antigen, the nanocarrier further comprises targeting agent. Again, the targeting agent mentioned here (and as described in more detail herein) is in addition to the plurality of moieties that are present on the immunofeature surface and that provide targeting of the nanocarriers to APCs. In some embodiments, the targeting agent is on the immunofeature surface of the nanocarrier, or on a second surface of the nanocarrier. In some embodiments, the targeting agent is associated with the nanocarrier. In some embodiments, the targeting agent is covalently associated with the nanocarrier. In some embodiments, the targeting agent is non-covalently associated with the nanocarrier.

In some embodiments, where a nanocarrier comprises both a B cell antigen and a T cell antigen, the nanocarrier further comprises an immunostimulatory agent and a targeting agent. In some embodiments, the immunostimulatory agent is on the surface of the nanocarrier (e.g., covalently or non-covalently associated) and/or is encapsulated within the nanocarrier (e.g., covalently or non-covalently associated), while the targeting agent is on the surface of the nanocarrier (e.g., covalently or non-covalently associated).

In some embodiments, the nanocarrier comprises an immunostimulatory agent. In some embodiments, the immunostimulatory agent is on the surface of the nanocarrier. In some embodiments, the immunostimulatory agent is encapsulated within the nanocarrier. In some embodiments, the immunostimulatory agent is both on the surface of the nanocarrier and encapsulated within the nanocarrier. In some embodiments, the immunostimulatory agent on the surface of the nanocarrier is different from the immunostimulatory agent encapsulated within the nanocarrier. In some embodiments, the immunostimulatory agent on the surface of and encapsulated within the nanocarrier is the same.

In some embodiments, the nanocarrier comprises more than one species of immunostimulatory agents, in which case the immunostimulatory agents are different.

In some embodiments, the nanocarrier comprises an immunofeature surface, an immunostimulatory agent and an antigen. In some embodiments, the antigen is a B cell antigen or a T cell antigen. In some embodiments, the immunostimulatory agent is an immunosuppressant (suppresses an immune response). In some embodiments, the immunosuppressant is cyclosporin, a steroid, methotrexate or any agent that interferes with T cell activation. In some embodiments, the immunostimulatory agent induces regulatory T cells (e.g., TGF-β, rapamycin or retinoic acid). In some embodiments, the immunosuppressant or agent that induces regulatory T cells promotes the acquisition of tolerance to an antigen. The nanocarrier, in some embodiments, further comprises a targeting agent. In some embodiments, the nanocarrier can be used to suppress the immune system and/or promote tolerance in a subject.

In some embodiments where the nanocarrier comprises an immunofeature surface, and an immunostimulatory agent, the nanocarrier further comprises a B cell antigen and/or a T cell antigen. In some embodiments, the B cell antigen is a poorly immunogenic antigen. In some embodiments, the B cell antigen is a small molecule. In some embodiments, the B cell antigen is a carbohydrate. In some embodiments, the B cell antigen is an addictive substance. In some embodiments, the B cell antigen is a toxin. In some embodiments, the T cell antigen is a degenerative disease antigen, an infectious disease antigen, a cancer antigen, an atopic disease antigen, an autoimmune disease antigen, an alloantigen, a xenoantigen, an addictive substance, or a metabolic disease enzyme or enzymatic product. In some embodiments, the T cell antigen is an universal T cell antigen. In some embodiments, the nanocarrier further comprises a targeting agent.

The nanocarrier, in some embodiments, can be used to induce or enhance an immune response to a poorly immunogenic antigen (e.g., a small molecule or carbohydrate) in a subject. In some embodiments, the nanocarrier can be used to induce or enhance an immune response to an addictive substance in a subject. In some embodiments, the nanocarrier can be used to induce or enhance an immune response to a toxin in a subject. The nanocarrier, in some embodiments, can be used to treat a subject that has or is susceptible to an addiction. The nanocarrier, in some embodiments, can be used to treat a subject that has been or will be exposed to a toxin. In some embodiments, the nanocarrier can be used to treat and/or prevent infectious disease, cancer, or autoimmune disease (including rheumatoid arthritis). In other embodiments, the nanocarriers can be used for immune suppression in connection with transplants to ameliorate transplant rejection.

In some embodiments, the nanocarrier further comprises a targeting moiety. In some embodiments, the targeting moiety is on the immunofeature surface, or on a second surface of the nanocarrier. In some embodiments, the targeting moiety is associated with the nanocarrier. In some embodiments, the targeting moiety is covalently associated with the nanocarrier. In some embodiments, the targeting moiety is non-covalently associated with the nanocarrier.

In some aspects a composition comprising a nanocarrier comprising (a) a conjugate of a polymer and an immunofeature moiety (i.e., one of the plurality of moieties on an immunofeature surface), (b) a conjugate of a polymer and an antigen, (c) a conjugate of a polymer and an immunostimulatory agent, and/or (d) a conjugate of a polymer and a targeting moiety is provided. In some embodiments, the nanocarrier comprises a conjugate of a polymer and an antigen and a conjugate of a polymer and an immunostimulatory agent. In some embodiments, the nanocarrier comprises a conjugate of a polymer and an antigen and a conjugate of a polymer and a targeting moiety. In some embodiments, the nanocarrier comprises a conjugate of a polymer and an immunostimulatory agent and a conjugate of a polymer and a targeting moiety. In some embodiments, the nanocarrier comprises a conjugate of a polymer and an antigen, a conjugate of a polymer and an immunostimulatory agent and a conjugate of a polymer and a targeting moiety. In some embodiments, the conjugate or conjugates is/are covalent conjugate/conjugates or non-covalent conjugate/conjugates or any combination thereof. In some embodiments, the antigen is a B cell antigen. In some embodiments, the nanocarrier further comprises a conjugate of a polymer and a T cell antigen. In some embodiments, such a conjugate is a covalent or non-covalent conjugate. In some embodiments, the antigen is a T cell antigen. In some embodiments, the nanocarrier further comprises a conjugate of a polymer and a B cell antigen. In some embodiments, such a conjugate is a covalent or non-covalent conjugate.

In some aspects, a composition comprising a nanocarrier comprising a molecule or molecules of the following formula X-L1-Y-L2-Z, wherein X is a biodegradable polymer, Y is a water soluble, non-adhesive polymer, Z is a targeting moiety, an immunomodulatory agent, an immunostimulatory agent, or a pharmaceutical agent, and L1 and L2 are bonds or linking molecules, wherein either Y or Z, but not both Y and Z, can be absent, is provided. In some embodiments, the nanocarrier comprises an antigen, an immunostimulatory agent, or both. In some embodiments, the pharmaceutical agent is an antigen. In some embodiments, the antigen is a degenerative disease antigen, an infectious disease antigen, a cancer antigen, an atopic disease antigen, an autoimmune disease antigen, an alloantigen, a xenoantigen, an addictive substance, or a metabolic disease enzyme or enzymatic product. Z may be any antigen described herein. In some embodiments, Z is a targeting moiety. In some embodiments, Z is a targeting moiety that binds a receptor expressed on the surface of a cell. In some embodiments, Z is a targeting moiety that binds a soluble receptor. In some embodiments, the soluble receptor is a complement protein or a pre-existing antibody. In some embodiments, the targeting moiety is for delivery of the nanocarrier to antigen presenting cells, T cells or B cells. In some embodiments, the antigen presenting cells are dendritic cells (DCs), follicular dendritic cells (FDCs), or macrophages. In some embodiments, the macrophages are subcapsular sinus macrophages (SCS-Mphs). In some embodiments, the Y is PEG or PEO. In some embodiments, Y is polyalkylene glycol or polyalkylene oxide. In some embodiments, X is PLGA, PLA or PGA. In some embodiments, Z is absent.

The nanocarriers of the invention comprise a surface comprising an immunofeature surface. In some aspects, the composition comprises a nanocarrier comprising a molecule or molecules of the following formula: X-L1-Y-L2-I, wherein X, L1, Y, and L2 are as described previously and I is an immunofeature moiety (i.e., one of the plurality of moieties on the immunofeature surface). As described herein, the immunofeature surface (via the plurality of moieties on the immunofeature surface) provides low affinity, high avidity binding to APCs.

In some aspects, a composition comprising a nanocarrier comprising an immunofeature surface is provided. In some aspects, a composition comprising a nanocarrier comprising an immunostimulatory agent is provided. In some embodiments, the composition further comprises an antigen and/or a targeting moiety. In some embodiments, at least one of the antigen, targeting moiety, and immunostimulatory agent is conjugated to a water soluble, non-adhesive polymer. In some embodiments, at least one of the antigen, targeting moiety, and immunostimulatory agent is conjugated to a biodegradable polymer. In some embodiments, at least one of the antigen, targeting moiety, and immunostimulatory agent is conjugated to a biocompatible polymer. In some embodiments, the biocompatible polymer is a conjugate of a water soluble, non-adhesive polymer conjugated to a biodegradable polymer. In some embodiments, the antigen is a B cell antigen. In some embodiments, the B cell antigen is not a T cell antigen. In some embodiments, the nanocarrier further comprises a T cell antigen. In some embodiments, the antigen is a T cell antigen.

In some aspects, a composition comprising a nanocarrier comprising an immunofeature surface, a small molecule, an immunostimulatory agent, and a T cell antigen is provided. In some embodiments, the small molecule is on the immunofeature surface, a second surface of the nanocarrier or is both on the surface of the nanocarrier and encapsulated within the nanocarrier. In some embodiments, the small molecule is an addictive substance. In some embodiments, the small molecule is a toxin. In some embodiments, the toxin is from a chemical weapon, an agent of biowarfare, or a hazardous environmental agent. In some embodiments, the small molecule is conjugated to a polymer. In some embodiments, the polymer is a water soluble, non-adhesive polymer, a biodegradable polymer, or a biocompatible polymer. In some embodiments, the polymer is a biocompatible polymer. In some embodiments, the immunostimulatory agent is on the surface of the nanocarrier or is both on the surface of the nanocarrier and encapsulated within the nanocarrier. In some embodiments, the immunostimulatory agent is conjugated to a polymer. In some embodiments, the polymer is a water soluble, non-adhesive polymer, a biodegradable polymer, or a biocompatible polymer biodegradable polymer. In some embodiments, the polymer is water soluble, non-adhesive polymer or a biodegradable polymer. In some embodiments, the nanocarrier further comprises a targeting moiety. In some embodiments, the targeting moiety is conjugated to a polymer. In some embodiments, the polymer is a water soluble, non-adhesive polymer, a biodegradable polymer, or a biocompatible polymer biodegradable polymer. In some embodiments, the polymer is a biocompatible polymer. In some embodiments, the water soluble, non-adhesive polymer is PEG or PEO. In some embodiments the water soluble, non-adhesive polymer is polyalkylene glycol or polyalkylene oxide. In some embodiments, the biodegradable polymer is PLGA, PLA, or PGA. In some embodiments, the biocompatible polymer is a conjugate of a water soluble, non-adhesive polymer and a biodegradable polymer.

In some embodiments, a composition comprising a nanocarrier comprising an immunofeature surface, an immunostimulatory agent, a T cell antigen, and a targeting moiety is provided. In some embodiments, the immunofeature surface comprises a plurality of moieties capable of providing low avidity binding to APC surfaces. In some embodiments, the immunostimulatory agent is a TLR 7/8 agonist. In some embodiments, the immunostimulatory agent is R848 (also referred to as Resiquimod) or imiquimod. In some embodiments, the plurality of moieties on the immunofeature surface are on the surface of the nanocarrier or are both on the surface of the nanocarrier and encapsulated within the nanocarrier. In some embodiments, the plurality of moieties on the immunofeature surface are conjugated to a polymer, preferably covalently conjugated. In some embodiments, the polymer is a water soluble, non-adhesive polymer, a biodegradable polymer, or a biocompatible polymer. In some embodiments, the plurality of moieties on the immunofeature surface are conjugated to a biocompatible polymer. In some embodiments, the immunostimulatory agent is on the surface of the nanocarrier, is encapsulated within the nanocarrier, or is both on the surface of the nanocarrier and encapsulated within the nanocarrier. In some embodiments, the immunostimulatory agent is conjugated to a polymer. In some embodiments, the polymer is a water soluble, non-adhesive polymer, a biodegradable polymer, or a biocompatible polymer biodegradable polymer. In some embodiments, immunostimulatory agent is conjugated to a biodegradable polymer. In some embodiments, the targeting moiety is conjugated to a polymer. In some embodiments, the polymer is a water soluble, non-adhesive polymer, a biodegradable polymer, or a biocompatible polymer biodegradable polymer. In some embodiments, targeting moiety is conjugated to a biocompatible polymer. In some embodiments, the water soluble, non-adhesive polymer is PEG or PEO. In some embodiments the water soluble, non-adhesive polymer is polyalkylene glycol or polyalkylene oxide. In some embodiments, the biodegradable polymer is PLGA, PLA, or PGA. In some embodiments, the biocompatible polymer is a conjugate of a water soluble, non-adhesive polymer and a biodegradable polymer.

In some embodiments of any of the nanocarriers provided herein, an immunostimulatory agent is encapsulated within the nanocarrier. In some of these embodiments, the immunostimulatory agent is R848, a TLR9 agonist (e.g., a CpG/CpG-containing nucleic acid). Such nanocarriers, in some embodiments, may be used to activate CD4 T cells and/or CD8 T cells. In some embodiments, the immunostimulatory agent, e.g., R848 or TLR9 agonist, is not conjugated. In some embodiments, the immunostimulatory agent, e.g., R848 or TLR9 agonist, is conjugated to a polymer. In some embodiments, the conjugation is covalent. In some embodiments, the conjugation is non-covalent. In some embodiments, the polymer is a water soluble, non-adhesive polymer. In some embodiments, the polymer is a biodegradable polymer. In some embodiments, the polymer is a biocompatible polymer. In some embodiments, the polymer is PEG-PLA or PLA. In any of these embodiments, the nanocarrier can further comprise a T cell antigen.

In some aspects, a composition comprising a nanocarrier comprising a poorly immunogenic antigen, an immunostimulatory agent, and a T cell antigen is provided. In some embodiments, the poorly immunogenic antigen is on the surface of the nanocarrier or is both on the surface of the nanocarrier and encapsulated within the nanocarrier. In some embodiments, the poorly immunogenic antigen is a small molecule or a carbohydrate. In some embodiments, the poorly immunogenic antigen is an addictive substance. In some embodiments, the poorly immunogenic antigen is a toxin. In some embodiments, the poorly immunogenic antigen is covalently conjugated to a polymer. In some embodiments, the polymer is a water soluble, non-adhesive polymer, a biodegradable polymer, or a biocompatible polymer biodegradable polymer. In some embodiments, the immunostimulatory agent is on the surface of the nanocarrier or is both on the surface of the nanocarrier and encapsulated within the nanocarrier. In some embodiments, the immunostimulatory agent is covalently conjugated to a polymer. In some embodiments, the polymer is a water soluble, non-adhesive polymer, a biodegradable polymer, or a biocompatible polymer biodegradable polymer. In some embodiments, the nanocarrier further comprises a targeting moiety. In some embodiments, the targeting moiety is covalently conjugated to a polymer. In some embodiments, the polymer is a water soluble, non-adhesive polymer, a biodegradable polymer, or a biocompatible polymer biodegradable polymer.

In some aspects, a composition comprising a nanocarrier that targets a specific cell, tissue or organ and modulates an immune response comprising a B cell antigen on its surface at a density that activates B cells and a immunostimulatory agent is provided. In some embodiments, the nanocarrier further comprises a targeting moiety. In some embodiments, the composition is a pharmaceutical composition and further comprises a pharmaceutically acceptable carrier. In some embodiments, the pharmaceutical composition is a vaccine composition.

In some aspects, a composition, such as a pharmaceutical composition, comprising an antigen presenting cell-targeting moiety and a nanocarrier is provided. In some embodiments, the antigen presenting cell-targeting moiety and nanocarrier are conjugated. In some embodiments, the conjugate is a covalent conjugate. In some embodiments, the conjugate is a non-covalent conjugate.

In some aspects, a composition, such as a pharmaceutical composition, comprising an immunostimulatory agent and a nanocarrier is provided. In some embodiments, the immunostimulatory agent and nanocarrier are conjugated. In some embodiments, the conjugate is a covalent conjugate. In some embodiments, the conjugate is a non-covalent conjugate.

In some aspects, a composition comprising a molecule with the formula X-L1-Y-L2-Z, wherein X is a biodegradable polymer, Y is a water soluble, non-adhesive polymer, Z is a targeting moiety, an immunostimulatory agent, or a pharmaceutical agent, and L1 and L2 are bonds or linking molecules, wherein either Y or Z, but not both Y and Z, can be absent is provided.

In some aspects, a composition comprising a molecule with the formula X-L1-Y-L2-I, wherein I is an immunofeature moiety, X is a biodegradable polymer, Y is a water soluble, non-adhesive polymer, and L1 and L2 are bonds or linking molecules, wherein either Y or I, but not both Y and I, can be absent is provided.

In some aspects, a composition comprising a molecule with the formula T-L1-X-L2-Y-L3-Z, where T is a T cell antigen, X is a biodegradable polymer, Y is a water soluble, non-adhesive polymer, Z is an Z is a targeting moiety, an immunostimulatory agent, or a pharmaceutical agent, wherein L1, L2, and L3 are bonds or linking molecules, and wherein any one or two of T, Y, and Z, but not all three of T, Y, and Z, can be absent is provided. In some embodiments, the pharmaceutical agent is an antigen. In some embodiments, the antigen is a B cell antigen or a T cell antigen.

In some aspects, a composition comprising a molecule with the formula T-L1-X-L2-Y-L3-I, where I is an immunofeature moiety, T is a T cell antigen, X is a biodegradable polymer, Y is a water soluble, non-adhesive polymer, Z is an Z is a targeting moiety, an immunostimulatory agent, or a pharmaceutical agent, wherein L1, L2, and L3 are bonds or linking molecules, and wherein any one or two of T, Y, and Z, but not all three of T, Y, and Z, can be absent is provided. In some embodiments, the pharmaceutical agent is an antigen. In some embodiments, the antigen is a B cell antigen or a T cell antigen.

In some embodiments, Z is a degenerative disease antigen, an infectious disease antigen, a cancer antigen, an atopic disease antigen, an autoimmune disease antigen, an alloantigen, a xenoantigen, a hapten, an addictive substance, or a metabolic disease enzyme or enzymatic product. In some embodiments, Z is any of the B cell antigens described herein. In some embodiments, Z is any of the T cell antigens provided herein.

In some embodiments, Z is a targeting moiety that binds a receptor expressed on the surface of a cell. In some embodiments, Z is a targeting moiety that binds a soluble receptor. In some embodiments, the soluble receptor is complement or a pre-existing antibody. In some embodiments, the targeting moiety is for targeting antigen presenting cells, T cells or B cells.

In some embodiments, Y is PEG or PEO. In some embodiments, Y is polyalkylene glycol or polyalkylene oxide.

In some embodiments, X is PLGA, PGA, or PLA.

In some embodiments, Z is absent. In some embodiments, Y is absent.

In some aspects, a pharmaceutical composition comprising a conjugate of a immunostimulatory agent and a polymer is provided. In some embodiments, the conjugate is a covalent conjugate. In some embodiments, the conjugate is a non-covalent conjugate. In some embodiments, the polymer is a water soluble, non-adhesive polymer, a biodegradable polymer, or a biocompatible polymer. In some embodiments, the polymer is a biocompatible polymer. In some embodiments, the biocompatible polymer is a biodegradable polymer or a water soluble, non-adhesive polymer. In some embodiments, the biocompatible polymer is a conjugate of a water soluble, non-adhesive polymer and a biodegradable polymer. In some embodiments, the polymer is synthetic. In some embodiments, the pharmaceutical composition comprises one or more nanocarriers wherein the conjugate is a component of the one or more nanocarriers. In some embodiments, the composition further comprises an antigen. In some embodiments, the pharmaceutical composition does not comprise an antigen. In some embodiments, the composition further comprises a targeting agent.

In some aspects, a vaccine composition comprising a conjugate of an immunostimulatory agent and a polymer is provided. In some embodiments, the conjugate is a covalent conjugate. In some embodiments, the conjugate is a non-covalent conjugate. In some embodiments, the polymer is a water soluble, non-adhesive polymer, a biodegradable polymer, or a biocompatible polymer. In some embodiments, the water soluble, non-adhesive polymer is polyethylene glycol. In some embodiments, the polymer is a biocompatible polymer. In some embodiments, the biocompatible polymer is a biodegradable polymer or a water soluble, non-adhesive polymer. In some embodiments, the biocompatible polymer is a conjugate of a water soluble, non-adhesive polymer and a biodegradable polymer. In some embodiments, the polymer is synthetic. In some embodiments, the pharmaceutical composition comprises one or more nanocarriers wherein the conjugate is a component of the one or more nanocarriers. In some embodiments, the composition further comprises an antigen. In some embodiments, the pharmaceutical composition does not comprise an antigen. In some embodiments, the composition further comprises a targeting agent.

In some embodiments, the B cell antigen is a protein or peptide. In some embodiments, the B cell antigen is a non-protein antigen (i.e., not a protein or peptide). In some embodiments, the protein or peptide is from an infectious agent. In some embodiments, the infectious agent is a bacterium, fungus, virus, protozoan, or parasite. In some embodiments, the virus is a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, or hepatitis E virus.

In some embodiments, the B cell antigen is a small molecule. In some embodiments, the small molecule is an abused substance, an addictive substance, or a toxin.

In some embodiments, the B cell antigen is an addictive substance. In some embodiments, the addictive substance is a narcotic, a hallucinogen, a stimulant, a cough suppressant, a tranquilizer, or a sedative. In some embodiments, the B cell antigen is an opiod or benzodiazepine.

In some embodiments, the B cell antigen is a toxin. In some embodiments, the toxin is from a chemical weapon. In some embodiments, the toxin from a chemical weapon is botulinum toxin or phosphene. Toxins from a chemical weapon also include, but are not limited to, O-Alkyl (<C10, incl. cycloalkyl) alkyl (Me, Et, n-Pr or i-Pr)-phosphonofluoridates (e.g. Sarin: O-Isopropyl methylphosphonofluoridate, Soman: O-Pinacolyl methylphosphonofluoridate), O-Alkyl (<C10, incl. cycloalkyl) N,N-dialkyl (Me, Et, n-Pr or i-Pr) phosphoramidocyanidates (e.g. Tabun: O-Ethyl N,N-dimethylphosphoramidocyanidate), O-Alkyl (H or <C10, incl. cycloalkyl) S-2-dialkyl (Me, Et, n-Pr or i-Pr)-aminoethyl alkyl (Me, Et, n-Pr or i-Pr) phosphonothiolates and corresponding alkylated or protonated salts (e.g. VX: O-Ethyl S-2-diisopropylaminoethyl methylphosphonothiolate), Sulfur mustards: 2-Chloroethylchloromethylsulfide, Mustard gas: Bis(2-chloroethyl)sulfide, Bis(2-chloroethylthio)methane, Sesquimustard: 1,2-Bis(2-chloroethylthio)ethane, 1,3-Bis(2-chloroethylthio)-n-propane, 1,4-Bis(2-chloroethylthio)-n-butane, 1,5-Bis(2-chloroethylthio)-n-pentane, Bis (2-chloroethylthiomethyl)ether, O-Mustard: Bis(2-chloroethylthioethyl)ether, Lewisites: Lewisite 1: 2-Chlorovinyldichloroarsine, Lewisite 2: Bis(2-chlorovinyl) chloroarsine, Lewisite 3: Tris(2-chlorovinyl)arsine, Nitrogen mustards: HN1: Bis(2-chloroethyl)ethylamine, HN2: Bis(2-chloroethyl)methylamine, HN3: Tris(2-chloroethyl)amine, Saxitoxin, Ricin, Amiton: O,O-Diethyl S-(2-(diethylamino) ethyl)phosphorothiolate and corresponding alkylated or protonated salts, PFIB: 1,1,3,3,3-Pentafluoro-2-(trifluoromethyl)-1-propene, 3-Quinuclidinyl benzilate (BZ), Phosgene: Carbonyl dichloride, Cyanogen chloride, Hydrogen cyanide and Chloropicrin: Trichloronitromethane. In some embodiments, the toxin for inclusion in a nanocarrier is a complete molecule of any of the foregoing or a portion thereof.

In some embodiments, the B cell antigen is a biohazard or hazardous environmental agent. In some embodiments, the hazardous environmental agent is arsenic, lead, mercury, vinyl chloride, polychlorinated biphenyls, benzene, polycyclic aromatic hydrocarbons, cadmium, benzo(a)pyrene, benzo(b)fluoranthene, chloroform, dichlor-diphenyl-trichlorethylene (DDT), P,P'-, aroclor 1254, aroclor 1260, dibenzo(a,h) anthracene, trichloroethylene, dieldrin, chromium hexavalent, or p,p'-dichlorodiphenyldichloroethene (DDE, P,P').

In some embodiments, the B cell antigen is a carbohydrate. In some embodiments, the carbohydrate is from an infectious agent. In some embodiments, the infectious agent is a bacterium, fungus, virus, protozoan, or parasite. In some embodiments, the bacterium is a *Pseudomonas, Pneumococcus, E. coli, Staphylococcus, Streptococcus, Treponema, Borrelia, Chlamydia, Haemophilus, Clostridium, Salmonella, Legionella, Vibrio* or Enterococci bacterium or a *Mycobacterium*. In some embodiments, the virus is a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, or hepatitis E virus.

In some embodiments, the B cell antigen is a self antigen. In some embodiments, the self antigen is a protein or peptide, lipoprotein, lipid, carbohydrate, or a nucleic acid. In some embodiments, the self antigen is an enzyme, a structural protein, a secreted protein, a cell surface receptor, or a cytokine. In some embodiments, the cytokine is TNF, IL-1, or IL-6. In some embodiments, the self antigen is cholesteryl ester transfer protein (CETP), the Aβ protein associated with Alzheimer's, a proteolytic enzyme that processes the pathological form of the Aβ protein, LDL associated with atherosclerosis, or a coreceptor for HIV-1. In some embodiments, the proteolytic enzyme that processes the pathological form of the Aβ protein is beta-secretase. In some embodiments, the LDL associated with atherosclerosis is oxidized or minimally modified. In some embodiments, the coreceptor for HIV-1 is CCR5. In some embodiments, the self antigen is an autoimmune disease antigen.

In some embodiments, the B cell antigen is a degenerative disease antigen, an infectious disease antigen, a cancer antigen, an atopic disease antigen, an autoimmune disease antigen, or a metabolic disease enzyme or enzymatic product thereof.

In some embodiments, the antigen is a cancer antigen. Is some embodiments, the cancer antigen is Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, or c-erbB-2.

In some embodiments, the infectious disease antigen is a viral antigen. In some embodiments, the viral antigen is an antigen from a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, or hepatitis E virus.

In some embodiments, the B cell antigen is a poorly immunogenic antigen. In some embodiments, the poorly immunogenic antigen is a non-protein antigen. In some embodiments, the poorly immunogenic antigen is a carbohydrate or small molecule. In some embodiments, the poorly immunogenic antigen is an abused substance, addictive substance, or toxin. In some embodiments, the toxin is from a chemical weapon. In some embodiments, the poorly immunogenic antigen is a hazardous environmental agent. In some embodiments, the poorly immunogenic antigen is a self antigen.

In general, the T cell antigen is a protein or peptide. In some embodiments, the T cell antigen is a degenerative disease antigen, an infectious disease antigen, a cancer antigen, an atopic disease antigen, an autoimmune disease antigen, an alloantigen, a xenoantigen, a contact sensitizer, a hapten, or a metabolic disease enzyme or enzymatic product.

In some embodiments, the T cell antigen is from an infectious agent. In some embodiments, the infectious agent is a bacterium, fungus, virus, protozoan, or parasite. In some embodiments, the infectious disease antigen is a viral antigen. In some embodiments, the viral antigen is an antigen from a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, or hepatitis E virus.

In some embodiments, T cell antigen is a universal T cell antigen. In some embodiments, the universal T cell antigen is one or more peptides derived from tetanus toxoid, Epstein-Barr virus, or influenza virus.

In some embodiments, immunostimulatory agents are interleukins, interferon, cytokines, etc. In some embodiments, the immunostimulatory agent is a toll-like receptor (TLR) agonist, cytokine receptor agonist, CD40 agonist, Fc receptor agonist, CpG-containing immunostimulatory nucleic acid, complement receptor agonist, or an adjuvant. In some embodiments, the TLR agonist is a TLR-1, TLR-2, TLR-3, TLR-4, TLR-5, TLR-6, TLR-7, TLR-8, TLR-9, or TLR-10 agonist. In some embodiments, the Fc receptor agonist is a Fc-gamma receptor agonist. In some embodiments, the complement receptor agonist binds to CD21 or CD35. In some embodiments, the complement receptor agonist induces endogenous complement opsonization of the nanocarrier. In some embodiments, the cytokine receptor agonist is a cytokine. In some embodiments, the cytokine receptor agonist is a small molecule, antibody, fusion protein, or aptamer. In some embodiments, the immunostimulatory agent is an adjuvant. In some embodiments, the adjuvant induces cytokine biosynthesis. In some embodiments, the adjuvant is alum, MF59, R848, cholera toxin, squalene, phosphate adjuvants, or tetrachlorodecaoxide. In some embodiments, the adjuvant is monophosphoryl lipid A (MPL, SmithKline Beecham); saponins including QS21 (SmithKline Beecham); immunostimulatory oligonucleotides (e.g., CpG immunostimulatory oligonucleotides first described by Kreig et al., *Nature* 374:546-9, 1995); incomplete Freund's adjuvant; complete Freund's adjuvant; montanide; vitamin E and various water-in-oil emulsions prepared from biodegradable oils such as squalene and/or tocopherol, Quil A, Ribi Detox, CRL-1005, or L-121.

In specific embodiments, an immunostimulatory agent may be a natural or synthetic agonist for a Toll-like receptor (TLR). In specific embodiments, an immunostimulatory agent may be a ligand for toll-like receptor (TLR)-7, such as CpGs, which induce type I interferon production; an agonist for the DC surface molecule CD40; an agent that promotes DC maturation; a TLR-4 agonist; a cytokine; proinflammatory stimuli released from necrotic cells (e.g. urate crystals); activated components of the complement cascade (e.g. CD21, CD35, etc.); and so forth.

In some embodiments, the targeting moiety binds a receptor expressed on the surface of a cell. In some embodiments, the targeting moiety binds a soluble receptor. In some embodiments, the soluble receptor is a complement protein or a pre-existing antibody. In some embodiments, the targeting moiety is for delivery of the nanocarrier to antigen presenting cells, T cells, or B cells. In some embodiments, the antigen presenting cells are macrophages. In some embodiments, the macrophages are subcapsular sinus macrophages. In some embodiments, the antigen presenting cells are dendritic cells. In some embodiments, the antigen presenting cells are follicular dendritic cells.

In some embodiments, the targeting moiety is a molecule that binds to CD11b, CD169, mannose receptor, DEC-205, CD11c, CD21/CD35, CX3CR1, or a Fc receptor. In some embodiments, the targeting moiety is a molecule that binds to CD169, CX3CR1, or a Fc receptor. In some embodiments, the molecule that binds to CD169 is an anti-CD169 antibody. In some embodiments, the molecule that binds CX3CR1 is CX3CL1 (fractalkine). In some embodiments, the targeting moiety comprises the Fc portion of an immunoglobulin. In some embodiments, the targeting moiety comprises the Fc portion of an IgG. In some embodiments, the Fc portion of an immunoglobulin is a human Fc portion of an immunoglobulin. In some embodiments, the Fc portion of an IgG is a human Fc portion of an IgG. In some embodiments, the targeting moiety is the soluble receptor, CRFc. In some embodiments, CRFc can be used to target macrophages in the subcapsular sinus but not macrophages of the medulla. In some embodiments, the targeting moiety is one or more amine moieties.

In some aspects, the compositions provided herein are immunogenic.

In some aspects, a method comprising administering any of the compositions provided herein to a subject in an amount effective to modulate an immune response is provided. In some embodiments, the composition is in an amount effective to induce or enhance an immune response. In some embodiments, the composition is in an amount effective to suppress an immune response. In some embodiments, the composition is in an amount effective to direct or redirect an immune response. In some embodiments, the method is for prophylaxis and/or treatment of the conditions identified herein.

In some embodiments, where the method is to induce or enhance an immune response, the subject has or is susceptible to having cancer, an infectious disease, a non-autoimmune metabolic or degenerative disease, an atopic disease, or an addiction. In some embodiments, the subject has been exposed to or may be exposed to a toxin. In some embodiments, the subject has been exposed to or may be exposed to a toxin from a chemical weapon. In some embodiments, the subject has been exposed to or may be exposed to a toxin from a hazardous environmental substance. In some embodiments, the nanocarrier comprises a B-cell antigen, an immunostimulatory agent, and a T cell antigen, such as an universal T cell antigen. In some embodiments, the nanocarrier further comprises a targeting moiety.

In some embodiments, where the method is for treating or preventing an addiction (or for treating a subject exposed to or who may be exposed to a toxin), the nanocarrier comprises the addictive substance or toxin, an adjuvant, and a T cell. In some embodiments, the method raises high titer antibodies that bind and neutralize the offending agent before it reaches its effector site (e.g., the brain). In some embodiments, the addictive substance or toxin is at a high density on the surface of the nanocarrier.

In some embodiments, the infectious disease is a chronic viral infection. In some embodiments, the chronic viral infection is HIV, HPV, HBV, or HCV infection. In some embodiments, the infectious disease is or is caused by a bacterial infection. In some embodiments, the subject has or is susceptible to having a *Pseudomonas* infection, a *Pneumococcus* infection, tuberculosis, malaria, leishmaniasis, *H. pylori*, a *Staphylococcus* infection, or a *Salmonella* infection. In some embodiments, the infectious disease is or is caused by a fungal infection. In some embodiments, the infectious disease is or is caused by a parasitic infection. In some embodiments, the infectious disease is or is caused by a protozoan infection. In some embodiments, the subject has or is susceptible to having influenza.

In some embodiments, the autoimmune disease is disease is lupus, multiple sclerosis, rheumatoid arthritis, diabetes mellitus type I, inflammatory bowel disease, thyroiditis, or celiac disease. In some embodiments, the subject has had or will have a transplant, and the method can be to prevent or ameliorate transplant rejection. In some embodiments, the nanocarrier comprises an antigen and an immune suppressant or an agent that induces regulatory T cells. In some embodiments, the nanocarrier further comprises a targeting moiety. Generally, where the method is one to suppress an immune response, the antigen is provided in the absence of an adjuvant.

In some aspects, vaccine nanocarriers for delivery of immunomodulatory agents to the cells of the immune system are provided. In some embodiments, vaccine nanocarriers comprise at least one immunomodulatory agent that is capable of inducing an immune response in B cells and/or in T cells. In certain embodiments, immunomodulatory agents presented on nanocarrier surfaces stimulate B cells, and immunomodulatory agents encapsulated within the nanocarriers are processed and presented to T cells. In some embodiments, vaccine nanocarriers comprise at least one targeting moiety that is useful for selective delivery of the vaccine nanocarrier to specific antigen-presenting cells (APCs).

In some embodiments, an immunomodulatory agent may comprise isolated and/or recombinant proteins or peptides, carbohydrates, glycoproteins, glycopeptides, proteoglycans, inactivated organisms and viruses, dead organisms and virus, genetically altered organisms or viruses, and cell extracts. In some embodiments, an immunomodulatory agent may comprise nucleic acids, carbohydrates, lipids, and/or small molecules. In some embodiments, an immunomodulatory agent is one that elicits an immune response. In some embodiments, an immunomodulatory agent is an antigen. In some embodiments, an immunomodulatory agent is used for vaccines.

In some embodiments, an immunomodulatory agent is any protein and/or other antigen derived from a pathogen. The pathogen may be a virus, bacterium, fungus, protozoan, parasite, etc. In some embodiments, an immunomodulatory agent may be in the form of whole killed organisms, peptides, proteins, glycoproteins, glycopeptides, proteoglycans, carbohydrates, or combinations thereof.

In some embodiments, all of the immunomodulatory agents of a vaccine nanocarrier are identical to one another. In some embodiments, all of the immunomodulatory agents of a vaccine nanocarrier are different. In some embodiments, a vaccine nanocarrier comprises exactly one distinct type (i.e., species) of immunomodulatory agent. For example, when the immunomodulatory agent is an antigen, all of the antigens that are in the vaccine nanocarrier are the same. In some embodiments, a vaccine nanocarrier comprises exactly two distinct types of immunomodulatory agents. In some embodiments, a vaccine nanocarrier comprises greater than two distinct types of immunomodulatory agents.

In some embodiments, a vaccine nanocarrier comprises a single type of immunomodulatory agent that stimulates an immune response in B cells. In some embodiments, a vaccine nanocarrier comprises a single type of immunomodulatory agent that stimulates an immune response in T cells. In some embodiments, a vaccine nanocarrier comprises two types of immunomodulatory agents, wherein the first immunomodulatory agent stimulates B cells, and the second immunomodulatory agent stimulates T cells. In certain embodiments, any of the aforementioned agents could stimulate both B cells and T cells, but this is not necessarily so. In certain embodiments, the aforementioned immunomodulatory agents stimulates only B cells or T cells, respectively. In some embodiments, a vaccine nanocarrier comprises greater than two types of immunomodulatory agents, wherein one or more types of immunomodulatory agents stimulate B cells, and one or more types of immunomodulatory agents stimulate T cells.

In some embodiments, a vaccine nanocarrier includes a lipid membrane (e.g. lipid bilayer, lipid monolayer, etc.). At least one immunomodulatory agent may be associated with the lipid membrane. In some embodiments, at least one immunomodulatory agent is embedded within the lipid membrane, embedded within the lumen of a lipid bilayer, associated with the interior surface of the lipid membrane, and/or encapsulated with the lipid membrane of a vaccine nanocarrier.

In some embodiments, a vaccine nanocarrier includes a polymer (e.g. a polymeric core). The immunomodulatory agent may be associated with the polymer, and in some embodiments, at least one type of immunomodulatory agent is associated with the polymer. In some embodiments, the immunomodulatory agent is embedded within the polymer, associated with the interior surface of the polymer, and/or encapsulated within the polymer of a vaccine nanocarrier, and, in some embodiments, at least one type of immunomodulatory agent is embedded within the polymer, associated with the interior surface of the polymer, and/or encapsulated within the polymer of a vaccine nanocarrier.

In some embodiments, inventive vaccine nanocarriers comprise less than less than 90% by weight, less than 75% by weight, less than 50% by weight, less than 40% by weight, less than 30% by weight, less than 20% by weight, less than 15% by weight, less than 10% by weight, less than 5% by weight, less than 1% by weight, or less than 0.5% by weight of the immunomodulatory agent.

In some embodiments, vaccine nanocarriers are associated with at least one targeting moiety in addition to the plurality of moieties associated with the immunofeature surface (i.e., the moieties that provide targeting of the nanocarriers to APCs). The additional targeting moieties are distinct from the plurality of moieties present on the immunofeature surface in that the additional targeting moieties typically provide high affinity binding to a receptor (and, therefore, may be alternatively referred to herein as "high affinity targeting moieties"). In some embodiments, a targeting moiety may be a nucleic acid, polypeptide, peptide, glycoprotein, glycopeptide, proteoglycan, carbohydrate, lipid, small molecule, etc. For example, a targeting moiety can be a nucleic acid targeting moiety (e.g. an aptamer, Spiegelmer®, etc.) that binds to a cell type specific marker. In some embodiments, a targeting moiety may be a naturally occurring or synthetic ligand for a cell surface protein, e.g., DEC-205, CD169, CD11b, etc. Examples of targeting moieties also include those provided elsewhere herein, such as those described above.

In accordance with the present invention, a targeting moiety recognizes one or more "targets" or "markers" associated with a particular organ, tissue, cell, and/or subcellular locale. In some embodiments, a target may be a marker that is exclusively or primarily associated with one or a few cell types, with one or a few diseases, and/or with one or a few developmental stages. Examples of cells that are targeted include antigen presenting cells (APCs), such as dendritic cells, follicular dendritic cells, and macrophages. One example of a macrophage is a subcapsular sinus macrophage. Other cells that are targeted include T cells and B cells. In some embodiments, a target can comprise a protein, a carbohydrate, a lipid, and/or a nucleic acid. In some embodiments, a target is a tumor marker. In some embodiments, a target is an APC marker. In certain embodiments, a target is a T cell marker. In some embodiments, the targeting moieties target secondary lymphoid tissues or organs. Secondary lympoid tissues or organs include lymph nodes, the spleen, Peyer's patches, the appendix, or tonsils.

In certain embodiments, a target is a dendritic cell marker. In some embodiments, DC markers include DC-205, CD11c, class II MHC, CD80, CD86, DC-SIGN, CD11b, BDCA-1, BDCA-2, BDCA-4, Siglec-H, CX3CR1, and/or Langerin. Examples of such markers are provided elsewhere herein.

In certain embodiments, a target is a subcapsular sinus macrophage marker. In some embodiments, SCS-Mph markers include CD169 (i.e. sialoadhesin), CD11b (i.e. CD11b/CD18, Mac-1, CR3 or αMβ2 integrin), Fc receptor, and/or the mannose receptor (i.e. a multi-valent lectin), proteins which are all prominently expressed on SCS-Mph. Examples of such markers are provided elsewhere herein.

In certain embodiments, a target is a B cell marker. In some embodiments, B cell markers may include complement receptors, CR1 (i.e. CD35) or CR2 (i.e. CD21), proteins which are expressed on B cells. In some embodiments, B cell targeting can be accomplished by B cell markers such as CD19, CD20, and/or CD22. In some embodiments, B cell targeting can be accomplished by B cell markers such as CD40, CD52, CD80, CXCR5, VLA-4, class II MHC, surface IgM or IgD, APRL, and/or BAFF-R. Examples of such markers are provided elsewhere herein.

In certain embodiments, a target is a FDC marker. In some embodiments, FDC markers include complement receptors, CR1 (i.e. CD35) or CR2 (i.e. CD21), proteins which are expressed on FDCs. Examples of such markers are provided elsewhere herein.

In some embodiments, a vaccine nanocarrier comprises a single type of targeting moiety that directs delivery of the vaccine nanocarrier to a single cell type (e.g. delivery to SCS-Mph only). In some embodiments, a vaccine nanocarrier comprises a single type of targeting moiety that directs delivery of the vaccine nanocarrier to multiple cell types (e.g. delivery to both SCS-Mphs and FDCs, or to both SCS-Mphs and DCs). In some embodiments, a vaccine nanocarrier comprises two types of targeting moieties, wherein the first type of targeting moiety directs delivery of the vaccine nanocarrier to one cell type, and the second type of targeting moiety directs delivery of the vaccine nanocarrier to a second cell type. For example, in some embodiments, the first type of targeting moiety directs delivery to SCS-Mphs, and the second type of targeting moiety directs delivery to DCs. As another example, the first type of targeting moiety directs delivery to SCS-Mphs, and the second type of targeting moiety directs delivery to FDCs.

In some embodiments, inventive vaccine nanocarriers comprise less than 50% by weight, less than 40% by weight, less than 30% by weight, less than 20% by weight, less than 15% by weight, less than 10% by weight, less than 5% by weight, less than 1% by weight, or less than 0.5% by weight of the targeting moiety.

In some embodiments, vaccine nanocarriers may transport one or more types of immunostimulatory agents which can help stimulate immune responses. In some embodiments, immunostimulatory agents boost immune responses by activating APCs to enhance their immunostimulatory capacity. In some embodiments, immunostimulatory agents boost immune responses by amplifying lymphocyte responses to specific antigens. In some embodiments, immunostimulatory agents boost immune responses by inducing the local release of mediators, such as cytokines from a variety of cell types.

In some embodiments, a vaccine nanocarrier comprises a single type of immunostimulatory agent that stimulates both B cells and T cells. In some embodiments, a vaccine nanocarrier comprises two types of immunostimulatory agents, wherein the first type of immunostimulatory agent stimulates B cells, and the second type of immunostimulatory agent stimulates T cells. In some embodiments, a vaccine nanocarrier comprises greater than two types of immunostimulatory agents, wherein one or more types of immunostimulatory agents stimulate B cells, and one or more types of immunostimulatory agents stimulate T cells.

In some embodiments, various assays can be utilized in order to determine whether an immune response has been modulated in a B cell or group of B cells or in a T cell or group of T cells. In some embodiments, the assay assesses whether or not the cell or group of cells has/have become "activated".

In some embodiments, various assays can be utilized in order to determine whether an immune response has been stimulated in a T cell or group of T cells. In some embodiments, stimulation of an immune response in T cells can be determined by measuring antigen-induced production of cytokines by T cells. In some embodiments, stimulation of an immune response in T cells can be determined by measuring antigen-induced proliferation of T cells. In some embodiments, an immune response in T cells is determined to be stimulated if cellular markers of T cell activation are expressed at different levels (e.g. higher or lower levels) relative to unstimulated cells.

In some embodiments, various assays can be utilized in order to determine whether an immune response has been stimulated in a B cell or group of B cells. In some embodiments, stimulation of an immune response in B cells can be determined by measuring antibody titers, antibody affinities, antibody performance in neutralization assays, class-switch recombination, affinity maturation of antigen-specific antibodies, development of memory B cells, development of long-lived plasma cells that can produce large amounts of high-affinity antibodies for extended periods of time, germinal center reactions, and/or antibody performance in neutralization assays.

A vaccine nanocarrier is an entity that comprises an immunofeature surface. The vaccine nanocarrier may also comprise at least one immunomodulatory agent which is capable of stimulating an immune response in B cells and/or T cells. Any vaccine nanocarrier can be used in accordance with the present invention.

In some embodiments, a nanocarrier has a greatest dimension (e.g., diameter) of less than 100 microns (µm). In some embodiments, inventive nanocarriers have a greatest dimension (e.g., diameter) of 300 nm or less. In some embodiments, inventive nanocarriers have a greatest dimension (e.g., diameter) of 250 nm or less. In some embodiments, inventive nanocarriers have a greatest dimension (e.g., diameter) of 200 nm or less. In some embodiments, inventive nanocarriers have a greatest dimension (e.g., diameter) of 150 nm or less. In some embodiments, inventive nanocarriers have a greatest dimension (e.g., diameter) of 100 nm or less. In some embodiments, inventive nanocarriers have a greatest dimension ranging between 25 nm and 200 nm. In some embodiments, inventive nanocarriers have a greatest dimension ranging between 20 nm and 100 nm.

A variety of different nanocarriers can be used in accordance with the present invention. In some embodiments, nanocarriers are spheres or spheroids. In some embodiments, nanocarriers are flat or plate-shaped. In some embodiments, nanocarriers are cubes or cuboids. In some embodiments, nanocarriers are ovals or ellipses. In some embodiments, nanocarriers are cylinders, cones, or pyramids. Nanocarriers comprise one or more surfaces, and at least one of the one or more surfaces comprises an immunofeature surface. Nanocarriers may be solid or hollow and may comprise one or more layers. In some embodiments, each layer has a unique composition and unique properties relative to the other layer(s). To give but one example, nanocarriers may have a core/shell structure, wherein the core is one layer (e.g. a polymeric core) and the shell is a second layer (e.g. a lipid bilayer or monolayer). Nanocarriers may comprise a plurality of different layers. In some embodiments, one layer may be substantially cross-linked, a second layer is not substantially cross-linked, and so forth. In some embodiments, one, a few, or all of the different layers may comprise one or more immunomodulatory agents, targeting moieties, immunostimulatory agents, and/or combinations thereof. In some embodiments, one layer comprises an immunomodulatory agent, targeting moiety, and/or immunostimulatory agent, a second layer does not comprise an immunomodulatory agent, targeting moiety, and/or immunostimulatory agent, and so forth. In some embodiments, each individual layer comprises a different immunomodulatory agent, targeting moiety, immunostimulatory agent, and/or combination thereof.

In some embodiments, nanocarriers may optionally comprise one or more lipids. In some embodiments, a nanocarrier is a liposome. In some embodiments, a nanocarrier comprises a lipid bilayer, and/or multiple lipid bilayers. For example, a lipid bilayer may form the exterior surface of a nanocarrier, in which case the nanocarrier comprising a lipid bilayer shell may be referred to as a liposome. Liposome nanocarriers typically have relatively moldable surfaces, and the nanocarriers may take on a variety of shapes (e.g., spherical, oblong, cylindrical, etc.) depending on environmental factors. It will be appreciated, therefore, that the maximum diameter of such nanocarriers may change in different environments. When referring to the diameter of such nanocarriers, Typically, liposome nanocarriers comprise phospholipids. In some embodiments, a nanocarrier comprises a lipid monolayer. In some embodiments, a nanocarrier is a micelle. In some embodiments, a nanocarrier comprises a core of a polymeric matrix surrounded by a lipid layer (e.g. lipid bilayer, lipid monolayer, etc.). In some embodiments, a nanocarrier comprises a non-polymeric core (e.g. metal particle, quantum dot, ceramic particle, bone particle, viral particle, etc.) surrounded by a lipid layer (e.g. lipid bilayer, lipid monolayer, etc.).

In some embodiments, a nanocarrier comprises one or more polymers. In some embodiments, a polymeric matrix can be surrounded by a coating layer (e.g. liposome, lipid monolayer, micelle, etc.). In some embodiments, an immunomodulatory agent, targeting moiety, and/or immunostimulatory agent can be associated with the polymeric matrix. In such embodiments, the immunomodulatory agent, targeting moiety, and/or immunostimulatory agent is effectively encapsulated within the nanocarrier. It will be appreciated, however, that the plurality of moieties on the immunofeature surface (i.e., that provide targeting to APCs) are on a surface of the nanocarriers, the surface being an exterior surface and exposed to the environment surrounding the nanocarriers.

In some embodiments, an immunomodulatory agent, targeting moiety, and/or immunostimulatory agent can be covalently associated with a nanocarrier. The targeting moieties mentioned here (and as described in more detail herein) are, for example, B-cell targeting moieties or T-cell targeting moieties. It will be appreciated that such moieties are in addition to the plurality of moieties that are present on the immunofeature surface and that provide targeting of the nanocarriers to APCs. In some embodiments, covalent association is mediated by a linker. In some embodiments, an immunomodulatory agent, targeting moiety, and/or immunostimulatory agent is non-covalently associated with a nanocarrier. For example, in some embodiments, an immunomodulatory agent, targeting moiety, and/or immunostimulatory agent is encapsulated within, surrounded by, and/or dispersed throughout a polymeric matrix, a lipid membrane, etc. Alternatively or additionally, an immunomodulatory agent, targeting moiety, and/or immunostimulatory agent may be associated with a polymeric matrix, a lipid membrane, etc. by hydrophobic interactions, charge interactions, van der Waals forces, etc.

A wide variety of polymers and methods for forming polymeric matrices therefrom are known in the art of drug delivery. In general, a polymeric matrix comprises one or more polymers. Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Polymers in accordance with the present invention may be organic polymers. In some embodiments, the polymers are dendritic polymers or blends of polymers.

Examples of polymers include polyethylenes, polycarbonates (e.g. poly(1,3-dioxan-2one)), polyanhydrides (e.g. poly(sebacic anhydride)), polyhydroxyacids (e.g. poly($\beta$-hydroxyalkanoate)), polypropylfumerates, polycaprolactones, polyamides (e.g. polycaprolactam), polyacetals, polyethers, polyesters (e.g. polylactide, polyglycolide), poly(orthoesters), polycyanoacrylates, polyvinyl alcohols, polyurethanes, polyphosphazenes, polyacrylates, polymethacrylates, polyureas, polystyrenes, and polyamines.

In some embodiments, nanocarriers comprise immunomodulatory agents embedded within reverse micelles. To give but one example, a liposome nanocarrier may comprise hydrophobic immunomodulatory agents embedded within the liposome membrane, and hydrophilic immunomodulatory agents embedded with reverse micelles found in the interior of the liposomal nanocarrier.

In some embodiments, a nanocarrier does not include a polymeric component. In some embodiments, nanocarriers comprise metal particles, quantum dots, ceramic particles, bone particles, viral particles, etc. In some embodiments, an immunomodulatory agent, targeting moiety, and/or immunostimulatory agent is associated with the surface of such a non-polymeric nanocarrier. In some embodiments, a non-polymeric nanocarrier is an aggregate of non-polymeric components, such as an aggregate of metal atoms (e.g. gold atoms). In some embodiments, an immunomodulatory agent, targeting moiety, and/or immunostimulatory agent is associated with the surface of, encapsulated within, surrounded by, and/or dispersed throughout an aggregate of non-polymeric components.

In some embodiments, nanocarriers may optionally comprise one or more amphiphilic entities (i.e., entities that possess both hydrophilic and hydrophobic properties). In some embodiments, an amphiphilic entity can promote the production of nanocarriers with increased stability, improved uniformity, or increased viscosity.

In some embodiments, a nanocarrier comprises one or more nanoparticles associated with the exterior surface of and/or encapsulated within the nanocarrier.

Nanocarriers may be prepared using any method known in the art. For example, particulate nanocarrier formulations can be formed by methods such as nanoprecipitation, flow focusing fluidic channels, spray drying, single and double emulsion solvent evaporation, solvent extraction, phase separation, milling, microemulsion procedures, nanopriting, microfabrication, nanofabrication, sacrificial layers, simple and complex coacervation, as well as other methods well known to those of ordinary skill in the art. Alternatively or additionally, aqueous and organic solvent syntheses for monodisperse semiconductor, conductive, magnetic, organic, and other nanoparticles may be utilized.

In some embodiments, immunomodulatory agents, targeting moieties, and/or immunostimulatory agents, are not covalently associated with a nanocarrier. For example, nanocarriers may comprise a polymeric matrix, and immunomodulatory agents, targeting moieties, and/or immunostimulatory agents, etc. are associated with the surface of, encapsulated within, and/or distributed throughout the polymeric matrix of an inventive nanocarrier. Immunomodulatory agents may be released by diffusion, degradation of the nanocarrier, and/or a combination thereof. In some embodiments, polymer(s) of the nanocarrier degrade by bulk erosion. In some embodiments, polymer(s) of the nanocarrier degrade by surface erosion.

In some embodiments, immunofeature moieties, immunomodulatory agents, targeting moieties, and/or immunostimulatory agents are covalently associated with a particle. In some embodiments, covalent association is mediated by one or more linkers. Any suitable linker can be used in accordance with the present invention. In some embodiments, the linker is a cleavable linker (e.g., an ester linkage, an amide linkage, a disulfide linkage, etc.).

In some embodiments, nanocarriers are made by self-assembly. As an example, lipids are mixed with a lipophilic immunomodulatory agent, and then formed into thin films on a solid surface. A hydrophilic immunomodulatory agent is dissolved in an aqueous solution, which is added to the lipid films to hydrolyze lipids under vortex. Liposomes with lipophilic immunomodulatory agents incorporated into the bilayer wall and hydrophilic immunomodulatory agents inside the liposome lumen are spontaneously assembled. In certain embodiments, pre-formulated polymeric nanoparticles are mixed with small liposomes under gentle vortex to induce liposome fusion onto polymeric nanoparticle surface.

As another example, a hydrophilic immunomodulatory agent to be encapsulated is first incorporated into reverse micelles by mixing with naturally derived and non-toxic amphiphilic entities in a volatile, water-miscible organic solvent. In some embodiments, a biodegradable polymer is added after reverse micelle formation is complete. The resulting biodegradable polymer-reverse micelle mixture is combined with a polymer-insoluble hydrophilic non-solvent to form nanoparticles by the rapid diffusion of the solvent into the non-solvent and evaporation of the organic solvent.

In some embodiments, lipid monolayer stabilized polymeric nanocarriers are used to deliver one or a plurality of immunomodulatory agents. In certain embodiments, a hydrophilic immunomodulatory molecule is first chemically conjugated to the polar headgroup of a lipid. The conjugate is mixed with a certain ratio of unconjugated lipid molecules in an aqueous solution containing one or more water-miscible solvents. A biodegradable polymeric material is mixed with the hydrophobic immunomodulatory agents to be encapsulated in a water miscible or partially water miscible organic solvent. The resulting polymer solution is added to the aqueous solution of conjugated and unconjugated lipid to yield nanoparticles by the rapid diffusion of the organic solvent into the water and evaporation of the organic solvent.

The compositions and methods described herein can be used for the prophylaxis and/or treatment of a variety of infectious diseases, disorders, and/or conditions. Examples of other diseases, disorders, and/or conditions are provided elsewhere herein. In some embodiments, vaccine nanocarriers in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive vaccine nanocarriers may be used to treat, alleviate, ameliorate, relieve, delay onset of, inhibit progression of, reduce severity of, and/or reduce incidence of one or more symptoms or features of microbial infection (e.g. bacterial infection, fungal infection, viral infection, parasitic infection, etc.). In some embodiments, the prophylaxis and/or treatment of microbial infection comprises administering a therapeutically effective amount of inventive vaccine nanocarriers to a subject in need thereof, in such amounts and for such time as is necessary to achieve the desired result. In certain embodiments of the present invention, a "therapeutically effective amount" of an inventive vaccine nanocarrier is that amount effective for treating, alleviating, ameliorating, relieving, delaying onset of, inhibiting progression of, reducing severity of, and/or reducing incidence of one or more symptoms or features of disease, disorder, and/or condition provided herein.

In some embodiments, inventive prophylactic and/or therapeutic protocols involve administering a therapeutically effective amount of one or more inventive vaccine nanocarriers to a subject such that an immune response is modulated (e.g., stimulated in both T cells and/or B cells).

The present invention provides novel compositions comprising a therapeutically effective amount of one or more vaccine nanocarriers and one or more pharmaceutically acceptable excipients. In some embodiments, the present invention provides for pharmaceutical compositions comprising inventive vaccine nanocarriers as described herein. The composition may include more than one type of nanocarrier, each type having different constituents (e.g., immunomodulatory agents, targeting agents, immunostimulatory agents, excipients, etc.). In accordance with some embodiments, a method of administering a pharmaceutical composition comprising inventive compositions to a subject (e.g. human) in need thereof is provided.

In some embodiments, a therapeutically effective amount of an inventive vaccine nanocarrier composition is delivered to a patient and/or animal prior to, simultaneously with, and/or after diagnosis with a disease, disorder, and/or condition. In some embodiments, a therapeutic amount of an inventive vaccine nanocarrier composition is delivered to a patient and/or animal prior to, simultaneously with, and/or after onset of symptoms of a disease, disorder, and/or condition. In certain embodiments, a therapeutic amount of an inventive vaccine nanocarrier composition is administered to a patient and/or animal prior to exposure to an infectious agent. In certain embodiments, a therapeutic amount of an inventive vaccine nanocarrier composition is administered to a patient and/or animal after exposure to an infectious agent. In certain embodiments, a therapeutic amount of an inventive vaccine nanocarrier composition is administered to a patient and/or animal prior to exposure to an addictive substance or a toxin. In certain embodiments, a therapeutic amount of an inventive vaccine nanocarrier composition is administered to a patient and/or animal after exposure to an addictive substance or a toxin.

In some embodiments, the pharmaceutical compositions of the present invention are administered by a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), transdermal, mucosal, nasal, buccal, enteral, sublingual; by intratracheal instillation, bronchial instillation, and/or inhalation; and/or as an oral spray, nasal spray, and/or aerosol. In certain embodiments, the composition is administered orally. In certain embodiments, the composition is administered parenterally. In certain embodiments, the composition is administered via intramuscular injection.

In certain embodiments, vaccine nanocarriers which delay the onset and/or progression of a disease, disorder, and/or condition (e.g., a particular microbial infection) may be administered in combination with one or more additional therapeutic agents which treat the symptoms of the disease, disorder, and/or condition. For example, the vaccine nanocarriers may be combined with the use of an anti-cancer agent, anti-inflammatory agent, antibiotic, or anti-viral agent.

The invention provides a variety of kits comprising one or more of the nanocarriers of the invention. For example, the invention provides a kit comprising an inventive nanocarrier and instructions for use. A kit may comprise multiple different nanocarriers. A kit may comprise any of a number of additional components or reagents in any combination. According to certain embodiments of the invention, a kit may include, for example, (i) a nanocarrier comprising at least one immunomodulatory agent, wherein the at least one immunomodulatory agent is capable of stimulating both a T cell and/or B cell response, at least one targeting moiety, and/or at least one immunostimulatory agent; (ii) instructions for administering the nanocarrier to a subject in need thereof. In certain embodiments, a kit may include, for example, (i) at least one immunomodulatory agent, wherein the at least one immunomodulatory agent is capable of stimulating both a T cell and B cell response; (ii) at least one targeting moiety; (iii) at least one immunostimulatory agent; (iv) a polymeric matrix precursor; (v) lipids and amphiphilic entities; (vi) instructions for preparing inventive vaccine nanocarriers from individual components (i)-(v).

In some embodiments, the kit comprises an inventive nanocarrier and instructions for mixing. Such kits, in some embodiments, also include an immunostimulatory agent and/or an antigen. The nanocarrier of such kits may comprise an immunomodulatory agent (e.g., a T cell antigen, such as a universal T cell antigen) and/or a targeting moiety. The T cell antigen and/or the targeting moiety may be on the surface of the nanocarrier. In some embodiments, the immunomodulatory agent and the antigen are the same. In some embodiments, they are different.

In some embodiments, the invention provides a composition comprising: (1) synthetic nanocarriers having a least one surface, wherein a first surface of the synthetic nanocarriers comprises an immunofeature surface: (2) an immunostimulatory moiety; (3) an MHC Class I, MHC Class II or CD-1 presentable polypeptide; and (4) a pharmaceutically acceptable excipient. The invention further includes a method for administering the composition to a subject.

In some embodiments, the invention provides a method for enhancing T-cell proliferation in a subject, the method comprising administering a composition comprising (1) synthetic nanocarriers having a least one surface, wherein a first surface of the synthetic nanocarriers comprises an immunofeature surface: (2) an immunostimulatory moiety; (3) an MHC Class I, MHC Class II or CD-1 presentable polypeptide; and (4) a pharmaceutically acceptable excipient.

In some embodiments, the invention provides a method for enhancing an immune system response in a subject, the method comprising administering an adjuvant as part of a composition comprising synthetic nanocarriers having a least one surface, wherein a first surface of the synthetic nanocarriers comprises an immunofeature surface.

In some embodiments, the invention provides a method for enhancing a cellular immune response in a subject by administering a composition as described herein. The cellular immune response involves enhanced T cell proliferation. In some embodiments, the cellular immune response is enhanced by administration of nanocarriers comprising an adjuvant, wherein the adjuvant stimulates cross priming (i.e., via cross presentation) by dendritic cells. In some embodiments, the cellular immune response is enhanced by administration of nanocarriers comprising a MHC 1 molecule that stimulates T cells via cross presentation. The cross presentation stimulates $CD8^+$ T cells. Delivery of adjuvant to dendritic cells by the nanocarriers of the invention provide an enhanced cross presentation effect (relative to the extent of cross presentation that may occur with nanocarriers in the abcense of adjuvant) and therefore enhanced proliferation of T cells.

As discussed below, experiments in FIGS. 29 and 33 demonstrate that synthetic nanocarriers that encapsulate a T cell antigen (OVA, ovalbumin protein) or an antigenic peptide (SIINFEKL (SEQ ID NO:1), derived from ovalbumin) together with covalently bound adjuvant (CL097 or R848) induce potent proliferation of antigen-specific OT-I CD8+ T cells. This T cell subset (also called cytotoxic T cells) only responds to antigens that are presented in the MHC class-I pathway. Exogenous antigens, such as those provided by conventional vaccines, are preferentially presented by MHC class-II molecules that are not recognized by CD8+ T cells. Only certain subsets of dendritic cells (DC) are capable of shunting some of the exogenous antigen they acquire to the MHC class-I pathway, a process called 'cross-presentation'. Methods and compositions that result in enhanced cross-presentation of vaccine antigens are desirable because they are predicted to result in improved cytotoxic effector responses that would be useful for the prevention and therapy of cancer and infectious microbes. The data in FIGS. 29 and 33 clearly show that exogenous antigens delivered by inventive synthetic nanocarriers can be cross-presented in vivo resulting in CD8 T cell proliferation in lymph nodes, even when the synthetic nanocarriers do not present an immunofeature surface. However, results shown in FIG. 38 show that synthetic nanocarrier targeting to lymph node DC can be substantially enhanced (at least 5-fold) when synthetic nanocarriers incorporate an immunofeature surface, such as an immunofeature surface comprising nicotine. This gain in targeting would be expected to result in a proportional increase in the amount of antigen and adjuvant that will be available to the DC for cross-presentation to CD8+ T cells. Thus, immunofeature surface-mediated targeting of synthetic nanocarriers would be expected to boost the capacity of synthetic nanocarrier vaccines to elicit cytotoxic T cell responses above and beyond that of synthetic nanocarrier vaccines lacking an immunofeature surface.

In any of the foregoing embodiments described above, the word conjugated means covalently or noncovalently conjugated, unless the context clearly indicates otherwise. In any of the foregoing embodiments described above, the word encapsulated means physically trapped within, whether by admixture, by a shell surrounding a core, by covalent bonding internal of the surface of the nanocarrier, and the like.

This application refers to various issued patents, published patent applications, journal articles, and other publications, all of which are incorporated herein by reference.

BRIEF DESCRIPTION OF THE DRAWING

Figure 28A:
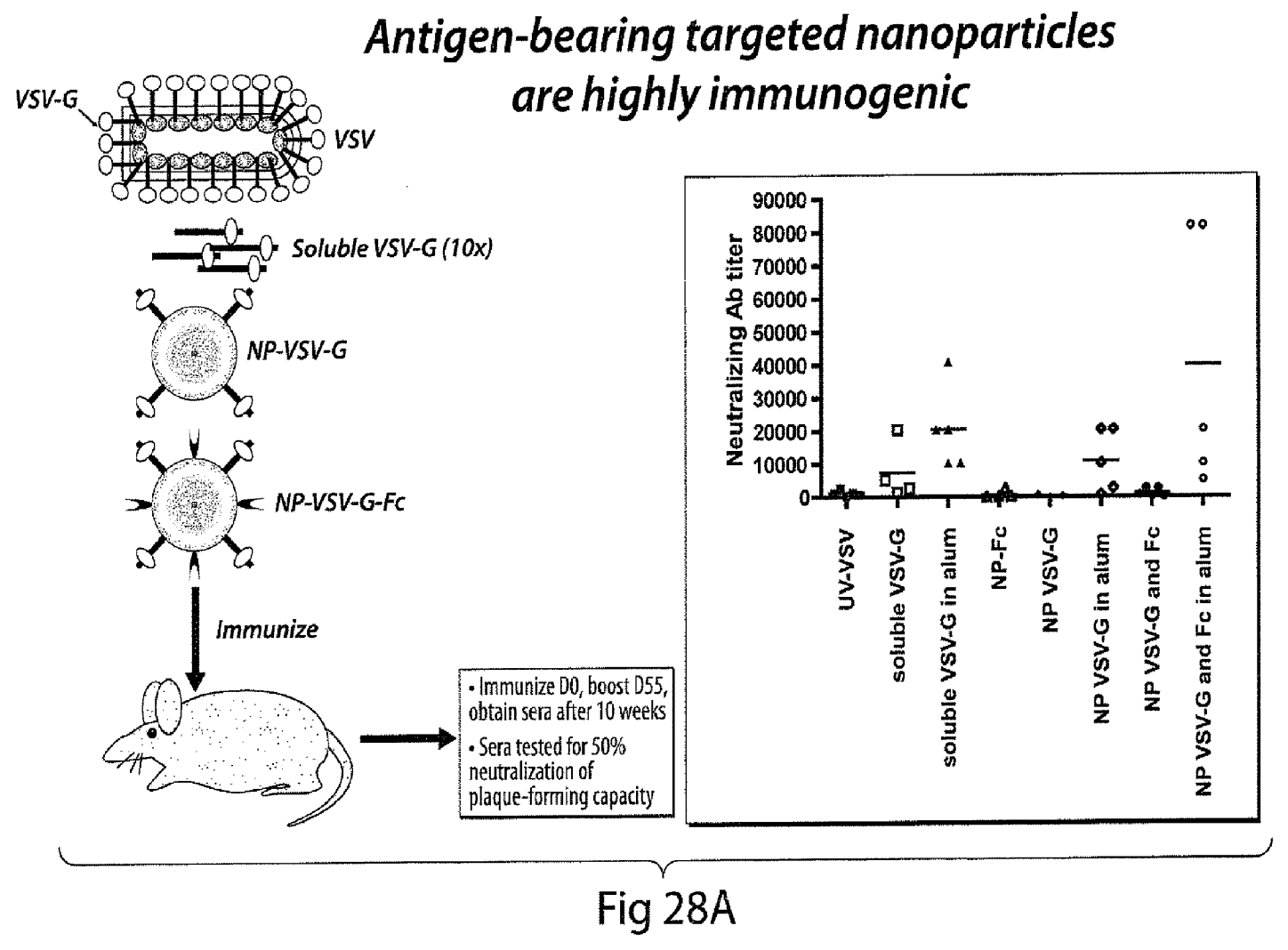

FIG. 28: (A) Antigen-bearing targeted nanoparticles are highly immunogenic and induce high antibody titers. (B) The induced immune response elicited by nanoparticle vaccines confers potent protection from a lethal dose of VSV.

DETAILED DESCRIPTION OF PREFERRED EMBODIMENT

Definitions

Figure 1:
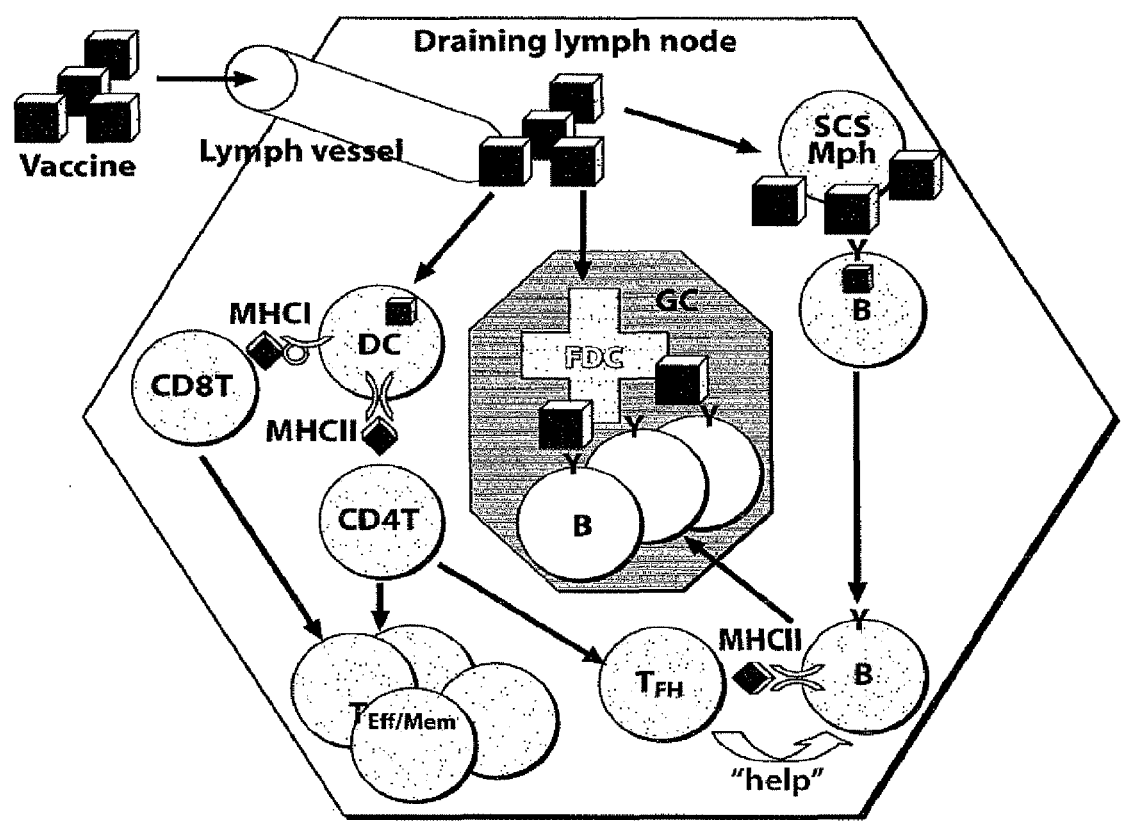
FIG. 1: Combined vaccine targeting strategy for optimal humoral and cellular immune response. The composite vaccine carries internal T cell antigens, adjuvants (not shown) and targeting moieties for DCs, FDC and SCS-Mph together with surface antigen for B cell recognition. Upon s.c. or i.m. injection, the material reaches lymph nodes via draining lymph vessels and accumulates on each APC (for clarity, only APC-specific targeting moieties are shown, but each APC acquires the entire complex). DCs internalize and digest the complex and present antigenic peptides in MHC class I and class II to CD8 and CD4 T cells, respectively. The activated T cells differentiate into effector/memory ($T_{Eff/Mem}$) cells that mediate cellular immune responses. $T_{FH}$ cells provide help to B cells that were initially stimulated by antigen on SCS-Mph and in the process have acquired and processed T cell antigens for restimulation of $T_{FH}$. The help provided by $T_{FH}$ cells allows the development of a GC reaction during which B cells proliferate and generate high-affinity antibodies.
Figure 2A:
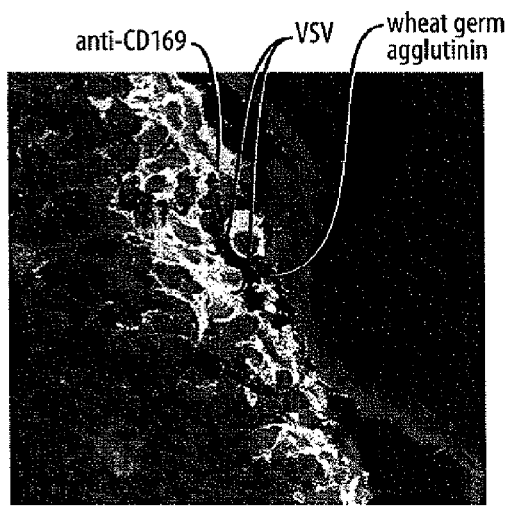
FIG. 2: SCS-Mph bind lymph-borne viral particles and present them to follicular B cells. (A) Immunohistochemical staining of the cortex of a mouse popliteal lymph node stained with anti-CD169 and counter-stained with wheat germ agglutinin. The lymph node was harvested 30 minutes after footpad injection of red fluorescent vesicular stomatitis virus (VSV). In the subcapsular sinus of the draining lymph node, the red virus colocalized exclusively with $CD169^+$ macrophages. (B) Electron micrograph of a lymph node macrophage (Mph) and a follicular B cell (B1) below the floor of the subcapsular sinus (SCSf) 30 minutes after VSV injection shows VSV at the surface and within a phagolysosome of the Mph and at the interface between Mph and B cells (arrowheads). (C) Injection of VSV into the footpad of untreated mice (B6) results in rapid downregulation of surface-expressed IgM on virus-specific B cells, a sign of B cell activation. Depletion of SCS-Mph after footpad injection of clodronate liposomes (CLL) abolished B cell activation, indicating that SCS-Mph are essential to present particulate antigen to B cells.
Figure 2B:
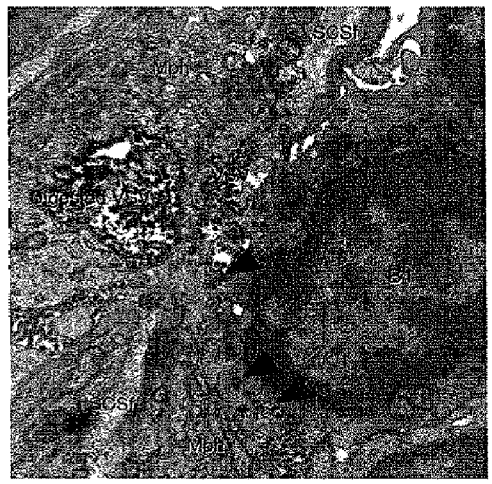
Figure 2C:
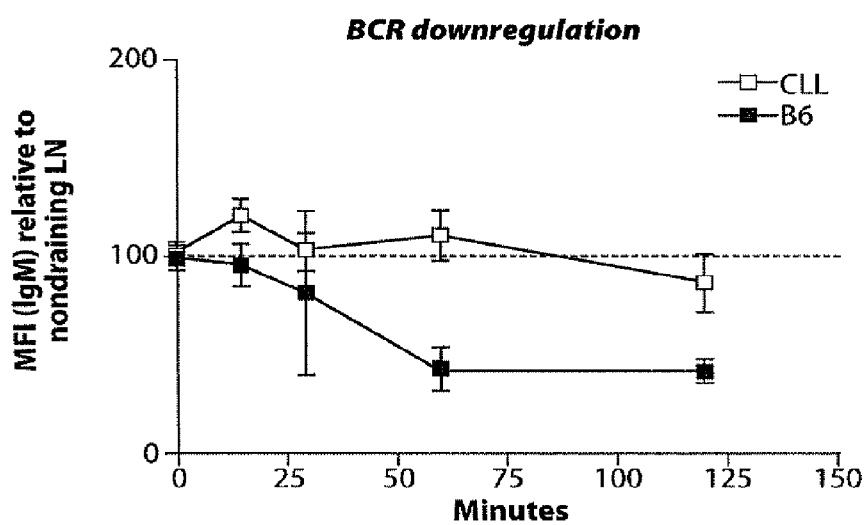

Abused Substance:

As used herein, the term "abused substance" is any substance taken by a subject (e.g., a human) for purposes other than those for which it is indicated or in a manner or in quantities other than directed by a physician. In some embodiments, the abused substance is a drug, such as an illegal drug. In certain embodiments, the abused substance is an over-the-counter drug. In some embodiments, the abused substance is a prescription drug. The abused substance, in some embodiments, is an addictive substance. In some embodiments, the abused substance has mood-altering effects, and, therefore, includes inhalants and solvents. In other embodiments, the abused substance is one that has no mood-altering effects or intoxication properties, and, therefore, includes anabolic steroids. Abused substances include, but are not limited to, cannabinoids (e.g., hashish, marijuana), depressants (e.g., barbituates, benodiazepines, flunitrazepam (Rohypnol), GHB, methaqualone (quaaludes)), dissociative anesthetics (e.g., ketamine, PCP), hallucinogens (e.g, LSD, mescaline, psilocybin), opioids and morphine derivatives (e.g., codeine, fentanyl, heroin, morphine, opium), stimulants (amphetamine, cocaine, Ecstacy (MDMA), methamphetamine, methylphenidate (Ritalin)), anabolic steriods, and inhalants. In some embodiments, the abused substance for inclusion in a nanocarrier is the complete molecule or a portion thereof.

Addictive Substance:

As used herein, the term "addictive substance" is a substance that causes obsession, compulsion, or physical dependence or psychological dependence. In some embodiments, the addictive substance is an illegal drug. In other embodiment, the addictive substance is an over-the-counter drug. In still other embodiments, the addictive substance is a prescription drug. Addictive substances include, but are not limited to, cocaine, heroin, marijuana, and methamphetamines. In some embodiments, the addictive substance for inclusion in a nanocarrier is the complete molecule or a portion thereof.

Administering or Administration:

(1) dosing a pharmacologically active material, such as an inventive composition, to a subject in a manner that is pharmacologically useful, (2) directing that such material be dosed to the subject in a pharmacologically useful manner, or (3) directing the subject to self-dose such material in a pharmacologically useful manner.

Amino Acid:

As used herein, term "amino acid," in its broadest sense, refers to any compound and/or substance that can be incorporated into a polypeptide chain. In some embodiments, an amino acid has the general structure $H_2N$—$C(H)(R)$—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" or "natural amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "non-natural amino acid" encompasses chemically produced or modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal:

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antibody:

As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. An antibody fragment can retain at least a significant portion of the full-length antibody's specific binding ability. Examples of such antibody fragments include, but are not limited to, Fab, Fab', F(ab')2, scFv, Fv, dsFv diabody, and Fd fragments. Antibody fragment also include Fc fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment will typically comprise at least about 50 amino acids and more typically will comprise at least about 200 amino acids.

Approximately:

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Associated with:

As used herein, the term "associated with" refers to the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g., charge interactions, affinity interactions, metal coordination, physical adsorption, host-guest interactions, hydrophobic interactions, ππ stacking interactions, hydrogen bonding interactions, van der Waals interactions, magnetic interactions, electrostatic interactions, dipole-dipole interactions, etc.). For example, in some embodiments, an entity (e.g., immunomodulatory agent, targeting moiety, immunostimulatory agent, nanoparticle, etc.) may be covalently associated with a vaccine nanocarrier. In some embodiments, an entity (e.g., immunomodulatory agent, targeting moiety, immunostimulatory agent, nanoparticle, etc.) may be non-covalently associated with a vaccine nanocarrier. For example, the entity may be associated with the surface of, encapsulated within, surrounded by, and/or distributed throughout a lipid bilayer, lipid monolayer, polymeric matrix, etc. of an inventive vaccine nanocarrier. Where an entity may be referred to by a particular name in the free (i.e., non-conjugated) form, it will be appreciated that, unless specified otherwise, the entity may also be referred to by the same name even when the entity is conjugated to a second entity.

Biocompatible:

As used herein, the term "biocompatible" refers to substances that are not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

Biodegradable:

As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

B Cell Antigen:

As used herein, the term "B cell antigen" refers to any antigen that is recognized by and triggers an immune response in a B cell. In some embodiments, an antigen that is a B cell antigen is also a T cell antigen. In certain embodiments, the B cell antigen is not also a T cell antigen. In certain embodiments, when a nanocarrier, as provided herein, comprises both a B cell antigen and a T cell antigen, the B cell antigen and T cell antigen are not the same antigen, although each of the B cell and T cell antigens may be, in some embodiments, both a B cell antigen and a T cell antigen. In other embodiments, the B cell antigen and T cell antigen of the nanocarrier are the same.

Cell Type:

As used herein, the term "cell type" refers to a form of cell having a distinct set of morphological, biochemical, and/or functional characteristics that define the cell type. One of skill in the art will recognize that a cell type can be defined with varying levels of specificity. For example, T cells and B cells are distinct cell types, which can be distinguished from one another but share certain features that are characteristic of the broader "lymphocyte" cell type of which both are members. Typically, cells of different types may be distinguished from one another based on their differential expression of a variety of genes which are referred to in the art as "markers" of a particular cell type or types (e.g., cell types of a particular lineage). In some embodiments, cells of different types may be distinguished from one another based on their differential functions. A "cell type-specific marker" is a gene product or modified version thereof that is expressed at a significantly greater level by one or more cell types than by all or most other cell types and whose expression is characteristic of that cell type. Many cell type specific markers are recognized as such in the art.

Dosage Form:

a drug in a medium, carrier, vehicle, or device suitable for administration to a subject. Examples of dosage forms are provided herein.

Hazardous Environmental Agent:

As used herein, the term "hazardous environmental agent" refers to any hazardous substance found in the environment. Such substances are generally believed to pose a health risk. Hazardous environmental agents include substances that are thought to pose a health risk even though they may not actually pose a risk. Hazardous environmental agents include, but are not limited to, arsenic, lead, mercury, vinyl chloride, polychlorinated biphenyls, benzene, polycyclic aromatic hydrocarbons, cadmium, benzo(a)pyrene, benzo(b)fluoranthene, chloroform, DDT, P,P'-, aroclor 1254, aroclor 1260, dibenzo(a,h)anthracene, trichloroethylene, dieldrin, chromium hexavalent, and DDE, P,P'. In some embodiments, the hazardous environmental agent for inclusion in a nanocarrier is the complete molecule or a portion thereof.

In Vitro:

As used herein, the term "in vitro" refers to events that occur in an artificial environment, e.g., in a test tube or reaction vessel, in cell culture, etc., rather than within an organism (e.g., animal, plant, and/or microbe).

In Vivo:

As used herein, the term "in vivo" refers to events that occur within an organism (e.g., animal, plant, and/or microbe).

Immunostimulatory Agent:

As used herein, the term "immunostimulatory agent" refers to an agent that modulates an immune response to an antigen but is not the antigen or derived from the antigen. "Modulate", as used herein, refers to inducing, enhancing, suppressing, directing, or redirecting an immune response. Such agents include immunostimulatory agents that stimulate (or boost) an immune response to an antigen but, as defined above, is not the antigen or derived from the antigen. Immunostimulatory agents, therefore, include adjuvants. In some embodiments, the immunostimulatory agent is on the surface of the nanocarrier and/or is encapsulated within the nanocarrier. In some embodiments, the immunostimulatory agent on the surface of the nanocarrier is different from the immunostimulatory agent encapsulated within the nanocarrier. In some embodiments, the nanocarrier comprises more than one type of immunostimulatory agent. In some embodiments, the more than one type of immunostimulatory agent act on different pathways. Examples of immunostimulatory agents include those provided elsewhere herein. In some embodiments, all of the immunostimulatory agents of a synthetic nanocarrier are identical to one another. In some embodiments, a synthetic nanocarrier comprises a number of different types of immunostimulatory agents. In some embodiments, a synthetic nanocarrier comprises multiple individual immunostimulatory agents, all of which are identical to one another. In some embodiments, a synthetic nanocarrier comprises exactly one type of immunostimulatory agent. In some embodiments, a synthetic nanocarrier comprises exactly two distinct types of immunostimulatory agents. In some embodiments, a synthetic nanocarrier comprises greater than two distinct types of immunostimulatory agents. In some embodiments, a synthetic nanocarrier comprises a lipid membrane (e.g., lipid bilayer, lipid monolayer, etc.), wherein at least one type of immunostimulatory agent is associated with the lipid membrane. In some embodiments, at least one type of immunostimulatory agent is embedded within the lipid membrane. In some embodiments, at least one type of immunostimulatory agent is embedded within the lumen of a lipid bilayer. In some embodiments, a synthetic nanocarrier comprises at least one type of immunostimulatory agent that is associated with the interior surface of the lipid membrane. In some embodiments, at least one type of immunostimulatory agent is encapsulated within the lipid membrane of a synthetic nanocarrier. In some embodiments, at least one type of immunostimulatory agent may be located at multiple locations of a synthetic nanocarrier. One of ordinary skill in the art will recognize that the preceding examples are only representative of the many different ways in which multiple immunostimulatory agents may be associated with different locales of synthetic nanocarriers. Multiple immunostimulatory agents may be located at any combination of locales of synthetic nanocarriers.

Nucleic Acid:

As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid", "DNA", "RNA", and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynylcytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Particle:

As used herein, a "particle" refers to any entity having a diameter of less than 10 microns (μm). Typically, particles have a longest dimension (e.g., diameter) of 1000 nm or less. In some embodiments, particles have a diameter of 300 nm or less. Particles include microparticles, nanoparticles, and picoparticles. In some embodiments, nanoparticles have a diameter of 200 nm or less. In some embodiments, nanoparticles have a diameter of 100 nm or less. In some embodiments, nanoparticles have a diameter of 50 nm or less. In some embodiments, nanoparticles have a diameter of 30 nm or less. In some embodiments, nanoparticles have a diameter of 20 nm or less. In some embodiments, nanoparticles have a diameter of 10 nm or less. In some embodiments, particles can be a matrix of polymers. In some embodiments, particles can be a non-polymeric particle (e.g., a metal particle, quantum dot, ceramic, inorganic material, bone, etc.). Particles may also be liposomes and/or micelles. As used herein, the term "nanoparticle" refers to any particle having a diameter of less than 1000 nm.

Pharmaceutically Acceptable Excipient:

a pharmacologically inactive substance added to an inventive composition to further facilitate administration of the composition. Examples, without limitation, of pharmaceutically acceptable excipients include calcium carbonate, calcium phosphate, various diluents, various sugars and types of starch, cellulose derivatives, gelatin, vegetable oils and polyethylene glycols.

Poorly Immunogenic Antigen:

As used herein, the term "poorly immunogenic antigen" refers to an antigen that does not trigger any or a sufficient level of a desired immune response. "Sufficient", as used herein, refers to the ability to elicit a detectable or protective immune response when administered in a composition that does not employ a nanocarrier described herein, e.g., as free antigen mixed with adjuvant in the absence of a nanocarrier. In some embodiments, the desired immune response is to treat or prevent a disease or condition. In certain embodiments, the desired immune response is to alleviate one or more symptoms of a disease or condition. Poorly immunogenic antigens include, but are not limited to, self antigens, small molecules, and carbohydrates.

Self Antigen:

As used herein, the term "self antigen" refers to a normal substance in the body of an animal that when an immune response against the antigen within the animal is triggered, autoimmunity (e.g., an autoimmune disease) can result. A self antigen can be a protein or peptide, lipoprotein, lipid, carbohydrate, or a nucleic acid. The nucleic acid can be a DNA or RNA. Self antigens include, but are not limited to, enzymes, structural proteins, secreted proteins, cell surface receptors, and cytokines. In some embodiments, the self antigen is a cytokine, and the cytokine is TNF, IL-1, or IL-6. In some embodiments, the self antigen is cholesteryl ester transfer protein (CETP), a serum protein responsible for cholesterol transfer from high-density lipoprotein (HDL) to low-density lipoprotein cholesterol (LDL), the Aβ protein associated with Alzheimer's, a proteolytic enzyme that processes the pathological form of the Aβ protein, LDL associated with atherosclerosis, or a coreceptor for HIV-1. In some embodiments, the proteolytic enzyme that processes the pathological form of the Aβ protein is beta-secretase. In some embodiments, the LDL associated with atherosclerosis is oxidized or minimally modified. In some embodiments, the coreceptor for HIV-1 is CCR5.

Small Molecule:

In general, a "small molecule" is understood in the art to be an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

Specific Binding:

As used herein, the term "specific binding" refers to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, $K_d$, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a $K_d$ of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include aptamer-aptamer target interactions, antibody-antigen interactions, avidin-biotin interactions, ligand-receptor interactions, metal-chelate interactions, hybridization between complementary nucleic acids, etc.

Subject:

As used herein, the term "subject" or "patient" refers to any organism to which a composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals) and/or plants. Typically, "subjects" are animals, including mammals such as humans and primates, and the like.

Suffering from:

An individual who is "suffering from" a disease, disorder, and/or condition has been diagnosed with, can be diagnosed with, or displays one or more symptoms of the disease, disorder, and/or condition.

Susceptible to:

An individual who is "susceptible to" a disease, disorder, and/or condition has not been diagnosed with and/or may not exhibit symptoms of the disease, disorder, and/or condition. In some embodiments, a disease, disorder, and/or condition is associated with a microbial infection (e.g., bacterial infection, viral infection, fungal infection, parasitic infection, etc.). In some embodiments, an individual who is susceptible to a microbial infection may be exposed to a microbe (e.g., by ingestion, inhalation, physical contact, etc.). In some embodiments, an individual who is susceptible to a microbial infection may be exposed to an individual who is infected with the microbe. In some embodiments, an individual who is susceptible to a microbial infection is one who is in a location where the microbe is prevalent (e.g., one who is traveling to a location where the microbe is prevalent). In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition. In some embodiments, the subject has or is susceptible to having cancer, an infectious disease, a non-autoimmune metabolic or degenerative disease, or an addiction. In some embodiments, the subject has or is susceptible to having a bacterial, fungal, protozoan, parisitic, or viral infection. The cause of such infection can be any of the organisms as provided herein. In some embodiments, the subject has or is susceptible to tuberculosis, malaria, leishmaniasis, *H. pylori*, a *Staphylococcus* infection, or a *Salmonella* infection. In some embodiments, the subject has or is susceptible to having influenza. In some embodiments, the subject has or is susceptible to an autoimmune disease.

Synthetic Nanocarrier(s):

"Synthetic nanocarrier(s)" means a discrete object that is not found in nature, and that possesses at least dimension that is less than or equal to 5 microns in size. Albumin nanoparticles are expressly included as synthetic nanocarriers. Synthetic nanocarriers according to the invention do not provoke a substantial vector effect; preferably they do not provoke a vector effect. In certain preferable embodiments, synthetic nanocarriers are modified to reduce or eliminate vector effects. This may be accomplished, for example, by coupling various materials (e.g. polyethylene glycols) to the synthetic nanocarrier to reduce the immunogenic nature of the synthetic nanocarrier.

A synthetic nanocarrier can be, but is not limited to, one or a plurality of lipid-based nanoparticles, polymeric nanoparticles, metallic nanoparticles, surfactant-based emulsions, dendrimers, buckyballs, nanowires, virus-like particles, peptide or protein-based particles (such as albumin nanoparticles) and/or nanoparticles that are developed using a combination of nanomaterials such as lipid-polymer nanoparticles. Synthetic nanocarriers may be a variety of different shapes, including but not limited to spheroidal, cubic, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., or (4) the lithographically constructed nanoparticles of Published US Patent Application 20090028910 to DeSimone et al. Synthetic nanocarriers according to the invention that have a minimum dimension of equal to or less than about 100 nm, preferably equal to or less than about 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than about 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than about 100 nm, do not comprise a surface that activates complement or alternatively comprise a surface that consists essentially of moieties that do not activate complement.

The terms "nanocarrier" "synthetic nanocarrier," and variations thereof are generally used interchangeably herein.

T Cell Antigen:

As used herein, the term "T cell antigen" refers to any antigen that is recognized by and triggers an immune response in a T cell (e.g., an antigen that is specifically recognized by a T cell receptor on a T cell via presentation of the antigen or portion thereof bound to a major histocompatiability complex molecule (MHC). In some embodiments, an antigen that is a T cell antigen is also a B cell antigen. In other embodiments, the T cell antigen is not also a B cell antigen. T cells antigens generally are proteins or peptides. T cell antigens may be an antigen that stimulates a CD8+ T cell response, a CD4+ T cell response, or both. The nanocarriers, therefore, in some embodiments can effectively stimulate both types of responses.

Target:

As used herein, the term "target" or "marker" refers to any entity that is capable of specifically binding to a particular targeting moiety. In some embodiments, targets are specifically associated with one or more particular tissue types. In some embodiments, targets are specifically associated with one or more particular cell types. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

Targeted:

A substance is considered to be "targeted" for the purposes described herein if it specifically binds to a target. In some embodiments, a targeting moiety specifically binds to a target under stringent conditions. An inventive nanocarrier, such as a vaccine nanocarrier, comprising a targeting moiety is considered to be "targeted" if the targeting moiety specifically binds to a target, thereby delivering the entire nanocarrier to a specific organ, tissue, cell, and/or subcellular locale.

Targeting Moiety:

As used herein, the terms "targeting moiety" and "high affinity targeting moiety" are used interchangeably and refer to any moiety that binds to a component of a cell. Typically, the binding of a targeting moiety to a component of a cell will be a high affinity binding interaction. In addition to the plurality of moieties that are present on the immunofeature surface and providing targeting (and high avidity binding) to APCs, the nanocarriers of the invention may further comprise one or more additional targeting moieties. In some embodiments, the targeting moiety specifically binds to a component of a cell. Such a component is referred to as a "target" or a "marker." A targeting moiety may be a polypeptide, glycoprotein, nucleic acid, small molecule, carbohydrate, lipid, etc. In some embodiments, a targeting moiety is an antibody or characteristic portion thereof. In some embodiments, a targeting moiety is a receptor or characteristic portion thereof. In some embodiments, a targeting moiety is a ligand or characteristic portion thereof. In some embodiments, a targeting moiety is a nucleic acid targeting moiety (e.g., an aptamer) that binds to a cell type specific marker. In some embodiments, a targeting moiety is a small molecule. The targeting moiety in some embodiments is on the surface of the nanocarrier. In other embodiments, the targeting moiety is encapsulated within the nanocarrier. In still other embodiments, the targeting moiety is associated with the nanocarrier. In some embodiments, the targeting moiety is covalently associated with the nanocarrier. In other embodiments, the targeting moiety is non-covalently associated with the nanocarrier. In yet other embodiments, the targeting moiety binds a receptor expressed on the surface of a cell. The targeting moiety, in some embodiments, binds a soluble receptor. In some embodiments, the soluble receptor is a complement protein or a pre-existing antibody. In further embodiments, the targeting moiety is for delivery of the nanocarrier to antigen presenting cells, T cells, or B cells. In some embodiments, the antigen presenting cells are macrophages. In other embodiments, the macrophages are subcapsular sinus macrophages. In still other embodiments, the antigen presenting cells are dendritic cells. In some embodiments, the antigen presenting cells are follicular dendritic cells. Specific non-limiting examples of targeting moieties include molecules that bind to CD11b, CD169, mannose receptor, DEC-205, CD11c, CD21/CD35, CX3CR1, or a Fc receptor. In some embodiments, the molecule that binds any of the foregoing is an antibody or antigen-binding fragment thereof (e.g., an anti-CD169 antibody). In some embodiments, the molecule that binds a Fc receptor is one that comprises the Fc portion of an immunoglobulin (e.g., IgG). In other embodiments, the Fc portion of an immunoglobulin is a human Fc portion. In some embodiments, the molecule that binds CX3CR1 is CX3CL1 (fractalkine). Targeting moieties that bind CD169 include anti-CD169 antibodies and ligands of CD169, e.g., sialylated CD227, CD43, CD206, or portions of these ligands that retain binding function, e.g., soluble portions.

Therapeutically Effective Amount:

As used herein, the term "therapeutically effective amount" means an amount of a therapeutic, prophylactic, and/or diagnostic agent (e.g., inventive vaccine nanocarrier) that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition. The term is also intended to refer to an amount of nanocarrier or composition thereof provided herein that modulates an immune response in a subject.

Therapeutic Agent:

As used herein, the term "therapeutic agent" refers to any agent that, when administered to a subject, has a therapeutic, prophylactic, and/or diagnostic effect and/or elicits a desired biological and/or pharmacological effect.

Treating:

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a microbial infection may refer to inhibiting survival, growth, and/or spread of the microbe. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of an inventive vaccine nanocarrier to a subject.

Universal T Cell Antigen:

As used herein, the term "universal T cell antigen" refers to a T cell antigen that can promote T cell help and enhance an immune response to a completely unrelated antigen. Universal T cell antigens include tetanus toxoid, as well as one or more peptides derived from tetanus toxoid, Epstein-Barr virus, or influenza virus. Universal T cell antigens also include a component of influenza virus, such as hemagglutinin, neuraminidase, or nuclear protein, or one or more peptides derived therefrom.

Vaccine Nanocarrier:

As used herein, the term "vaccine nanocarrier" refers to a synthetic nanocarrier comprising at least one immunomodulatory agent or immunostimulatory agent. In certain embodiments, a vaccine nanocarrier includes at least two types of immunomodulatory agents. In some embodiments, the immunomodulatory agents are antigens, and the vaccine nanocarrier comprises 2, 3, 4, 5, 6, 7, 8, 9, 10, or more antigens. The different antigens can be or be derived from completely different antigenic molecules, or the different antigens can be different epitopes from the same antigenic molecule. In other embodiments, the vaccine nanocarrier comprises 2, 3, 4, 5, 6, 7, 8, 9, 10, or more different epitopes from the same antigenic molecule. A vaccine nanocarrier may be any form of particle. A vaccine nanocarrier, in some embodiments, is capable of stimulating an immune response in T cells and/or B cells. In other embodiments, the vaccine nanocarrier is capable of enhancing, suppressing, directing, or redirecting an immune response. In some embodiments, any assay available in the art may be used to determine whether T cells and/or B cells have been stimulated. In some embodiments, T cell stimulation may be assayed by monitoring antigen-induced production of cytokines, antigen-induced proliferation of T cells, and/or antigen-induced changes in protein expression. In some embodiments, B cell stimulation may be assayed by monitoring antibody titers, antibody affinities, antibody performance in neutralization assays, class-switch recombination, affinity maturation of antigen-specific antibodies, development of memory B cells, development of long-lived plasma cells that can produce large amounts of high-affinity antibodies for extended periods of time, germinal center reactions, and/or antibody performance in neutralization assays. In some embodiments, a vaccine nanocarrier further comprises at least one targeting moiety that can help deliver the vaccine nanocarrier to a particular target (e.g., organ, tissue, cell, and/or subcellular locale) within a subject. In some embodiments, a vaccine nanocarrier further comprises at least one immunostimulatory agent that can help stimulate an immune response in T cells and/or B cells. In some embodiments, a vaccine nanocarrier further comprises at least one nanoparticle that allows for tunable membrane rigidity and controllable liposome stability. In some embodiments, vaccine nanocarriers comprise lipids, amphiphilic compounds, polymers, sugars, polymeric matrices, and/or non-polymeric particles.

Vector Effect:

the establishment of an immune response to a synthetic nanocarrier, rather than to an antigen to which an adaptive immune response is desired. Vector effects can occur when the material of the synthetic nanocarrier is capable of stimulating a strong immune response because of its chemical composition or structure.

Water Soluble, Non-Adhesive Polymer:

As used herein, the term "water soluble, non-adhesive polymer" refers to a polymer that is soluble in water and that can confer reduced biofouling properties. In some embodiments, the water soluble, non-adhesive polymer is polyethylene glycol, polyethylene oxide, polyalkylene glycol, and polyalkylene oxide.

Vaccines

Vaccinations are typically either passive or active in nature. In general, active vaccinations involve the exposure of a subject's immune system to one or more agents that are recognized as unwanted, undesired, and/or foreign and elicit an endogenous immune response resulting in the activation of antigen-specific naive lymphocytes that then give rise to antibody-secreting B cells or antigen-specific effector and memory T cells or both. This approach can result in long-lived protective immunity that may be boosted from time to time by renewed exposure to the same antigenic material. The prospect of longevity of a successful immune response to active vaccination makes this strategy more desirable in most clinical settings than passive vaccination whereby a recipient is injected with preformed antibodies or with antigen-specific effector lymphocytes, which may confer rapid ad hoc protection, but typically do not establish persistent immunity.

A large variety of vaccine formulations are being or have been employed in humans. The most common route of administration in humans is by intramuscular (i.m.) injection, but vaccines may also be applied or administered orally, intranasally, subcutaneously, inhalationly, or intravenously. In most cases, vaccine-derived antigens are initially presented to naive lymphocytes in regional lymph nodes.

Some current vaccines against, e.g., microbial pathogens, consist of live attenuated or non-virulent variant strains of microorganisms, or killed or otherwise inactivated organisms. Other vaccines utilize more or less purified components of pathogen lysates, such as surface carbohydrates or recombinant pathogen-derived proteins that are sometimes fused to other molecules, particularly proteins that can confer adjuvant activity.

Vaccines that utilize live attenuated or inactivated pathogens typically yield a vigorous immune response, but their use has limitations. For example, live vaccine strains can sometimes cause infectious pathologies, especially when administered to immune-compromised recipients. Moreover, many pathogens, particularly viruses, undergo continuous rapid mutations in their genome, which allow them to escape immune responses to antigenically distinct vaccine strains. However, most or all pathogens are thought to possess certain antigenic determinants that are not easily mutated because they are associated with essential functions. Antibodies directed against these conserved epitopes, rather than more variable, non-essential epitopes can protect against highly mutable viruses (Baba et al., 2000, *Nat. Med.,* 6:200; incorporated herein by reference). Vaccines based on live or killed intact pathogens do not necessarily promote the recognition of these critical epitopes, but may essentially "distract" the immune system to focus its assault on highly variable determinants. Thus, the present invention encompasses the recognition that an engineered vaccine nanocarrier that mimics the highly immunogenic particulate nature of viral particles, but presents selectively essential, immutable epitopes, could yield much more potent and "escape-proof" neutralizing antibody and effector T cell responses than intact microorganisms.

The precise mechanisms by which vaccines stimulate antibody responses in draining lymph nodes (or fail to do so) are still incompletely understood. B and T cells are initially sequestered in distinct anatomic regions, the superficially located B follicles and the surrounding paracortex and deep cortex, respectively. Upon antigen challenge, antigen-specific B cells in follicles as well as CD4 T cells in the T cell area become activated and then migrate toward the border zone between the two compartments. B cells that have phagocytosed lymph-borne antigens process the acquired material and begin to present antigenic peptides in MHC class-II surface molecules that are then recognized by the activated CD4 T cells (the $T_{FH}$ cells). Antigen-recognition allows the $T_{FH}$ cells to provide help to B cells, which constitutes a potent survival signal and triggers the formation of germinal centers (GCs) within B follicles. The GC reaction promotes class-switch recombination, affinity maturation of antigen-specific antibodies, and the formation of memory B cells and long-lived plasma cells that can produce large amounts of high-affinity antibodies for extended periods of time. Thus, the present invention encompasses the recognition that a vaccine nanocarrier may have components that allow antigenic material to be efficiently recognized by both B and T cells and to induce vigorous GC reactions (FIG. 1).

The present invention describes systems for developing vaccine nanocarriers for vaccine delivery that can overcome these aforementioned limitations of current vaccine technology. The present invention encompasses the recognition that lymph-borne viral particles that measure tens to hundreds of nanometers in diameter and induce potent cellular and antibody responses are captured and retained on the surface of macrophages in the subcapsular sinus of draining lymph nodes (i.e., subcapsular sinus macrophages, abbreviated SCS-Mph). These macrophages are involved in the efficient early presentation of intact viral particles to follicular B cells. In some embodiments, inventive nanocarriers mimic viral particles and target SCS-Mph. As shown in Example 1, upon subcutaneous injection of Cy5 encapsulated poly(lactic-coglycolic acid) (PLGA) nanoparticles (50 nm-150 nm) that are surface stabilized with a monolayer of lipid and polyethylene glycol, the injected nanoparticles readily enter lymphatics and are bound in the subcapsular sinus of draining lymph nodes similar to lymph-borne viruses. Similar nanocarriers carrying immunomodulatory agent(s) that stimulate B cells and/or T cells are particularly useful in vaccinating a subject.

Thus, the present invention encompasses the recognition that nanocarriers, such as lymph-borne virus-sized nanocarriers carrying an immunomodulatory agent can be recognized in lymph nodes as if they were viruses and may elicit a potent immune response, for example, when the particles include immunomodulatory agent(s) that are recognized by B cells and/or T cells.

By carrying immunomodulatory agents on the surface and/or loading similar or distinct immunomodulatory agents inside, nanocarriers can simultaneously deliver these immunomodulatory agents to distinct cells of the immune system and stimulate them. In certain embodiments, immunomodulatory agents presented on nanocarrier surfaces stimulate B cells, and immunomodulatory agents encapsulated within the nanocarriers are processed by antigen-presenting cells (APCs), such as dendritic cells (DCs), in lymphoid tissues (and by B cells after activation) and presented to T cells. In some embodiments, by modifying the surface of nanocarriers with a targeting moiety (e.g., antibody or fragment thereof, peptide or polypeptide, Affibody®, Nanobody™, AdNectin™, Avimer™, aptamer, Spiegelmer®, small molecule, lipid, carbohydrate, etc.), nanocarriers can selectively deliver immunomodulatory agents to specific antigen presenting cells, such as DCs, SCS-Mph, FDCs, T Cells, B cells, and/or combinations thereof. A nanocarrier can be, but is not limited to, one or a plurality of lipid nanoparticles, polymeric nanoparticles, metallic nanoparticles, surfactant-based emulsions, dendrimers, and/or nanoparticles that are developed using a combination of nanomaterials such as lipid-polymer nanoparticles. Vaccine nanocarriers are described in further detail in the section entitled "Vaccine Nanocarriers."

T Cells

The present invention provides vaccine nanocarriers for delivery of, for example, immunomodulatory agents to the cells of the immune system. In some embodiments, vaccine nanocarriers comprise at least one immunomodulatory agent which can be delivered to APCs, which then process and deliver the immunomodulatory agent(s) to T cells.

Professional APCs are very efficient at internalizing antigen, either by phagocytosis or by endocytosis, and then display a fragment of the antigen, bound to either a class II major histocompatibility complex (class II MHC) molecule or a class I MHC molecule on the APC membrane. CD4 T cells recognize and interact with the antigen-class II MHC molecule complex on the APC membrane, whereas CD8 T cells recognize and interact with the antigen-class I MHC molecule complex. An additional co-stimulatory signal as well as modulating cytokines are then produced by the APC, leading to T cell activation.

In some embodiments, the nanocarriers of the invention comprise one or more of an MHC I, MHC II, or CD-1 presentable polypeptide. Typically, the MHC I, MHC II, or CD-1 presentable polypeptide will be located on a surface of the nanocarrier.

Examples of MHC I presentable polypeptides include antigens (such as antigens derived from viruses, bacteria, fungi, tumors, self proteins, or synthetic peptides); SIINFEKL (SEQ ID NO:1) (derived from OVA); GP33 (derived from the surface glycoprotein of LCMV Ann); Core 18-27 (derived from HbcAg from hepatitis B virus), and MAGE (derived from melanoma.

Examples of MHC II presentable polypeptides include antigens (such as antigens derived from viruses, bacteria, fungi, tumors, self proteins, or synthetic peptides); OVA323-339 (derived from OVA), GP61 (derived from the surface glycoprotein of LCMV Arm); MAGE-A4 280-299, tetanus toxoid, CTP (peptides corresponding to various segments of the B subunit of cholera toxin), diphtheria toxoid, PADRE peptide. Preferred antigens are those that are recognized by most of the MHC present in humans and to which exists preexisting immunity (e.g., because of prior infections or prior vaccinations).

Examples of CD-1 presentable polypeptides include lipid antigens derived from self, from pathogens, from tumors, or synthetic antigens; mycolic acid (from *Mycobacterium tubercolosis*), sulpholipids (from mycobacteria), lipophosphoglycan (from *Leishmania donovani*), diacylglycerols (from *Borrelia Burgdoferi*), glycoshpingolipids, alpha-galactosylceramide (from marine sponge), isoglobotrihexosylceramide (self), ganglioside GD3 (self), and the like.

In some embodiments, the nanocarriers of the invention comprise a plurality of different moieties selected from MHC I, MHC II, or CD-1 presentable polypeptides.

The MHC I, MHC II, or CD-1 presentable polypeptides may be associated with the immunofeature surface of the nanocarriers, or associated with a second surface of the nanocarriers. Alternatively or in addition, the MHC I, MHC II, or CD-1 presentable polypeptides may be encapsulated within a core region of the nanocarrier.

As will be appreciated by those of skill in the art, Natural Killer T cells (NKT cells) are T cells that share properties with natural killer cells. In particular, NKT cells recognize and bind CD-1 polypeptides. Accordingly, in some embodiments, compositions of the invention that comprise CD-1 presentable polypeptides are able to bind to NKT cells.

Immunomodulatory Agents

The present invention provides vaccine nanocarriers comprising one or more immunomodulatory agents. In some embodiments, inventive nanocarriers comprising one or more immunomodulatory agents are used as vaccines. In some embodiments, an immunomodulatory agent may comprise isolated and/or recombinant proteins or peptides, carbohydrates, glycoproteins, glycopeptides, proteoglycans, inactivated organisms and viruses, dead organisms and virus, genetically altered organisms or viruses, and cell extracts. In some embodiments, an immunomodulatory agent may comprise nucleic acids, carbohydrates, lipids, and/or small molecules. In some embodiments, an immunomodulatory agent is one that elicits an immune response. In other embodiments, an immunomodulatory agent is a polynucleotide that encodes a protein or peptide that when the protein or peptide is expressed an immune response is elicited. In some embodiments, an immunomodulatory agent is an antigen. In some embodiments, an immunomodulatory agent is a protein or peptide. In some embodiments, an immunomodulatory agent is used for vaccines.

In some embodiments, an immunomodulatory agent is any protein and/or other antigen derived from a pathogen. The pathogen may be a virus, bacterium, fungus, protozoan, parasite, etc. In some embodiments, immunomodulatory agents may include antigens of bacterial organisms such as *Borrelia* species, *Bacillus anthracis, Borrelia burgdorferi, Bordetella pertussis, Camphylobacter jejuni, Chlamydia* species, *Chlamydial psittaci, Chlamydial trachomatis, Clostridium* species, *Clostridium tetani, Clostridium botulinum, Clostridium perfringens, Corynebacterium diphtheriae, Coxiella* species, an *Enterococcus* species, *Erlichia* species, *Escherichia coli, Francisella tularensis, Haemophilus* species, *Haemophilus influenzae, Haemophilus parainfluenzae, Lactobacillus* species, a *Legionella* species, *Legionella pneumophila, Leptospirosis interrogans, Listeria* species, *Listeria monocytogenes, Mycobacterium* species, *Mycobacterium tuberculosis, Mycobacterium leprae, Mycoplasma* species, *Mycoplasma pneumoniae, Neisseria* species, *Neisseria meningitidis, Neisseria gonorrhoeae, Pneumococcus* species, *Pseudomonas* species, *Pseudomonas aeruginosa, Salmonella* species, *Salmonella typhi, Salmonella enterica, Rickettsia* species, *Rickettsia ricketsii, Rickettsia typhi, Shigella* species, *Staphylococcus* species, *Staphylococcus aureus, Streptococcus* species, *Streptococcus pnuemoniae, Streptococcus pyrogenes, Streptococcus mutans, Treponema* species, *Treponema pallidum*, a *Vibrio* species, *Vibrio cholerae, Yersinia pestis*, and the like.

In some embodiments, immunomodulatory agents may include antigens of viral organisms such as pox viruses, smallpox (variola), ebola virus, hepadnavirus, marburg virus, dengue fever virus, influenza A and B, parainfluenza, respiratory syncytial virus, measles (rubeola virus), human immunodeficiency virus (HIV), human papillomavirus (HPV), varicella-zoster, herpes simplex 1 and 2, cytomegalovirus, Epstein-Barr virus, JC virus, rhabdovirus, rotavirus, rhinovirus, adenovirus, orthomyxovirus, papillomavirus, parvovirus, picornavirus, poliovirus, mumps, rabies, reovirus, rubella, togavirus, retrovirus, coxsackieviruses, equine encephalitis, Japanese encephalitis, yellow fever, Rift Valley fever, hepatitis A, B, C, D, and E virus, and the like. Viral organisms include those that are dsDNA viruses, ssDNA viruses, dsRNA viruses, (+) ssRNA viruses (−) sRNA viruses, ssRNA-RT viruses, and dsDNA-RT viruses.

In some embodiments, immunomodulatory agents may include antigens of fungal, protozoan, and/or parasitic organisms such as *Aspergillus* species, *Candida* species, *Candida albicans*, *Candida tropicalis*, *Cryptococcus* species, *Cryptococcus neoformans*, *Entamoeba histolytica*, *Histoplasma capsulatum*, *Leishmania* species, *Nocardia asteroides*, *Plasmodium falciparum*, *Toxoplasma gondii*, *Trichomonas vaginalis*, *Toxoplasma* species, *Trypanosoma brucei*, *Schistosoma mansoni*, and the like.

In some embodiments, immunomodulatory agents may include E1 and/or E2 proteins of HCV. In some embodiments, immunomodulatory agents may include gp120 of HIV. In some embodiments, immunomodulatory agents may include hemagglutinin and/or neuraminidase of influenza virus. In some embodiments, immunomodulatory agents may include pneumococcal polysaccharide or family 1 and/or family 2 PspA of *Streptococcus pneumoniae* or capsular polysaccharides types 5 and 8 or microbial surface components recognizing adhesive matrix molecule of *Staphylococcus aureus*. In some embodiments, immunomodulatory agents may include mannan of *Candida albicans* or cryptococcal capsular polysaccharide of *Cryptococcus neoformans*. In some embodiments, immunomodulatory agents may include PfEMP1 of *Plasmodium falciparum* or other parasite-derived antigens expressed on *plasmodium*-infected red blood cells or GRA7 of *Toxoplasma gondi*.

Any of the antigens described herein may be in the form of whole killed organisms, peptides, proteins, glycoproteins, glycopeptides, proteoglycans, nucleic acids that encode a protein or peptide, carbohydrates, small molecules, or combinations thereof.

In some embodiments, an immunomodulatory agent is derived from a microorganism for which at least one vaccine already exists. In some embodiments, an immunomodulatory agent is derived from a microorganism for which no vaccines have been developed.

In some embodiments, a vaccine nanocarrier comprises at least one type of immunomodulatory agent. In some embodiments, all of the immunomodulatory agents of a vaccine nanocarrier are identical to one another. In some embodiments, a vaccine nanocarrier comprises a number of different immunomodulatory agents. In some embodiments, a vaccine nanocarrier comprises multiple individual immunomodulatory agents, all of which are the same. In some embodiments, a vaccine nanocarrier comprises exactly one type of immunomodulatory agent. In some embodiments, a vaccine nanocarrier comprises exactly two distinct types of immunomodulatory agents. In some embodiments, a vaccine nanocarrier comprises greater than two distinct types of immunomodulatory agents. In some embodiments, a vaccine nanocarrier comprises 3, 4, 5, 6, 7, 8, 9, 10, or more distinct types of immunomodulatory agents.

In some embodiments, a vaccine nanocarrier comprises two types of immunomodulatory agents which are both derived from a single genus of microorganism. In some embodiments, a vaccine nanocarrier comprises two types of immunomodulatory agents which are both derived from a single genus and species of microorganism. In some embodiments, a vaccine nanocarrier comprises two types of immunomodulatory agents which are both derived from a single genus, species, and strain of microorganism. In some embodiments, a vaccine nanocarrier comprises two types of immunomodulatory agents which are both derived from a single clone of a microorganism.

In some embodiments, a vaccine nanocarrier comprises more than two types of immunomodulatory agents which are all derived from a single genus of microorganism. In some embodiments, a vaccine nanocarrier comprises more than two types of immunomodulatory agents which are all derived from a single genus and species of microorganism. In some embodiments, a vaccine nanocarrier comprises more than two types of immunomodulatory agents which are all derived from a single genus, species, and strain of microorganism. In some embodiments, a vaccine nanocarrier comprises more than two types of immunomodulatory agents which are all derived from a single clone of a microorganism.

In some embodiments, a vaccine nanocarrier comprises two or more types of immunomodulatory agent which are all derived from a single genus of microorganism. In some embodiments, a vaccine nanocarrier comprises two or more types of immunomodulatory agent which are all derived from a single genus and species of microorganism. In some embodiments, a vaccine nanocarrier comprises two or more types of immunomodulatory agent which are all derived from a single genus, species, and strain of microorganism.

In some embodiments, a vaccine nanocarrier comprises two or more types of immunomodulatory agents which are derived from different strains of a single species of microorganism. In some embodiments, a vaccine nanocarrier comprises two or more types of immunomodulatory agents which are derived from different species of the same genus of microorganism. In other embodiments, a vaccine nanocarrier comprises two or more types of immunomodulatory agents each derived from different genera of microorganism.

In some embodiments, a vaccine nanocarrier comprises a single type of immunomodulatory agent that stimulates an immune response in both B cells and T cells. In some embodiments, a vaccine nanocarrier comprises two types of immunomodulatory agents, wherein the first immunomodulatory agent stimulates B cells, and the second type of immunomodulatory agent stimulates T cells. In certain embodiments, one or both agents may stimulate T cells and B cells. In some embodiments, a vaccine nanocarrier comprises greater than two types of immunomodulatory agents, wherein one or more types of immunomodulatory agents stimulate B cells, and one or more types of immunomodulatory agents stimulate T cells.

In some embodiments, a vaccine nanocarrier comprises at least one type of immunomodulatory agent that is associated with the exterior surface of the vaccine nanocarrier. In some embodiments, the association is covalent. In some embodiments, the covalent association is mediated by one or more linkers. In some embodiments, the association is non-covalent. In some embodiments, the non-covalent association is mediated by charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. For a more detailed description of how an immunomodulatory agent may be associated with a vaccine nanocarrier, please see the section below entitled "Production of Vaccine Nanocarriers."

In some embodiments, a vaccine nanocarrier includes a lipid membrane (e.g., lipid bilayer, lipid monolayer, etc.). At least one immunomodulatory agent may be associated with the lipid membrane. In some embodiments, at least one immunomodulatory agent is embedded within the lipid membrane. In some embodiments, at least one immunomodulatory agent is embedded within the lumen of a lipid bilayer. In some embodiments, a vaccine nanocarrier comprises at least one immunomodulatory agent that is associated with the interior surface of the lipid membrane. In some embodiments, at least one immunomodulatory agent is encapsulated within the lipid membrane of a vaccine nanocarrier. In some embodiments, at least one type of immunomodulatory agent may be located at multiple locations of a vaccine nanocarrier. For example, a first type of immunomodulatory agent may be embedded within a lipid membrane, and a second type of immunomodulatory agent may be encapsulated within the lipid membrane of a vaccine nanocarrier. To give another example, a first type of immunomodulatory agent may be associated with the exterior surface of a lipid membrane, and a second type of immunomodulatory agent may be associated with the interior surface of the lipid membrane of a vaccine nanocarrier. In some embodiments, a first type of immunomodulatory agent may be embedded within the lumen of a lipid bilayer of a vaccine nanocarrier, and the lipid bilayer may encapsulate a polymeric matrix throughout which a second type of immunomodulatory agent is distributed. In some embodiments, a first type of immunomodulatory agent and a second type of immunomodulatory agent may be in the same locale of a vaccine nanocarrier (e.g., they may both be associated with the exterior surface of a vaccine nanocarrier; they may both be encapsulated within the vaccine nanocarrier; etc.).

In some embodiments, a vaccine nanocarrier includes a polymer (e.g., a polymeric core). At least one type of immunomodulatory agent may be associated with the polymer. In some embodiments, at least one type of immunomodulatory agent is embedded within the polymer. In some embodiments, a vaccine nanocarrier comprises at least one type of immunomodulatory agent that is associated with the interior surface of the polymer. In some embodiments, at least one type of immunomodulatory agent is encapsulated with the polymer of a vaccine nanocarrier. In some embodiments, at least one type of immunomodulatory agent may be located at multiple locations of a vaccine nanocarrier. For example, a first type of immunomodulatory agent may be embedded within a polymer, and a second type of immunomodulatory agent may be encapsulated within a lipid membrane surrounding the polymeric core of a vaccine nanocarrier. To give another example, a first type of immunomodulatory agent may be associated with the exterior surface of a polymer, and a second type of immunomodulatory agent may be embedded within the polymer of a vaccine nanocarrier.

One of ordinary skill in the art will recognize that the preceding examples are only representative of the many different ways in which multiple immunomodulatory agents may be associated with different locales of vaccine nanocarriers. Multiple immunomodulatory agents may be located at any combination of locales of vaccine nanocarriers. Additionally, the aforementioned examples can also apply to the other agents of a nanocarrier (e.g., a immunostimulatory agent).

In some embodiments, the immunomodulatory agent is a T cell antigen, and the T cell antigen is derived from the same pathogen against which vaccination is intended. In this case, an initially small number of naive T cells are stimulated to generate pathogen-specific effector and memory T cells. In some embodiments, the antigen may be taken from an unrelated source, such as an infectious agent to which wide-spread immunity already exists (e.g., tetanus toxoid or a common component of influenza virus, such as hemagglutinin, neuraminidase, or nuclear protein). In the latter case, the vaccine exploits the presence of memory T cells that have arisen in response to prior infections or vaccinations. Memory cells in general react more rapidly and vigorously to antigen rechallenge and, therefore, may provide a superior source of help to B cells.

Other T cell antigens include, but are not limited to, degenerative disease antigens, infectious disease antigens, cancer antigens, alloantigens, atopic disease antigens, autoimmune disease antigens, contact sensitizers, haptens, xenoantigens, or metabolic disease enzymes or enzymatic products thereof. In some embodiments, the infectious disease antigen is a viral antigen, which includes any antigen derived from any of the viruses described herein. Examples of T cell antigens include those provided elsewhere herein.

In some embodiments, T cell antigens are incorporated into nanocarriers as intact proteins. In some embodiments, T cell antigens are incorporated into nanocarriers as modified proteins. In some embodiments, T cell antigens are incorporated into nanocarriers as mutated proteins. In some embodiments, T cell antigens are provided as a collection of overlapping peptides, which can boost antigen incorporation into MHC class II complexes and, therefore, further promote a helper response. In some embodiments, T cell antigens are provided as a collection of non-overlapping peptides, which can boost antigen incorporation into MHC class II complexes and, therefore, further promote a helper response. In some embodiments, T cell antigens are provided as nucleic acids that encode the antigens.

In some embodiments, inventive nanocarriers, such as vaccine nanocarriers, comprise less than less than 90% by weight, less than 75% by weight, less than 50% by weight, less than 40% by weight, less than 30% by weight, less than 20% by weight, less than 15% by weight, less than 10% by weight, less than 5% by weight, less than 1% by weight, or less than 0.5% by weight of the immunomodulatory agent.

Targeting Moieties

In some embodiments, inventive nanocarriers comprise one or more targeting moieties. In certain embodiments of the invention, nanocarriers are associated with one or more targeting moieties. A targeting moiety is any moiety that binds to a component associated with an organ, tissue, cell, extracellular matrix, and/or subcellular locale. In some embodiments, such a component is referred to as a "target" or a "marker," and these are discussed in further detail below.

A targeting moiety may be a nucleic acid, polypeptide, glycoprotein, carbohydrate, lipid, small molecule, etc. For example, a targeting moiety can be a nucleic acid targeting moiety (e.g. an aptamer, Spiegelmer®, etc.) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain antibodies, etc. Synthetic binding proteins such as Affibodies®, Nanobodies™, AdNectins™, Avimers™, etc., can be used. Peptide targeting moieties can be identified, e.g., using procedures such as phage display. This widely used technique has been used to identify cell specific ligands for a variety of different cell types.

In accordance with the present invention, a targeting moiety recognizes one or more "targets" or "markers" associated with a particular organ, tissue, cell, and/or subcellular locale. In some embodiments, a target may be a marker that is exclusively or primarily associated with one or a few cell types, with one or a few diseases, and/or with one or a few developmental stages. A cell type specific marker is typically expressed at levels at least 2 fold greater in that cell type than in a reference population of cells which may consist, for example, of a mixture containing an approximately equal amount of cells (e.g., approximately equal numbers of cells, approximately equal volume of cells, approximately equal mass of cells, etc.). In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, at least 500 fold, at least 1000 fold, at least 5000 fold, or at least 10,000 fold greater than its average expression in a reference population. Detection or measurement of a cell type specific marker may make it possible to distinguish the cell type or types of interest from cells of many, most, or all other types.

In some embodiments, a target can comprise a protein, a carbohydrate, a lipid, and/or a nucleic acid. In certain embodiments, a target can comprise a protein and/or characteristic portion thereof, such as a tumor-marker, integrin, cell surface receptor, transmembrane protein, intercellular protein, ion channel, membrane transporter protein, enzyme, antibody, chimeric protein, glycoprotein, etc. In certain embodiments, a target can comprise a carbohydrate and/or characteristic portion thereof, such as a glycoprotein, sugar (e.g., monosaccharide, disaccharide, polysaccharide), glycocalyx (i.e., the carbohydrate-rich peripheral zone on the outside surface of most eukaryotic cells) etc. In certain embodiments, a target can comprise a lipid and/or characteristic portion thereof, such as an oil, fatty acid, glyceride, hormone, steroid (e.g., cholesterol, bile acid), vitamin (e.g. vitamin E), phospholipid, sphingolipid, lipoprotein, etc. In certain embodiments, a target can comprise a nucleic acid and/or characteristic portion thereof, such as a DNA nucleic acid; RNA nucleic acid; modified DNA nucleic acid; modified RNA nucleic acid; nucleic acid that includes any combination of DNA, RNA, modified DNA, and modified RNA; etc.

In some embodiments, a targeting moiety could be the surface glycoprotein molecule from VSV. VSV comprises a single surface molecule, VSV-G, which is a toll-like receptor agonist. VSV is efficiently targeted to cells of the immune system, so in some embodiments, vaccine nanocarriers could comprise the VSV surface molecule in order to target vaccine nanocarriers to cells of the immune system.

In some embodiments, a target is a tumor marker. In some embodiments, a tumor marker is an antigen that is expressed in tumor cells but not in healthy and/or normal cells. In some embodiments, a tumor marker is an antigen that is more prevalent in tumor cells than in healthy and/or normal cells. Exemplary tumor markers include, but are not limited to, gp100; Melan-A; tyrosinase; PSMA; HER-2/neu; MUC-1; topoisomerase IIα; sialyl-Tn; carcinoembryonic antigen; ErbB-3-binding protein-1; alpha-fetoprotein; and the cancer-testis antigens MAGE-A1, MAGE A4, and NY-ESO-1.

In some embodiments, a target is an APC marker. In some embodiments, an APC target is an antigen that is expressed in APCs but not in non-APCs. In some embodiments, an APC target is an antigen that is more prevalent in APCs than in non-APCs. Exemplary APC markers include, but are not limited to, CD11c, CD11b, CD14, CD40, CD45, CD163, CD169 (sialoadhesin), DEC205 (CD205), MHC class II, DC-SIGN, CD21/CD35, and Fc γ RI, PD-L2. In some embodiments, APC markers include any of DC and/or macrophage markers, examples of which are described herein.

In certain embodiments, a target is a DC marker. In some embodiments, a DC target is an antigen that is expressed in DCs but not in non-DCs. In some embodiments, a DC target is an antigen that is more prevalent in DCs than in non-DCs. Exemplary DC markers are listed below in the section entitled "Dendritic Cells" and include those provided elsewhere herein.

In certain embodiments, a target is a T cell marker. In some embodiments, a T cell target is an antigen that is expressed in T cells but not in non-T cells. In some embodiments, a T cell target is an antigen that is more prevalent in T cells than in non-T cells. Exemplary T cell markers are listed below in the section entitled "T Cell Targeting Moieties" and include those provided elsewhere herein.

In some embodiments, a target is preferentially expressed in particular cell types. For example, expression of an APC, DC, and/or T cell target in APCs, DCs, and/or T cells is at least 2-fold, at least 3-fold, at least 4-fold, at least 5-fold, at least 10-fold, at least 20-fold, at least 50-fold, at least 100-fold, at least 500-fold, or at least 1000-fold overexpressed in APCs, DCs, and/or T cells relative to a reference population. In some embodiments, a reference population may comprise non-APCs, FDCs, and/or T cells.

In some embodiments, expression of an APC, DC, and/or T cell target in activated APCs, DCs, and/or T cells is at least 2-fold, at least 3-fold, at least 4-fold, at least 5-fold, at least 10-fold, at least 20-fold, at least 50-fold, at least 100-fold, at least 500-fold, or at least 1000-fold overexpressed in activated APCs, DCs, and/or T cells relative to a reference population. In some embodiments, a reference population may comprise non-activated APCs, DCs, and/or T cells.

In some embodiments, inventive nanocarriers, such as vaccine nanocarriers, comprise less than 50% by weight, less than 40% by weight, less than 30% by weight, less than 20% by weight, less than 15% by weight, less than 10% by weight, less than 5% by weight, less than 1% by weight, or less than 0.5% by weight of the targeting moiety.

In some embodiments, targeting moieties are covalently associated with a nanocarrier. In some embodiments, covalent association is mediated by a linker. In some embodiments, targeting moieties are not covalently associated with a nanocarrier. For example, targeting moieties may be associated with the surface of, encapsulated within, surrounded by, and/or distributed throughout the polymeric matrix of an inventive particle. For example, in some embodiments, a targeting moiety can be encapsulated within, surrounded by, and/or dispersed throughout the liposomal membrane and/or polymeric matrix of a nanocarrier. Alternatively or additionally, a targeting moiety can be associated with a nanocarrier by charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Association of targeting moieties with vaccine nanocarriers is described in further detail below, in the section entitled "Production of Vaccine Nanocarriers."

Dendritic Cells

Dendritic Cells (DCs) are a type of myeloid leukocytes; they are among the most potent antigen presenting cells for T lymphocytes. Resting DCs reside in many tissues, including lymph nodes, in an immature, tolerogenic state, i.e., they present intermediate to high levels of peptide-MHC complexes, but with little or no costimulatory molecules and without secreting cytokines that T cells need to differentiate into effector cells. T cells that are presented with a specific antigen by immature DCs begin to proliferate for a few days, but then they die by apoptosis or become unresponsive to further activation. The ensuing depletion of antigen-specific T cell responses renders the host selectively tolerant to this antigen. By contrast, when DCs acquire antigens while they are exposed to maturation stimuli, the cells rapidly up-regulate MHC and costimulatory molecules and secrete several cytokines. The now mature DCs are potent inducers of effector T cells and immunological memory. DC maturation can be induced by many signals, such as certain inflammatory cytokines, ligation of DC-expressed CD40, agonists for TLRs, (e.g., bacterial endotoxin), immune complexes, activated complement, necrotic cells, apoptotic cells, free urate, urate crystals, and/or HMGB-1.

DEC-205 (i.e., CD205) is a surface-expressed multi-functional lectin that is selectively expressed on DCs and thymic epithelial cells in lymphoid tissues. In vivo experiments with subcutaneously injected chimeric α-DEC-205 monoclonal antibodies have shown that ligand binding to DEC-205 induces efficient internalization and subsequent processing of the endocytosed material for presentation in MHC molecules in both mice and humans (Hawiger et al., 2001, *J. Exp. Med.* 194:769; Bonifaz et al., 2002, *J. Exp. Med.*, 196:1627; and Bozzacco et al., 2007, *Proc. Natl. Acad. Sci., USA,* 104:1289; each of which is incorporated herein by reference). Upon intra-cutaneous or subcutaneous injection, the chimeric antibody is transported via lymph vessels to the draining lymph nodes where it binds specifically to resident DCs, thus providing the means to target antigens to resting DCs without causing their maturation. The targeted DCs will then induce T cell tolerance to the presented antigen, rather than immunity. However, when DEC-205 is targeted together with an immunostimulatory agent that induces DC maturation (e.g., α-CD40 or one or more ligands for DC-expressed TLRs; discussed in further detail below in the section entitled "Immunostimulatory Agents"), then the vaccine acts as a potent immunostimulant promoting preferentially cytotoxic and Th1-type effector T cell responses.

DC targeting can be accomplished by moieties that bind DC-205, CD11c, class II MHC, CD80, CD86, DC-SIGN, CD11b, BDCA-1, BDCA-2, BDCA-4, Siglec-H, CX3CR1, and/or Langerin.

In some embodiments, DC targeting can be accomplished by any targeting moiety that specifically binds to any entity (e.g., protein, lipid, carbohydrate, small molecule, etc.) that is prominently expressed and/or present on DCs (i.e., a DC marker). Exemplary DC markers include, but are not limited to, CD1a (R4, T6, HTA-1); CD1b (R1); CD1c (M241, R7); CD1d (R3); CD1e (R2); CD11b (αM Integrin chain, CR3, Mo1, C3niR, Mac-1); CD11c (αX Integrin, p150, 95, AXb2); CDw117 (Lactosylceramide, LacCer); CD19 (B4); CD33 (gp67); CD 35 (CR1, C3b/C4b receptor); CD 36 (GpIIIb, GPIV, PASIV); CD39 (ATPdehydrogenase, NTPdehydrogenase-1); CD40 (Bp50); CD45 (LCA, T200, B220, Ly5); CD45RA; CD45RB; CD45RC; CD45RO (UCHL-1); CD49d (VLA-4α, α4 Integrin); CD49e (VLA-5α, α5 Integrin); CD58 (LFA-3); CD64 (FcγRI); CD72 (Ly-19.2, Ly-32.2, Lyb-2); CD73 (Ecto-5' nucloticlase); CD74 (Ii, invariant chain); CD80 (B7, B7-1, BB1); CD81 (TAPA-1); CD83 (HB15); CD85a (ILT5, LIR3, HL9); CD85d (ILT4, LIR2, MIR10); CD85j (ILT2, LIR1, MIR7); CD85k (ILT3, LIR5, HM18); CD86 (B7-2/B70); CD88 (C5aB); CD97 (BL-KDD/F12); CD101 (IGSF2, P126, V7); CD116 (GM-CSFRα); CD120a (TMFRI, p55); CD120b (TNFRII, p75, TNFR p80); CD123 (IL-3Rα); CD139; CD148 (HPTP-η, p260, DEP-1); CD150 (SLAM, IPO-3); CD156b (TACE, ADAM17, cSVP); CD157 (Mo5, BST-1); CD167a (DDR1, trkE, cak); CD168 (RHAMM, IHABP, HMMR); CD169 (Sialoadhesin, Siglec-1); CD170 (Siglec-5); CD171 (L1CAM, NILE); CD172 (SIRP-1α, MyD-1); CD172b (SIRPβ); CD180 (RP105, Bgp95, Ly64); CD184 (CXCR4, NPY3R); CD193 (CCR3); CD196 (CCR6); CD197 (CCR7 (ws CDw197)); CDw197 (CCR7, EBI1, BLR2); CD200 (OX2); CD205 (DEC-205); CD206 (MMR); CD207 (Langerin); CD208 (DC-LAMP); CD209 (DC-SIGN); CDw218a (IL18Rα); CDw218b (IL8Rβ); CD227 (MUC1, PUM, PEM, EMA); CD230 (Prion Protein (PrP)); CD252 (OX40L, TNF (ligand) superfamily, member 4); CD258 (LIGHT, TNF (ligand) superfamily, member 14); CD265 (TRANCE-R, TNF-R superfamily, member 11a); CD271 (NGFR, p75, TNFR superfamily, member 16); CD273 (B7DC, PDL2); CD274 (B7H1, PDL1); CD275 (B7H2, ICOSL); CD276 (B7H3); CD277 (BT3.1, B7 family: Butyrophilin 3); CD283 (TLR3, TOLL-like receptor 3); CD289 (TLR9, TOLL-like receptor 9); CD295 (LEPR); CD298 (ATP1B3, Na K ATPase β3 submit); CD300a (CMRF-35H); CD300c (CMRF-35A); CD301 (MGL1, CLECSF14); CD302 (DCL1); CD303 (BDCA2); CD304 (BDCA4); CD312 (EMR2); CD317 (BST2); CD319 (CRACC, SLAMF7); CD320 (8D6); and CD68 (gp110, Macrosialin); class II MHC; BDCA-1; Siglec-H; wherein the names listed in parentheses represent alternative names.

T Cell Targeting Moieties

In some embodiments, T cell targeting can be accomplished by any targeting moiety that specifically binds to any entity (e.g., protein, lipid, carbohydrate, small molecule, etc.) that is prominently expressed and/or present on T cells (i.e., a T cell marker). Exemplary T cell markers include, but are not limited to, CD2 (E-rosette R, T11, LFA-2); CD3 (T3); CD3α; CD3β; CD3ε; CD4 (L3T4, W3/25, T4); CD5 (T1, Tp67, Leu-1, LY-1); CD6 (T12); CD7 (gp40, Leu 9); CD8a (Leu2, T8, Lyt2,3); CD8b (CD8, Leu2, Lyt3); CD11a (LFA-1α, α Integrin chain); CD11b (αM Integrin chain, CR3, Mo1, C3niR, Mac-1); CD11c (αX Integrin, p150, 95, AXb2); CD15s (Sialyl Lewis X); CD15u (3' sulpho Lewis X); CD15su (6 sulpho-sialyl Lewis X); CD16b (FcgRlllb); CDw17 (Lactosylceramide, LacCer); CD18 (Integrin β2 CD11a, b, c β-subunit); CD26 (DPP IV ectoeneyme, ADA binding protein); CD27 (T14, S152); CD28 (Tp44, T44); CD29 (Platelet GPlla, β-1 integrin, GP); CD31 (PECAM-1, Endocam); CD35 (CR1, C3b/C4b receptor); CD37 (gp52-40); CD38 (ADP-ribosyl/cyclase, T10); CD43 (Sialophorin, Leukosialin); CD44 (ECMRII, H-CAM, Pgp-1); CD45 (LCA, T200, B220, Ly5); CD45RA (p56lck, p59fyn, Src kinases); CD45RB (p56lck, p59fyn, Src kinases); CD45RC (p56lck, p59fyn, Src kinases); CD46 (MCP); CD47 (gp42, IAP, OA3, Neurophillin); CD47R (MEM-133); CD48 (Blast-1, Hulym3, BCM-1, OX-45); CD49c (VLA-3α, α3 Integrin); CD49d (VLA-4α, α4 Integrin); CD49e (VLA-5α, α5 Integrin); CD49f (VLA-6α, α6 Integrin gplc); CD50 (ICAM-3); CD52 (CAMPATH-1, HES); CD53 (OX-44); CD54 (ICAM-1); CD55 (DAF); CD56 (Leu-19, NKH-1, NCAM); CD57 (HNK1, Leu-7); CD58 (LFA-3); CD59 (1F5Ag, H19, Protectin, MACIF, MIRL, P-18); CD60a (GD3); CD60b (9-O-acetyl GD3); CD60c (7-O acetyl GD3); CD62L (L-selectin, LAM-1, LECAM-1, MEL-14, Leu8, TQ1); CD73 (Ecto-5'-nucleotidase); CD75 (sialo-masked Lactosamine); CD75S (α2, 6 sialylated Lactosamine); CD81 (TAPA-1); CD82 (4F9, C33, IA-4, KAI1, R2); CD84 (P75, GR6); CD85a (ILT5, LIR3, HL9); CD85j (ILT2, LIR1, MIR7); CD87 (uPAR); CDw92 (p70); CD94 (Kp43); CD95 (APO-1, FAS, TNFRSF6); CD98 (4F2, FRP-1, RL-388); CD99 (MIC2, E2); CD99R (CD99 Mab restricted); CD100 (SEMA4D); CD102 (ICAM-2); CD108 (SEMA7A, JMH blood group antigen); CDw119 (IFNγR, IFNγRα); CD120a (TNFRI, p55); CD120b (TNFRII, p75, TNFR p80); CD121a (Type 1 IL-1R); CD121b (Type 2 IL-1R); CD122 (IL2Rβ); CD124 (IL-4Rα); CD126 (IL-6Rα); CD127 (p90, IL-7R, IL-7Rα); CD128a (IL-8Ra, CXCR1, (Tentatively renamed as CD181)); CD128b (IL-8Rb, CXCR2, (Tentatively renamed as CD182)); CD130 (gp130); CD132 (Common γ chain, IL-2Rγ); CD147 (Basigin, EMMPRIN, M6, OX47); CD148

(HPTP-η, p260, DEP-1); CD150 (SLAM, IPO-3); CD153 (CD3OL, TNSF8); CD156b (TACE, ADAM17, cSVP); CD158a (KIR2DL1, p58.1); CD158b1 (KIR2DL2, p58.2); CD158b2 (KIR2DL3, p58.3); CD158c (KIR2DS6, KIRX); CD158|e1/e2 (KIR3DLI/S1, p70); CD159F (KIR2DL5); CD158g (KIR2DS5); CD158h (KIR2DS1, p50.1); CD158i (KIR2DS4, p50.3); CD158j (KIR2DS2, p50.2); CCD158k (KIR3DL2, p140); CD159a (NKG2A); CD160 (BY55, NK1, NK28); CD161 (NKR, NKRP1A); CD162 (PSGL-1); CD164 (MGC-24, MUC-24); CD171 (L1CAM, NILE); CD172g (SIRPg); CD181 (CXCR1, (Formerly known as CD128a)); CD182 (CXCR2, (Formerly known as CD128b)); CD183 (CXCR3, GPR9); CD184 (CXCR4, NPY3R); CD185 (CXCR5); CD186 (CXCR6); CD191 (CCR1); CD192 (CCR2); CD193 (CCR3); CD195 (CCR5); CD196 (CCR6); CD197 (CCR7 (was CDw197)); CDw197 (CCR7, EBI1, BLR2); CDw198 (CCR8); CDw199 (CCR9); CD205 (DEC-205); CDw210 (CK); CDw217 (CK); CDw218a (IL18Rα); CDw218b (IL18Rβ); CD220 (Insulin R); CD221 (IGF1 R); CD222 (M6P-R, IGFII-R); CD223 (LAG-3); CD224 (GGT); CD225 (Leu13); CD226 (DNAM-1, PTA1); CD229 (Ly9); CD230 (Prion Protein (PrP)); CD244 (2B4, P38, NAIL); CD245 (p220/240); CD247 (CD3 Zeta Chain); CD261 (TRAIL-R1, TNF-R superfamily, member 10a); CD262 (TRAIL-R2, TNF-R superfamily, member 10b); CD263 (TRAIL-R3, TNF-R superfamily, member 10c); CD264 (TRAIL-R4, TNF-R superfamily, member 10d); CD265 (TRANCE-R, TNF-R superfamily, member 11a); CD268 (BAFFR, TNF-R superfamily, member 13C); CD272 (BTLA); CD275 (B7H2, ICOSL); CD277 (BT3.1, B7 family: Butyrophilin 3); CD294 (CRTH2, PGRD2, G protein-coupled receptor 44); CD295 (LEPR); CD296 (ART1, ADP-ribosyltransferase 1); CD298 (ATP1B3, Na K ATPase β3 subunit); CD300a (CMRF-35H); CD300c (CMRF-35A); CD305 (LAIR1); CD314 (NKG2D); CD316 (EW12); CD317 (BST2); CD319 (CRACC, SLAMF7); CD321 (JAM1); CD322 (JAM2); CDw328 (Siglec7); and CD68 (gp 110, Macrosialin); wherein the names listed in parentheses represent alternative names.

In some embodiments, T cell targeting can be accomplished by any targeting moiety that binds, such as specifically binds, to any entity (e.g., protein, lipid, carbohydrate, small molecule, etc.) that is prominently expressed and/or present on T cells upon activation (i.e., activated T cell targets). Exemplary activated T cell targeting moieties include, but are not limited to, CD1a (RA, T6, HTA-1); CD1b (R1); Cd1c (M241,R7); CD1d (R3); CD9 (p24, DRAP-1, MRP-1); CD25 (Tac antigen, IL-2Rα, p55); CD30 (Ber-H2, Ki-1); CD39 (ATPdehydrogenase, NTPdehydrogenase-1); CD45RO (UCHL-1); CD49a (VLA-1α, α1 Integrin); CD49b (VLA-2α, gpla, α2 Integrin); CD69 (AIM, EA 1, MLR3, gp34/28, VEA); CD70 (Ki-24, CD27 ligand); CD74 (Ii, invariant chain); CD80 (B7, B7-1, BB1); CD86 (B7-2/B70); CD96 (TACTILE); CD97 (BL-KDD/F12); CD101 (IGSF2, P126, V7); CD103 (HML-1, Integrin αE, ITGAE); CD107a (LAMP-1); CD107b (LAMP-2); CD109 (8A3, E123 7D1); CD134 (OX40, TNFRSF4); CDw137 (4-1BB, ILA); CD146 (Muc 18, S-endo, MCAM, Mel-CAM); CD152 (CTLA-4); CD154 (CD40L, gp39, TRAP-1, T-BAM); CD166 (AL-CAM, KG-CAM, SC-1, BEN, DM-GRASP); CD178 (Fas Ligand); CD227 (MUC1, PUM, PEM, EMA); CD253 (TRAIL, TNF (ligand) superfamily, member 10); CD254 (TRANCE, RANKL, TNF (ligand) superfamily, member 11); CD258 (LIGHT, TMF (ligand) superfamily, member 14); CD267 (TACI, TNF-R superfamily, member 13B); CD273 (B7DC, PDL2); CD274 (B7H1, PDL1); CD278 (ICOS); CD279 (PD1); and CD312 (EMR2); wherein the names listed in parentheses represent alternative names.

Molecular Characteristics of Targeting Moieties

Nucleic Acid Targeting Moieties.

As used herein, a "nucleic acid targeting moiety" is a nucleic acid that binds selectively to a target. In some embodiments, a nucleic acid targeting moiety is a nucleic acid aptamer. An aptamer is typically a polynucleotide that binds to a specific target structure that is associated with a particular organ, tissue, cell, extracellular matrix component, and/or subcellular locale. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g., hairpin loops) that disrupt base pairing.

In some embodiments, a nucleic acid targeting moiety is a Spiegelmer®. In general, Spiegelmers® are high-affinity L-enantiomeric oligonucleotide ligands that display high resistance to enzymatic degradation compared with D-oligonucleotides. In some embodiments, Spiegelmers® can be designed and utilized just as an aptamer would be designed and utilized.

One of ordinary skill in the art will recognize that any nucleic acid that is capable of specifically binding to a target, as described herein, can be used in accordance with the present invention.

Nucleic acids of the present invention (including nucleic acid targeting moieties and/or functional RNAs to be delivered, e.g., RNAi agents, ribozymes, tRNAs, etc., described in further detail below) may be prepared according to any available technique including, but not limited to chemical synthesis, enzymatic synthesis, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in molecular biology, v. 288 (Clifton, N.J.) Totowa, N.J.: Humana Press, 2005; both of which are incorporated herein by reference).

The nucleic acid that forms the nucleic acid targeting moiety may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid targeting moiety can be replaced with a hydrocarbon linker or a polyether linker provided that the binding affinity and selectivity of the nucleic acid targeting moiety is not substantially reduced by the substitution (e.g., the dissociation constant of the nucleic acid targeting moiety for the target should not be greater than about $1 \times 10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) *Antisense Drug Technology: Principles, Strategies, and Applications* (1$^{st}$ ed), Marcel Dekker; ISBN: 0824705661, 1st edition (2001); incorporated herein by reference; and references therein. For example, 2'-modifications include halo, alkoxy and allyloxy groups. In some embodiments, the 2'-OH group is replaced by a group selected from H, OR, R, halo, SH, $SR_1$, $NH_2$, $NH_R$, $NR_2$ or CN, wherein R is $C_1$-$C_6$ alkyl, alkenyl, or alkynyl, and halo is F, Cl, Br or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleosides (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of an aptamer such that the ability of the aptamer to specifically bind to the aptamer target is not substantially affected. The modified region may be at the 5'-end and/or the 3'-end of one or both strands. For example, modified aptamers in which approximately 1 to approximately 5 residues at the 5' and/or 3' end of either of both strands are nucleotide analogs and/or have a backbone modification can be employed. The modification may be a 5' or 3' terminal modification. A nucleic acid strand may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic agent, improved specific binding of an aptamer to an aptamer target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the aptamer are inverted to yield a linkage such as a 3'-3' linkage or a 5'-5' linkage.

In some embodiments, nucleic acids in accordance with the present invention are not synthetic, but are naturally-occurring entities that have been isolated from their natural environments.

Small Molecule Targeting Moieties.

In some embodiments, a targeting moiety in accordance with the present invention may be a small molecule. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

In certain embodiments, a small molecule is oligomeric. In certain embodiments, a small molecule is non-oligomeric. In certain embodiments, a small molecule is a natural product or a natural product-like compound having a partial structure (e.g., a substructure) based on the full structure of a natural product. In certain embodiments, a small molecule is a synthetic product. In some embodiments, a small molecule may be from a chemical library. In some embodiments, a small molecule may be from a pharmaceutical company historical library. In certain embodiments, a small molecule is a drug approved by the U.S. Food and Drug Administration as provided in the U.S. Code of Federal Regulations (C.F.R.).

One of ordinary skill in the art will appreciate that any small molecule that specifically binds to a desired target, as described herein, can be used in accordance with the present invention.

Protein Targeting Moieties.

In some embodiments, a targeting moiety in accordance with the present invention may be a protein or peptide. In certain embodiments, peptides range from about 5 to about 100, from about 5 to about 50, from about 10 to about 75, from about 15 to about 50, or from about 20 to about 25 amino acids in size. In some embodiments, a peptide sequence can be based on the sequence of a protein. In some embodiments, a peptide sequence can be a random arrangement of amino acids.

The terms "polypeptide" and "peptide" are used interchangeably herein, with "peptide" typically referring to a polypeptide having a length of less than about 100 amino acids. Polypeptides may contain L-amino acids, D-amino acids, or both and may contain any of a variety of amino acid modifications or analogs known in the art. Useful modifications include, e.g., terminal acetylation, amidation, lipidation, phosphorylation, glycosylation, acylation, farnesylation, sulfation, etc.

Exemplary proteins that may be used as targeting moieties in accordance with the present invention include, but are not limited to, antibodies, receptors, cytokines, peptide hormones, glycoproteins, glycopeptides, proteoglycans, proteins derived from combinatorial libraries (e.g., Avimers™, Affibodies®, etc.), and characteristic portions thereof. Synthetic binding proteins such as Nanobodies™, AdNectins™, etc., can be used. In some embodiments, protein targeting moieties can be peptides.

One of ordinary skill in the art will appreciate that any protein and/or peptide that specifically binds to a desired target, as described herein, can be used in accordance with the present invention.

In some embodiments, a targeting moiety may be an antibody and/or characteristic portion thereof. The term "antibody" refers to any immunoglobulin, whether natural or wholly or partially synthetically produced and to derivatives thereof and characteristic portions thereof. An antibody may be monoclonal or polyclonal. An antibody may be a member of any immunoglobulin class, including any of the human classes: IgG, IgM, IgA, IgD, and IgE.

As used herein, an antibody fragment (i.e. characteristic portion of an antibody) refers to any derivative of an antibody which is less than full-length. In some embodiments, an antibody fragment retains at least a significant portion of the full-length antibody's specific binding ability. Examples of such antibody fragments include, but are not limited to, Fab, Fab', F(ab')2, scFv, Fv, dsFv diabody, and Fd fragments. Antibody fragments also include, but are not limited, to Fc fragments.

An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment will typically comprise at least about 50 amino acids and more typically will comprise at least about 200 amino acids.

In some embodiments, antibodies may include chimeric (e.g. "humanized") and single chain (recombinant) antibodies. In some embodiments, antibodies may have reduced effector functions and/or bispecific molecules. In some embodiments, antibodies may include fragments produced by a Fab expression library.

Single-chain Fvs (scFvs) are recombinant antibody fragments consisting of only the variable light chain (VL) and variable heavy chain (VH) covalently connected to one another by a polypeptide linker. Either VL or VH may comprise the NH2-terminal domain. The polypeptide linker may be of variable length and composition so long as the two variable domains are bridged without significant steric interference. Typically, linkers primarily comprise stretches of glycine and serine residues with some glutamic acid or lysine residues interspersed for solubility.

Diabodies are dimeric scFvs. Diabodies typically have shorter peptide linkers than most scFvs, and they often show a preference for associating as dimers.

An Fv fragment is an antibody fragment which consists of one VH and one VL domain held together by noncovalent interactions. The term "dsFv" as used herein refers to an Fv with an engineered intermolecular disulfide bond to stabilize the VH-VL pair.

An F(ab')2 fragment is an antibody fragment essentially equivalent to that obtained from immunoglobulins by digestion with an enzyme pepsin at pH 4.0-4.5. The fragment may be recombinantly produced.

A Fab' fragment is an antibody fragment essentially equivalent to that obtained by reduction of the disulfide bridge or bridges joining the two heavy chain pieces in the F(ab')2 fragment. The Fab' fragment may be recombinantly produced.

A Fab fragment is an antibody fragment essentially equivalent to that obtained by digestion of immunoglobulins with an enzyme (e.g., papain). The Fab fragment may be recombinantly produced. The heavy chain segment of the Fab fragment is the Fd piece.

Carbohydrate Targeting Moieties.

In some embodiments, a targeting moiety in accordance with the present invention may comprise a carbohydrate. In some embodiments, a carbohydrate may be a polysaccharide comprising simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, the carbohydrate may be aminated, carboxylated, and/or sulfated. In some embodiments, hydrophilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

One of ordinary skill in the art will appreciate that any carbohydrate that specifically binds to a desired target, as described herein, can be used in accordance with the present invention.

Lipid Targeting Moieties.

In some embodiments, a targeting moiety in accordance with the present invention may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be a $C_{15}$-$C_{25}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

One of ordinary skill in the art will appreciate that any fatty acid group that specifically binds to a desired target, as described herein, can be used in accordance with the present invention.

Novel Targeting Moieties

Any novel targeting moiety can be utilized in the nanocarriers in accordance with the present invention. Any method known in the art can be used to design, identify, and/or isolate novel targeting moieties. For example, standard techniques utilizing libraries of molecules and in vitro binding assays can be utilized to identify novel targeting moieties.

Nucleic acid targeting moieties (e.g. aptamers, Spiegelmers®) may be designed and/or identified using any available method. In some embodiments, nucleic acid targeting moieties are designed and/or identified by identifying nucleic acid targeting moieties from a candidate mixture of nucleic acids. Systemic Evolution of Ligands by Exponential Enrichment (SELEX), or a variation thereof, is a commonly used method of identifying nucleic acid targeting moieties that bind to a target from a candidate mixture of nucleic acids (see, e.g., U.S. Pat. Nos. 6,482,594; 6,458,543; 6,458,539; 6,376,190; 6,344,318; 6,242,246; 6,184,364; 6,001,577; 5,958,691; 5,874,218; 5,853,984; 5,843,732; 5,843,653; 5,817,785; 5,789,163; 5,763,177; 5,696,249; 5,660,985; 5,595,877; 5,567,588; and 5,270,163; each of which is incorporated herein by reference). Alternatively or additionally, Polyplex In Vivo Combinatorial Optimization (PICO) is a method that can be used to identify nucleic acid targeting moieties (e.g. aptamers) that bind to a target from a candidate mixture of nucleic acids in vivo and/or in vitro and is described in co-pending PCT Application US06/47975, entitled "System for Screening Particles," filed Dec. 15, 2006, which is incorporated herein by reference.

Immunostimulatory Agents

In some embodiments, nanocarriers may transport one or more immunostimulatory agents which can help stimulate immune responses. In some embodiments, immunostimulatory agents boost immune responses by activating APCs to enhance their immunostimulatory capacity. In some embodiments, immunostimulatory agents boost immune responses by amplifying lymphocyte responses to specific antigens. In some embodiments, immunostimulatory agents boost immune responses by inducing the local release of mediators, such as cytokines from a variety of cell types. In some embodiments, the immunostimulatory agents suppress or redirect an immune response. In some embodiments, the immunostimulatory agents induce regulatory T cells.

In some embodiments, all of the immunostimulatory agents of a vaccine nanocarrier are identical to one another. In some embodiments, a vaccine nanocarrier comprises a number of different types of immunostimulatory agents. In some embodiments, a vaccine nanocarrier comprises multiple individual immunostimulatory agents, all of which are identical to one another. In some embodiments, a vaccine nanocarrier comprises exactly one type of immunostimulatory agent. In some embodiments, a vaccine nanocarrier comprises exactly two distinct types of immunostimulatory agents. In some embodiments, a vaccine nanocarrier comprises greater than two distinct types of immunostimulatory agents.

In some embodiments, a vaccine nanocarrier comprises a single type of immunostimulatory agent that stimulates both B cells and T cells. In some embodiments, a vaccine nanocarrier comprises two types of immunostimulatory agents, wherein first type of immunostimulatory agent stimulates B cells, and the second type of immunostimulatory agent stimulates T cells. In some embodiments, a vaccine nanocarrier comprises greater than two types of immunostimulatory agents, wherein one or more types of immunostimulatory agents stimulate B cells, and one or more types of immunostimulatory agents stimulate T cells.

In some embodiments, a vaccine nanocarrier comprises at least one type of immunostimulatory agent that is associated with the exterior surface of the vaccine nanocarrier. In some embodiments, the association is covalent. In some embodiments, the covalent association is mediated by one or more linkers. In some embodiments, the association is non-covalent. In some embodiments, the non-covalent association is mediated by charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Association of immunostimulatory agents with vaccine nanocarriers is described in further detail below, in the section entitled "Production of Vaccine Nanocarriers."

In some embodiments, a vaccine nanocarrier comprises a lipid membrane (e.g., lipid bilayer, lipid monolayer, etc.), wherein at least one type of immunostimulatory agent is associated with the lipid membrane. In some embodiments, at least one type of immunostimulatory agent is embedded within the lipid membrane. In some embodiments, at least one type of immunostimulatory agent is embedded within the lumen of a lipid bilayer. In some embodiments, a vaccine nanocarrier comprises at least one type of immunostimulatory agent that is associated with the interior surface of the lipid membrane. In some embodiments, at least one type of immunostimulatory agent is encapsulated with the lipid membrane of a vaccine nanocarrier. In some embodiments, at least one type of immunostimulatory agent may be located at multiple locations of a vaccine nanocarrier. For example, a first type of immunostimulatory agent may be embedded within a lipid membrane, and a second type of immunostimulatory agent may be encapsulated within the lipid membrane of a vaccine nanocarrier. To give another example, a first type of immunostimulatory agent may be associated with the exterior surface of a lipid membrane, and a second type of immunostimulatory agent may be associated with the interior surface of the lipid membrane of a vaccine nanocarrier. In some embodiments, a first type of immunostimulatory agent may be embedded within the lumen of a lipid bilayer of a vaccine nanocarrier, and the lipid bilayer may encapsulate a polymeric matrix throughout which a second type of immunostimulatory agent is distributed. In some embodiments, a first type of immunostimulatory agent and a second type of immunostimulatory agent may be in the same locale of a vaccine nanocarrier (e.g., they may both be associated with the exterior surface of a vaccine nanocarrier; they may both be encapsulated within the vaccine nanocarrier; etc.). One of ordinary skill in the art will recognize that the preceding examples are only representative of the many different ways in which multiple immunostimulatory agents may be associated with different locales of vaccine nanocarriers. Multiple immunostimulatory agents may be located at any combination of locales of vaccine nanocarriers.

In certain embodiments, immunostimulatory agents may be interleukins, interferon, cytokines, etc. In specific embodiments, an immunostimulatory agent may be a natural or synthetic agonist for a Toll-like receptor (TLR). In specific embodiments, vaccine nanocarriers incorporate a ligand for toll-like receptor (TLR)-7, such as CpGs, which induce type I interferon production. In specific embodiments, an immunostimulatory agent may be an agonist for the DC surface molecule CD40. In certain embodiments, to stimulate immunity rather than tolerance, a nanocarrier incorporates an immunostimulatory agent that promotes DC maturation (needed for priming of naive T cells) and the production of cytokines, such as type I interferons, which promote antibody responses and anti-viral immunity. In some embodiments, an immunomodulatory agent may be a TLR-4 agonist, such as bacterial lipopolysacharide (LPS), VSV-G, and/or HMGB-1. In some embodiments, immunomodulatory agents are cytokines, which are small proteins or biological factors (in the range of 5 kD-20 kD) that are released by cells and have specific effects on cell-cell interaction, communication and behavior of other cells. In some embodiments, immunostimulatory agents may be proinflammatory stimuli released from necrotic cells (e.g., urate crystals). In some embodiments, immunostimulatory agents may be activated components of the complement cascade (e.g., CD21, CD35, etc.). In some embodiments, immunostimulatory agents may be activated components of immune complexes. The immunostimulatory agents include TLR-1, TLR-2, TLR-3, TLR-4, TLR-5, TLR-6, TLR-7, TLR-8, TLR-9, and TLR-10 agonists. The immunostimulatory agents also include complement receptor agonists, such as a molecule that binds to CD21 or CD35. In some embodiments, the complement receptor agonist induces endogenous complement opsonization of the nanocarrier. Immunostimulatory agents also include cytokine receptor agonists, such as a cytokine. In some embodiments, the cytokine receptor agonist is a small molecule, antibody, fusion protein, or aptamer.

In some embodiments, there are more than one type of immunostimulatory agent. In some embodiments, the different immunostimulatory agents each act on a different pathway. The immunostimulatory agents, therefore, can be different Toll-like receptors, a Toll-like receptor and CD40, a Toll-like receptor and a component of the inflammasome, etc.

In some embodiments, the immunostimulatory agent may be an adjuvant. Thus, in some embodiments, the present invention provides pharmaceutical compositions comprising vaccine nanocarriers formulated with one or more adjuvants. The term "adjuvant", as used herein, refers to an agent that does not constitute a specific antigen, but boosts the immune response to the administered antigen.

In some embodiments, the present invention is directed to delivery of adjuvant using nanocarriers capable of carrying the adjuvant (encapsulated and/or on a surface) to targeted locations such as the cell surface of Antigen Presenting Cells (APCs), wherein the nanocarriers comprise: (i) one or more molecules on a surface to target specific cells; (iii) one or more molecules that are capable of eliciting an immunogenic response when covalently attached to a polymer or encapsulated inside the nanoparticles. The embodiment is directed to enhancing the potentiating of an immune response in a mammal, comprising administering an effective amount of a nanoparticle delivery of adjuvant of the present invention to enhance the immune response of a mammal to one or more antigens. The embodiment is also directed to a method of vaccination using the compositions of the present invention.

For example, in some embodiments, the adjuvant is encapsulated within the nanoparticles of the invention. Typically, in such cases, the adjuvant is present in free form, i.e., the adjuvant is not conjugated to the polymers that form the nanoparticles. Adjuvant is encapsulated during the preparation of the nanoparticles in the usual manner, as exemplified herein. The release profile of the adjuvant from the nanoparticles when administered to a patient will depend upon a variety of factors, including the size of the nanoparticles, rate of dissolution of the polymer forming the nanoparticles (if dissolution occurs), the molecular weight of the polymer forming the nanoparticles, and the chemical characteristics of the adjuvant (which, in turn, will influence the location of the adjuvant within the nanoparticles, diffusion rates, etc.). The amount of adjuvant encapsulated in the polymer nanoparticles will be determined during the process of formation of the nanoparticles.

For example, in some embodiments, the adjuvant is conjugated to the polymers that form the nanoparticles. Typically, in such cases, the adjuvant is expressed on or near the surface of the nanoparticles. In some embodiments, an amphilic polymer capable of self-assembling into nanoparticles is used, and the adjuvant is covalently attached to one terminus of the polymer. For example, the adjuvant may be used as an initiating species in the polymerization reaction used to form the polymers. When the adjuvant is conjugated (i.e., covalently bonded) to a terminus of the polymer, upon self-assembly of the polymer, the adjuvant is concentrated at the periphery or at the core of the nanoparticles. For example, in a polymer comprising a hydrophobic block and a hydrophilic block, wherein the polymer is allowed to self-assemble into nanoparticles having a hydrophobic core and a hydrophilic periphery, adjuvant that is conjugated to the terminus of the hydrophilic block will be concentrated at the periphery of the nanoparticles. In some preferred embodiments, the adjuvant is concentrated at the surface of the nanoparticles and remains in a position to act as an immunostimulant. For nanoparticle formulations comprising conjugated adjuvant, the density of adjuvant on the surface of the nanoparticles will be a function of a variety of factors, including the molecular weight of the polymers forming the nanoparticles, the density of the nanoparticles, and the chemical characteristics of the adjuvant.

In some embodiments, a combination of encapsulated and conjugated adjuvant is used.

For example, in some embodiments, vaccine nanocarriers are formulated with one or more adjuvants such as gel-type adjuvants (e.g., aluminum hydroxide, aluminum phosphate, calcium phosphate, etc.), microbial adjuvants (e.g., immunomodulatory DNA sequences that include CpG motifs; endotoxins such as monophosphoryl lipid A; exotoxins such as cholera toxin, E. coli heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.), surfactant based adjuvants, and/or combinations thereof. Other exemplary adjuvants include some polymers (e.g., polyphosphazenes, described in U.S. Pat. No. 5,500,161, which is incorporated herein by reference), QS21, squalene, tetrachlorodecaoxide, etc.

The term "adjuvant" is intended to include any substance which is incorporated into or administered simultaneously with the conjugates of the invention and which nonspecifically potentiates the immune response in the subject. Adjuvants include aluminum compounds, e.g., gels, aluminum hydroxide and aluminum phosphate, and Freund's complete or incomplete adjuvant (in which the conjugate is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U) leutinan, pertussis toxin, cholera toxin, lipid A, saponins and peptides, e.g. muramyl dipeptide. Rare earth salts, e.g., lanthanum and cerium, may also be used as adjuvants. The amount of adjuvants depends on the subject and the particular conjugate used and can be readily determined by one skilled in the art without undue experimentation. The adjuvant to be incorporated in the nanoparticle system and delivered to a target cell or tissue of the present invention may be combined with a diagnostic, antigen, prophylactic or prognostic agents. Any chemical compound to be administered to an individual may be delivered using the adjuvant nanoparticle delivery system of the invention.

In some embodiments, the adjuvant will be contained within or upon the surface of a biodegradable nanocarrier, for example by covalent linkage to the excipient (e.g., covalent linkage to the polymer forming the nanocarrier). The invention is not limited to adjuvant conjugates, but also includes embodiments comprising free adjuvant encapsulated inside the nanocarrier or adsorbed on the surface of the nanoparticle. Although reference may be made to "the encapsulated adjuvant" or to "the conjugated adjuvant," it will be appreciated that (unless otherwise specified) the description above and below pertains to both cases. The encapsulated adjuvant will stimulate intracellular pattern recognition receptors such as APCs, endosomal Toll-like receptor (TLR)-3, TLR-7, TLR-8 and TLR-9, or components of the cytoplasmic inflammasome, such as NOD2 or NALP3. The encapsulated adjuvant can be used for therapeutic applications of genital warts, basal cell carcinoma, actinic keratosis, cHPV, melanoma, leukemias, chicken pox, dengue, hog cholera, Influenza, rabies, yellow fever, carcinomas, HBV, HCV, genital herpes, sarcoidosis, hepatitis C, hepatitis B, HIV, lupus etc.

The nanoparticle delivery of adjuvant of the present invention can be utilized to enhance the immune response to one or more antigens. Antigens from a variety of pathogenic agents can be employed to form the conjugates of the present invention. Typical antigens suitable for the immune-response provoking conjugates of the present invention include antigens derived from any of the following: bacteria, such as the ethiological agents of anthrax, leprosy, tuberculosis, diphtheria, Lyme disease, syphilis, typhoid fever, and gonorrhea; protozoans, such as *Babeosis bovis, Plasmodium, Leishmania* spp. *Toxoplasma gondii*, and *Trypanosoma cruzi*; fungi, such as *Aspergillus* sp., *Candida albicans, Cryptococcus neoformans*, and *Histoplasma capsulatum*; and tumor antigens, such as carcinoembryonic antigen, prostate-specific membrane antigen, prostate specific antigen, protein MZ2-E, polymorphic epithelial mucin (PEM), folate-binding-protein LK26, truncated epidermal growth factor receptor (EGRF), Thomsen-Friedenreich (T) antigen, GM-2 and GD-2 gangliosides. The antigen can be a protein, peptide, polysaccharide or oligosaccharide (free or conjugated to a protein carrier), or mixtures thereof. The proteins and peptides may be purified from a natural source, synthesized by means of solid phase synthesis, or may be obtained means of recombinant genetics. The polysaccharides and oligosaccharides may be isolated from a natural source, or may be synthesized using enzymatic procedures and/or organic synthesis approaches. Adjuvants that stimulate endosomal TLRs include imidazoquinoline compounds (e.g. loxoribine, gardiquimod, imiquimod, propirimine, resiquimod, CL097, 3M-002, 851 (3M PharmaJTakeda), sotirimod (3M Pharma), 852A (3M Pharma), Isatoribine (Anadys), ANA975 (Anadys/Novartis), SM360320 (Sumitomo), R1354 (Coley Pharmaceuticals), 3M-854 (3M Pharma), single- and double-stranded such as $R_{CpG7909}$ (Coley Pharmaceuticals), $R_{CpG2006}$ (Coley Pharmaceuticals), $R_{CpG10101}$ (Coley Pharmaceutical), AVE675 (Coley Pharmaceuticals), 10101, Tolamba (Dynavax Technologies), Heplisav (Dynavax Technologies), 1018ISS (Dynavax Technologies), IM02055 (Idera Pharmaceuticals), IRS 954 (Dynavax Technologies), etc. In some embodiments, the nanocarrier will present one or more adjuvants linked (conjugated) to the surface or encapsulated as free molecule or conjugates inside nanocarrier. Surface-presented adjuvants may stimulate either the intracellular pattern recognition receptors listed above or cell surface expressed receptors on APCs, such as TLR-1, TLR-2, TLR-4, TLR-5, TLR-6, TLR-10, TLR-1 1, CD40, TNFR or IL-1 R described above. In another embodiment, the nanocarrier adjuvant conjugate will contain one or more adjuvants on both its surface and its interior.

Nanocarrier adjuvant conjugates may comprise multi entities bound to one another by any physicochemical means, including hydrophobic interaction between delivery system and the non-specific hydrophobic portions of an antibody molecule, antibody-controlled drug delivery particle specific binding, electrostatic interaction, and covalent coupling. The nature of the preferred bonding will depend, among other things, upon the mode of administration and the pharmaceutical carriers used to deliver the conjugate to the selected epithelial barrier. For example, some bonds are not as well suited as others to withstand certain environments such as the stomach, but can be protected by delivery systems which bypass the stomach. It is, of course, important that the bond between adjuvant and polymer and be of such a nature that it does not destroy or reduce the adjuvant efficacy. Such bonds are well known to those of ordinary skill in the art; examples are provided in greater detail below. For example, the adjuvant may be attached by means of an ester, ether, amide or carbamoyl link, among which ester, amide and carbamoyl links have the advantage that they can be hydrolysed in the cell. The linkage between the conjugates and the adjuvant is effected with or without a spacer arm consisting of a branched or unbranched alkyl chain comprising carbon atoms. The amphipathic compounds obtained in alcoholic solution can then be dispersed in water or in an aqueous buffer, and can yield a suspension of micelles or of liposomes. Advantageously, the amphipathic compounds of the invention are combined with a neutral lipid such as a phospholipid, for example dioleoylphosphatidylethanol-amine (DOPE) or dioleoylphosphatidylcholine (DOPC). This combination causes the amphipathic compounds according to the invention to organize themselves in the form of liposomes rather than micelles during the phase of dispersion in an aqueous environment.

In another embodiment, the nanocarrier-adjuvant may additionally incorporate a targeting moiety, such as an antibody, fragment of an antibody, polypeptides, recombinant native or modified proteins or fusion proteins, aptamers, oligonucleotides composed of either RNA or DNA, carbohydrates, polymers or small molecules, which direct the preferential binding and/or uptake of a carrier to APCs such as DCs, subcapsular sinus macrophages or follicular dendritic cells (FDC), or any combination of these target cells. In another embodiment the nanoparticle-adjuvant is combined with an encapsulated or surface presented antigen, such as polypeptides, recombinant native or modified proteins or fusion proteins, oligonucleotides composed of either RNA or DNA, carbohydrates, polymers or small molecules. In another embodiment, the nanoparticle-adjuvant incorporates both a targeting moiety and one or more antigen.

Conjugates of the present invention can include one or more bacterial antigens from a particular bacteria, including:

*Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospira* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichia* spp., and *Rickettsia* spp.

Bacterial antigens can be native, recombinant or synthetic. Such bacterial antigens include, but are not limited to, selectins or lectins from bacteria that bind to carbohydrate determinants present on cell surfaces; and bacteria receptors for proteins, such as fibronectin, laminin, and collagens. Nanoparticle delivery of adjuvant can include one or more one or more antigens from a particular virus, including: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-11, FeLV, Bovine LV, FeIV, Canine distemper virus, Canine contagious hepatitis virus, Feline calicivirus, Feline rhinotracheitis virus, TGE virus (swine), and Foot and mouth disease.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses.

Nanoparticle delivery of adjuvant can include one or more tumor associated antigens. Tumor associated antigens can be native, recombinant or synthetic. Such tumor associated antigens include, but are not limited to, protein MZ2-E, polymorphic epithelial mucin, folate-binding protein LK26, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, MUC-1 and peptide fragments thereof, CA 125, 15-3, 19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Herllneu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein p210 BCR-ABL.

Useful peptides or polypeptides may comprise an epitope-bearing portion of a polypeptide known to elicit an antibody and/or an antigen-specific cytotoxic T lymphocyte (CTL) response when the whole polypeptide is administered to an animal. The epitope of this polypeptide portion is an immunogenic or antigenic epitope of the polypeptide. An "immunogenic epitope" is defined as a part of a protein that elicits an antibody and/or an antigen-specific cytotoxic T lymphocyte (CTL) response when the whole protein is the immunogen. On the other hand, a region of a protein molecule to which an antibody can bind is defined as an "antigenic epitope."

As to the selection of peptides or polypeptides bearing an antigenic epitope (i.e., that contain a region of a protein molecule to which an antibody can bind), relatively short synthetic peptides that mimic part of a protein sequence are capable of eliciting an antiserum that reacts with the partially mimicked protein. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides that can be employed to form conjugates of the invention are therefore useful to raise antibodies, including monoclonal antibodies, that bind specifically to a particular polypeptide. Antigenic epitope-bearing peptides and polypeptides of the invention preferably contain a sequence of at least seven, more preferably at least nine and most preferably between about at least 15 to about 30 amino acids contained within the amino acid sequence of a particular polypeptide.

Epitopes recognized by the T-cell receptors on CTLs may be different from those seen by antibodies. Usually, CTLs recognize peptides (derived from proteins enzymatically degraded in the cytosol compartment) which are bound to MHC class I molecules and exposed on the cell surface. These CTL-recognized peptides bind selectively to MHC class I molecules according to the MHC allele specific sequence motifs. These peptides can be identified by expression cloning. Alternatively, CTL-recognized peptides can be identified by induction of CTLs by in vitro stimulation with peptides derived from the protein antigen used for immunization. The particular CTL-recognized epitope-bearing peptides and polypeptides of the invention preferably are sequences of at least six amino acids, and more preferably between 7 to 20 amino acids. These peptides can be used to form conjugates of the invention and are useful to raise antibodies as well as antigen specific CTLs or T-cell immunity. Epitope-bearing peptides and polypeptides may be produced by any conventional means.

The disclosed invention capitalizes on insights into the cellular and molecular mechanisms by which adjuvants induce immune responses following subcutaneous injection. Nanocanier-based adjuvant application has several advantages over conventional approaches, some of which are: 1. minimal off-target action of adjuvants resulting in reduced side effects; 2. enhanced targetting to APCs leading to enhanced therapeutic and prophylactic immune responses to vaccines; 3. nanoparticle-adjuvants can induce desired immunization effects with lower doses of adjuvant and/or antigen and may require fewer booster inoculations; 4. reduced toxicity allows the safe administration of larger doses of adjuvants to maximize immune responses to poorly immunogenic antigens; and 5. controlled or triggered release of the adjuvant from hours to days.

Assays for T Cell Activation

In some embodiments, various assays can be utilized in order to determine whether an immune response has been stimulated in a T cell or group of T cells (i.e., whether a T cell or group of T cells has become "activated"). In some embodiments, stimulation of an immune response in T cells can be determined by measuring antigen-induced production of cytokines by T cells. In some embodiments, stimulation of an immune response in T cells can be determined by measuring antigen-induced production of IFNγ, IL-4, IL-2, IL-10, IL-17 and/or TNFα by T cells. In some embodiments, antigen-produced production of cytokines by T cells can be measured by intracellular cytokine staining followed by flow cytometry. In some embodiments, antigen-induced production of cytokines by T cells can be measured by surface capture staining followed by flow cytometry. In some embodiments, antigen-induced production of cytokines by T cells can be measured by determining cytokine concentration in supernatants of activated T cell cultures. In some embodiments, this can be measured by ELISA.

In some embodiments, antigen-produced production of cytokines by T cells can be measured by ELISPOT assay. In general, ELISPOT assays employ a technique very similar to the sandwich enzyme-linked immunosorbent assay (ELISA) technique. An antibody (e.g. monoclonal antibody, polyclonal antibody, etc.) is coated aseptically onto a PVDF (polyvinylidene fluoride)-backed microplate. Antibodies are chosen for their specificity for the cytokine in question. The plate is blocked (e.g. with a serum protein that is non-reactive with any of the antibodies in the assay). Cells of interest are plated out at varying densities, along with antigen or mitogen, and then placed in a humidified 37° C. $CO_2$ incubator for a specified period of time. Cytokine secreted by activated cells is captured locally by the coated antibody on the high surface area PVDF membrane. After washing the wells to remove cells, debris, and media components, a secondary antibody (e.g., a biotinylated polyclonal antibody) specific for the cytokine is added to the wells. This antibody is reactive with a distinct epitope of the target cytokine and thus is employed to detect the captured cytokine. Following a wash to remove any unbound biotinylated antibody, the detected cytokine is then visualized using an avidin-HRP, and a precipitating substrate (e.g., AEC, BCIP/NBT). The colored end product (a spot, usually a blackish blue) typically represents an individual cytokine-producing cell. Spots can be counted manually (e.g., with a dissecting microscope) or using an automated reader to capture the microwell images and to analyze spot number and size. In some embodiments, each spot correlates to a single cytokine-producing cell.

In some embodiments, an immune response in T cells is said to be stimulated if between about 1% and about 100% of antigen-specific T cells produce cytokines. In some embodiments, an immune response in T cells is said to be stimulated if at least about 1%, at least about 5%, at least about 10%, at least about 25%, at least about 50%, at least about 75%, at least about 90%, at least about 95%, at least about 99%, or about 100% of antigen-specific T cells produce cytokines.

In some embodiments, an immune response in T cells is said to be stimulated if immunized subjects comprise at least about 10-fold, at least about 50-fold, at least about 100-fold, at least about 500-fold, at least about 1000-fold, at least about 5000-fold, at least about 10,000-fold, at least about 50,000-fold, at least about 100,000-fold, or greater than at least about 100,000-fold more cytokine-producing cells than do naive controls.

In some embodiments, stimulation of an immune response in T cells can be determined by measuring antigen-induced proliferation of T cells. In some embodiments, antigen-induced proliferation may be measured as uptake of $H^3$-thymidine in dividing T cells (sometimes referred to as "lymphocyte transformation test, or "LTT"). In some embodiments, antigen-induced proliferation is said to have occurred if $H^3$-thymidine uptake (given as number of counts from a γ counter) is at least about 5-fold, at least about 10-fold, at least about 20-fold, at least about 50-fold, at least about 100-fold, at least about 500-fold, at least about 1000-fold, at least about 5000-fold, at least about 10,000-fold, or greater than at least about 10,000-fold higher than a naïve control.

In some embodiments, antigen-induced proliferation may be measured by flow cytometry. In some embodiments, antigen-induced proliferation may be measured by a carboxyfluorescein succinimidyl ester (CFSE) dilution assay. CFSE is a non-toxic, fluorescent, membrane-permeating dye that binds the amino groups of cytoplasmic proteins with its succinimidyl-reactive group (e.g. T cell proteins). When cells divide, CFSE-labeled proteins are equally distributed between the daughter cells, thus halving cell fluorescence with each division. Consequently, antigen-specific T cells lose their fluorescence after culture in the presence of the respective antigen ($CFSE^{low}$) and are distinguishable from other cells in culture ($CFSE^{high}$). In some embodiments, antigen-induced proliferation is said to have occurred if CFSE dilution (given as the percentage of $CFSE^{low}$ cells out of all $CFSE^+$ cells) is at least about 5%, at least about 10%, at least about 25%, at least about 50%, at least about 75%, at least about 90%, at least about 95%, or at least about 100%.

In some embodiments, an immune response in T cells is said to be stimulated if cellular markers of T cell activation are expressed at different levels (e.g. higher or lower levels) relative to unstimulated cells. In some embodiments, CD11a CD27, CD25, CD40L, CD44, CD45RO, and/or CD69 are more highly expressed in activated T cells than in unstimulated T cells. In some embodiments, L-selectin (CD62L), CD45RA, and/or CCR7 are less highly expressed in activated T cells than in unstimulated T cells.

In some embodiments, an immune response in T cells is measured by assaying cytotoxicity by effector $CD8^+$ T cells against antigen-pulsed target cells. For example, a $^{51}$chromium ($^{51}Cr$) release assay can be performed. In this assay, effector $CD8^+$ T cells bind infected cells presenting virus peptide on class I MHC and signal the infected cells to undergo apoptosis. If the cells are labeled with $^{51}Cr$ before the effector $CD8^+$ T cells are added, the amount of $^{51}Cr$ released into the supernatant is proportional to the number of targets killed.

One of ordinary skill in the art will recognize that the assays described above are only exemplary methods which could be utilized in order to determine whether T cell activation has occurred. Any assay known to one of skill in the art which can be used to determine whether T cell activation has occurred falls within the scope of this invention. The assays described herein as well as additional assays that could be used to determine whether T cell activation has occurred are described in *Current Protocols in Immunology* (John Wiley & Sons, Hoboken, N.Y., 2007; incorporated herein by reference).

B Cells

The present invention provides vaccine nanocarriers for delivery of, for example, immunomodulatory agents to the cells of the immune system. In some embodiments, vaccine nanocarriers comprise at least one immunomodulatory agent which can be presented to B cells (i.e., B cell antigens).

Immunomodulatory Agents

B cells and T cells recognize antigen by different mechanisms. As described above, T cells recognize antigen in a processed form (e.g., as a peptide fragment presented by an APC's MHC molecule to the T cell receptor). B cells recognize antigens in their native form. B cells recognize free (e.g., soluble) antigen in blood or lymph using B cell receptors (BCRs) and/or membrane bound-immunoglobulins.

The immunomodulatory agent can be a B cell antigen. B cell antigens include, but are not limited to proteins, peptides, small molecules, and carbohydrates. In some embodiments, the B cell antigen is a non-protein antigen (i.e., not a protein or peptide antigen). In some embodiments, the B cell antigen is a carbohydrate associated with an infectious agent. In some embodiments, the B cell antigen is a glycoprotein or glycopeptide associated with an infectious agent. The infectious agent can be a bacterium, virus, fungus, protozoan, or parasite. In some embodiments, the B cell antigen is a poorly immunogenic antigen. In some embodiments, the B cell antigen is an abused substance or a portion thereof. In some embodiments, the B cell antigen is an addictive substance or a portion thereof.

Addictive substances include, but are not limited to, drugs known to cause addiction including stimulants, sedatives and opiates, amphetamine, cocaine, heroine, caffeine, alcohol, barbiturates, benzodiazepines, methaqualone, morphine, phentanyl, solvents, anabolic steroids, *cannabis*, narcotics, cough suppressants, tranquilizers, sedatives and all metabolites, analogues, and derivatives thereof. Further examples of addictive substances include those provided elsewhere herein.

In some embodiments, the addictive substance comprises one or more chiral carbon centers, and may, accordingly, be present in an enantiomerically pure form or a mixture of isomers. In some embodiments, where the addictive qualities of the addictive substance are dependent on the stereochemistry of the ciral carbon(s), the addictive substance used in the compositions described herein is present as the isomer that is most addictive, or as the isomer that is most commonly available, or as the isomer that is most commonly responsible for addiction among users.

Drug addiction is considered a pathological state, involving the progression of acute drug use to the development of drug-seeking behavior, the vulnerability to relapse, and the decreased, slowed ability to respond to naturally rewarding stimuli. The Diagnostic and Statistical Manual of Mental Disorders, Fourth Edition (DSM-IV) has categorized three stages of addiction: preoccupation/anticipation, bingelintoxication, and withdrawal/negative affect. These stages are characterized, respectively, everywhere by constant cravings and preoccupation with obtaining the substance; using more of the substance than necessary to experience the intoxicating effects; and experiencing tolerance, withdrawal symptoms, and decreased motivation for normal life activities. By the American Society of Addiction Medicine definition, drug addiction differs from drug dependence and drug tolerance. The term drug addiction is also used as a category which may include the same persons who can be given the diagnosis of substance dependence or substance abuse.

In some embodiments, the B cell antigen is a toxin, such as a toxin from a chemical weapon. In some embodiments, the toxin from a chemical weapon is botulinum toxin or phosphene. Toxins from a chemical weapon include, but are not limited to, O-Alkyl (<C10, incl. cycloalkyl) alkyl (Me, Et, n-Pr or i-Pr)-phosphonofluoridates (e.g. Sarin: O-Isopropyl methylphosphonofluoridate, Soman: O-Pinacolyl methylphosphonofluoridate), O-Alkyl (<C 10, incl. cycloalkyl) N,N-dialkyl (Me, Et, n-Pr or i-Pr) phosphoramidocyanidates (e.g. Tabun: O-Ethyl N,N-dimethylphosphoramidocyanidate), O-Alkyl (H or <C10, incl. cycloalkyl) S-2-dialkyl (Me, Et, n-Pr or i-Pr)-aminoethyl alkyl (Me, Et, n-Pr or i-Pr) phosphonothiolates and corresponding alkylated or protonated salts (e.g. VX: O-Ethyl S-2-diisopropylaminoethyl methylphosphonothiolate), Sulfur mustards: 2-Chloroethylchloromethylsulfide, Mustard gas: Bis(2-chloroethyl)sulfide, Bis(2-chloroethylthio)methane, Sesquimustard: 1,2-Bis(2-chloroethylthio)ethane, 1,3-Bis(2-chloroethylthio)-n-propane, 1,4-Bis(2-chloroethylthio)-n-butane, 1,5-Bis(2-chloroethylthio)-n-pentane, Bis(2-chloroethylthiomethyl)ether, O-Mustard: Bis(2-chloroethylthioethyl)ether, Lewisites: Lewisite 1: 2-Chlorovinyldichloroarsine, Lewisite 2: Bis(2-chlorovinyl)chloroarsine, Lewisite 3: Tris(2-chlorovinyl)arsine, Nitrogen mustards: HN1: Bis(2-chloroethyl)ethylamine, HN2: Bis(2-chloroethyl)methylamine, HN3: Tris(2-chloroethyl)amine, Saxitoxin, Ricin, Amiton: O,O-Diethyl S-(2-(diethylamino)ethyl)phosphorothiolate and corresponding alkylated or protonated salts, PFIB: 1,1,3,3,3-Pentafluoro-2-(trifluoromethyl)-1-propene, 3-Quinuclidinyl benzilate (BZ), Phosgene: Carbonyl dichloride, Cyanogen chloride, Hydrogen cyanide and Chloropicrin: Trichloronitromethane.

The B cell antigen may also be a hazardous environmental agent. Hazardous environmental agents include, but are not limited to, arsenic, lead, mercury, vinyl chloride, polychlorinated biphenyls, benzene, polycyclic aromatic hydrocarbons, cadmium, benzo(a)pyrene, benzo(b)fluoranthene, chloroform, DDT, P,P'-, aroclor 1254, aroclor 1260, dibenzo(a,h) anthracene, trichloroethylene, dieldrin, chromium hexavalent, and DDE, P,P'. Examples of such agents include those provided elsewhere herein.

In some embodiments, the B cell antigen is a self antigen. In other embodiments, the B cell antigen is an alloantigen, a contact sensitizer, a degenerative disease antigen, a hapten, an infectious disease antigen, a cancer antigen, an atopic disease antigen, an autoimmune disease antigen, an addictive substance, a xenoantigen, or a metabolic disease enzyme or enzymatic product thereof. Examples of such antigens include those provided elsewhere herein.

As described above, the present invention provides vaccine nanocarriers comprising, for example, one or more immunomodulatory agents. In some embodiments, inventive nanocarriers comprising one or more immunomodulatory agents are used as vaccines. In some embodiments, antigen presentation to B cells can be optimized by presenting structurally intact immunomodulatory agents on the surface of nanocarriers. In some embodiments, structurally intact immunomodulatory agents are presented on the surface of vaccine nanocarriers at high copy number and/or density.

In some embodiments, an immunomodulatory agent may comprise isolated and/or recombinant proteins or peptides, inactivated organisms and viruses, dead organisms and virus, genetically altered organisms or viruses, and cell extracts. In some embodiments, an immunomodulatory agent may comprise nucleic acids, carbohydrates, lipids, and/or small molecules. In some embodiments, an immunomodulatory agent is one that elicits an immune response. In some embodiments, an immunomodulatory agent is an antigen. In some embodiments, an immunomodulatory agent is used for vaccines. Further description of immunomodulatory agents can be found in the section above entitled "B Cells."

As discussed above, a vaccine nanocarrier may comprise a single type of immunomodulatory agent that stimulates both B cells and T cells. In some embodiments, a vaccine nanocarrier comprises two types of immunomodulatory agents, wherein first type of immunomodulatory agent stimulates B cells, and the second type of immunomodulatory agent stimulates T cells. In some embodiments, a vaccine nanocarrier comprises greater than two types of immunomodulatory agents, wherein one or more types of immunomodulatory agents stimulate B cells, and one or more types of immunomodulatory agents stimulate T cells.

Targeting Moieties As discussed above, inventive nanocarriers comprise one or more targeting moieties. For a discussion of general and specific properties of targeting moieties in accordance with the present invention, see the subheading entitled "Targeting Moieties" in the section above entitled "T Cells." In some embodiments, targeting moieties target particular cell types. In certain embodiments, a target is a B cell marker. In some embodiments, a B cell target is an antigen that is expressed in B cells but not in non-B cells. In some embodiments, a B cell target is an antigen that is more prevalent in B cells than in non-B cells.

In certain embodiments, a target is a SCS-Mph marker. In some embodiments, an SCS-Mph target is an antigen that is expressed in SCS-Mph but not in non-SCS-Mph. In some embodiments, an SCS-Mph target is an antigen that is more prevalent in SCS-Mph than in non-SCS-Mph. Exemplary SCS-Mph markers are listed below in the section entitled "Subcapsular Sinus Macrophage Cells" and include those provided elsewhere herein.

In certain embodiments, a target is a FDC marker. In some embodiments, an FDC target is an antigen that is expressed in FDCs but not in non-FDCs. In some embodiments, an FDC target is an antigen that is more prevalent in FDCs than in non-FDCs. Exemplary FDC markers are listed below in the section entitled "Follicular Dendritic Cells" and include those provided elsewhere herein.

In some embodiments, a target is preferentially expressed in particular cell types. For example, expression of an SCS-Mph, FDC, and/or B cell target in SCS-Mph, FDCs, and/or B cells is at least 2-fold, at least 3-fold, at least 4-fold, at least 5-fold, at least 10-fold, at least 20-fold, at least 50-fold, at least 100-fold, at least 500-fold, or at least 1000-fold overexpressed in SCS-Mph, FDCs, and/or B cells relative to a reference population. In some embodiments, a reference population may comprise non-SCS-Mph, FDCs, and/or B cells.

In some embodiments, expression of an SCS-Mph, FDC, and/or B cell target in activated SCS-Mph, FDCs, and/or B cells is at least 2-fold, at least 3-fold, at least 4-fold, at least 5-fold, at least 10-fold, at least 20-fold, at least 50-fold, at least 100-fold, at least 500-fold, or at least 1000-fold overexpressed in activated SCS-Mph, FDCs, and/or B cells relative to a reference population. In some embodiments, a reference population may comprise non-activated SCS-Mph, FDCs, and/or B cells.

Subcapsular Sinus Macrophage Cells

Figure 17A:
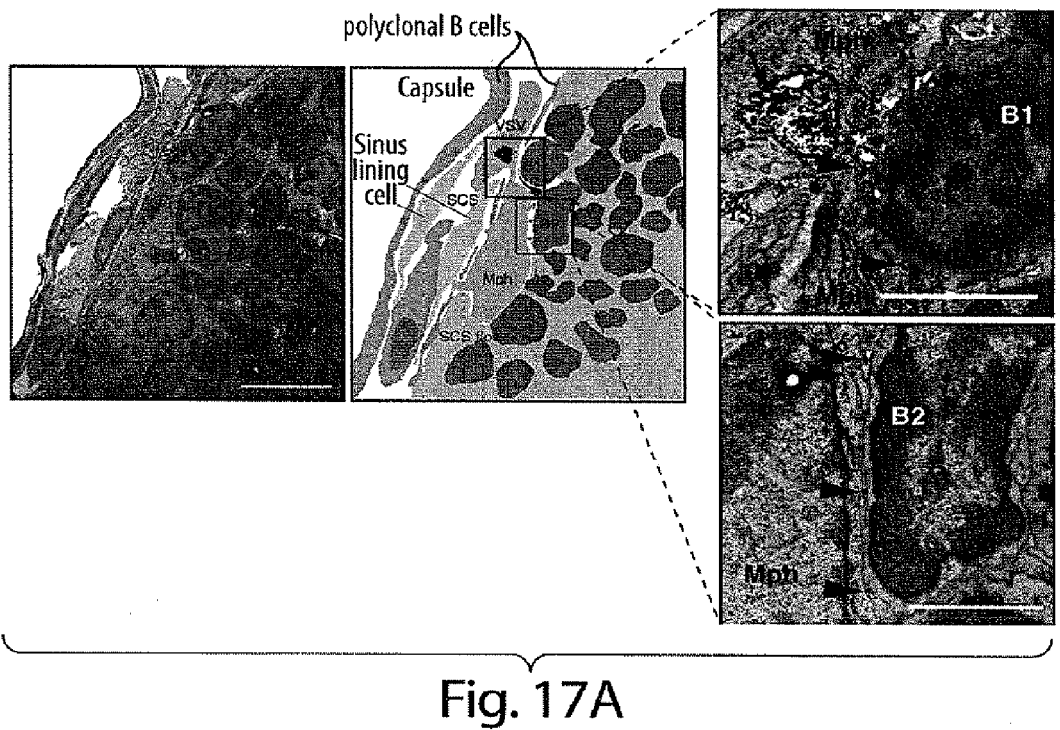
Figure 17B:
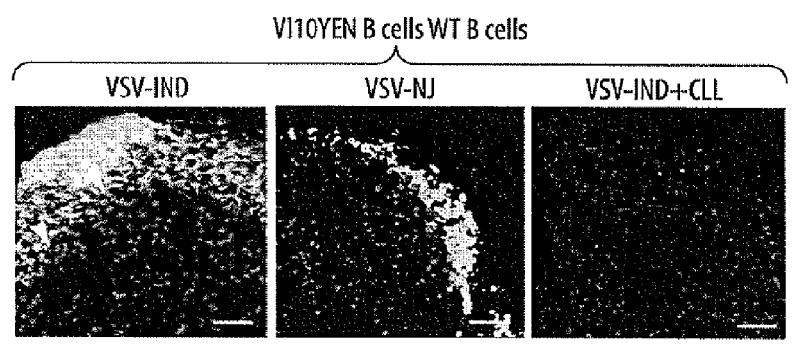
Figures 1, 17C:
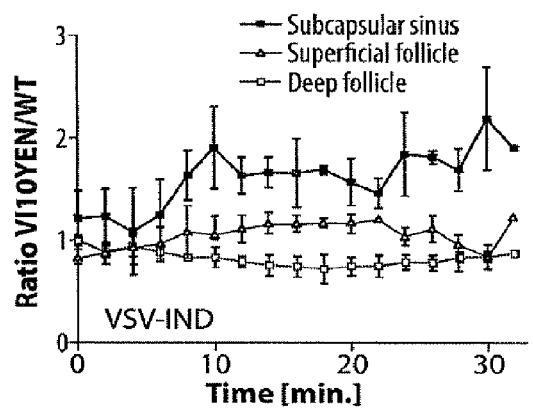
Figures 2, 17C:
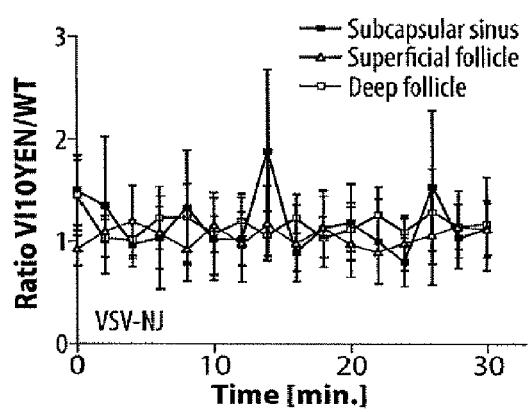
Figures 3, 17C:
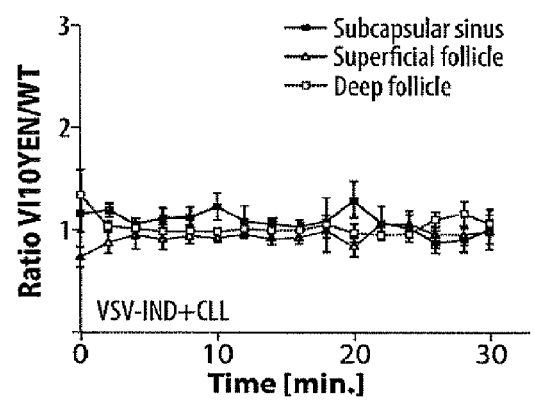
Figures 4, 17C:
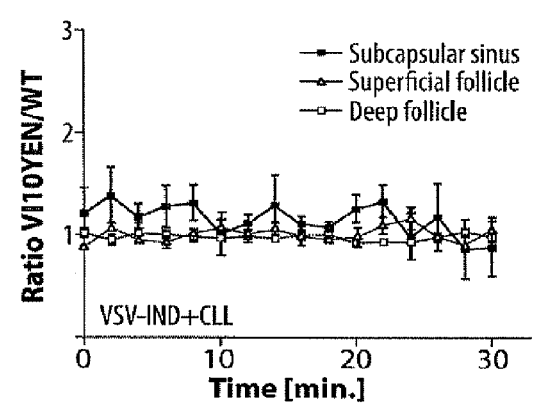
Figure 17D:
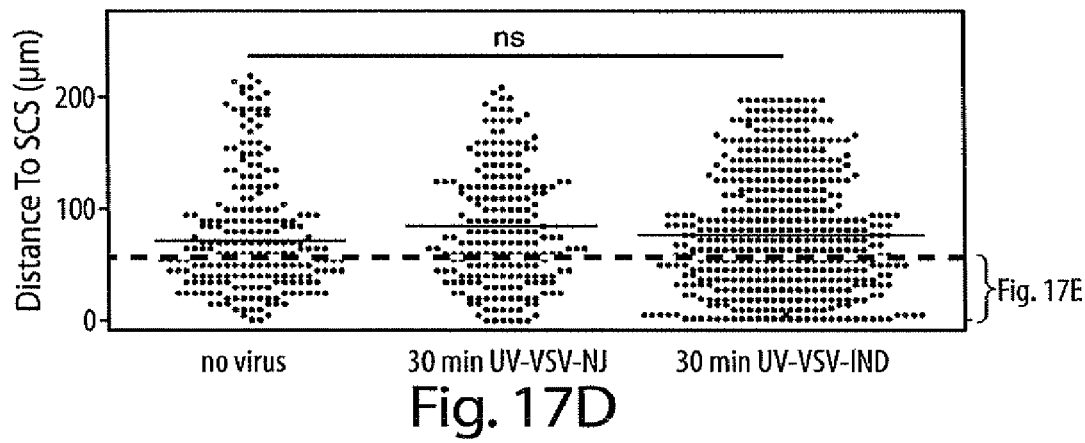

The present invention encompasses the recognition that targeting of antigens to subcapsular sinus macrophages (SCS-Mph) is involved in efficient early presentation of lymph-borne pathogens, such as viruses, to follicular B cells (FIG. 2). As described in Example 1, following subcutaneous injection of vesicular stomatitis virus (VSV) or adenovirus (AdV) into the footpad of mice, viral particles were efficiently and selectively retained by CD169+ SCS-Mph in the draining popliteal lymph nodes. VSV-specific B cell receptor (BCR) transgenic B cells in these lymph nodes were rapidly activated and generated extremely high antibody titers upon this viral challenge. Depletion of SCS-Mph by injection of liposomes laden with clodronate (which is toxic for Mph) abolished early B cell activation, indicating that SCS-Mph are essential for the presentation of lymph-borne particulate antigens to B cells.

B cells are more potently activated by polyvalent antigens that are presented to them on a fixed surface, rather than in solution. While not wishing to be bound by any one theory, the present invention suggests a reason why many enveloped viruses (such as VSV) elicit potent neutralizing antibody responses to their envelope glycoprotein: the antigenic protein is presented at a very high density on the surface of the viral particles, and the viral particles are presented to B cells in a relatively immotile manner, i.e., bound to the plasma membrane of SCS-Mph. The present invention encompasses the recognition that vaccine carriers that mimic viral particles by targeting SCS-Mph upon subcutaneous injection and presenting polyvalent conformationally intact antigens on their surface can stimulate a potent B cell response.

In some embodiments, SCS-Mph targeting is accomplished by moieties that bind CD169 (i.e., sialoadhesin), CD11b (i.e., CD11b/CD18, Mac-1, CR3 or $\alpha M\beta 2$ integrin), and/or the mannose receptor (i.e., a multi-valent lectin), proteins which are all prominently expressed on SCS-Mph. Examples of such moieties include those provided elsewhere herein.

In some embodiments, SCS-Mph targeting can be accomplished by any targeting moiety that specifically binds to any entity (e.g., protein, lipid, carbohydrate, small molecule, etc.) that is prominently expressed and/or present on macrophages (i.e., SCS-Mph markers). Exemplary SCS-Mph markers include, but are not limited to, CD4 (L3T4, W3/25, T4); CD9 (p24, DRAP-1, MRP-1); CD11a (LFA-1α, α L Integrin chain); CD11b (αM Integrin chain, CR3, Mo1, C3niR, Mac-1); CD11c (αX Integrin, p150, 95, AXb2); CDw12 (p90-120); CD13 (APN, gp150, EC 3.4.11.2); CD14 (LPS-R); CD15 (X-Hapten, Lewis, X, SSEA-1, 3-FAL); CD15s (Sialyl Lewis X); CD15u (3' sulpho Lewis X); CD15su (6 sulpho-sialyl Lewis X); CD16a (FCRIIIA); CD16b (FcgRIIIb); CDw17 (Lactosylceramide, LacCer); CD18 (Integrin β2, CD11a,b,c β-subunit); CD26 (DPP IV ectoeneyme, ADA binding protein); CD29 (Platelet GPIIa, β-1 integrin, GP); CD31 (PECAM-1, Endocam); CD32 (FCγRII); CD33 (gp67); CD35 (CR1, C3b/C4b receptor); CD36 (GpIIIb, GPIV, PASIV); CD37 (gp52-40); CD38 (ADP-ribosyl cyclase, T10); CD39 (ATPdehydrogenase, NTPdehydrogenase-1); CD40 (Bp50); CD43 (Sialophorin, Leukosialin); CD44 (EMCRII, H-CAM, Pgp-1); CD45 (LCA, T200, B220, Ly5); CD45RA; CD45RB; CD45RC; CD45RO (UCHL-1); CD46 (MCP); CD47 (gp42, IAP, OA3, Neurophillin); CD47R (MEM-133); CD48 (Blast-1, Hulym3, BCM-1, OX-45); CD49a (VLA-1α, α1 Integrin); CD49b (VLA-2α, gpla, α2 Integrin); CD49c (VLA-3α, α3 Integrin); CD49e (VLA-5α, α5 Integrin); CD49f (VLA-6α, α6 Integrin, gplc); CD50 (ICAM-3); CD51 (Integrin α, VNR-α, Vitronectin-Rα); CD52 (CAMPATH-1, HE5); CD53 (OX-44); CD54 (ICAM-1); CD55 (DAF); CD58 (LFA-3); CD59 (1F5Ag, H19, Protectin, MACIF, MIRL, P-18); CD60a (GD3); CD60b (9-O-acetyl GD3); CD61 (GP IIIa, β3 Integrin); CD62L (L-selectin, LAM-1, LECAM-1, MEL-14, Leu8, TQ1); CD63 (LIMP, MLA1, gp55, NGA, LAMP-3, ME491); CD64 (FcγRI); CD65 (Ceramide, VIM-2); CD65s (Sialylated-CD65, VIM2); CD72 (Ly-19.2, Ly-32.2, Lyb-2); CD74 (Ii, invariant chain); CD75 (sialo-masked Lactosamine); CD75S (α2,6 sialylated Lactosamine); CD80 (B7, B7-1, BB1); CD81 (TAPA-1); CD82 (4F9, C33, IA4, KAI1, R2); CD84 (p75, GR6); CD85a (ILT5, LIR2, HL9); CD85d (ILT4, LIR2, MIR10); CD85j (ILT2, LIR1, MIR7); CD85k (ILT3, LIR5, HM18); CD86 (B7-2/B70); CD87 (uPAR); CD88 (C5aR); CD89 (IgA Fc receptor, FcαR); CD91 (α2M-R, LRP); CDw92 (p70); CDw93 (GR11); CD95 (APO-1, FAS, TNFRSF6); CD97 (BL-KDD/F12); CD98 (4F2, FRP-1, RL-388); CD99 (MIC2, E2); CD99R (CD99 Mab restricted); CD100 (SEMA4D); CD101 (IGSF2, P126, V7); CD102 (ICAM-2); CD111 (PVRL1, HveC, PRR1, Nectin 1, HIgR); CD112 (HveB, PRR2, PVRL2, Nectin2); CD114 (CSF3R, G-CSRF, HG-CSFR); CD115 (c-fms, CSF-1R, M-CSFR);

CD116 (GM-CSFRα); CDw119 (IFNγR, IFNγRA); CD120a (TNFRI, p55); CD120b (TNFRII, p75, TNFR p80); CD121b (Type 2 IL-1R); CD122 (IL2Rβ); CD123 (IL-3Rα); CD124 (IL-4Rα); CD127 (p90, IL-7R, IL-7Rα); CD128a (IL-8Ra, CXCR1, (Tentatively renamed as CD181)); CD128b (IL-8Rb, CSCR2, (Tentatively renamed as CD182)); CD130 (gp130); CD131 (Common β subunit); CD132 (Common γ chain, IL-2Rγ); CDw136 (MSP-R, RON, p158-ron); CDw137 (4-1BB, ILA); CD139; CD141 (Thrombomodulin, Fetomodulin); CD147 (Basigin, EMMPRIN, M6, OX47); CD148 (HPTP-η, p260, DEP-1); CD155 (PVR); CD156a (CD156, ADAM8, MS2); CD156b (TACE, ADAM17, cSVP); CDw156C (ADAM10); CD157 (Mo5, BST-1); CD162 (PSGL-1); CD164 (MGC-24, MUC-24); CD165 (AD2, gp37); CD168 (RHAMM, IHABP, HMMR); CD169 (Sialoadhesin, Siglec-1); CD170 (Siglec 5); CD171 (L1CAM, NILE); CD172 (SIRP-1α, MyD-1); CD172b (SIRPβ); CD180 (RP105, Bgp95, Ly64); CD181 (CXCR1, (Formerly known as CD128a)); CD182 (CXCR2, (Formerly known as CD128b)); CD184 (CXCR4, NPY3R); CD191 (CCR1); CD192 (CCR2); CD195 (CCR5); CDw197 (CCR7 (was CDw197)); CDw198 (CCR8); CD204 (MSR); CD205 (DEC-25); CD206 (MMR); CD207 (Langerin); CDw210 (CK); CD213a (CK); CDw217 (CK); CD220 (Insulin R); CD221 (IGF1 R); CD222 (M6P-R, IGFII-R); CD224 (GGT); CD226 (DNAM-1, PTA1); CD230 (Prion Protein (PrP)); CD232 (VESP-R); CD244 (2B4, P38, NAIL); CD245 (p220/240); CD256 (APRIL, TALL2, TNF (ligand) superfamily, member 13); CD257 (BLYS, TALL1, TNF (ligand) superfamily, member 13b); CD261 (TRAIL-R1, TNF-R superfamily, member 10a); CD262 (TRAIL-R2, TNF-R superfamily, member 10b); CD263 (TRAIL-R3, TNBF-R superfamily, member 10c); CD264 (TRAIL-R4, TNF-R superfamily, member 10d); CD265 (TRANCE-R, TNF-R superfamily, member 11a); CD277 (BT3.1, B7 family: Butyrophilin 3); CD280 (TEM22, ENDO180); CD281 (TLR1, TOLL-like receptor 1); CD282 (TLR2, TOLL-like receptor 2); CD284 (TLR4, TOLL-like receptor 4); CD295 (LEPR); CD298 (ATP1B3, Na K ATPase, β3 subunit); CD300a (CMRF-35H); CD300c (CMRF-35A); CD300e (CMRF-35L1); CD302 (DCL1); CD305 (LAIR1); CD312 (EMR2); CD315 (CD9P1); CD317 (BST2); CD321 (JAM1); CD322 (JAM2); CDw328 (Siglec7); CDw329 (Siglec9); CD68 (gp 110, Macrosialin); and/or mannose receptor; wherein the names listed in parentheses represent alternative names. Examples of such markers include those provided elsewhere herein.

In some embodiments, SCS-Mph targeting can be accomplished by any targeting moiety that specifically binds to any entity (e.g., protein, lipid, carbohydrate, small molecule, etc.) that is prominently expressed and/or present on macrophages upon activation (i.e., activated SCS-Mph marker). Exemplary activated SCS-Mph markers include, but are not limited to, CD1a (R4, T6, HTA-1); CD1b (R1); CD1c (M241, R7); CD44R (CD44v, CD44v9); CD49d (VLA-4α, α4 Integrin); CD69 (AIM, EA 1, MLR3, gp34/28, VEA); CD105 (Endoglin); CD142 (Tissue factor, Thromboplastin, F3); CD143 (ACE, Peptidyl dipeptidase A, Kininase II); CD153 (CD3OL, TNSF8); CD163 (M130, GHI/61, RM3/1); CD166 (AL-CAM, KG-CAM, SC-1, BEN, DM-GRASP); CD227 (MUC1, PUM, PEM, EMA); CD253 (TRAIL, TNF (ligand) superfamily, member 10); CD273 (B7DC, PDL2); CD274 (B7H1,PDL1); CD275 (B7H2, ICOSL); CD276 (B7H3); CD297 (ART4, ADP-ribosyltransferase 4; and Dombrock blood group glycoprotein; wherein the names listed in parentheses represent alternative names. Examples of such markers include those provided elsewhere herein.

B Cell Targeting Moieties

In some embodiments, B cell targeting can be accomplished by moieties that bind the complement receptors, CR1 (i.e., CD35) or CR2 (i.e., CD21), proteins which are expressed on B cells as well as FDCs. In some embodiments, B cell targeting can be accomplished by B cell markers such as CD19, CD20, and/or CD22. In some embodiments, B cell targeting can be accomplished by B cell markers such as CD40, CD52, CD80, CXCR5, VLA-4, class II MHC, surface IgM or IgD, APRL, and/or BAFF-R. The present invention encompasses the recognition that simultaneous targeting of B cells by moieties specific for complement receptors or other APC-associated molecules boosts humoral responses.

In some embodiments, B cell targeting can be accomplished by any targeting moiety that specifically binds to any entity (e.g., protein, lipid, carbohydrate, small molecule, etc.) that is prominently expressed and/or present on B cells (i.e., B cell marker). Exemplary B cell markers include, but are not limited to, CD1c (M241, R7); CD1d (R3); CD2 (E-rosette R, T11, LFA-2); CD5 (T1, Tp67, Leu-1, Ly-1); CD6 (T12); CD9 (p24, DRAP-1, MRP-1); CD11a (LFA-1α, αL Integrin chain); CD11b (αM Integrin chain, CR3, Mo1, C3niR, Mac-1); CD11c (αX Integrin, P150, 95, AXb2); CDw17 (Lactosylceramide, LacCer); CD18 (Integrin β2, CD11a, b, c β-subunit); CD19 (B4); CD20 (B1, Bp35); CD21 (CR2, EBV-R, C3dR); CD22 (BL-CAM, Lyb8, Siglec-2); CD23 (FceRII, B6, BLAST-2, Leu-20); CD24 (BBA-1, HSA); CD25 (Tac antigen, IL-2Rα, p55); CD26 (DPP IV ectoeneyme, ADA binding protein); CD27 (T14, S152); CD29 (Platelet GPIIa, β-1 integrin, GP); CD31 (PECAM-1, Endocam); CD32 (FCγRII); CD35 (CR1, C3b/C4b receptor); CD37 (gp52-40); CD38 (ADP-ribosyl cyclase, T10); CD39 (ATPdehydrogenase, NTPdehydrogenase-1); CD40 (Bp50); CD44 (ECM-RII, H-CAM, Pgp-1); CD45 (LCA, T200, B220, Ly5); CD45RA; CD45RB; CD45RC; CD45RO (UCHL-1); CD46 (MCP); CD47 (gp42, IAP, OA3, Neurophilin); CD47R (MEM-133); CD48 (Blast-1, Hulym3, BCM-1, OX-45); CD49b (VLA-2α, gpla, α2 Integrin); CD49c (VLA-3α, α3 Integrin); CD49d (VLA-4α, α4 Integrin); CD50 (ICAM-3); CD52 (CAMPATH-1, HES); CD53 (OX-44); CD54 (ICAM-1); CD55 (DAF); CD58 (LFA-3); CD60a (GD3); CD62L (L-selectin, LAM-1, LECAM-1, MEL-14, Leu8, TQ1); CD72 (Ly-19.2, Ly-32.2, Lyb-2); CD73 (Ecto-5'-nuciotidase); CD74 (Ii, invariant chain); CD75 (sialo-masked Lactosamine); CD75S (α2, 6 sialytated Lactosamine); CD77 (Pk antigen, BLA, CTH/Gb3); CD79a (Igα, MB1); CD79b (Igβ, B29); CD80; CD81 (TAPA-1); CD82 (4F9, C33, IA4, KAI1, R2); CD83 (HB15); CD84 (P75, GR6); CD85j (ILT2, LIR1, MIR7); CDw92 (p70); CD95 (APO-1, FAS, TNFRSF6); CD98 (4F2, FRP-1, RL-388); CD99 (MIC2, E2); CD100 (SEMA4D); CD102 (ICAM-2); CD108 (SEMA7A, JMH blood group antigen); CDw119 (IFNγR, IFNγRα); CD120a (TNFRI, p55); CD120b (TNFRII, p75, TNFR p80); CD121b (Type 2 IL-1R); CD122 (IL2Rβ); CD124 (IL-4Rα); CD130 (gp130); CD132 (Common γ chain, IL-2Rγ); CDw137 (4-1BB, ILA); CD139; CD147 (Basigin, EMMPRIN, M6, OX47); CD150 (SLAM, IPO-3); CD162 (PSGL-1); CD164 (MGC-24, MUC-24); CD166 (ALCAM, KG-CAM, SC-1, BEN, DM-GRASP); CD167a (DDR1, trkE, cak); CD171 (L1CMA, NILE); CD175s (Sialyl-Tn (S-Tn)); CD180 (RP105, Bgp95, Ly64); CD184 (CXCR4, NPY3R); CD185 (CXCR5); CD192 (CCR2); CD196 (CCR6); CD197 (CCR7 (was CDw197)); CDw197 (CCR7, EBI1, BLR2); CD200 (OX2); CD205 (DEC-205); CDw210 (CK); CD213a (CK); CDw217 (CK); CDw218a (IL18Rα); CDw218b (IL18Rβ); CD220 (Insulin R); CD221 (IGF1 R); CD222 (M6P-R, IGFII-R); CD224 (GGT); CD225 (Leu13); CD226 (DNAM- 1, PTA1); CD227 (MUC1, PUM, PEM, EMA); CD229 (Ly9); CD230 (Prion Protein (Prp)); CD232 (VESP-R); CD245 (p220/240); CD247 (CD3 Zeta Chain); CD261 (TRAIL-R1, TNF-R superfamily, member 10a); CD262 (TRAIL-R2, TNF-R superfamily, member 10b); CD263 (TRAIL-R3, TNF-R superfamily, member 10c); CD264 (TRAIL-R4, TNF-R superfamily, member 10d); CD265 (TRANCE-R, TNF-R superfamily, member 11a); CD267 (TACI, TNF-R superfamily, member 13B); CD268 (BAFFR, TNF-R superfamily, member 13C); CD269 (BCMA, TNF-R superfamily, member 16); CD275 (B7H2, ICOSL); CD277 (BT3.1.B7 family: Butyrophilin 3); CD295 (LEPR); CD298 (ATP1B3 Na K ATPase β3 subunit); CD300a (CMRF-35H); CD300c (CMRF-35A); CD305 (LAIR1); CD307 (IRTA2); CD315 (CD9P1); CD316 (EW12); CD317 (BST2); CD319 (CRACC, SLAMF7); CD321 (JAM1); CD322 (JAM2); CDw327 (Siglec6, CD33L); CD68 (gp 100, Macrosialin); CXCR5; VLA-4; class II MHC; surface IgM; surface IgD; APRL; and/or BAFF-R; wherein the names listed in parentheses represent alternative names. Examples of markers include those provided elsewhere herein.

In some embodiments, B cell targeting can be accomplished by any targeting moiety that specifically binds to any entity (e.g., protein, lipid, carbohydrate, small molecule, etc.) that is prominently expressed and/or present on B cells upon activation (i.e., activated B cell marker). Exemplary activated B cell markers include, but are not limited to, CD1a (R4, T6, HTA-1); CD1b (R1); CD15s (Sialyl Lewis X); CD15u (3' sulpho Lewis X); CD15su (6 sulpho-sialyl Lewis X); CD30 (Ber-H2, Ki-1); CD69 (AIM, EA 1, MLR3, gp34/28, VEA); CD70 (Ki-24, CD27 ligand); CD80 (B7, B7-1, BB1); CD86 (B7-2/B70); CD97 (BL-KDD/F12); CD125 (IL-5Rα); CD126 (IL-6Rα); CD138 (Syndecan-1, Heparan sulfate proteoglycan); CD152 (CTLA-4); CD252 (OX40L, TNF (ligand) superfamily, member 4); CD253 (TRAIL, TNF(ligand) superfamily, member 10); CD279 (PD1); CD289 (TLR9, TOLL-like receptor 9); and CD312 (EMR2); wherein the names listed in parentheses represent alternative names. Examples of markers include those provided elsewhere herein.

Follicular Dendritic Cells

B cells that initially detect a previously unknown antigen typically express a B cell receptor (BCR, i.e., an antibody with a transmembrane domain) with suboptimal binding affinity for that antigen. However, B cells can increase by several orders of magnitude the affinity of the antibodies they make when they enter into a germinal center (GC) reaction. This event, which typically lasts several weeks, depends on FDC that accumulate, retain and present antigenic material to the activated B cells. B cells, while proliferating vigorously, repeatedly mutate the genomic sequences that encode the antigen binding site of their antibody and undergo class-switch recombination to form secreted high-affinity antibodies, mostly of the IgG isotype. GC reactions also stimulate the generation of long-lived memory B cells and plasma cells that maintain high protective antibody titers, often for many years. Vaccine carriers that target FDC upon subcutaneous injection and that are retained on the FDC surface for long periods of time are predicted to boost GC reactions in response to vaccination and improve the affinity and longevity of desired humoral immune responses.

In some embodiments, FDC targeting can be accomplished by moieties that bind the complement receptors, CR1 (i.e., CD35) or CR2 (i.e., CD21), proteins which are expressed on FDCs as well as B cells. Examples of moieties include those provided elsewhere herein.

Vaccine Nanocarriers Comprising Multiple Targeting Moieties

GC reactions and B cell survival not only require FDC, but also are dependent on help provided by activated CD4 T cells. Help is most efficiently provided when a CD4 T cell is first stimulated by a DC that presents a cognate peptide in MHC class II (pMHC) to achieve a follicular helper ($T_{FH}$) phenotype. The newly generated $T_{FH}$ cell then migrates toward the B follicle and provides help to those B cells that present them with the same pMHC complex. For this, B cells first acquire antigenic material (e.g., virus or virus-like vaccine), internalize and process it (i.e., extract peptide that is loaded into MHC class II), and then present the pMHC to a $T_{FH}$ cell.

Thus, the present invention encompasses the recognition that a vaccine that stimulates optimal humoral immunity can combine several features and components (FIG. 1): (a) antigenic material for CD4 T cells that is targeted to and presented by DCs; (b) surface antigens that can be presented in their native form by SCS-Mph to antigen-specific follicular B cells; (c) the capacity to be acquired and processed by follicular B cells for presentation to $T_{FH}$ cells (the present invention encompasses the recognition that B cells readily acquire and internalize particulate matter from SCS-Mph); (d) the ability to reach FDC and be retained on FDC in intact form and for long periods of time; and (e) adjuvant activity to render APC fully immunogenic and to avoid or overcome tolerance.

In some embodiments, a vaccine nanocarrier comprises at least one targeting moiety. In some embodiments, all of the targeting moieties of a vaccine nanocarrier are identical to one another. In some embodiments, a vaccine nanocarrier a number of different types of targeting moieties. In some embodiments, a vaccine nanocarrier comprises multiple individual targeting moieties, all of which are identical to one another. In some embodiments, a vaccine nanocarrier comprises exactly one type of targeting moiety. In some embodiments, a vaccine nanocarrier comprises exactly two distinct types of targeting moieties. In some embodiments, a vaccine nanocarrier comprises greater than two distinct types of targeting moieties.

In some embodiments, a vaccine nanocarrier comprises a single type of targeting moiety that directs delivery of the vaccine nanocarrier to a single cell type (e.g., delivery to SCS-Mph only). In some embodiments, a vaccine nanocarrier comprises a single type of targeting moiety that directs delivery of the vaccine nanocarrier to multiple cell types (e.g., delivery to both SCS-Mph and FDCs). In some embodiments, a vaccine nanocarrier comprises two types of targeting moieties, wherein the first type of targeting moiety directs delivery of the vaccine nanocarrier to one cell type, and the second type of targeting moiety directs delivery of the vaccine nanocarrier to a second cell type. In some embodiments, a vaccine nanocarrier comprises greater than two types of targeting moieties, wherein one or more types of targeting moieties direct delivery of the vaccine nanocarrier to one cell type, and one or more types of targeting moieties direct delivery of the vaccine nanocarrier to a second cell type. To give but one example, a vaccine nanocarrier may comprise two types of targeting moieties, wherein the first type of targeting moiety directs delivery of the vaccine nanocarrier to DCs, and the second type of targeting moiety directs delivery of the vaccine nanocarrier to SCS-Mph.

In some embodiments, a vaccine nanocarrier comprises at least one targeting moiety that is associated with the exterior surface of the vaccine nanocarrier. In some embodiments, the association is covalent. In some embodiments, the covalent association is mediated by one or more linkers. In some embodiments, the association is non-covalent. In some embodiments, the non-covalent association is mediated by charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof.

In some embodiments, a vaccine nanocarrier comprises a lipid membrane (e.g., lipid bilayer, lipid monolayer, etc.), wherein at least one targeting moiety is associated with the lipid membrane. In some embodiments, at least one targeting moiety is embedded within the lipid membrane. In some embodiments, at least one targeting moiety is embedded within the lumen of a lipid bilayer. In some embodiments, at least one targeting moiety may be located at multiple locations of a vaccine nanocarrier. For example, a first targeting moiety may be embedded within a lipid membrane, and a second immunostimulatory agent may be associated with the exterior surface of a vaccine nanocarrier. To give another example, a first targeting moiety and a second targeting moiety may both be associated with the exterior surface of a vaccine nanocarrier.

Immunostimulatory Agents

As described above, in some embodiments, vaccine nanocarriers may transport one or more immunostimulatory agents which can help stimulate immune responses. In some embodiments, a vaccine nanocarrier comprises a single type of immunostimulatory agent that stimulates both B cells and T cells. In some embodiments, a vaccine nanocarrier comprises two types of immunostimulatory agents, wherein first type of immunostimulatory agent stimulates B cells, and the second type of immunostimulatory agent stimulates T cells. In some embodiments, a vaccine nanocarrier comprises greater than two types of immunostimulatory agents, wherein one or more types of immunostimulatory agents stimulate B cells, and one or more types of immunostimulatory agents stimulate T cells. See the section above for a more detailed description of immunostimulatory agents that can be used in accordance with the present invention.

Assays for B Cell Activation

In some embodiments, various assays can be utilized in order to determine whether an immune response has been stimulated in a B cell or group of B cells (i.e., whether a B cell or group of B cells has become "activated"). In some embodiments, stimulation of an immune response in B cells can be determined by measuring antibody titers. In general, "antibody titer" refers to the ability of antibodies to bind and neutralize antigens at particular dilutions. For example, a high antibody titer refers to the ability of antibodies to bind and neutralize antigens even at high dilutions. In some embodiments, an immune response in B cells is said to be stimulated if antibody titers are measured to be positive at dilutions at least about 5-fold greater, at least about 10-fold greater, at least about 20-fold greater, at least about 50-fold greater, at least about 100-fold greater, at least about 500-fold greater, at least about 1000 fold greater, or more than about 1000-fold greater than in non-immunized individuals or pre-immune serum.

In some embodiments, stimulation of an immune response in B cells can be determined by measuring antibody affinity. In particular, an immune response in B cells is said to be stimulated if an antibody has an equilibrium dissociation constant ($K_d$) less than $10^{-7}$ M, less than $10^{-8}$ M, less than $10^{-9}$ M, less than $10^{-10}$ M, less than $10^{-11}$ M, less than $10^{-12}$ M, or less.

In some embodiments, a T cell-dependent immune response in B cells is said to be stimulated if class-switch recombination has occurred. In particular, a switch from IgM to an IgG isotype or to IgA or to a mixture of these isotypes is indicative of a T cell dependent immune response in B cells.

In some embodiments, an immune response in B cells is determined by measuring affinity maturation of antigen-specific antibodies. Affinity maturation occurs during the germinal center reaction whereby activated B cells repeatedly mutate a region of the immunoglobulin gene that encodes the antigen-binding region. B cells producing mutated antibodies which have a higher affinity for antigen are preferentially allowed to survive and proliferate. Thus, over time, the antibodies made by B cells in GCs acquire incrementally higher affinities. In some embodiments, the readout of this process is the presence of high antibody titer (e.g. high affinity IgG antibodies that bind and neutralize antigens even at high dilutions).

In some embodiments, an immune response in B cells is said to be stimulated if memory B cells and/or long-lived plasma cells that can produce large amounts of high-affinity antibodies for extended periods of time have formed. In some embodiments, antibody titers are measured after different time intervals (e.g. 2 weeks, 1 month, 2 months, 6 months, 1 year, 2 years, 5 years, 10 years, 15 years, 20 years, 25 years, or longer) after vaccination in order to test for the presence of memory B cells and/or long-lived plasma cells that can produce large amounts of high-affinity antibodies for extended periods of time. In some embodiments, memory B cells and/or long-lived plasma cells that can produce large amounts of high-affinity antibodies for extended periods of time are said to be present by measuring humoral responses (e.g., if humoral responses are markedly more rapid and result in higher titers after a later booster vaccination than during the initial sensitization).

In some embodiments, an immune response in B cells is said to be stimulated if a vigorous germinal center reaction occurs. In some embodiments, a vigorous germinal center reaction can be assessed visually by performing histology experiments. In some embodiments, vigorous germinal center reaction can be assayed by performing immunohistochemistry of antigen-containing lymphoid tissues (e.g., vaccine-draining lymph nodes, spleen, etc.). In some embodiments, immunohistochemistry is followed by flow cytometry.

In some embodiments, stimulation of an immune response in B cells can be determined by identifying antibody isotypes (e.g., IgG, IgA, IgE, IgM). In certain embodiments, production of IgG isotype antibodies by B cells is a desirable immune response in a B cell.

In some embodiments, an immune response in B cells is determined by analyzing antibody function in neutralization assays. In particular, the ability of a microorganism (e.g., virus, bacterium, fungus, protozoan, parasite, etc.) to infect a susceptible cell line in vitro in the absence of serum is compared to conditions when different dilutions of immune and non-immune serum are added to the culture medium in which the cells are grown. In certain embodiments, an immune response in a B cell is said to be stimulated if infection of a microorganism is neutralized at a dilution of about 1:5, about 1:10, about 1:50, about 1:100, about 1:500, about 1:1000, about 1:5000, about 1:10,000, or less.

In some embodiments, the efficacy of vaccines in animal models may be determined by infecting groups of immunized and non-immunized mice (e.g., 3 or more weeks after vaccination) with a dose of a microorganism that is typically lethal. The magnitude and duration of survival of both group is monitored and typically graphed a Kaplan-Meier curves. To assess whether enhanced survival is due to B cell responses, serum from immune mice can be transferred as a "passive vaccine" to assess protection of non-immune mice from lethal infection.

One of ordinary skill in the art will recognize that the assays described above are only exemplary methods which could be utilized in order to determine whether B cell activation has occurred. Any assay known to one of skill in the art which can be used to determine whether B cell activation has occurred falls within the scope of this invention. The assays described herein as well as additional assays that could be used to determine whether B cell activation has occurred are described in *Current Protocols in Immunology* (John Wiley & Sons, Hoboken, N.Y., 2007; incorporated herein by reference).

Nanocarriers

Any of the nanocarriers described herein may be vaccine nanocarriers. Although some of disclosure provided herein specifically mentions vaccine nanocarriers, it will be appreciated that, unless otherwise specified, the disclosure is not limited to vaccine nanocarriers but applies to any of the nanocarriers described herein.

In some embodiments, a vaccine nanocarrier is a synthetic nanocarrier that comprises, for example, at least one immunomodulatory agent which is capable of stimulating an immune response in one or both of B cells and T cells. The immunomodulatory agent may be associated with the nanocarriers in any way as described in more detail herein.

In some embodiments, nanocarriers are biodegradable and biocompatible. In general, a biocompatible substance is not toxic to cells. In some embodiments, a substance is considered to be biocompatible if its addition to cells results in less than a certain threshold of cell death (e.g. less than 50%, 20%, 10%, 5%, or less cell death). In some embodiments, a substance is considered to be biocompatible if its addition to cells does not induce adverse effects. In general, a biodegradable substance is one that undergoes breakdown under physiological conditions over the course of a therapeutically relevant time period (e.g., weeks, months, or years). In some embodiments, a biodegradable substance is a substance that can be broken down by cellular machinery. In some embodiments, a biodegradable substance is a substance that can be broken down by chemical processes. In some embodiments, a nanocarrier is a substance that is both biocompatible and biodegradable. In some embodiments, a nanocarrier is a substance that is biocompatible, but not biodegradable. In some embodiments, a nanocarrier is a substance that is biodegradable, but not biocompatible.

In some embodiments, a nanocarrier in accordance with the present invention is any entity having a greatest dimension (e.g., diameter) of less than 5 microns (μm). In some embodiments, inventive nanocarriers have a greatest dimension of less than 3 μm. In some embodiments, inventive nanocarriers have a greatest dimension of less than 1000 nanometers (nm). In some embodiments, inventive nanocarriers have a greatest dimension of less than 900 nm, 800 nm, 700 nm, 600 nm, 500 nm, 400 nm, 300 nm, 200 nm, or 100 nm. In some embodiments, inventive nanocarriers have a greatest dimension (e.g., diameter) of 300 nm or less. In some embodiments, inventive nanocarriers have a greatest dimension (e.g., diameter) of 250 nm or less. In some embodiments, inventive nanocarriers have a greatest dimension (e.g., diameter) of 200 nm or less. In some embodiments, inventive nanocarriers have a greatest dimension (e.g., diameter) of 150 nm or less. In some embodiments, inventive nanocarriers have a greatest dimension (e.g., diameter) of 100 nm or less. Smaller nanocarriers, e.g., having a greatest dimension of 50 nm or less are used in some embodiments of the invention. In some embodiments, inventive nanocarriers have a greatest dimension ranging between 25 nm and 200 nm. In some embodiments, inventive nanocarriers have a greatest dimension ranging between 20 nm and 100 nm. The nanocarriers of the compositions provided herein, in some embodiments, have a mean geometric diameter that is less than 500 nm. In some embodiments, the nanocarriers have mean geometric diameter that is greater than 50 nm but less than 500 nm. In some embodiments, the mean geometric diameter of a population of nanocarriers is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75-250 nm.

In some embodiments, inventive nanocarriers have a greatest dimension of greater than 1000 nanometers (nm). In some embodiments, inventive nanocarriers have a greatest dimension of greater than 900 nm, 800 nm, 700 nm, 600 nm, 500 nm, 400 nm, 300 nm, 200 nm, or 100 nm. In some embodiments, inventive nanocarriers have a greatest dimension (e.g., diameter) of 300 nm or more. In some embodiments, inventive nanocarriers have a greatest dimension (e.g., diameter) of 250 nm or more. In some embodiments, inventive nanocarriers have a greatest dimension (e.g., diameter) of 200 nm or more. In some embodiments, inventive nanocarriers have a greatest dimension (e.g., diameter) of 150 nm or more. In some embodiments, inventive nanocarriers have a greatest dimension (e.g., diameter) of 100 nm or more. Smaller nanocarriers, e.g., having a greatest dimension of 50 nm or more are used in some embodiments of the invention.

In some embodiments, nanocarriers have a diameter of less than 1000 nm. In some embodiments, nanocarriers have a diameter of approximately 750 nm. In some embodiments, nanocarriers have a diameter of approximately 500 nm. In some embodiments, nanocarriers have a diameter of approximately 450 nm. In some embodiments, nanocarriers have a diameter of approximately 400 nm. In some embodiments, nanocarriers have a diameter of approximately 350 nm. In some embodiments, nanocarriers have a diameter of approximately 300 nm. In some embodiments, nanocarriers have a diameter of approximately 275 nm. In some embodiments, nanocarriers have a diameter of approximately 250 nm. In some embodiments, nanocarriers have a diameter of approximately 225 nm. In some embodiments, nanocarriers have a diameter of approximately 200 nm. In some embodiments, nanocarriers have a diameter of approximately 175 nm. In some embodiments, nanocarriers have a diameter of approximately 150 nm. In some embodiments, nanocarriers have a diameter of approximately 125 nm. In some embodiments, nanocarriers have a diameter of approximately 100 nm. In some embodiments, nanocarriers have a diameter of approximately 75 nm. In some embodiments, nanocarriers have a diameter of approximately 50 nm. In some embodiments, nanocarriers have a diameter of approximately 25 nm.

In certain embodiments, nanocarriers are greater in size than the renal excretion limit (e.g., nanocarriers having diameters of greater than 6 nm). In certain embodiments, nanocarriers are small enough to avoid clearance of nanocarriers from the bloodstream by the liver (e.g., nanocarriers having diameters of less than 1000 nm). In general, physiochemical features of nanocarriers should allow a nanocarrier to circulate longer in plasma by decreasing renal excretion and liver clearance.

It is often desirable to use a population of nanocarriers that is relatively uniform in terms of size, shape, and/or composition so that each nanocarrier has similar properties. For example, at least 80%, at least 90%, or at least 95% of the nanocarriers may have a diameter or greatest dimension that falls within 5%, 10%, or 20% of the average diameter or greatest dimension. In some embodiments, a population of nanocarriers may be heterogeneous with respect to size, shape, and/or composition. In some embodiments, 30%, 40%, 50%, 60%, 70%, 80%, 90%, or more of the nanocarriers of a population of nanocarriers have a diameter that is less than 500 nM. In some embodiments, 10%, 20%, 30%, 40%, 50%, 60%, 70%, 80%, 90%, or more of the nanocarriers of a population of nanocarriers have a diameter that is greater than 50 nm but less than 500 nm. In some embodiments, 10%, 20%, 30%, 40%, 50%, 60%, 70%, 80%, 90%, or more of the nanocarriers of a population of nanocarriers have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the nanocarriers of a population of nanocarriers have a diameter that is between 100-400 nm, 100-300 nm, 100-250 nm, or 100-200 nm. In some embodiments, 10%, 20%, 30%, 40%, 50%, 60%, 70%, 80%, 90%, or more of the nanocarriers of a population of nanocarriers have a diameter that is between 60-400 nm, 60-350 nm, 60-300 nm, 60-250 nm, or 60-200 nm.

A variety of different nanocarriers can be used in accordance with the present invention. In some embodiments, nanocarriers are spheres or spheroids. In some embodiments, nanocarriers are flat or plate-shaped. In some embodiments, nanocarriers are cubes or cuboids. In some embodiments, nanocarriers are ovals or ellipses. In some embodiments, nanocarriers are cylinders, cones, toroids (i.e., donut shaped), or pyramids. In some embodiments, particles are liposomes. In some embodiments, particles are micelles. It will be appreciated that each of these shapes fall within the general category of "particles," and that the nanocarriers of the invention may comprise nanoparticles (i.e., a particle having a diameter of less than 1000 nm), microparticles (i.e., particles having a diameter of less than 1000 micrometers), or picoparticles (i.e., particles having a diameter of less than 1 nm). It will further be appreciated that, in some embodiments (such as lipid-based nanocarriers, as described in more detail below), the nanocarriers are not rigid and may have a shape and diameter that changes based on the environment.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheriodal synthetic nanocarrier, the maximum and minimum dimension of a synthetic nanocarrier would be substantially identical, and would be the size of its diameter. Similarly, for a cubic synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably 80%, more preferably 90%, of the synthetic nanocarriers in a sample, based on the total number of synthetic nanocarriers in the sample, is greater than 100 nm. In a embodiment, a maximum dimension of at least 75%, preferably 80%, more preferably 90%, of the synthetic nanocarriers in a sample, based on the total number of synthetic nanocarriers in the sample, is equal to or less than 5 μm. Preferably, a minimum dimension of at least 75%, preferably 80%, more preferably 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Preferably, a maximum dimension of at least 75%, preferably 80%, more preferably 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred embodiments, a maximum dimension of at least 75%, preferably 80%, more preferably 90%, of the synthetic nanocarriers in a sample, based on the total number of synthetic nanocarriers in the sample, is equal to or greater than 100 nm, more preferably equal to or greater than 120, more preferably greater than 130 nm, more preferably greater than 140 nm, and more preferably still greater than 150 nm. Measurement of synthetic nanocarrier sizes is obtained by suspending the synthetic nanocarriers in a liquid (usually aqueous) media and using dynamic light scattering (e.g. using a Brookhaven ZetaPALS instrument) Nanocarriers can be solid or hollow and can comprise one or more layers. In some embodiments, each layer has a unique composition and unique properties relative to the other layer(s). To give but one example, nanocarriers may have a core/shell structure, wherein the core is one layer (e.g. a polymeric core) and the shell is a second layer (e.g. a lipid bilayer or monolayer). Nanocarriers may comprise a plurality of different layers. In some embodiments, one layer may be substantially cross-linked, a second layer is not substantially cross-linked, and so forth. In some embodiments, one, a few, or all of the different layers may comprise one or more immunomodulatory agents, targeting moieties, immunostimulatory agents, and/or combinations thereof. In some embodiments, one layer comprises an immunomodulatory agent, targeting moiety, and/or immunostimulatory agent, a second layer does not comprise an immunomodulatory agent, targeting moiety, and/or immunostimulatory agent, and so forth. In some embodiments, each individual layer comprises a different immunomodulatory agent, targeting moiety, immunostimulatory agent, and/or combination thereof.

In some preferred embodiments of the present invention, vaccine nanocarriers comprise an antigen (e.g., a B-cell antigen or a T-cell antigen) and an immunostimulatory agent such as an adjuvant, wherein the antigen and immunostimulatory agent are associated with the same nanocarrier. The immunofeature surface on inventive nanocarriers containing both an antigen and the immunostimulatory agent enhances the uptake of both components by antigen presenting cells, which results in enhanced antigen presentation and lymphocyte activation. This promotes the situation where the activating/proinflammatory effects of adjuvants are concentrated on those cells that will also acquire a sufficient dose of antigen, and vice versa.

Lipid Nanocarriers

In some embodiments, nanocarriers may optionally comprise one or more lipids. In some embodiments, a nanocarrier may comprise a liposome. In some embodiments, a nanocarrier may comprise a lipid bilayer. In some embodiments, a nanocarrier may comprise a lipid monolayer. In some embodiments, a nanocarrier may comprise a micelle. In some embodiments, a nanocarrier may comprise a core comprising a polymeric matrix surrounded by a lipid layer (e.g., lipid bilayer, lipid monolayer, etc.). In some embodiments, a nanocarrier may comprise a non-polymeric core (e.g., metal particle, quantum dot, ceramic particle, bone particle, viral particle, etc.) surrounded by a lipid layer (e.g., lipid bilayer, lipid monolayer, etc.).

In some embodiments, nanocarriers may comprise a lipid bilayer oriented such that the interior and exterior of the nanocarrier are hydrophilic, and the lumen of the lipid bilayer is hydrophobic. Examples of vaccine nanocarriers comprising lipid bilayers are described in Example 2 and shown in FIGS. 3-8. In some embodiments, hydrophobic immunomodulatory agents, targeting moieties, and/or immunostimulatory agents may be associated with (e.g., embedded within) the lumen of the lipid bilayer. In some embodiments, hydrophilic immunomodulatory agents, targeting moieties, and/or immunostimulatory agents may be associated with (e.g., covalently or non-covalently associated with, encapsulated within, etc.) the interior and/or exterior of the nanocarrier. In some embodiments, hydrophilic immunomodulatory agents, targeting moieties, and/or immunostimulatory agents may be associated with (e.g., covalently or non-covalently associated with, encapsulated within, etc.) the interior and/or exterior surface of the lipid bilayer. In some embodiments, the interior, hydrophilic surface of the lipid bilayer is associated with an amphiphilic entity. In some embodiments, the amphiphilic entity is oriented such that the hydrophilic end of the amphiphilic entity is associated with the interior surface of the lipid bilayer, and the hydrophobic end of the amphiphilic entity is oriented toward the interior of the nanocarrier, producing a hydrophobic environment within the nanocarrier interior.

In some embodiments, nanocarriers may comprise a lipid monolayer oriented such that the interior of the nanocarrier is hydrophobic, and the exterior of the nanocarrier is hydrophilic. Examples of vaccine nanocarriers comprising lipid monolayers are described in Example 2 and shown in FIGS. 9 and 10. In some embodiments, hydrophobic immunomodulatory agents, targeting moieties, and/or immunostimulatory agents may be associated with (e.g., covalently or non-covalently associated with, encapsulated within, etc.) the interior of the nanocarrier and/or the interior surface of the lipid monolayer. In some embodiments, hydrophilic immunomodulatory agents, targeting moieties, and/or immunostimulatory agents may be associated with (e.g., covalently or non-covalently associated with, encapsulated within, etc.) the exterior of the nanocarrier and/or the exterior surface of the lipid monolayer. In some embodiments, the interior, hydrophobic surface of the lipid bilayer is associated with an amphiphilic entity. In some embodiments, the amphiphilic entity is oriented such that the hydrophobic end of the amphiphilic entity is associated with the interior surface of the lipid bilayer, and the hydrophilic end of the amphiphilic entity is oriented toward the interior of the nanocarrier, producing a hydrophilic environment within the nanocarrier interior.

In some embodiments, a nanocarrier may comprise one or more nanoparticles associated with the exterior surface of the nanocarrier. Examples of vaccine nanocarriers comprising nanoparticles associated with the exterior surface of the nanocarrier are described in Example 2 and shown in FIGS. 4, 6, and 8.

The percent of lipid in nanocarriers can range from 0% to 99% by weight, from 10% to 99% by weight, from 25% to 99% by weight, from 50% to 99% by weight, or from 75% to 99% by weight. In some embodiments, the percent of lipid in nanocarriers can range from 0% to 75% by weight, from 0% to 50% by weight, from 0% to 25% by weight, or from 0% to 10% by weight. In some embodiments, the percent of lipid in nanocarriers can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

In some embodiments, lipids are oils. In general, any oil known in the art can be included in nanocarriers. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be a $C_{15}$-$C_{25}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In some embodiments, the oil is a liquid triglyceride.

Suitable oils for use with the present invention include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, and combinations thereof. Suitable oils for use with the present invention include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In some embodiments, a lipid is a hormone (e.g. estrogen, testosterone), steroid (e.g., cholesterol, bile acid), vitamin (e.g. vitamin E), phospholipid (e.g. phosphatidyl choline), sphingolipid (e.g. ceramides), or lipoprotein (e.g. apolipoprotein).

Nanocarriers Comprising a Polymeric Matrix

In some embodiments, nanocarriers can comprise one or more polymers. In some embodiments, a polymeric matrix can be surrounded by a coating layer (e.g., liposome, lipid monolayer, micelle, etc.). In some embodiments, an immunomodulatory agent, targeting moiety, and/or immunostimulatory agent can be associated with the polymeric matrix. In such embodiments, the immunomodulatory agent, targeting moiety, and/or immunostimulatory agent is effectively encapsulated within the nanocarrier.

In some embodiments, an immunomodulatory agent, targeting moiety, and/or immunostimulatory agent can be covalently associated with a polymeric matrix. In some embodiments, covalent association is mediated by a linker. In some embodiments, an immunomodulatory agent, targeting moiety, and/or immunostimulatory agent can be non-covalently associated with a polymeric matrix. For example, in some embodiments, an immunomodulatory agent, targeting moiety, and/or immunostimulatory agent can be encapsulated within, surrounded by, and/or dispersed throughout a polymeric matrix. Alternatively or additionally, an immunomodulatory agent, targeting moiety, and/or immunostimulatory agent can be associated with a polymeric matrix by hydrophobic interactions, charge interactions, van der Waals forces, etc.

A wide variety of polymers and methods for forming polymeric matrices therefrom are known in the art of drug delivery. In general, a polymeric matrix comprises one or more polymers. Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

Examples of polymers include polyethylenes, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumerates, polycaprolactones, polyamides (e.g. polycaprolactam), polyacetals, polyethers, polyesters (e.g., polylactide, polyglycolide), poly(orthoesters), polycyanoacrylates, polyvinyl alcohols, polyurethanes, polyphosphazenes, polyacrylates, polymethacrylates, polyureas, polystyrenes, and polyamines.

In some embodiments, polymers in accordance with the present invention include polymers which have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a nanocarrier comprising a hydrophilic polymeric matrix generates a hydrophilic environment within the nanocarrier. In some embodiments, hydrophilic immunomodulatory agents, targeting moieties, and/or immunostimulatory agents may be associated with hydrophilic polymeric matrices.

In some embodiments, polymers can be hydrophobic. In some embodiments, a nanocarrier comprising a hydrophobic polymeric matrix generates a hydrophobic environment within the nanocarrier. In some embodiments, hydrophobic immunomodulatory agents, targeting moieties, and/or immunostimulatory agents may be associated with hydrophobic polymeric matrices.

In some embodiments, polymers may be modified with one or more moieties and/or functional groups. Any moiety or functional group can be used in accordance with the present invention. In some embodiments, polymers may be modified with polyethylene glycol (PEG), with a carbohydrate, and/or with acyclic polyacetals derived from polysaccharides (Papisov, 2001, *ACS Symposium Series*, 786:301; incorporated herein by reference).

In some embodiments, polymers may be modified with a lipid or fatty acid group, properties of which are described in further detail below. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethylene imine), poly(ethylene imine)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.*, 30:97; and Kabanov et al., 1995, *Bioconjugate Chem.*, 6:7; both of which are incorporated herein by reference), poly (ethylene imine) (PEI; Boussif et al., 1995, *Proc. Natl. Acad. Sci., USA*, 1995, 92:7297; incorporated herein by reference), and poly(amidoamine) dendrimers (Kukowska-Latallo et al., 1996, *Proc. Natl. Acad. Sci., USA*, 93:4897; Tang et al., 1996, *Bioconjugate Chem.*, 7:703; and Haensler et al., 1993, *Bioconjugate Chem.*, 4:372; all of which are incorporated herein by reference) are positively-charged at physiological pH, form ion pairs with nucleic acids, and mediate transfection in a variety of cell lines.

In some embodiments, polymers can be degradable polyesters bearing cationic side chains (Putnam et al., 1999, *Macromolecules*, 32:3658; Barrera et al., 1993, *J. Am. Chem. Soc.*, 115:11010; Kwon et al., 1989, *Macromolecules*, 22:3250; Lim et al., 1999, *J. Am. Chem. Soc.*, 121:5633; and Zhou et al., 1990, *Macromolecules*, 23:3399; all of which are incorporated herein by reference). Examples of these polyesters include poly(L-lactide-co-L-lysine) (Barrera et al., 1993, *J. Am. Chem. Soc.*, 115:11010; incorporated herein by reference), poly(serine ester) (Zhou et al., 1990, *Macromolecules*, 23:3399; incorporated herein by reference), poly(4-hydroxy-L-proline ester) (Putnam et al., 1999, *Macromolecules*, 32:3658; and Lim et al., 1999, *J. Am. Chem. Soc.*, 121:5633; both of which are incorporated herein by reference), and poly(4-hydroxy-L-proline ester) (Putnam et al., 1999, *Macromolecules*, 32:3658; and Lim et al., 1999, *J. Am. Chem. Soc.*, 121:5633; both of which are incorporated herein by reference).

In some embodiments, polymers in accordance with the present invention may be carbohydrates, properties of which are described in further detail below. In some embodiments, a carbohydrate may be a polysaccharide comprising simple sugars (or their derivatives) connected by glycosidic bonds, as known in the art. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, a polymer in accordance with the present invention may be a protein or peptide, properties of which are described in further detail below. Exemplary proteins that may be used in accordance with the present invention include, but are not limited to, albumin, collagen, a poly(amino acid) (e.g., polylysine), an antibody, etc.

In some embodiments, a polymer in accordance with the present invention may be a nucleic acid (i.e., polynucleotide), properties of which are described in further detail below. Exemplary polynucleotides that may be used in accordance with the present invention include, but are not limited to, DNA, RNA, etc.

In some embodiments, the present invention relates to the use of polymeric nanoparticle-antigen bioconjugate systems as a platform to induce the formation of antibodies. A controlled release polymer system or vesicle based system, as used herein, is a polymer combined with an active agent, such as a therapeutic agent, a diagnostic agent, a prognostic, or prophylactic agent, so that the active agent is released and/or triggered from the material in a predesigned manner. The polymer-antigen bioconjugates system may be synthesized as a homopolymer, diblock triblock and/or multiblock copolymer. The synthesis of the polymer-antigen bioconjugates system includes polymerization from monomers and conjugation of different polymers. The nanoparticle system may include a polymer that is biologically degradable, chemically degradable, or both biologically and chemically degradable. Examples of suitable polymers for controlled release polymer systems include, but are not limited to, poly(lactic acid), derivatives of poly(lactic acid), PEGylated poly(lactic acid), poly(lactic-co-glycolic acid), derivatives of poly(lacticco-glycolic acid), PEGylated poly(lactic-co-glycolic acid), poly (anhydrides), PEGylated poly(anhydrides), poly(ortho esters) derivatives of pholy(ortho esters), PEGylated poly (ortho esters), poly(caprolactones), derivatives of poly(caprolactone), PEGylated poly(caprolactones), polylysine, derivatives of polylysine, PEGylated polylysine, poly(ethylene imine), derivatives of poly(ethylene imine), PEGylated poly(ethylene imine), poly(acrylic acid), derivatives of poly (acrylic acid), PEGylated poly(acrylic acid), poly(urethane), PEGylated poly(urethane), derivatives of poly(urethane), and combinations thereof.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, *J. Am. Chem. Soc.*, 123:9480; Lim et al., 2001, *J. Am. Chem. Soc.*, 123:2460; Langer, 2000, *Acc. Chem. Res.*, 33:94; Langer, 1999, *J. Control. Release*, 62:7; and Uhrich et al., 1999, *Chem. Rev.*, 99:3181; all of which are incorporated herein by reference). More generally, a variety of methods for synthesizing suitable polymers are described in *Concise Encyclopedia of Polymer Science and Polymeric Amines and Ammonium Salts*, Ed. by Goethals, Pergamon Press, 1980; *Principles of Polymerization* by Odian, John Wiley & Sons, Fourth Edition, 2004; *Contemporary Polymer Chemistry* by Allcock et al., Prentice-Hall, 1981; Deming et al., 1997, *Nature*, 390:386; and in U.S. Pat. Nos. 6,506,577, 6,632,922, 6,686,446, and 6,818,732; all of which are incorporated herein by reference.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step.

It is further to be understood that inventive nanocarriers may comprise block copolymers, graft copolymers, blends, mixtures, and/or adducts of any of the foregoing and other polymers.

Those skilled in the art will recognize that the polymers listed herein represent an exemplary, not comprehensive, list of polymers that can be of use in accordance with the present invention.

In some embodiments, vaccine nanocarriers comprise immunomodulatory agents embedded within reverse micelles. To give but one example, a liposome nanocarrier may comprise hydrophobic immunomodulatory agents embedded within the liposome membrane, and hydrophilic immunomodulatory agents embedded with reverse micelles found in the interior of the liposomal nanocarrier.

Non-Polymeric Nanocarriers

In some embodiments, nanocarriers may not comprise a polymeric component. In some embodiments, nanocarriers may comprise metal particles, quantum dots, ceramic particles, bone particles, viral particles, etc. In some embodiments, an immunomodulatory agent, targeting moiety, and/or immunostimulatory agent can be associated with the surface of such a non-polymeric nanocarrier. In some embodiments, a non-polymeric nanocarrier is an aggregate of non-polymeric components, such as an aggregate of metal atoms (e.g., gold atoms). In some embodiments, an immunomodulatory agent, targeting moiety, and/or immunostimulatory agent can be associated with the surface of, encapsulated within, surrounded by, and/or dispersed throughout an aggregate of non-polymeric components.

In certain embodiments of the invention, non-polymeric nanocarriers comprise gradient or homogeneous alloys. In certain embodiments of the invention, nanocarriers comprise particles which possess optically and/or magnetically detectable properties.

Nanocarriers Comprising Amphiphilic Entities

In some embodiments, nanocarriers may optionally comprise one or more amphiphilic entities. In some embodiments, an amphiphilic entity can promote the production of nanocarriers with increased stability, improved uniformity, or increased viscosity. In some embodiments, amphiphilic entities can be associated with the interior surface of a lipid membrane (e.g., lipid bilayer, lipid monolayer, etc.). For example, if the interior surface of a lipid membrane is hydrophilic, the space encapsulated within the lipid nanocarrier is hydrophilic. However, if an amphiphilic entity is associated with the interior surface of the hydrophilic lipid membrane such that the hydrophilic end of the amphiphilic entity is associated with the interior surface of the hydrophilic lipid membrane and the hydrophobic end of the amphiphilic entity is associated with the interior of the nanocarrier, the space encapsulated within the nanocarrier is hydrophobic.

The percent of amphiphilic entity in nanocarriers can range from 0% to 99% by weight, from 10% to 99% by weight, from 25% to 99% by weight, from 50% to 99% by weight, or from 75% to 99% by weight. In some embodiments, the percent of amphiphilic entity in nanocarriers can range from 0% to 75% by weight, from 0% to 50% by weight, from 0% to 25% by weight, or from 0% to 10% by weight. In some embodiments, the percent of amphiphilic entity in nanocarriers can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Any amphiphilic entity known in the art is suitable for use in making nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween® 85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. These amphiphilic entities may be extracted and purified from a natural source or may be prepared synthetically in a laboratory. In certain specific embodiments, amphiphilic entities are commercially available.

Those skilled in the art will recognize that this is an exemplary, not comprehensive, list of substances with surfactant activity. Any amphiphilic entity may be used in the production of nanocarriers to be used in accordance with the present invention.

Vaccine Nanocarriers Comprising Carbohydrates

In some embodiments, nanocarriers may optionally comprise one or more carbohydrates. The percent of carbohydrate in nanocarriers can range from 0% to 99% by weight, from 10% to 99% by weight, from 25% to 99% by weight, from 50% to 99% by weight, or from 75% to 99% by weight. In some embodiments, the percent of carbohydrate in nanocarriers can range from 0% to 75% by weight, from 0% to 50% by weight, from 0% to 25% by weight, or from 0% to 10% by weight. In some embodiments, the percent of carbohydrate in nanocarriers can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Carbohydrates may be natural or synthetic. A carbohydrate may be a derivatized natural carbohydrate. In certain embodiments, a carbohydrate is a monosaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a disaccharide, including but not limited to lactose, sucrose, maltose, trehalose, and cellobiose. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In certain embodiments, the carbohydrate is a sugar alcohol, including but not limited to mannitol, sorbitol, xylitol, erythritol, maltitol, and lactitol.

Particles and Particles Associated with Vaccine Nanocarriers

In some embodiments, vaccine nanocarriers in accordance with the present invention may comprise one or more particles. In some embodiments, one or more particles are associated with a vaccine nanocarrier. In some embodiments, vaccine nanocarriers comprise one or more particles associated with the outside surface of the nanocarrier. In some embodiments, particles may be associated with vaccine nanocarriers via covalent linkage. In some embodiments, particles may be associated with vaccine nanocarriers via non-covalent interactions (e.g., charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof). In some embodiments, vaccine nanocarriers comprise one or more particles encapsulated within the nanocarrier. In some embodiments, vaccine nanocarriers comprise one or more particles embedded within the surface of the nanocarrier (e.g., embedded within a lipid bilayer). In some embodiments, particles associated with a nanocarrier allow for tunable membrane rigidity and controllable liposome stability.

In some embodiments, vaccine nanocarrier particles or particles to be associated with a vaccine nanocarrier may comprise a polymeric matrix, as described above. In some embodiments, vaccine nanocarrier particles or particles to be associated with a vaccine nanocarrier may comprise non-polymeric components (e.g., metal particles, quantum dots, ceramic particles, bone particles, viral particles, etc.), as described above.

In some embodiments, vaccine nanocarrier particles or particles to be associated with a vaccine nanocarrier may have a negative charge. In some embodiments, vaccine nanocarrier particles or particles to be associated with a vaccine nanocarrier may have a positive charge. In some embodiments, vaccine nanocarrier particles or particles to be associated with a vaccine nanocarrier may be electrically neutral.

In some embodiments, the particles have one or more amine moieties on a surface. The amine moieties can be, for example, aliphatic amine moieties. In certain embodiments, the amine is a primary, secondary, tertiary, or quaternary amine. In certain embodiments, the particle comprises an amine-containing polymer. In certain embodiments, the particle comprises an amine-containing lipid. In certain embodiments, the particles comprises a protein or a peptide that is positively charged at neutral pH. In some embodiments, the particle with the one or more amine moieties on its surface has a net positive charge at neutral pH. Other chemical moieties that provide a positive charge at neutral pH may also be used in the inventive particles.

In some embodiments, the particles have one or more negatively charged (at neutral pH) moieties on a surface. For example, the particles have one or more carboxylic acid or phosphoric acid groups on the surface. In some embodiments, the particle with the one or more carboxylic acid or phosphoric acid moieties on its surface has a net negative charge at neutral pH. Other chemical moieties that provide a negative charge at neutral pH may also be used in the inventive particles.

In some embodiments, the particles have one or more substantially neutral (at neutral pH) moieties on a surface. For example, the particles have one or more ether groups on the surface. In some embodiments, the particle with the one or more ether moieties on its surface has substantially no net charge at neutral pH. Other chemical moieties that provide a neutral charge at neutral pH may also be used in the inventive particles.

Some non-limiting examples of compounds that can be present at the surface of the nanocarriers in order to effect the charge at the surface include 1-palmitoyl-2-oleoyl-sn-glycero-3-phosphocholine (POPC), 1,2-dioleoyl-3-trimethylammonium-propane, chloride salt (DOTAP), monosialoganglioside GM3, 1,2-dihexadecanoyl-sn-glycero-3-phospho-L-serine, sodium salt (DPPS), monophosphoryl Lipid A, and N-4-nitrobenzo-2-oxa-1,3-diazole phosphatidylethanolamine (NBD-PE).

Zeta potential is a measurement of surface potential of a particle. In some embodiments, the nanocarrier particles or particles associated with the nanocarriers have a positive zeta potential. In some embodiments, particles have a zeta potential ranging between −50 mV and +50 mV. In some embodiments, particles have a zeta potential ranging between −25 mV and +25 mV. In some embodiments, particles have a zeta potential ranging between −10 mV and +10 mV. In some embodiments, particles have a zeta potential ranging between −5 mV and +5 mV. In some embodiments, particles have a zeta potential ranging between 0 mV and +50 mV. In some embodiments, particles have a zeta potential ranging between 0 mV and +25 mV. In some embodiments, particles have a zeta potential ranging between 0 mV and +10 mV. In some embodiments, particles have a zeta potential ranging between 0 mV and +5 mV. In some embodiments, particles have a zeta potential ranging between −50 mV and 0 mV. In some embodiments, particles have a zeta potential ranging between −25 mV and 0 mV. In some embodiments, particles have a zeta potential ranging between −10 mV and 0 mV. In some embodiments, particles have a zeta potential ranging between −5 mV and 0 mV. In some embodiments, particles have a substantially neutral zeta potential (i.e. approximately 0 mV).

Particles (e.g., nanoparticles, microparticles) may be prepared using any method known in the art. For example, particulate formulations can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanoparticles have been described (Pellegrino et al., 2005, *Small*, 1:48; Murray et al., 2000, *Ann. Rev. Mat. Sci.*, 30:545; and Trindade et al., 2001, *Chem. Mat.*, 13:3843; all of which are incorporated herein by reference).

In certain embodiments, particles are prepared by the nanoprecipitation process or spray drying. Conditions used in preparing particles may be altered to yield particles of a desired size or property (e.g., hydrophobicity, hydrophilicity, external morphology, "stickiness," shape, etc.). The method of preparing the particle and the conditions (e.g., solvent, temperature, concentration, air flow rate, etc.) used may depend on the therapeutic agent to be delivered and/or the composition of the polymer matrix.

Methods for making microparticles for delivery of encapsulated agents are described in the literature (see, e.g., Doubrow, Ed., "Microcapsules and Nanoparticles in Medicine and Pharmacy," CRC Press, Boca Raton, 1992; Mathiowitz et al., 1987, *J. Control. Release*, 5:13; Mathiowitz et al., 1987, *Reactive Polymers*, 6:275; and Mathiowitz et al., 1988, *J. Appl. Polymer Sci.*, 35:755; all of which are incorporated herein by reference).

If particles prepared by any of the above methods have a size range outside of the desired range, particles can be sized, for example, using a sieve.

Immunofeature Surface

The synthetic nanocarriers of the invention comprise one or more surfaces, and in some embodiments at least one surface comprises an immunofeature surface.

An immunofeature surface is a surface that comprises multiple moieties, wherein: (1) the immunofeature surface excludes moieties that are the Fc portion of an antibody; and (2) the moieties are present in an amount effective to provide avidity-based binding to mammalian antigen presenting cells.

Avidity-based binding is binding that is based on an avidity effect (this type of binding may also be referred to as "high avidity" binding). In a preferred embodiment, the presence of an immunofeature surface can be determined using an in vivo assay followed by an in vitro assay as follows (although other methods that ascertain the presence of binding based on an avidity effect (i.e. "high avidity" binding) may be used in the practice of the present invention as well.)

The in vivo assay makes use of two sets of synthetic nanocarriers carrying different fluorescent labels, with one set of synthetic nanocarriers having the immunofeature surface and the other set serving as a control. To test whether the immunofeature surface can target synthetic nanocarriers to Antigen Presenting Cells in vivo, both sets of synthetic nanocarriers are mixed 1:1 and injected into the footpad of a mouse. Synthetic nanocarrier accumulation on dendritic cells and subcapsular sinus macrophages is measured by harvesting the draining popliteal lymph node of the injected mouse at a time point between 1 to 4 hours and 24 hours after nanocarrier injection, respectively. Lymph nodes are processed for confocal fluorescence immunohistology of frozen sections, counterstained with fluorescent antibodies to mouse-CD11c (clone HL3, BD BIOSCIENCES® or mouse-CD169 (clone 3D6.112 from SEROTEC®) and analyzed by planimetry using a suitable image processing software, such as ADOBE® PHOTOSHOP®). Targeting of antigen presenting cells by the immunofeature surface is established if synthetic nanocarriers comprising the immunofeature surface associate with dendritic cells and/or subcapsular sinus macrophages at least 1.2-fold, preferably at least 1.5-fold, more preferably at least 2-fold more frequently than control nanocarriers.

In a preferred embodiment, the in vitro assay that accompanies the in vivo assay determines the immobilization of human or murine dendritic cells or murine subcapsular sinus macrophages (collectively "In Vitro Antigen Presenting Cells") on a biocompatible surface that is coated with either the moieties of which the immunofeature surface is comprised, or an antibody that is specific for an In Vitro Antigen Presenting Cell-expressed surface antigen (for human dendritic cells: anti-CD1c (BDCA-1) clone AD5-8E7 from Miltenyi BIOTEC®, for mouse dendritic cells: anti-CD11c (αX integrin) clone HL3, BD BIOSCIENCES®, or for murine subcapsular sinus macrophages: anti-CD169 clone 3D6.112 from SEROTEC®) such that (i) an optimal coating density corresponding to maximal immobilization of the In Vitro Antigen Presenting Cells to the surface which has been coated with the moieties of which the immunofeature surface is comprised is either undetectable or at least 10%, preferably at least 20%, more preferably at least 25%, of that observed with the antibody coated surface; and (ii) if immobilization of In Vitro Antigen Presenting Cells by the immunofeature surface is detectable, the immunofeature surface that is being tested supports half maximal binding at a coating density of moieties of which the immunofeature surface is comprised that is at least 2-fold, preferably at least 3-fold, more preferably at least 4-fold higher than the antibody coating density that supports half maximal binding.

Immunofeature surfaces may be positively charged, negatively charged or neutrally charged at pH=7.2-7.4. Immunofeature surfaces may be made up of the same moiety or a mixture of different moieties. In embodiments, the immunofeature surfaces may comprise B cell antigens. Examples of moieties potentially useful in immunofeature surfaces comprise: methoxy groups, positively charged amine groups (e.g. tertiary amines), sialyllactose, avidin and/or avidin derivatives such as NeutrAvidin, and residues of any of the above. In an embodiment, the moieties of which the immunofeature surface is comprised are coupled to a surface of the inventive nanocarriers. In another embodiment, the immunofeature surface is coupled to a surface of the inventive nanocarriers.

It should be noted that moieties of which immunofeature surfaces are comprised confer high avidity binding. Not all moieties that could be present on a nanocarrier will confer high avidity binding, as defined specifically in this definition, and described generally throughout the present specification. Accordingly, even though a surface may comprise multiple moieties (sometimes referred to as an "array"), this does not mean that such a surface inherently is an immunofeature surface absent data showing that such a surface confers binding according to the present definition and disclosure.

In some embodiments, the plurality of moieties are other than the Fc portion of an antibody. In some embodiments, the plurality of moieties are selected from immunostimulatory moieties (as described herein), immunomodulatory moieties (as described herein), targeting moieties (as described herein), small organic moieties (e.g., nicotine), oligomers, and polymers (including synthetic polymers such as PEG), inorganic moieties, nucleic acids and polynucleotides (e.g., DNA and RNA fragments), amino acids, polypeptides, glycoproteins, biologically active substances (as described herein), gangliosides, lipids, phospholipids, carbohydrates, polysaccharides, and fragments of any of the foregoing. In some embodiments, the immunofeature surfaces may comprise B-cell antigens or T-cell antigens. Any combination of the foregoing moieties are also within the scope of the invention. It will be appreciated that bonding of such moieties to the immunofeature surface may involve appropriate modification such as replacement of a bond to an atom in the moiety with a bond to the surface.

In some embodiments, bonding of the plurality of moieties to the immunofeature surface is via covalent bonds between the moiety and a component of the nanocarrier. For example, in the case of nanocarriers comprising polymeric materials, the plurality of moieties may be covalently bonded to the polymers. In some cases, however, non-covalent interactions may be used, including ionic or hydrogen bonding, or dispersion forces.

Immunofeature surfaces may comprise a plurality of moieties that are the same moiety or a mixture of different moieties. For example, 2, 3, 4, 5, 6, 7, 8, 9, or 10 different types of moieties may be present in the immunofeature surface.

Immunofeature surfaces may be overall positively charged, negatively charged or neutrally charged when the immunofeature surface is present in buffered aqueous solution at pH in the range 7.2-7.4. It will be appreciated that, where a mixture of different moieties are present one the immunofeature surface, the immunofeature surface may be associated with a combination of positively charged, negatively charged, and/or neutrally charged moieties at any particular pH.

The immunofeature surface provides high avidity binding to an antigen presenting cell (APC), particularly APCs expressing MHC II molecules. For example, in some embodiments, the immunofeature surface provides high avidity binding to dendritic cells (DCs). In some other embodiments, the immunofeature surface provides high avidity binding to macrophages, for example subcapsular sinus macrophages (SCS Mphs). In some embodiments, the immunofeature surface provides high avidity binding to B-cells (i.e., the immunofeature surfaces comprises B-cell antigens). In preferred embodiments the immunofeature surface provides high avidity and low affinity binding to DCs, SCS Mphs, or B-cells.

Immunofeature surfaces comprise a plurality of moieties, and the plurality of moieties may be all the same moiety or a mixture of different moieties. The plurality of moieties are present on a surface that is capable of binding to APC surfaces with high avidity. In some embodiments, The plurality of moieties are present on a surface that is capable of binding to APC surfaces with high avidity and low affinity. Examples of moieties useful in immunofeature surfaces include: small organic molecules such as mannose, maleimide, POPC, DPPS, DOPS, monophosphoryl Lipid A, NBD-PE, and derivatives thereof; functional groups such as methoxy, amine, carboxylic acid, and analogues thereof; polysaccharides such as silalylactose and monosialoganglioside GM3; proteins and polypeptides such as avidin, NeutrAvidin, lysozyme, oligomer G, protein G, and derivatives thereof, and the like.

The extent to which the moieties present in an immunofeature surface are capable of directing nanocarriers to APCs will vary. For example, moieties that provide an immunofeature surface that is more specifically targeted to APCs (i.e., more specifically able to bind to APCs with high avidity and low affinity) will result in nanocarrier formulations that exhibit greater accumulation in areas such as the SCS.

It should be noted that moieties of which immunofeature surfaces are comprised confer high avidity binding. Not all moieties that are present on a nanocarrier will confer high avidity binding, as set forth specifically in this definition, and generally throughout the present specification. Accordingly, even though a surface may comprise multiple moieties (sometimes referred to as an "array"), this does not mean that such a surface inherently is an immunofeature surface absent data showing that such a surface confers binding according to the present definition and disclosure.

In some embodiments, nanocarriers having a surface comprising an immunofeature surface are able to target specific APCs when administered to a subject. For example, in some embodiments, the nanocarriers with an immunofeature surface are able to target DCs. In some embodiments, the nanocarriers with an immunofeature surface are able to target macrophages, such as SCS-Mphs. In some embodiments, the nanocarriers with an immunofeature surface are able to target B-cells. In this context, the terms "target" are used to indicate that compositions of nanocarriers having an immunofeature surface tend to accumulate in a specific region upon administration to a subject. Such accumulation may occur within minutes (e.g., less than 1 minute, less than 5 minutes, or less than 10 minutes, or less than 30 minutes), hours (e.g., less than 1 hour, or less than 2 hours, or less than 5 hours, or less than 10 hours), or days (e.g., less than 1 day, or less than 2 days, or less than 5 days) of administration.

In some embodiments, the complement system is not substantially activated by the nanocarriers of the invention. For example, in some embodiments, the nanocarriers do not activate the classical complement pathway and/or the alternative complement pathway. Nanocarriers that substantially do not activate complement show less than 50%, preferably less than 35%, more preferably less than 25%, of the amount of C3a increase compared to the hydroxylated nanocarriers disclosed in Example 9 of US Published Patent Application 2008/0031899, and determined using the methods of the same Example 9.

Production of Nanocarriers

Synthetic nanocarriers may be prepared using any method known in the art. For example, particulate nanocarrier formulations can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanoparticles have been described (Pellegrino et al., 2005, *Small*, 1:48; Murray et al., 2000, *Ann. Rev. Mat. Sci.*, 30:545; and Trindade et al., 2001, *Chem. Mat.*, 13:3843; all of which are incorporated herein by reference).

In certain embodiments, nanocarriers are prepared by the nanoprecipitation process or spray drying. Conditions used in preparing nanocarriers may be altered to yield particles of a desired size or property (e.g., hydrophobicity, hydrophilicity, external morphology, "stickiness," shape, etc.). The method of preparing the nanocarrier and the conditions (e.g., solvent, temperature, concentration, air flow rate, etc.) used may depend on the composition and/or resulting architecture of the nanocarrier.

Methods useful in making synthetic nanocarriers according to the invention are described in the literature (see, e.g., Doubrow, Ed., "Microcapsules and Nanoparticles in Medicine and Pharmacy," CRC Press, Boca Raton, 1992; Mathiowitz et al., 1987, *J. Control. Release*, 5:13; Mathiowitz et al., 1987, *Reactive Polymers*, δ: 275; and Mathiowitz et al., 1988, *J. Appl. Polymer Sci.*, 35:755; all of which are incorporated herein by reference).

In some embodiments, inventive vaccine nanocarriers comprise at least one immunomodulatory agent and, optionally, a lipid membrane, a polymeric matrix, and/or a non-polymeric particle. In certain embodiments, inventive vaccine nanocarriers comprise at least one immunomodulatory agent; a lipid membrane, a polymeric matrix, and/or a non-polymeric particle; and at least one targeting moiety. In certain embodiments, inventive vaccine nanocarriers comprise at least one immunomodulatory agent; a lipid membrane, a polymeric matrix, and/or a non-polymeric particle; at least one targeting moiety; and at least one immunostimulatory agent. In certain embodiments, inventive vaccine nanocarriers comprise at least one immunomodulatory agent; a lipid membrane, a polymeric matrix, and/or a non-polymeric particle; at least one targeting moiety; at least one immunostimulatory agent; and at least one nanoparticle.

Inventive nanocarriers may be manufactured using any available method. It is desirable to associate immunomodulatory agents, targeting moieties, and/or immunostimulatory agents to vaccine nanocarriers without adversely affecting the 3-dimensional characteristic and conformation of the immunomodulatory agents, targeting moieties, and/or immunostimulatory agents. It is desirable that the vaccine nanocarrier should be able to avoid uptake by the mononuclear phagocytic system after systemic administration so that it is able to reach specific cells in the body.

In some embodiments, immunomodulatory agents, targeting moieties, immunostimulatory agents, and/or nanoparticles are not covalently associated with a vaccine nanocarrier. For example, vaccine nanocarriers may comprise a polymeric matrix, and immunomodulatory agents, targeting moieties, immunostimulatory agents, and/or nanoparticles may be associated with the surface of, encapsulated within, and/or distributed throughout the polymeric matrix of an inventive vaccine nanocarrier. Immunomodulatory agents are released by diffusion, degradation of the vaccine nanocarrier, and/or combination thereof. In some embodiments, polymers degrade by bulk erosion. In some embodiments, polymers degrade by surface erosion.

In some embodiments, immunomodulatory agents, targeting moieties, immunostimulatory agents, and/or nanoparticles are covalently associated with a vaccine nanocarrier. For such vaccine nanocarriers, release and delivery of the immunomodulatory agent to a target site occurs by disrupting the association. For example, if an immunomodulatory agent is associated with a nanocarrier by a cleavable linker, the immunomodulatory agent is released and delivered to the target site upon cleavage of the linker.

In some embodiments, immunomodulatory agents, targeting moieties, immunostimulatory agents, and/or nanoparticles are not covalently associated with a vaccine nanocarrier. For example, vaccine nanocarriers may comprise polymers, and immunomodulatory agents, targeting moieties, immunostimulatory agents, and/or nanoparticles may be associated with the surface of, encapsulated within, surrounded by, and/or distributed throughout the polymer of an inventive vaccine nanocarrier. In some embodiments, immunomodulatory agents, targeting moieties, immunostimulatory agents, and/or nanoparticles are physically associated with a vaccine nanocarrier.

Physical association can be achieved in a variety of different ways. Physical association may be covalent or non-covalent. The vaccine nanocarrier, immunomodulatory agent, targeting moiety, immunostimulatory agent, and/or nanoparticle may be directly associated with one another, e.g., by one or more covalent bonds, or may be associated by means of one or more linkers. In one embodiment, a linker forms one or more covalent or non-covalent bonds with the immunomodulatory agent, targeting moiety, immunostimulatory agent, and/or nanoparticle and one or more covalent or non-covalent bonds with the immunomodulatory agent, targeting moiety, immunostimulatory agent, and/or nanoparticle, thereby attaching them to one another. In some embodiments, a first linker forms a covalent or non-covalent bond with the vaccine nanocarrier and a second linker forms a covalent or non-covalent bond with the immunomodulatory agent, targeting moiety, immunostimulatory agent, and/or nanoparticle. The two linkers form one or more covalent or non-covalent bond(s) with each other.

Any suitable linker can be used in accordance with the present invention. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to 25 atoms long, 1 to 20 atoms long, 1 to 15 atoms long, 1 to 10 atoms long, or 1 to 10 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted.

In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker.

In some embodiments, the linker is a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with a vaccine nanocarrier. General strategies include passive adsorption (e.g., via electrostatic interactions), multivalent chelation, high affinity non-covalent binding between members of a specific binding pair, covalent bond formation, etc. (Gao et al., 2005, *Curr. Op. Biotechnol.*, 16:63; incorporated herein by reference). In some embodiments, click chemistry can be used to associate a linker with a particle.

A bifunctional cross-linking reagent can be employed. Such reagents contain two reactive groups, thereby providing a means of covalently associating two target groups. The reactive groups in a chemical cross-linking reagent typically belong to various classes of functional groups such as succinimidyl esters, maleimides, and pyridyldisulfides. Exemplary cross-linking agents include, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol] ester (NHS-PEO12), etc. For example, carbodiimide-mediated amide formation and active ester maleimide-mediated amine and sulfhydryl coupling are widely used approaches.

In some embodiments, a vaccine nanocarrier can be formed by coupling an amine group on one molecule to a thiol group on a second molecule, sometimes by a two- or three-step reaction sequence. A thiol-containing molecule may be reacted with an amine-containing molecule using a heterobifunctional cross-linking reagent, e.g., a reagent containing both a succinimidyl ester and either a maleimide, a pyridyldisulfide, or an iodoacetamide. Amine-carboxylic acid and thiol-carboxylic acid cross-linking, maleimide-sulfhydryl coupling chemistries (e.g., the maleimidobenzoyl-N-hydroxysuccinimide ester (MBS) method), etc., may be used. Polypeptides can conveniently be attached to particles via amine or thiol groups in lysine or cysteine side chains respectively, or by an N-terminal amino group. Nucleic acids such as RNAs can be synthesized with a terminal amino group. A variety of coupling reagents (e.g., succinimidyl 3-(2-pyridyldithio)propionate (SPDP) and sulfosuccinimidyl-4-(N-maleimidomethyl)cyclohexane-1-carboxylate (sulfo-SMCC) may be used to associate the various components of vaccine nanocarriers. Vaccine nanocarriers can be prepared with functional groups, e.g., amine or carboxyl groups, available at the surface to facilitate association with a biomolecule.

Non-covalent specific binding interactions can be employed. For example, either a particle or a biomolecule can be functionalized with biotin with the other being functionalized with streptavidin. These two moieties specifically bind to each other non-covalently and with a high affinity, thereby associating the particle and the biomolecule. Other specific binding pairs could be similarly used. Alternately, histidine-tagged biomolecules can be associated with particles conjugated to nickel-nitrolotriaceteic acid (Ni-NTA).

Any biomolecule to be attached to a particle, targeting moiety, and/or therapeutic agent. The spacer can be, for example, a short peptide chain, e.g., between 1 and 10 amino acids in length, e.g., 1, 2, 3, 4, or 5 amino acids in length, a nucleic acid, an alkyl chain, etc.

For additional general information on association and/or conjugation methods and cross-linkers, see the journal *Bioconjugate Chemistry*, published by the American Chemical Society, Columbus Ohio, PO Box 3337, Columbus, Ohio, 43210; "Cross-Linking," Pierce Chemical Technical Library, available at the Pierce web site and originally published in the 1994-95 Pierce Catalog, and references cited therein; Wong S S, *Chemistry of Protein Conjugation and Cross-linking*, CRC Press Publishers, Boca Raton, 1991; and Hermanson, G. T., *Bioconjugate Techniques*, Academic Press, Inc., San Diego, 1996.

Alternatively or additionally, vaccine nanocarriers can be attached to immunomodulatory agents, targeting moieties, immunostimulatory agents, and/or nanoparticles directly or indirectly via non-covalent interactions. Non-covalent interactions include but are not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof.

In some embodiments, a vaccine nanocarrier may be associated with an immunomodulatory agent, targeting moiety, immunostimulatory agent, and/or nanoparticle via charge interactions. For example, a vaccine nanocarrier may have a cationic surface or may be reacted with a cationic polymer, such as poly(lysine) or poly(ethylene imine), to provide a cationic surface. The vaccine nanocarrier surface can then bind via charge interactions with a negatively charged immunomodulatory agent, targeting moiety, immunostimulatory agent, and/or nanoparticle. One end of the immunomodulatory agent, targeting moiety, immunostimulatory agent, and/or nanoparticle is, typically, attached to a negatively charged polymer (e.g., a poly(carboxylic acid)) or an additional oligonucleotide sequence that can interact with the cationic polymer surface without disrupting the function of the immunomodulatory agent, targeting moiety, immunostimulatory agent, and/or nanoparticle.

In some embodiments, a vaccine nanocarrier may be associated with an immunomodulatory agent, targeting moiety, immunostimulatory agent, and/or nanoparticle via affinity interactions. For example, biotin may be attached to the surface of the vaccine nanocarrier and streptavidin may be attached to the immunomodulatory agent, targeting moiety, immunostimulatory agent, and/or nanoparticle; or conversely, biotin may be attached to the immunomodulatory agent, targeting moiety, immunostimulatory agent, and/or nanoparticle and the streptavidin may be attached to the surface of the vaccine nanocarrier. The biotin group and streptavidin may be attached to the vaccine nanocarrier or to the immunomodulatory agent, targeting moiety, immunostimulatory agent, and/or nanoparticle via a linker, such as an alkylene linker or a polyether linker. Biotin and streptavidin bind via affinity interactions, thereby binding the vaccine nanocarrier to the immunomodulatory agent, targeting moiety, immunostimulatory agent, and/or nanoparticle.

In some embodiments, a vaccine nanocarrier may be associated with an immunomodulatory agent, targeting moiety, immunostimulatory agent, and/or nanoparticle via metal coordination. For example, a polyhistidine may be attached to one end of the immunomodulatory agent, targeting moiety, immunostimulatory agent, and/or nanoparticle, and a nitrilotriacetic acid can be attached to the surface of the vaccine nanocarrier. A metal, such as $Ni^{2+}$, will chelate the polyhistidine and the nitrilotriacetic acid, thereby binding the immunomodulatory agent, targeting moiety, immunostimulatory agent, and/or nanoparticle to the vaccine nanocarrier.

In some embodiments, a vaccine nanocarrier may be associated with an immunomodulatory agent, targeting moiety, immunostimulatory agent, and/or nanoparticle via physical adsorption. For example, a hydrophobic tail, such as polymethacrylate or an alkyl group having at least about 10 carbons, may be attached to one end of the immunomodulatory agent, targeting moiety, immunostimulatory agent, and/or nanoparticle. The hydrophobic tail will adsorb onto the surface of a hydrophobic vaccine nanocarrier, thereby binding the immunomodulatory agent, targeting moiety, immunostimulatory agent, and/or nanoparticle to the vaccine nanocarrier.

In some embodiments, a vaccine nanocarrier may be associated with an immunomodulatory agent, targeting moiety, immunostimulatory agent, and/or nanoparticle via host-guest interactions. For example, a macrocyclic host, such as cucurbituril or cyclodextrin, may be attached to the surface of the vaccine nanocarrier and a guest group, such as an alkyl group, a polyethylene glycol, or a diaminoalkyl group, may be attached to the immunomodulatory agent, targeting moiety, immunostimulatory agent, and/or nanoparticle; or conversely, the host group may be attached to the immunomodulatory agent, targeting moiety, immunostimulatory agent, and/or nanoparticle and the guest group may be attached to the surface of the vaccine nanocarrier. In some embodiments, the host and/or the guest molecule may be attached to the immunomodulatory agent, targeting moiety, immunostimulatory agent, and/or nanoparticle or the vaccine nanocarrier via a linker, such as an alkylene linker or a polyether linker.

In some embodiments, a vaccine nanocarrier may be associated with an immunomodulatory agent, targeting moiety, immunostimulatory agent, and/or nanoparticle via hydrogen bonding interactions. For example, an oligonucleotide having a particular sequence may be attached to the surface of the vaccine nanocarrier, and an essentially complementary sequence may be attached to one or both ends of the immunomodulatory agent, targeting moiety, immunostimulatory agent, and/or nanoparticle such that it does not disrupt the function of the immunomodulatory agent, targeting moiety, immunostimulatory agent, and/or nanoparticle. The immunomodulatory agent, targeting moiety, immunostimulatory agent, and/or nanoparticle then binds to the vaccine nanocarrier via complementary base pairing with the oligonucleotide attached to the vaccine nanocarrier. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with a base on the second oligonucleotide. Typically, it is desirable for an oligonucleotide sequence attached to the vaccine nanocarrier to form at least about 6 complementary base pairs with a complementary oligonucleotide attached to the immunomodulatory agent, targeting moiety, immunostimulatory agent, and/or nanoparticle.

Figure 3:
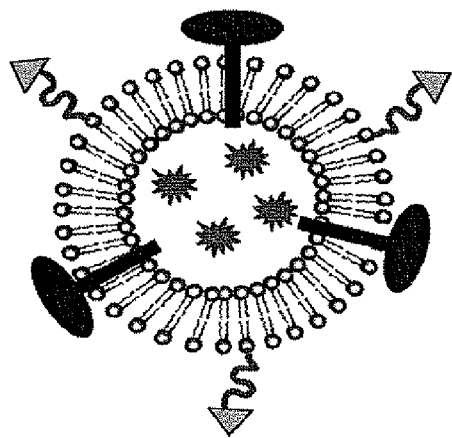
FIG. 3: An exemplary liposome nanocarrier with a lipophilic immunomodulatory agent incorporated in the membrane, and a hydrophilic immunomodulatory agent encapsulated within the liposome.

In some embodiments, vaccine nanocarriers are made by self-assembly. For a detailed example of self-assembly of vaccine nanocarriers, see Examples 1 and 2. In certain embodiments, small liposomes (10 nm-1000 nm) are manufactured and employed to deliver one or multiple immunomodulatory agents to cells of the immune system (FIG. 3). In general, liposomes are artificially-constructed spherical lipid vesicles, whose controllable diameter from tens to thousands of nm signifies that individual liposomes comprise biocompatible compartments with volume from zeptoliters ($10^{-21}$ L) to femtoliters ($10^{-15}$ L) that can be used to encapsulate and store various cargoes such as proteins, enzymes, DNA and drug molecules. Liposomes may comprise a lipid bilayer which has an amphiphilic property: both interior and exterior surfaces of the bilayer are hydrophilic, and the bilayer lumen is hydrophobic. Lipophilic molecules can spontaneously embed themselves into liposome membrane and retain their hydrophilic domains outside, and hydrophilic molecules can be chemically conjugated to the outer surface of liposome taking advantage of membrane biofunctionality.

In certain embodiments, lipids are mixed with a lipophilic immunomodulatory agent, and then formed into thin films on a solid surface. A hydrophilic immunomodulatory agent is dissolved in an aqueous solution, which is added to the lipid films to hydrolyze lipids under vortex. Liposomes with lipophilic immunomodulatory agents incorporated into the bilayer wall and hydrophilic immunomodulatory agents inside the liposome lumen are spontaneously assembled.

In certain embodiments, a lipid to be used in liposomes can be, but is not limited to, one or a plurality of the following: phosphatidylcholine, lipid A, cholesterol, dolichol, sphingosine, sphingomyelin, ceramide, glycosylceramide, cerebroside, sulfatide, phytosphingosine, phosphatidyl-ethanolamine, phosphatidylglycerol, phosphatidylinositol, phosphatidylserine, cardiolipin, phosphatidic acid, and lysophophatides. In certain embodiments, an immunomodulatory agent can be conjugated to the surface of a liposome. In some embodiments, the liposome carries an identical or a non-identical immunomodulatory agent inside. In some embodiments, the liposome surface membrane can be modified with targeting moieties that can selectively deliver the immunomodulatory agent(s) to specific antigen expressing cells.

Figure 4:
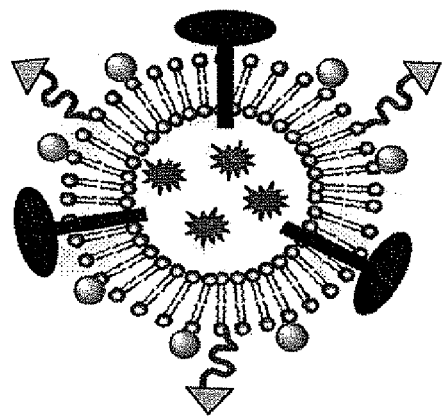
FIG. 4: An exemplary nanoparticle-stabilized liposome nanocarrier with a lipophilic immunomodulatory agent incorporated into the membrane, and a hydrophilic immunomodulating agent encapsulated within the liposome.

In some embodiments, nanoparticle-stabilized liposomes are used to deliver one or a plurality of immunomodulatory agents to cells of the immune system (FIG. 4). By allowing small charged nanoparticles (1 nm-30 nm) to adsorb on liposome surface, liposome-nanoparticle complexes have not only the merits of aforementioned bare liposomes (FIG. 3), but also tunable membrane rigidity and controllable liposome stability. When small charged nanoparticles approach the surface of liposomes carrying either opposite charge or no net charge, electrostatic or charge-dipole interaction between nanoparticles and membrane attracts the nanoparticles to stay on the membrane surface, being partially wrapped by lipid membrane. This induces local membrane bending and globule surface tension of liposomes, both of which enable tuning of membrane rigidity. This aspect is significant for vaccine delivery using liposomes to mimic viruses whose stiffness depends on the composition of other biological components within virus membrane. Moreover, adsorbed nanoparticles form a charged shell which protects liposomes against fusion, thereby enhancing liposome stability. In certain embodiments, small nanoparticles are mixed with liposomes under gentle vortex, and the nanoparticles stick to liposome surface spontaneously. In specific embodiments, small nanoparticles can be, but are not limited to, polymeric nanoparticles, metallic nanoparticles, inorganic or organic nanoparticles, hybrids thereof, and/or combinations thereof.

Figure 5:
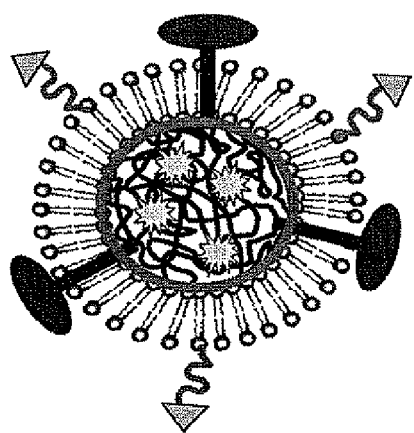
FIG. 5: An exemplary liposome-polymer nanocarrier with a lipophilic immunomodulatory agent incorporated into the membrane, and a hydrophobic immunomodulating agent encapsulated within the polymeric nanoparticle.

In some embodiments, liposome-polymer nanocarriers are used to deliver one or a plurality of immunomodulatory agents to cells of the immune system (FIG. 5). Instead of keeping the liposome interior hollow, hydrophilic immunomodulatory agents can be encapsulated. FIG. 3 shows liposomes that are loaded with di-block copolymer nanoparticles to form liposome-coated polymeric nanocarriers, which have the merits of both liposomes and polymeric nanoparticles, while excluding some of their limitations. In some embodiments, the liposome shell can be used to carry lipophilic or conjugate hydrophilic immunomodulatory agents, and the polymeric core can be used to deliver hydrophobic immunomodulatory agents.

In certain embodiments, pre-formulated polymeric nanoparticles (40 nm-1000 nm) are mixed with small liposomes (20 nm-100 nm) under gentle vortex to induce liposome fusion onto polymeric nanoparticle surface. In specific embodiments, di-block copolymer nanoparticles can be, but are not limited to, one or a plurality of following: poly($_{D,L}$ lactic acid)-block-poly(ethylene glycol) (PLA-b-PEG), poly ($_{D,L}$glycolic acid)-block-poly(ethylene glycol) (PLG-b-PEG), poly($_{D,L}$lactic-co-glycolic acid)-block-poly(ethylene glycol) (PLGA-b-PEG), and poly(ε-caprolactone)-block-poly(ethylene glycol) (PCL-b-PEG).

Figure 6:
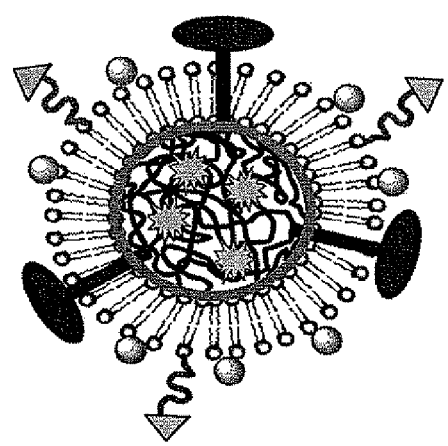
FIG. 6: An exemplary nanoparticle-stabilized liposome-polymer nanocarrier with a lipophilic immunomodulatory agent incorporated into the membrane, and a hydrophobic immunomodulating agent encapsulated within the polymeric nanoparticle.

In some embodiments, nanoparticle-stabilized liposome-polymer nanocarriers are used to deliver one or a plurality of immunomodulatory agents (FIG. 6). By adsorbing small nanoparticles (1 nm-30 nm) to the liposome-polymer nanocarrier surface, the nanocarrier has not only the merit of both aforementioned nanoparticle-stabilized liposomes (FIG. 4) and aforementioned liposome-polymer nanoparticles (FIG. 5), but also tunable membrane rigidity and controllable liposome stability.

Figure 7:
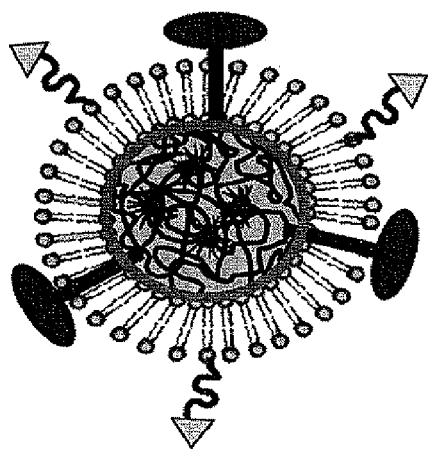
FIG. 7: An exemplary liposome-polymer nanocarrier containing reverse micelles with a lipophilic immunomodulatory agent incorporated into the membrane, and a hydrophilic immunomodulatory agent encapsulated within the reverse micelles.

In some embodiments, liposome-polymer nanocarriers containing reverse micelles are used to deliver one or a plurality of immunomodulatory agents (FIG. 7). Since the aforementioned liposome-polymer nanocarriers (FIGS. 5 and 6) are limited to carry hydrophobic immunomodulatory agents within polymeric nanoparticles, here small reverse micelles (1 nm-20 nm) are formulated to encapsulate hydrophilic immunomodulatory agents and then mixed with the di-block copolymers to formulate polymeric core of liposomes.

In certain embodiments, a hydrophilic immunomodulatory agent to be encapsulated is first incorporated into reverse micelles by mixing with naturally derived and non-toxic amphiphilic entities in a volatile, water-miscible organic solvent. In certain embodiments, the amphiphilic entity can be, but is not limited to, one or a plurality of the following: phosphatidylcholine, lipid A, cholesterol, dolichol, shingosine, sphingomyelin, ceramide, glycosylceramide, cerebroside, sulfatide, phytosphingosine, phosphatidylethanolamine, phosphatidylglycerol, phosphatidylinositol, phosphatidylserine, cardiolipin, phosphatidic acid, and lysophophatides. In some embodiments, the volatile, water-miscible organic solvent can be, but is not limited to: tetrahydrofuran, acetone, acetonitrile, or dimethylformamide. In some embodiments, a biodegradable polymer is added to this mixture after reverse micelle formation is complete. The resulting biodegradable polymer-reverse micelle mixture is combined with a polymer-insoluble hydrophilic non-solvent to form nanoparticles by the rapid diffusion of the solvent into the non-solvent and evaporation of the organic solvent. In certain embodiments, the polymer-insoluble hydrophilic non-solvent can be, but is not limited to one or a plurality of the following: water, ethanol, methanol, and mixtures thereof. Reverse micelle contained polymeric nanoparticles are mixed with lipid molecules to form the aforementioned liposome-polymer complex structure (FIG. 5).

Figure 8:
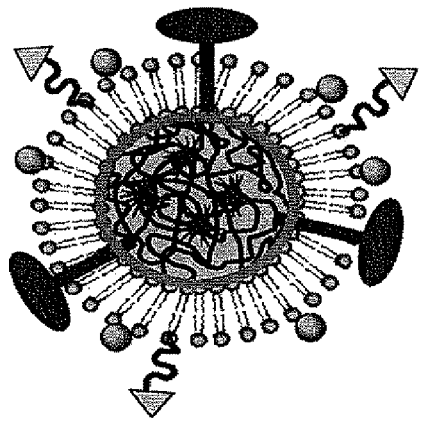
FIG. 8: An exemplary nanoparticle-stabilized liposome-polymer nanocarrier containing reverse micelles with a lipophilic immunomodulatory agent incorporated into the memb Arrowheads: virions in contact zone between macrophage and B cells. (B) MP-IVM of polyclonal and VI10YEN B cells in popliteal LNs. Scale bars: 50 μm. (C) Regional ratios of VI10YEN B cells/control B cells following VSV injection. Results are from 3 movies/group. (D,E) Localization of VI10YEN B cells in popliteal LNs relative to the SCS. **: p<0.01 (one-way ANOVA with Bonferroni's post-test).

In some embodiments, nanoparticle-stabilized liposome-polymer nanocarriers containing reverse micelles are used to deliver one or a plurality of immunomodulatory agents (FIG. 8). By adsorbing small nanoparticles (1 nm-30 nm) to a liposome-polymer nanocarrier surface, the nanocarrier has not only the merit of both aforementioned nanoparticle-stabilized liposomes (FIG. 4) and aforementioned reverse micelle contained liposome-polymer nanoparticles (FIG. 7), but also tunable membrane rigidity and controllable liposome stability.

Figure 9:
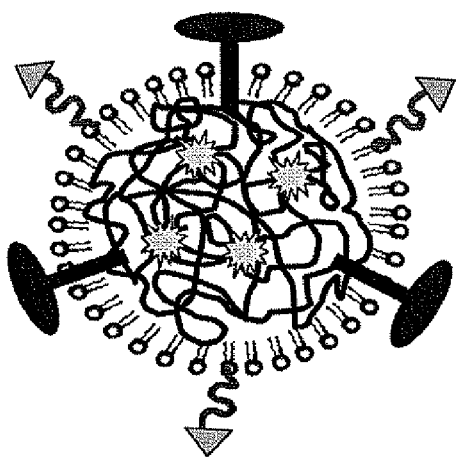

In some embodiments, lipid monolayer stabilized polymeric nanocarriers are used to deliver one or a plurality of immunomodulatory agents (FIG. 9). As compared to aforementioned liposome-polymer nanocarrier (FIGS. 5-8), this system has the merit of simplicity in terms to both agents and manufacturing. In some embodiments, a hydrophobic homopolymer can form the polymeric core in contrast to the di-block copolymer used in FIGS. 5-8, which has both hydrophobic and hydrophilic segments. Lipid-stabilized polymeric nanocarriers can be formed within one single step instead of formulating polymeric nanoparticle and liposome separately followed by fusing them together.

In certain embodiments, a hydrophilic immunomodulatory molecule is first chemically conjugated to lipid headgroup. The conjugate is mixed with a certain ratio of unconjugated lipid molecules in an aqueous solution containing one or more water-miscible solvents. In certain embodiments, the amphiphilic entity can be, but is not limited to, one or a plurality of the following: phosphatidylcholine, lipid A, cholesterol, dolichol, shingosine, sphingomyelin, ceramide, cerebroside, sulfatide, phytosphingosine, phosphatidylethanolamine, glycosylceramide, phosphatidylglycerol, phosphatidylinositol, phosphatidylserine, cardiolipin, phosphatidic acid, and lysophosphatides. In some embodiments, the water miscible solvent can be, but is not limited to: acetone, ethanol, methanol, and isopropyl alcohol. A biodegradable polymeric material is mixed with the hydrophobic immunomodulatory agents to be encapsulated in a water miscible or partially water miscible organic solvent. In specific embodiments, the biodegradable polymer can be, but is not limited to one or a plurality of the following: poly(D,L-lactic acid), poly(D,L-glycolic acid), poly(ε-caprolactone), or their copolymers at various molar ratios. In some embodiments, the water miscible organic solvent can be but is not limited to: acetone, ethanol, methanol, or isopropyl alcohol. In some embodiments, the partially water miscible organic solvent can be, but is not limited to: acetonitrile, tetrahydrofuran, ethyl acetate, isopropyl alcohol, isopropyl acetate, or dimethylformamide. The resulting polymer solution is added to the aqueous solution of conjugated and unconjugated lipid to yield nanoparticles by the rapid diffusion of the organic solvent into the water and evaporation of the organic solvent.

Figure 10:
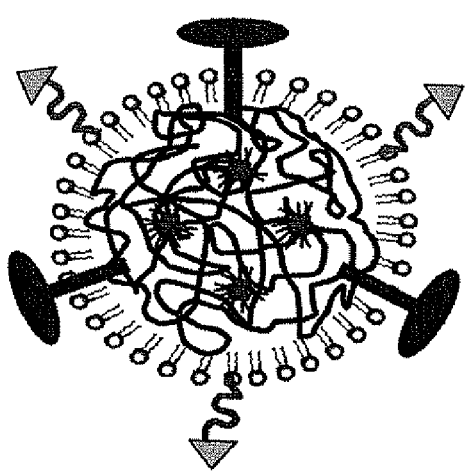

In some embodiments, lipid monolayer stabilized polymeric nanoparticles comprising reverse micelles are used to deliver one or a plurality of immunomodulatory agents (FIG. 10). Since the aforementioned lipid-stabilized polymeric nanocarriers (FIG. 9) are limited to carry hydrophobic immunomodulatory agents, here, small reverse micelles (1 nm-20 nm) are formulated to encapsulate hydrophilic immunomodulatory agents and mixed with biodegradable polymers to form polymeric nanocarrier core.

It is to be understood that the compositions of the invention can be made in any suitable manner, and the invention is in no way limited to compositions that can be produced using the methods described herein. Selection of an appropriate method may require attention to the properties of the particular moieties being associated.

If desired, various methods may be used to separate vaccine nanocarriers with an attached immunomodulatory agent, targeting moiety, immunostimulatory agent, and/or nanoparticle from vaccine nanocarriers to which the immunomodulatory agent, targeting moiety, immunostimulatory agent, and/or nanoparticle has not become attached, or to separate vaccine nanocarriers having different numbers of immunomodulatory agents, targeting moieties, immunostimulatory agents, and/or nanoparticles attached thereto. For example, size exclusion chromatography, agarose gel electrophoresis, or filtration can be used to separate populations of vaccine nanocarriers having different numbers of entities attached thereto and/or to separate vaccine nanocarriers from other entities. Some methods include size-exclusion or anion-exchange chromatography.

In some embodiments, inventive vaccine nanocarriers are manufactured under sterile conditions. This can ensure that resulting vaccines are sterile and non-infectious, thus improving safety when compared to live vaccines. This provides a valuable safety measure, especially when subjects receiving vaccine have immune defects, are suffering from infection, and/or are susceptible to infection.

In some embodiments, inventive vaccine nanocarriers may be lyophilized and stored in suspension or as lyophilized powder depending on the formulation strategy for extended periods without losing activity.

Applications

The compositions and methods described herein can be used to induce, enhance, suppress, direct, or redirect an immune response. The compositions and methods described herein can be used for the prophylaxis and/or treatment of any cancer, infectious disease, metabolic disease, degenerative disease, autoimmune disease, inflammatory disease, immunological disease, or other disorder and/or condition. The compositions and methods described herein can also be used for the treatment of an addiction, such as an addiction to any of the addictive substances described herein. The compositions and methods described herein can also be used for the prophylaxis and/or treatment of a condition resulting from the exposure to a toxin, hazardous substance, environmental toxin, or other harmful agent. Subjects include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

In some embodiments, vaccine nanocarriers in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive vaccine nanocarriers may be used to treat, alleviate, ameliorate, relieve, delay onset of, inhibit progression of, reduce severity of, and/or reduce incidence of one or more symptoms or features of microbial infection (e.g. bacterial infection, fungal infection, viral infection, parasitic infection, etc.).

In one aspect of the invention, a method for the prophylaxis and/or treatment of a disease, disorder, or condition (e.g., a microbial infection) is provided. In some embodiments, the prophylaxis and/or treatment of the disease, disorder, or condition comprises administering a therapeutically effective amount of inventive vaccine nanocarriers to a subject in need thereof, in such amounts and for such time as is necessary to achieve the desired result. In certain embodiments of the present invention a "therapeutically effective amount" of an inventive vaccine nanocarrier is that amount effective for treating, alleviating, ameliorating, relieving, delaying onset of, inhibiting progression of, reducing severity of, and/or reducing incidence of one or more symptoms or features of microbial infection. In some embodiments, a "therapeutically effective amount" is an amount effective to modulate the immune system. Such an amount may be an immunogenic amount, i.e., an amount sufficient to elicit a detectable immune response in a subject, e.g., a detectable antibody response and/or detectable T cell response.

Inventive prophylactic and/or therapeutic protocols involve administering a therapeutically effective amount of one or more inventive vaccine nanocarriers to a healthy subject (e.g., a subject who does not display any symptoms of microbial infection and/or who has not been diagnosed with microbial infection; a subject who has not yet been exposed to a toxin, a subject who has not yet ingested an abused or addictive substance, etc.). For example, healthy individuals may be vaccinated using inventive vaccine nanocarrier(s) prior to development of microbial infection, exposure to the toxin, abused substance, addictive substance, etc. and/or onset of symptoms related thereto; at risk individuals (e.g., patients exposed to individuals suffering from microbial infection, traveling to locations where microbes/toxins are prevalent; etc.) can be treated substantially contemporaneously with (e.g., within 48 hours, within 24 hours, or within 12 hours of) the onset of symptoms of and/or exposure/ingestion. Of course individuals known to have microbial infection, have been exposed to a toxin, or ingested an abused or additive substance may receive treatment at any time.

In some embodiments, inventive prophylactic and/or therapeutic protocols involve administering a therapeutically effective amount of one or more inventive vaccine nanocarriers to a subject such that an immune response is stimulated in both T cells and B cells.

In some embodiments, by combining selected immunomodulatory agents with targeting moieties and immunostimulatory agents for different APCs, immune responses (e.g. effector responses) can be tailored to preferentially elicit the most desirable type of immune response for a given indication, e.g., humoral response, type 1 T cell response, type 2 T cell response, cytotoxic T cell, response, and/or a combination of these responses. Thus, the same platform may be used for a broad range of different clinical applications, including prophylactic vaccines to a host of pathogens as well as immunotherapy of existing diseases, such as infections, autoimmune diseases, and/or cancer.

Cancers include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

Autoimmune diseases include, but are not limited to, rheumatoid arthritis, rheumatic fever, ulcerative colitis, celiac disease, Crohn's disease, inflammatory bowel disease, insulin-dependent diabetes mellitus, diabetes mellitus, juvenile diabetes, spontaneous autoimmune diabetes, gastritis, autoimmune atrophic gastritis, autoimmune hepatitis, thyroiditis, Hashimoto's thyroiditis, autoimmune thyroiditis, insulitis, oophoritis, orchitis, uveitis, phacogenic uveitis, multiple sclerosis, myasthenia gravis, primary myxoedema, thyrotoxicosis, pernicious anemia, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, sympathetic opthalmia, idiopathic thrombocylopenic purpura, idiopathic leucopenia, Siogren's syndrome, Wegener's granulomatosis, poly/dermatomyositis or systemic lupus erythematosus.

Inflammatory disease/disorders include, for example, cardiovascular disease, chronic obstructive pulmonary disease (COPD), bronchiectasis, chronic cholecystitis, tuberculosis, Hashimoto's thyroiditis, sepsis, sarcoidosis, silicosis and other pneumoconioses, and an implanted foreign body in a wound, but are not so limited. As used herein, the term "sepsis" refers to a well-recognized clinical syndrome associated with a host's systemic inflammatory response to microbial invasion. The term "sepsis" as used herein refers to a condition that is typically signaled by fever or hypothermia, tachycardia, and tachypnea, and in severe instances can progress to hypotension, organ dysfunction, and even death.

Pharmaceutical Compositions

The present invention provides novel compositions comprising a therapeutically effective amount of one or more vaccine nanocarriers and one or more pharmaceutically acceptable excipients. In some embodiments, the present invention provides for pharmaceutical compositions comprising inventive vaccine nanocarriers and/or any of the compositions thereof described herein. Such pharmaceutical compositions may optionally comprise one or more additional therapeutically-active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive vaccine nanocarrier comprising at least one immunomodulatory agent and optionally comprising one or more targeting moieties, immunostimulatory agents, and/or nanoparticles.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient(s), and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span® 65], glyceryl monooleate, sorbitan monooleate [Span® 80]), polyoxyethylene esters (e.g. polyoxyethylene monostearate [Myrj®45], polyoxyethylene hydrogenated castor oil, polyethoxylated castor oil, polyoxymethylene stearate, and Solutol), sucrose fatty acid esters, polyethylene glycol fatty acid esters (e.g. Cremophor®), polyoxyethylene ethers, (e.g. polyoxyethylene lauryl ether [Brij® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, vaccine nanocarriers of the invention are mixed with solubilizing agents such as Cremophor®, alcohols, oils, modified oils, glycols, polysorbates, cyclodextrins, polymers, and combinations thereof.

Injectable formulations, for example, sterile injectable aqueous or oleaginous suspensions may be formulated according to the known art using suitable dispersing or wetting agents and suspending agents. A sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing vaccine nanocarriers of this invention with suitable non-irritating excipients such as cocoa butter, polyethylene glycol or a suppository wax which are solid at ambient temperature but liquid at body temperature and therefore melt in the rectum or vaginal cavity and release active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

Active ingredients can be in micro-encapsulated form with one or more excipients as noted above. Solid dosage forms of tablets, dragees, capsules, pills, and granules can be prepared with coatings and shells such as enteric coatings, release controlling coatings and other coatings well known in the pharmaceutical formulating art. In such solid dosage forms, active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of vaccine nanocarriers in accordance with the invention may include ointments, pastes, creams, lotions, gels, powders, solutions, sprays, inhalants and/or patches. Generally, active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 μm to about 7 μm or from about 1 μm to about 6 μm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 μm and at least 95% of the particles by number have a diameter less than 7 μm. Alternatively, at least 95% of the particles by weight have a diameter greater than 1 μm and at least 90% of the particles by number have a diameter less than 6 μm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and the active ingredient may constitute 0.1% to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 μm to about 200 μm.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 μm to about 500 μm. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 µm to about 200 µm, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1%/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

In some embodiments, a therapeutically effective amount of an inventive vaccine nanocarrier composition is delivered to a patient and/or animal prior to, simultaneously with, and/or after diagnosis with a disease, disorder, and/or condition. In some embodiments, a therapeutic amount of an inventive composition is delivered to a patient and/or animal prior to, simultaneously with, and/or after onset of symptoms of a disease, disorder, and/or condition. In some embodiments, the amount of a vaccine nanocarrier is sufficient to treat, alleviate, ameliorate, relieve, delay onset of, inhibit progression of, reduce severity of, and/or reduce incidence of one or more symptoms or features of the disease, disorder, and/or condition. In some embodiments, the amount of a vaccine nanocarrier is sufficient to elicit a detectable immune response in a subject. In some embodiments, the amount of a vaccine nanocarrier is sufficient to elicit a detectable antibody response in a subject. In some embodiments, the amount of a vaccine nanocarrier is sufficient to elicit a detectable T cell response in a subject. In some embodiments, the amount of a vaccine nanocarrier is sufficient to elicit a detectable antibody and T cell response in a subject. In some embodiments, an advantage of the nanocarriers provided is that the nanocarriers can elicit potent responses with a much lower concentration of antigen than required with a conventional vaccine.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered by a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), transdermal, mucosal, nasal, buccal, enteral, sublingual; by intratracheal instillation, bronchial instillation, and/or inhalation; and/or as an oral spray, nasal spray, and/or aerosol. Specifically contemplated routes are oral administration, intravenous injection, intramuscular injection, and/or subcutaneous injection. In some embodiments, inventive vaccine nanocarriers are administered parenterally. In some embodiments, inventive vaccine nanocarriers are administered intravenously. In some embodiments, inventive vaccine nanocarriers are administered orally.

In general the most appropriate route of administration will depend upon a variety of factors including the nature of the vaccine nanocarrier (e.g., its stability in the environment of the gastrointestinal tract), the condition of the subject (e.g., whether the subject is able to tolerate oral administration), etc. The invention encompasses the delivery of the inventive pharmaceutical composition by any appropriate route taking into consideration likely advances in the sciences of drug delivery.

In certain embodiments, the vaccine nanocarriers of the invention may be administered in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the present invention encompasses "therapeutic cocktails" comprising populations of inventive vaccine nanocarriers. In some embodiments, all of the vaccine nanocarriers within a population of vaccine nanocarriers comprise a single species of targeting moiety which can bind to multiple targets (e.g. can bind to both SCS-Mph and FDCs). In some embodiments, different vaccine nanocarriers within a population of vaccine nanocarriers comprise different targeting moieties, and all of the different targeting moieties can bind to the same target. In some embodiments, different vaccine nanocarriers comprise different targeting moieties, and all of the different targeting moieties can bind to different targets. In some embodiments, such different targets may be associated with the same cell type. In some embodiments, such different targets may be associated with different cell types.

Where appropriate, the nanoparticle bioconjugates of the invention may be administered per se (neat) or in the form of a pharmaceutically acceptable salts. When used in medicine the salts should be pharmaceutically acceptable, but non-pharmaceutically acceptable salts may conveniently be used to prepare pharmaceutically acceptable salts thereof and are not excluded from the scope of the invention. Such pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

In some embodiments of the invention, administration of the nanocarriers occurs in a plurality of doses. For example, 2, 3, 4, 5, 6, 7, 8, 9, or 10 doses may be administered to a patient. As-needed dosing is also within the scope of the invention, and may include recurring doses on a regular schedule. The doses may be separated by any interval appropriate to achieve the desired biological effect, such as between 1 day and 1 year, or between 1 day and 1 month, or between 1 day and 1 week.

In some embodiments, the first dose of nanocarriers elicits antigen-specific T cell proliferation and effector differentiation in a subject one week after receiving the dose. Antigen-specific T cell proliferation in the subject may be determined in the subject's peripheral blood lymphocytes by measuring the frequency of specific peptide-MHC tetramer binding T cells using flow cytometry or the uptake of H3-thymidine upon in vitro rechallenge with the antigen. Effector T cell frequency and function in a subject may be determined in peripheral blood lymphocytes by measuring the frequency of cytokine-producing T cells using an ELISPOT assay. In some embodiments, one week after administration of a first dose of nanocarriers to a patient, the blood concentration of antigen-specific T cells in the subject, as determined by the above methods, is greater than 10-fold, or greater than 100-fold, or greater than 1000-fold higher than the concentration of T cells responding to an irrelevant antigen, such as bovine serum albumin, to which the subject has no immunological memory. In some embodiments, such blood concentrations of T cells in the subject are achieved and/or maintained and/or enhanced one week after administration of a first subsequent dose of the nanocarriers, or one week after administration of any (i.e., first, second, third, etc.) subsequent dose of the nanocarriers.

Combination Therapies

It will be appreciated that vaccine nanocarriers and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive vaccine nanocarrier useful for vaccinating against a particular type of microbial infection may be administered concurrently with another agent useful for treating the same microbial infection), or they may achieve different effects (e.g., control of any adverse effects attributed to the vaccine nanocarrier).

In some embodiments, pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive vaccine nanocarrier may be administered concurrently with another therapeutic agent used to treat the same disorder), and/or they may achieve different effects (e.g., control of any adverse effects attributed to the vaccine nanocarrier). In some embodiments, vaccine nanocarriers of the invention are administered with a second therapeutic agent that is approved by the U.S. Food and Drug Administration.

In will further be appreciated that therapeutically active agents utilized in combination may be administered together in a single composition or administered separately in different compositions.

In general, it is expected that agents utilized in combination with be utilized at levels that do not exceed the levels at which they are utilized individually. In some embodiments, the levels utilized in combination will be lower than those utilized individually.

In some embodiments, inventive vaccine nanocarriers may be administered in combination with an agent, including, for example, therapeutic, diagnostic, and/or prophylactic agents. Exemplary agents to be delivered in accordance with the present invention include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof.

In certain embodiments, vaccine nanocarriers which delay the onset and/or progression of a particular microbial infection may be administered in combination with one or more additional therapeutic agents which treat the symptoms of microbial infection. To give but one example, upon exposure to rabies virus, nanocarriers comprising immunomodulatory agents useful for vaccination against rabies virus may be administered in combination with one or more therapeutic agents useful for treatment of symptoms of rabies virus (e.g. antipsychotic agents useful for treatment of paranoia that is symptomatic of rabies virus infection).

In some embodiments, pharmaceutical compositions comprising inventive vaccine nanocarriers comprise less than 50% by weight, less than 40% by weight, less than 30% by weight, less than 20% by weight, less than 15% by weight, less than 10% by weight, less than 5% by weight, less than 1% by weight, or less than 0.5% by weight of an agent to be delivered.

The pharmaceutical compositions provided herein may further comprise one or more additional biologically active substances. Generally, non-limiting examples of such substances include eukaryotic and prokaryotic cells, viruses, vectors, proteins, peptides, nucleic acids, polysaccharides and carbohydrates, lipids, glycoproteins, and synthetic organic and inorganic drugs that exert a biological effect when administered to an animal. Combinations of such biologically active substances are also within the scope of the invention. For ease of reference, and unless indicated otherwise, the term "active substance" is also used to include detectable compounds such as radiopaque compounds including air and barium, magnetic compounds, and the like. The additional active substances can be soluble or insoluble in water. Further examples of biologically active substances include antiangiogenesis factors, antibodies, antimicrobials, antimalarials, amebicides, antiprotazoal, antifungals, antivirals, antineoplastic compounds, growth factors hormones, enzymes, immunoactives, and drugs such as steroids or antibiotics. Non-limiting examples of these and other classes of biologically active substances are listed below and may be encapsulated in the nanoparticle delivery system for the purposes of delivery to targeted cells or tissues.

In some embodiments, vaccine nanocarriers are administered in combination with one or more small molecules and/or organic compounds with pharmaceutical activity. In some embodiments, the agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis, etc.

In certain embodiments, a small molecule agent can be any drug. In some embodiments, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

A more complete listing of classes and specific drugs suitable for use in the present invention may be found in *Pharmaceutical Drugs: Syntheses, Patents, Applications* by Axel Kleemann and Jurgen Engel, Thieme Medical Publishing, 1999, Goodman and Gilman, *The Pharmacological Basis of Therapeutics*. 9th ed. McGraw-Hill 1996, and the *Merck Index An Encyclopedia of Chemicals, Drugs and Biologicals*, Ed. by Budavari et al., CRC Press, 1996. The relevant portions of these texts are incorporated herein by reference.

In some embodiments, vaccine nanocarriers are administered in combination with one or more nucleic acids (e.g. functional RNAs, functional DNAs, etc.) to a specific location such as a tissue, cell, or subcellular locale. For example, inventive vaccine nanocarriers which are used to delay the onset and/or progression of a particular microbial infection may be administered in combination with RNAi agents which reduce expression of microbial proteins. Molecular properties of nucleic acids are described in the section above entitled "Nucleic Acid Targeting Moieties."

In some embodiments, vaccine nanocarriers are administered in combination with one or more proteins or peptides. In some embodiments, the agent to be delivered may be a peptide, hormone, erythropoietin, insulin, cytokine, antigen for vaccination, etc. In some embodiments, the agent to be delivered may be an antibody and/or characteristic portion thereof. Molecular properties of which are described in the section above entitled "Protein Targeting Moieties."

In some embodiments, vaccine nanocarriers are administered in combination with one or more carbohydrates, such as a carbohydrate that is associated with a protein (e.g. glycoprotein, proteogycan, etc.). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol. Molecular properties of carbohydrates are described in the section above entitled "Vaccine Nanocarriers Comprising Carbohydrates."

In some embodiments, vaccine nanocarriers are administered in combination with one or more lipids, such as a lipid that is associated with a protein (e.g. lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g. vitamin E), phospholipids, sphingolipids, and lipoproteins. Molecular properties of lipids are described in the section above entitled "Lipid Vaccine Nanocarriers."

Further examples of therapeutic agents include the following:

Antineoplastic compounds. Examples include nitrosoureas (e.g., carmustine, lomustine, semustine, streptozotocin), methylhydrazines (e.g., procarbazine, dacarbazine).

Steroid hormones. Examples include glucocorticoids, estrogens, progestins, androgens, tetrahydrodesoxycaricosterone, cytokines and growth factors, Asparaginase.

Immunoactive compounds. Examples include immunosuppressives (e.g., pyrimethamine, trimethopterin, penicillamine, cyclosporine, azathioprine) and immunostimulants (e.g., levamisole, diethyl dithiocarbamate, enkephalins, endorphins).

Antimicrobial compounds. Examples include antibiotics, e.g., β-lactam, penicillin, cephalosporins, carbapenims and monobactams, β-lactamase inhibitors, aminoglycosides, macrolides, tetracycline, and spectinomycin.

Antimalarials, amebicides, antiprotazoal, antivirals, and antifungals. Examples include amphotericin β, acyclovir, idoxuridine, ribavirin, trifluridine, vidarbine, gancyclovir. Further antiviral agents include reverse transcriptase inhibitors and nucleoside analogs, e.g. ddI, ddC, 3TC, ddA, AZT; protease inhibitors, e.g., Invirase, ABT-538; inhibitors of in RNA processing, e.g., ribavirin.

Parasiticides, antihalmintics, radiopharmaceutics, gastrointestinal drugs, hematologic compounds, and immunoglobulins. Blood clotting proteins, e.g., antihemophilic factor and factor IX complex. Anticoagulants, e.g., dicumarol, and heparin Na. Fibrolysin inhibitors, such as tranexamic acid.

Cardiovascular Drugs and peripheral antiadrenergic drugs. Centrally acting antihypertensive drugs, e.g., methyldopa, methyldopa HCl, Antihypertensive direct vasodilators, e.g., diazoxide, hydralazine HCl. Drugs affecting renin-angiotensin system. Peripheral vasodilators such as phentolamine. Antianginal drugs and cardiac glycosides. Inodilators, e.g., aminone, milrinone, enoximone, fenoximone, imazodan, and sulmazole. Antidysrhythmics, calcium entry blockers, and drugs affecting blood lipids, e.g., ranitidine, bosentan, rezulin.

Respiratory Drugs. Sypathomimetic drugs, e.g., albuterol, bitolterol mesylate, dobutamine HCl, dopamine HCl, ephedrine So, epinephrine, fenfluramine HCl, isoproterenol HCl, methoxamine HCl, norepinephrine bitartrate, phenylephrine HCl, ritodrine HCl.

Cholinomimetic drugs, e.g., acetylcholine Cl. Anticholinesterases, e.g., edrophonium Cl. Cholinesterase reactivators. Adrenergic blocking drugs, e.g., acebutolol HCl, atenolol, esmolol HCl, labetalol HCl, metoprolol, nadolol, phentolamine mesylate, and propanolol HCl. Antimuscarinic drugs, e.g., anisotropine methylbromide, atropine S04, clinidium Br, glycopyrrolate, ipratropiur Br, and scopolamine HBr.

Neurotransmitters and neurotransmitter agents, e.g., acetylcholine, adenosine, adenosine triphosphate. Amino acid neurotransmitters, e.g., excitatory amino acids, GABA, glycine. Biogenic amine neurotransmitters, e.g., dopamine, epinephrine, histamine, norepinephrine, octopamine, serotonin, tyramine. Neuropeptides, nitric oxide, and K+ channel toxins. Antiparkinson drugs. Examples include amaltidine HCl, benztropine mesylate, e.g., carbidopa.

Hormones. Pituitary hormones, e.g., chorionic gonadotropin, cosyntropin, menotropins, somatotropin, iorticotropin, protirelin, thyrotropin, vasopressin, and lypressin. Adrenal hormones, e.g., beclomethasone dipropionate, betamethasone, dexamethasone, and triamcinolone. Pancreatic hormones, e.g., glucagon, and insulin. Parathyroid hormone, e.g., dihydrochysterol. Thyroid hormones, e.g., calcitonin etidronate disodium, levothyroxine Na, liothyronine Na, liotrix, thyroglobulin, teriparatide acetate. Antithyroid drugs. Estrogenic hormones. Progestins and antagonists, and hormonal contraceptives. Testicular hormones. Gastrointestinal hormones, e.g., cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, sincalide.

Enzymes. Examples include hyaluronidase, streptokinase, tissue plasminogen activator, urokinase, PGE-adenosine deaminase.

Peptides and proteins. The nanoparticle bioconjugate system may encapsulate peptides/proteins and/or may have surfaces functionalized with peptides/proteins. Examples of peptides and proteins include ankyrins, arrestins, bacterial membrane proteins, clathrin, connexins, ovalbumin, viral proteins from capsid or the envelop like HA or VSVG, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor α, transforming growth factor β, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocye function-associated antigen, intercellular adhesion molecule, vascular cell adhesion molecule, Thy-1, antiporters, CA-15-3 antigen, fibronectins, laminin, myelin-associated glycoprotein, GAP, GAP-43.

Cytokines and Cytokine Receptors. Examples of cytokines and receptors thereof which may be delivered via the nanoparticle carriers of the present invention include, but are not limited to: Interleulun-1 (IL-1), IL-2, IL-3, IL-4, IL-5, IL-6, IL-7, IL-8, IL-9, IL-10, IL11, IL-12, IL-13, IL-14, L-15, IL-16, IL-17, IL-18, IL-1 receptor, IL-2 receptor, IL-3 receptor, IL-4 receptor, IL-5 receptor, L-6 receptor, L-7 receptor, IL-8 receptor, IL-9 receptor, IL-10 receptor, IL-11 receptor, IL-12 receptor, IL-13 receptor, L-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor β, tumor necrosis factor, lymphotoxin, Fas, granulocyte colony stimulating factor, granulocyte macrophage colony stimulating factor, interferon α, interferon β, interferon γ.

Growth Factors, Protein Hormones, and receptors thereof. Examples include erythropoietin, angiogenin, hepatocyte growth factor, fibroblast growth factor, keratinocyte growth factor, nerve growth factor, tumor growth factor α, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II.

Chemokines and receptors thereof. Examples include: ENA-78, ELC, GRO-α, GRO-β, GRO-γ, HRG, LIF, IP-10, MCP-1, MCP-2, MCP-3, MCP-4, MIP-1α, MIP-1β, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, α-chemokine receptors: CXCR1, CXCR2, CXCR3, CXCR4, CXCRS, CXCR6, CXCR7 β-chemokine receptors: CCR1, CCR2, CCR3, CCR4, CCR5, CCR6, CCR7.

Antibodies. Examples of antibodies which may be used as targeting ligand via the nanoparticle carriers of the present invention include: (a) anti-cluster of differentiation antigen CD-1 through CD-166 and the ligands or counter receptors for these molecules; (b) anti-cytokine antibodies, e.g., anti-IL-1 through anti-IL-18 and the receptors for these molecules; (c) anti-immune receptor antibodies, antibodies against T cell receptors, major histocompatibility complexes I and II, B cell receptors, selectin killer inhibitory receptors, killer activating receptors, OX-40, MadCAM-1, Gly-CAM1, integrins, cadherens, sialoadherens, Fas, CTLA-4, Fcγ-receptors, Fcα-receptors, Fcε-receptors, Fcμ-receptors, and their ligands; (d) anti-metalloproteinase antibodies, e.g., collagenase, MMP-1 through MMP-8, TIMP-1, TIMP-2; anti-cell lysislproinflammatory molecules, e.g., perforin, complement components, prostanoids, nitron oxide, thromboxanes; and (e) anti-adhesion molecules, e.g., carcioembryonic antigens, lamins, fibronectins.

Specific examples of known therapeutics which may be delivered via a nanoparticle delivery of the invention include, but are not limited to: (a) Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb); (b) Ceclor, Lorabid, Dynabac, Prozac, Darvon, Permax, Zyprexa, Humalog, Axid, Gemzar, Evista (Eli Lily); (c) VasotecNaseretic, Mevacor, Zocor, Prinivil/Prinizide, Plendil, CozaarlHyzaar, Pepcid, Prilosec, Primaxin, Noroxin, Recombivax HB, Varivax, TimopticlXE, Trusopt, Proscar, Fosamax, Sinemet, Crixivan, Propecia, Vioxx, Singulair, Maxalt, Ivermectin (Merck & Co.); (d) Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer); (e) Vantin, Rescriptor, Vistide, Genotropin, Micronase/Glyn./Glyb., Fragrnin, Total Medrol, Xanaxlalprazolam, Sermion, Halcionitriazolam, Freedox, Dostinex, Edronax, Mirapex, Pharmorubicin, Adriamycin, Carnptosar, Remisar, Depo-Provera, Caverject, Detrusitol, Estring, Healon, Xalatan, Rogaine (Pharmacia & Upjohn); (f) Lopid, Accrupil, Dilantin, Cognex, Neurontin, Loestrin, Dilzem, Fempatch, Estrostep, Rezulin, Lipitor, Omnicef, FemHRT, Suramin, and Clinafloxacin (Warner Lambert).

Those skilled in the art will recognize that this is an exemplary, not comprehensive, list of therapeutic, diagnostic, and/or prophylactic agents that can be delivered in combination with the vaccine nanocarriers of the present invention. Any therapeutic, diagnostic, and/or prophylactic agent may be administered with vaccine nanocarriers in accordance with the present invention.

Kits

The invention provides a variety of kits comprising one or more of the nanocarriers of the invention. For example, the invention provides a kit comprising an inventive vaccine nanocarrier and instructions for use. A kit may comprise multiple different vaccine nanocarriers. A kit may comprise any of a number of additional components or reagents in any combination. All of the various combinations are not set forth explicitly but each combination is included in the scope of the invention.

According to certain embodiments of the invention, a kit may include, for example, (i) a vaccine nanocarrier comprising at least one immunomodulatory agent, wherein the at least one immunomodulatory agent is capable of stimulating both a T cell and B cell response; (ii) instructions for administering the vaccine nanocarrier to a subject in need thereof.

In certain embodiments, a kit may include, for example, (i) a vaccine nanocarrier comprising at least one immunomodulatory agent, wherein the at least one immunomodulatory agent is capable of stimulating both a T cell and B cell response, at least one targeting moiety, and/or at least one immunomodulatory agent; (ii) instructions for administering the vaccine nanocarrier to a subject in need thereof.

In certain embodiments, a kit may include, for example, (i) at least one immunomodulatory agent, wherein the at least one immunomodulatory agent is capable of stimulating both a T cell and B cell response; (ii) at least one targeting moiety; (iii) at least one immunostimulatory agent; (iv) a polymeric matrix precursor; (v) lipids and amphiphilic entities; (vi) instructions for assembling inventive vaccine nanocarriers from individual components (i)-(v).

In some embodiments, the kit comprises an inventive nanocarrier and instructions for mixing. Such kits, in some embodiments, also include an immunostimulatory agent and/or an immunomodulatory agent (e.g., a B cell or T cell antigen) The nanocarrier of such kits may comprise an immunomodulatory agent (e.g., a T cell antigen, such as a universal T cell antigen) and/or a targeting moiety. The T cell antigen and/or the targeting moiety may be on the surface of the nanocarrier. In some embodiments, the immunomodulatory agent and the antigen are the same. In some embodiments, they are different.

Kits typically include instructions for use of inventive vaccine nanocarriers. Instructions may, for example, comprise protocols and/or describe conditions for production of vaccine nanocarriers, administration of vaccine nanocarriers to a subject in need thereof, etc. Kits generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

EXEMPLIFICATION

Example 1

Subcapsular Sinus Macrophages in Lymph Nodes Clear Lymph-Borne Viruses and Present them to Antiviral B Cells Materials and Methods Method Summary VSV-IND and VSV-NJ virions were purified from culture supernatants of infected BSRT7 cells and used either unmodified or fluorescently labeled with Alexa-568 (red) or Alexa-488 (green). Fluorescent viruses used for tissue imaging were UV-irradiated to prevent generation of non-fluorescent progeny. Fluorescent labeling or UV-irradiation of VSV-IND particles did not affect their antigenicity or their ability to elicit a calcium flux in VI10YEN cells (not shown). Following fluorescent virus injection into footpads, draining popliteal LNs were harvested for analysis by electron microscopy or to generate frozen sections for immunostaining and confocal microscopy. To image adoptively transferred B cells in LNs, VI10YEN and wildtype B cells were fluorescently labeled and co-transferred by i.v. injection into wildtype or mutant recipient mice. 18 hours later, when B cells had homed to B cell follicles, mice were injected with labeled or unlabeled VSV in the right footpad. At different time intervals thereafter, the draining popliteal LN was observed by MP-IVM or harvested for confocal microscopy or for flow cytometry to analyze the activation state of virus-specific and control B cells. In some experiments, macrophages in the popliteal LN were depleted by sc injections of CLL, and animals were used for experiments 7-10 days later. MP-IVM, electron microscopy, immunohistochemistry and flow cytometry for various markers was performed on LNs with and without prior CLL treatment. VSV propagation from the footpad injection site to the blood and other organs was assessed by injecting a defined amount of live VSV into footpads followed by tissue harvest at two hours or six hours after VSV injection. To measure viral titers, tissues were homogenized and used in plaque assays. Some viral propagation experiments were performed after cannulation of the thoracic duct.

Mice and Antibodies

C57BL/6 and BALB/c mice were purchased from Taconic Farms (Germantown, N.Y.). VI10YEN (Hangartner et al., 2003, *Proc. Natl. Acad. Sci., USA*, 100:12883; incorporated herein by reference), $C3^{-/-}$ (Wessels et al., 1995, *Proc. Natl. Acad. Sci., USA*, 92:11490; incorporated herein by reference), MHCII-EGFP (Boes et al., 2002, *Nature*, 418: 983; incorporated herein by reference), Act-EGFP (Wright et al., 2001, *Blood*, 97:2278), and DH-LMP2A mice (Casola et al., 2004, *Nat. Immunol.*, 5:317; incorporated herein by reference) were bred in barrier animal facilities at Harvard Medical School and the Immune Disease Institute (IDI). Radiation chimeras were generated by irradiation of Act(EGFP) mice with two doses of 650 rad and reconstitution with C57BL/6 bone marrow, and were allowed to reconstitute for 8 weeks prior to use. In some experiments, SCS macrophages were depleted by footpad injections of 30 μl clodronate liposomes (CLL), 7-10 days prior to the experiment.

Clodronate was a gift of Roche Diagnostics GmbH, Mannheim, Germany. Other reagents for preparation of liposomes were: Phosphatidylcholine (LIPOID E PC, Lipoid GmbH, Ludwigshafen, Germany) and cholesterol (Sigma-Aldrich).

Mice were housed under specific pathogen-free and antiviral antibody-free conditions in accordance with National Institutes of Health guidelines. All experimental animal procedures were approved by the Institutional Animal Committees of Harvard Medical School and the IDI.

Antibodies were purchased from BD Biosciences (San Jose, Calif.), except anti-B220-Alexa647 (Invitrogen-Caltag), anti-LYVE-1 (Millipore-Upstate), goat-anti-rabbit-APC (Invitrogen), goat-anti-GFP-FITC (Rockland), anti-FITC-Alexa488 (Invitrogen), and Fab anti-IgM-FITC (Jackson Immunoresearch). The following antibodies were purchased from AbD-Serotec: anti-CD68-Alexa647, anti-CD11b-Alexa647, F4/80-Alexa647, anti-CD169-FITC (3D6). The anti-idiotypic antibody 35.61 for detection of the VI10 BCR in VI10YEN mice (Hangartner et al., 2003, *Proc. Natl. Acad. Sci., USA*, 100:12883; incorporated herein by reference) was produced from hybridoma supernatants according to standard methods.

Flow Cytometry

Flow cytometric analysis of blood samples was performed after retro-orbital phlebotomy of mice and lysis of erythrocytes with ACK buffer (0.15 M $NH_4Cl$, 1 mM $KHCO_3$, 0.1 mM EDTA (disodium salt), pH 7.2). Single-cell suspensions of LNs and spleens for flow cytometry were generated by careful mincing of tissues and subsequent digestion at 37° C. for 40 minutes in DMEM (Invitrogen-Gibco) in the presence of 250 μg/ml liberase CI (Roche) plus 50 μg/ml DNase-I (Roche). After 20 minutes of digestion, samples were vigorously passed through an 18 G needle to ensure complete organ dissociation. All flow cytometric analyses were performed in FACS buffer containing PBS with 2 mM EDTA and 2% FBS (Invitrogen-GIBCO) on a FACScalibur (BD Pharmingen), and analyzed by FlowJo software (Treestar Inc., Ashland, Oreg.). For calcium flux, cells were labeled with 4 μM Fluo-LOJO (Teflabs) in DMEM containing 10% FCS for 90 minutes at 37° C. Cells were spun through FCS and used immediately.

Viruses and VSV Plaque Assay

VSV serotypes Indiana (VSV-IND, Mudd-Summers derived clone, in vitro rescued (Whelan et al., 1995, *Proc. Natl. Acad. Sci., USA*, 92:8388; incorporated herein by reference) and plaque purified) or New Jersey (VSV-NJ, Pringle Isolate, plaque purified) were propagated at a MOI of 0.01 on BSRT7 cells. Supernatants of infected cells were cleared from cell debris by centrifugation at 2000×g, filtered through 0.45 μm sterile filters and subjected to ultracentrifugation at 40,000×g for 90 minutes. Pellets were resuspended in PBS and purified by ultracentrifugation (157,000×g, 60 minutes) through a cushion of 10% sucrose in NTE (0.5 mM NaCl, 10 mM Tris-HCl pH 7.5, 5 mM EDTA pH 8). After resuspension in PBS overnight, virus protein was quantified by BCA assay (Pierce), and infectivity was quantified by plaque assay. Some batches were labeled with carboxylic acid succinimidyl esters of AlexaFluor-488 or AlexaFluor-568 (Invitrogen-Molecular Probes) at a 104-105-fold molar excess of Alexa dye over virus particles. Unconjugated dye was removed by ultracentrifugation through 10% sucrose in NTE, pellets resuspended in PBS and stored frozen. Infectivity of VSV preparations was quantified by plaque assay on green monkey kidney cells (Vero). VSV titers from organs of infected mice were determined similarly, after homogenization of the organs with a Potter-Elvejhem homogenizer. When necessary, during viral preparation, the approximately 4 ml supernatants from the 157,000×g ultracentrifugation were collected and concentrated with a 10,000 MWCO Amicon Ultra (Millipore). In order to account for residual infectivity in concentrated supernatants, VSV stocks were diluted to levels of infectivity equal to that of the concentrated supernatants and calcium flux in VI10YEN B cells was compared over further 100 fold dilutions of VSV and supernatant. UV-inactivated, AlexaFluor-568 labeled Adenovirus 5 (AdV5) was generated following standard procedures (Leopold et al., 1998, *Human Gene Therapy*, 9:367; incorporated herein by reference). All infectious work was performed in designated BL2+ workspaces, in accordance with institutional guidelines, and approved by the Harvard Committee on Microbiological Safety.

VSV Neutralization Assay

Serum of immunized mice was prediluted 40-fold in MEM containing 2% FCS. Serial two-fold dilutions were mixed with equal volumes of VSV (500 pfu/ml) and incubated for 90 minutes at 37° C. in 5% $CO_2$. 100 μl of serum-virus mixture was transferred onto Vero cell monolayers in 96-well plates and incubated for 1 hour at 37° C. The monolayers were overlaid with 100 μl DMEM containing 1% methylcellulose and incubated for 24 hours at 37° C. Subsequently, the overlay was discarded, and the monolayer was fixed and stained with 0.5% crystal violet. The highest dilution of serum that reduced the number of plaques by 50% was taken as titer. To determine IgG titers, undiluted serum was pretreated with an equal volume of 0.1 mM β-mercaptoethanol in saline.

Adhesion Assays 96-well plates (Corning) were coated overnight with dilutions of recombinant murine VCAM-1-Fc or ICAM-1-Fc (R&D systems), or purified VSV-IND in PBS in triplicates. Negative control wells were coated with 4% BSA, positive control wells were coated with 1 mg/ml poly-L-lysine. Plates were blocked for 1-2 h at 4° C. with Hanks Balanced Salt Solution (HBSS)/1% BSA and washed. Naïve B cells from VI10YEN or C57BL/6 mice were negatively selected by magnetic cell separation using CD43 magnetic beads (Miltenyi, Bergisch Gladbach, Germany) and added to the plates at $3\times10^5$/well in HBSS with 1% BSA, 1 mM $Ca_2^+$ and 1 mM $Mg_2^+$ in the presence or absence of UV-inactivated VSV-IND (MOI of 1000) for 30 minutes at 37° C. After gentle washing (3 times in HBSS with 1% BSA), plates were fixed for 10 minutes with PBS/10% glutaraldehyde, stained for 45 minutes with 0.5% crystal violet/20% methanol, and washed in water. Dye was eluted by addition of 1% SDS and absorbance at 570 nm was spectrophotometrically determined (SpectraMax340PC microplate reader and SoftmaxPro 3.1.2 software, Molecular Devices Corporation) after 30 minutes.

Confocal Microscopy

For some analyses, C57BL/6 mice were injected into both hind footpads with 20 µg AlexaFluor-568 or AlexaFluor-488 labeled VSV-IND or VSV-NJ for 30 minutes. For other experiments, mice were transfused with $1\times10^7$ negatively selected naïve B cells from VI10YEN×MHCII-EGFP mice one day prior to the experiment. At predetermined time points, popliteal LNs were fixed in situ by footpad injections of phosphate buffered L-lysine with 1% paraformaldehyde/periodate (PLP). After removal of popliteal LNs and 3-5 hours incubation in PLP at 4° C., popliteal LNs were washed in 0.1 M PBS, pH 7.2 and cryoprotected by an ascending series of 10%, 20%, and 30% sucrose in PBS. Samples were snap-frozen in TBS tissue freezing liquid (Triangle Biomedical Sciences, Durham N.C.) and stored at −80° C. Sections of 40 µm thickness were mounted on Superfrost Plus slides (Fisherbrand) and stained with fluorescent antibodies in a humidified chamber after Fc receptor blockade with 1 µg/ml antibody 2.4G2 (BD Pharmingen). Samples were mounted in Fluor Save reagent solution (EMD-Calbiochem) and stored at 4° C. until analysis. Images were collected with a BioRad confocal microscopy system using an Olympus BX50WI microscope and 10×/0.4 or 60×/1.2W objectives. Images were analyzed using LaserSharp2000 software (BioRad Cell Science, Hemel Hempstead, Great Britain) and Photoshop CS (Adobe). Quantification of T/B border localized B cells was done by counting cells that were within 50 µm of the T/B border, as denoted by B220 counterstain, any cells localized in more central regions were considered follicular.

Electron Microscopy

Popliteal LNs were fixed in situ by footpad injection of 2% formaldehyde and 2.5% glutaraldehyde in 0.1 M sodium cacodylate buffer, pH 7.4. The LNs were excised and immersed in the same buffer overnight at 4° C., washed in cacodylate buffer, and osmicated with 1% Osmium tetroxide/ 1.5% Potassium ferrocyanide (in water) for 1 hour at room temperature in the dark. After washing in water, samples were washed 3-4 times in 0.05 M malelate buffer pH 5.15. Samples were counterstained for 2 hours in 1% uranyl acetate in maleate buffer and washed three times in water. Samples were dehydrated by incubation for 15 minutes in dilutions of ethanol in water (70%-90%-100%), incubated in propylene oxide for 1 hour, and transferred into Epon mixed 1:1 with propylene oxide RT overnight. Samples were moved to embedding mold filled with freshly mixed Epon, and heated for 24-48 hours at 60° C. for polymerization. Samples were analyzed on a Tecnai G2 Spirit BioTWIN electron microscope at the Harvard Medical School EM facility.

Intravital Multiphoton Microscopy (MP-IVM) of the Popliteal LN

Naïve B cells were negatively selected by magnetic isolation using CD43 beads (Miltenyi). VI10YEN B cells were labeled for 20 minutes at 37° C. with 10 µM 5-(and 6-)-(((4-chloromethyl)benzoyl)amino)tetramethylrhodamine (CMTMR; Invitrogen), C57BL/6 B cells were labeled for 25 minutes at 37° C. with 10 µM 7-amino-4-chloromethylcoumarin (CMAC; Invitrogen). In some experiments, labels were swapped between wildtype and VI10YEN B cells to exclude unspecific dye effects. 5-6×10⁶ B cells of each population were mixed and adoptively transferred by tail vein injection into C57BL/6 recipient mice one day before analysis. In some experiments, recipient C57BL/6 mice had received an injection of 30 µl CLL into the hind footpad 7-10 days before the experiment to eliminate SCS macrophages (Delemarre et al., 1990, *J. Leukoc. Biol.*, 47:251; incorporated herein by reference). Eighteen hours following adoptive B cell transfer, recipient mice were anaesthetized by intraperitoneal injection on of ketamine (50 mg/kg) and xylazine (10 mg/kg). The right popliteal LN was prepared microsurgically for MP-IVM and positioned on a custom-built microscope stage as described (Mempel et al., 2004, *Nature*, 427:154; incorporated herein by reference). Care was taken to spare blood vessels and afferent lymph vessels. The exposed LN was submerged in normal saline and covered with a glass coverslip. A thermocouple was placed next to the LN to monitor local temperature, which was maintained at 36-38° C. MP-IVM was performed on a BioRad 2100 MP system at an excitation wavelength of 800 nm, from a tunable MaiTai Ti:sapphire laser (Spectra-Physics). Fluorescently labeled VSV (20 µg in 20 µl) was injected through a 31 G needle into the right hind footpad of recipient mice concomitant to observation. For four-dimensional off-line analysis of cell migration, stacks of 11 optical x-y sections with 4 µm z spacing were acquired every 15 seconds with electronic zooming to 1.8×-3× through a 20×/0.95 water immersion objective (Olympus). Emitted fluorescence and second harmonic signals were detected through 400/40 nm, 450/80 nm, 525/50 nm, and 630/120 nm band-pass filters with non-descanned detectors to generate three-color images. Sequences of image stacks were transformed into volume-rendered, four-dimensional time-lapse movies using Volocity software (Improvision). 3D instantaneous velocities were determined by semi-automated cell tracking with Volocity and computational analysis by Matlab (Mathworks). Accumulation of cells at the SCS was determined by manual movie analysis performed by blinded observers. Every 2 minutes, the VI10YEN B cells and polyclonal B cells were counted at the SCS, in the superficial follicle (<50 µm distance from the SCS) and the deep follicle (>50 µm distance from the SCS), and ratios of VI10YEN/polyclonal B cells was expressed for each compartment in the entire 30 minute movie.

Thoracic Duct Cannulation

Figure 11A:
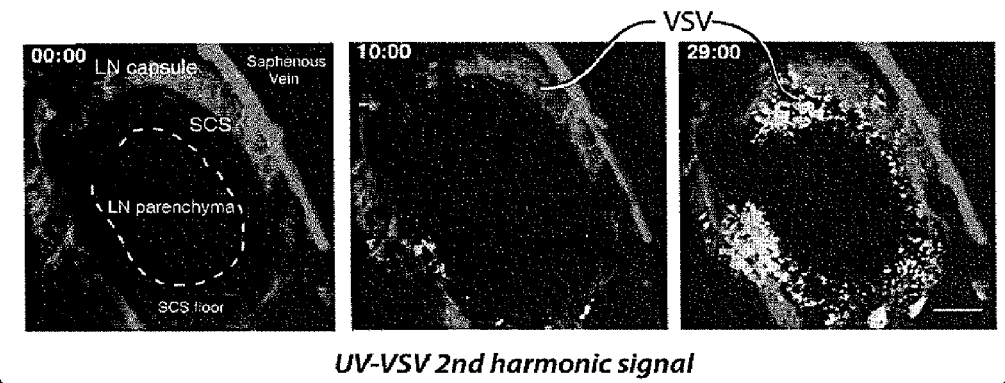
Figure 11B:
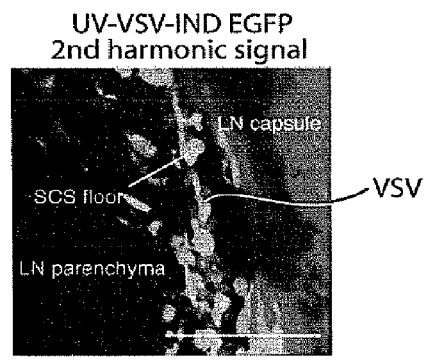
Figure 11C:
Figure 11D:
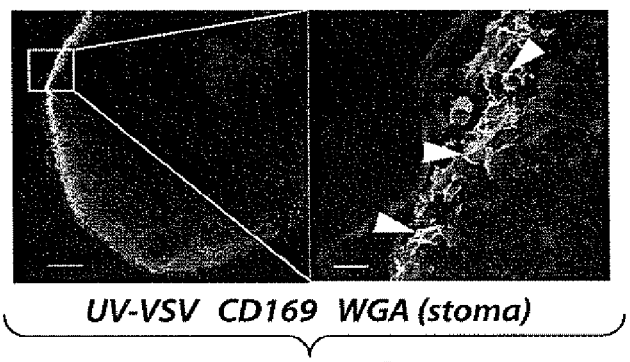
Figure 11E:
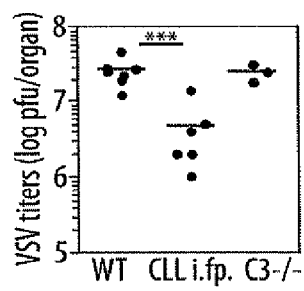
Figure 11F:
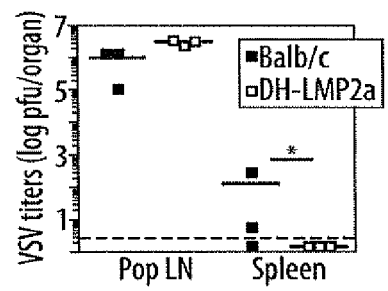
Figure 11G:
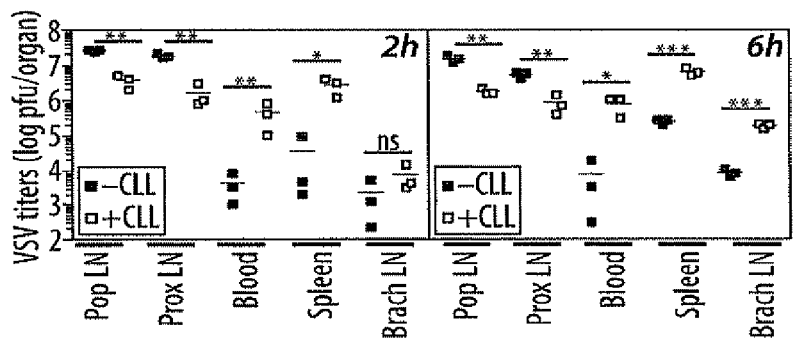
Figure 11H:
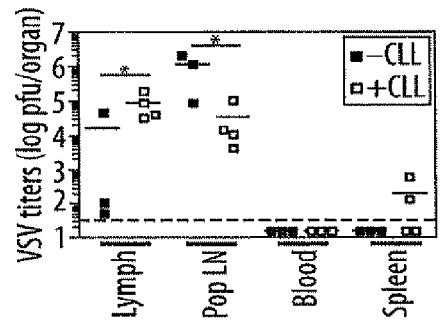
Figure 12A:
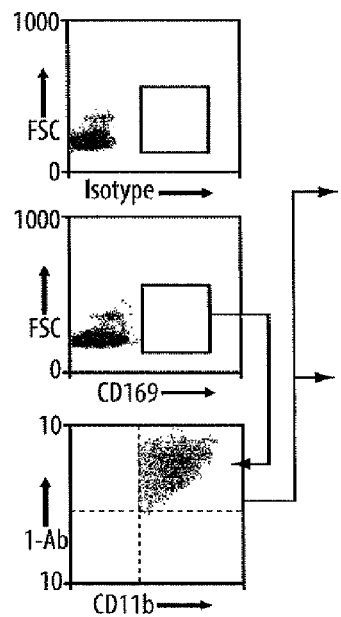
Figure 12B:
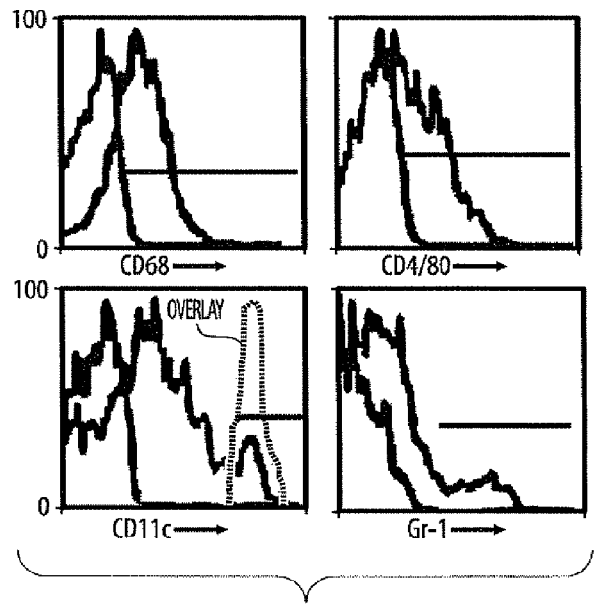
Figure 12C:
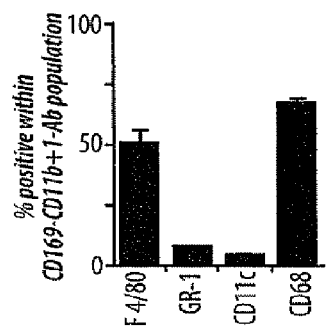
Figure 12D:
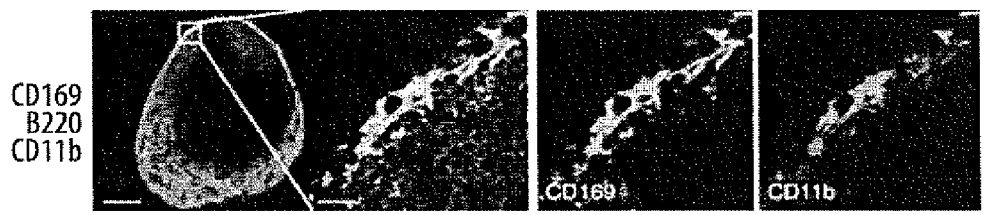
Figure 12E:
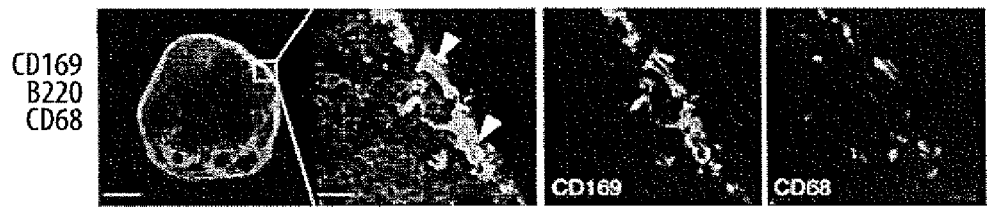
Figure 12F:
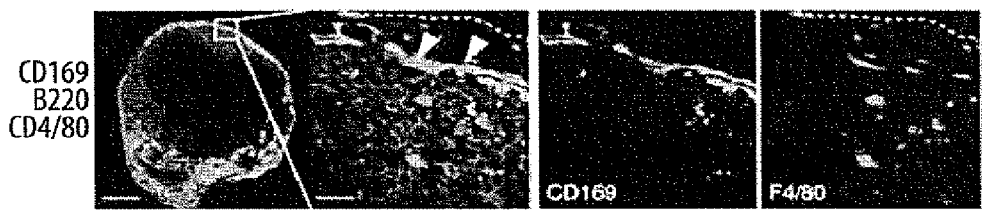
Figure 12G:
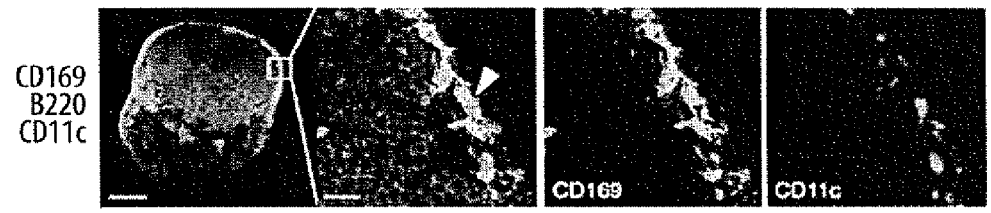
Figure 13A:
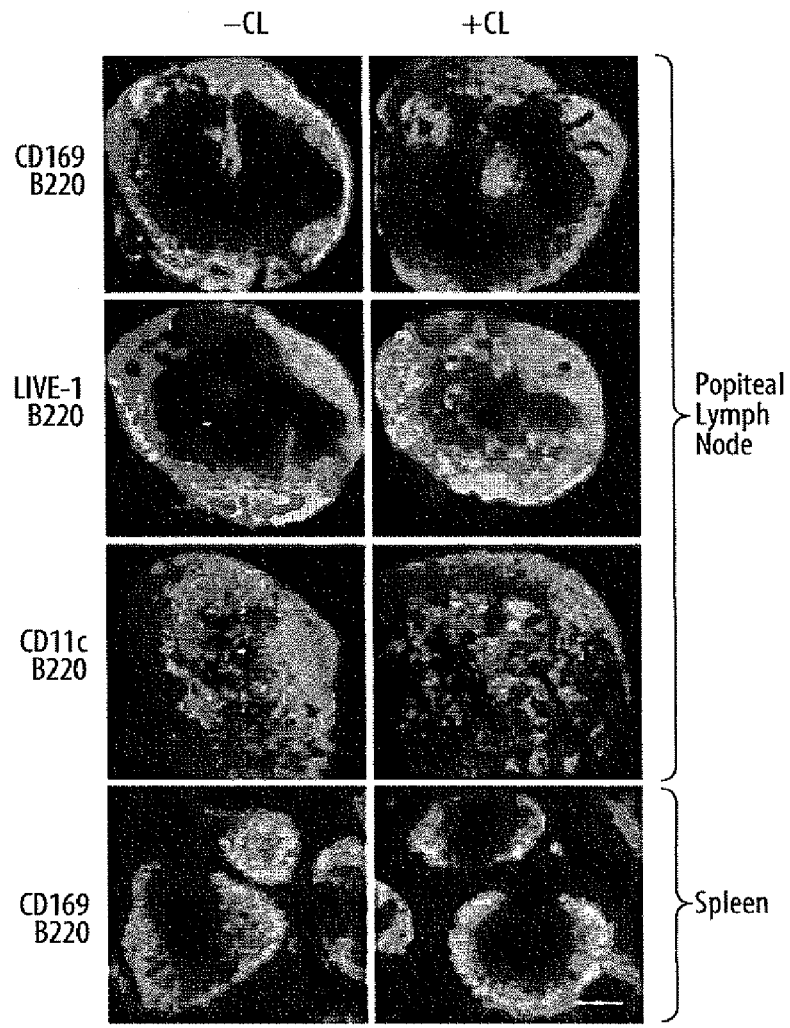
Figure 13B:
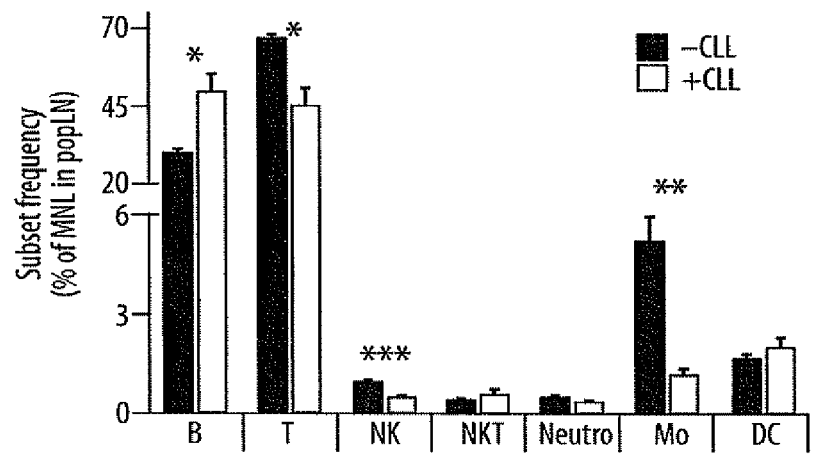
Figure 13C:
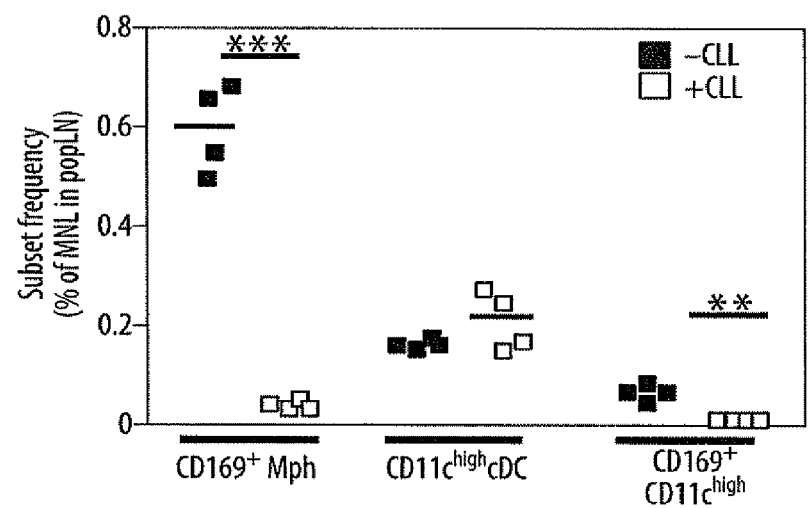
Figure 13D:
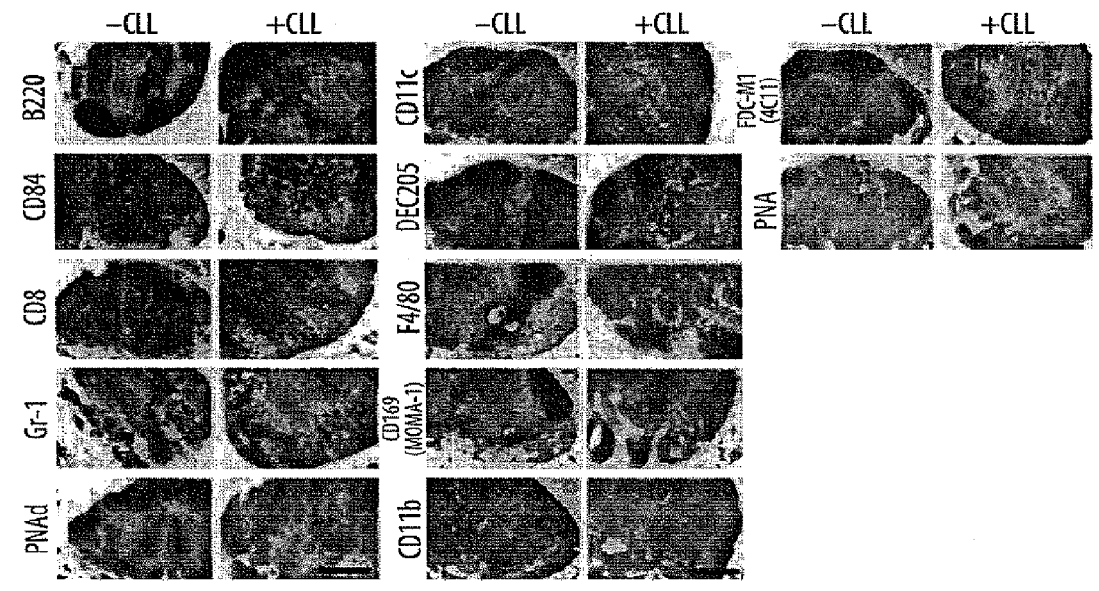
Figure 13E:
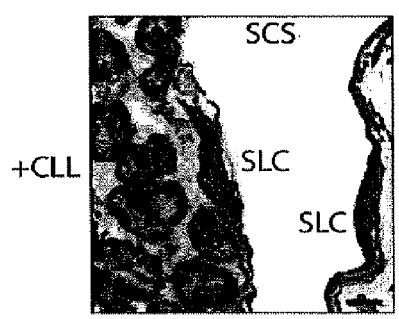

For thoracic duct cannulation, mice received 200 µl olive oil p.o. 30 minutes prior to cannulation to facilitate visualization of the lymph vessels. Animals were then anesthetized with xylazine (10 mg/kg) and ketamine HCl (50 mg/kg). A polyethylene catheter (PE-10) was inserted into the right jugular vein for continuous infusion (2 ml/hour) of Ringer's lactate (Abbott Laboratories, North Chicago, Ill.) containing 1 U/ml heparin (American Pharmaceutical partners, Los Angeles, Calif.). Using a dissecting microscope, the TD was exposed through a left subcostal incision. Silastic® silicon tubing (0.012" I.D., Dow Corning, Midland, USA) was flushed with heparinised (50 U/ml) phosphate-buffered saline (DPBS, Mediatech, Herndon, Va.), inserted into the cisterna chyli through an approximately 0.3 mm incision and fixed with isobutyl cyanoacrylate monomer (Nexaband®, Abbott Laboratories). The remaining part of the tubing was exteriorized through the posterior abdominal wall. Subsequently, the abdominal incision was closed using a 6-0 nonabsorbable running suture (Sofsilk, Tyco Healthcare Group, Norwalk, Colo.). Following a 30 minute equilibration of lymph flow, animals were footpad injected with 108 pfu of VSV-IND and lymph samples were collected on ice for 6 hours. Lymph and organs were taken after 6 hours of thoracic duct lymph collection and plagued as described above. Lymph and organs were plagued as described above. In some experiments the draining popliteal and paraaortic lymph nodes were surgically excised and the surrounding lymph vessels cauterized to prevent lymph borne viral access to the blood.

Results and Discussion

Lymph nodes (LNs) prevent systemic dissemination of pathogens, such as viruses that enter the body's surfaces, from peripheral sites of infection. They are also the staging ground of adaptive immune responses to pathogen-derived antigens (von Andrian and Mempel, 2003, *Nat. Rev. Immunol.,* 3:867; and Karrer et al., 1997, *J. Exp. Med.,* 185:2157; both of which are incorporated herein by reference). It is unclear how virus particles are cleared from afferent lymph and presented to cognate B cells to induce antibody responses. Here, we identify a population of $CD11b^+CD169^+$ $MHCII^+$ macrophages on the floor of the subcapsular sinus (SCS) and in the medulla of LNs that capture viral particles within minutes after subcutaneous (s.c.) injection. SCS macrophages translocated surface-bound viral particles across the SCS floor and presented them to migrating B cells in the underlying follicles. Selective depletion of these macrophages compromised local viral retention, exacerbated viremia of the host, and impaired local B cell activation. These findings indicate that $CD169^+$ macrophages have a dual physiological function. They act as innate "flypaper" by preventing the systemic spread of lymph-borne pathogens and as critical gatekeepers at the lymph-tissue interface that facilitate B cell recognition of particulate antigens and initiate humoral immune responses.

We have investigated how virus particles that enter peripheral tissues are handled within draining LNs. Hind footpads of mice were injected with fluorescently labeled UV-inactivated vesicular stomatitis virus (VSV), a cytopathic rhabdovirus that is transmittable by insect bites (Mead et al., 2000, *Ann. N.Y. Acad. Sci.,* 916:437; incorporated herein by reference) and elicits T-independent neutralizing B cell responses (Bachmann et al., 1995, *Eur. J. Immunol.,* 25:3445; incorporated herein by reference). Using multiphoton intravital microscopy (MP-IVM) in popliteal LNs (Mempel et al., 2004, *Nature,* 427:154; incorporated herein by reference) draining the injected footpad, we observed that VSV accumulated in discrete patches on the SCS floor within minutes after sc injection, while the parenchyma and roof of the SCS remained free of virus (FIG. 11A). The viral deposits became progressively denser forming conspicuous irregular reticular patterns, which remained fixed in place for hours.

To characterize the predilection sites for VSV binding in LNs, we reconstituted irradiated Act(EGFP) mice with wild-type bone marrow. The resulting B6→Act(EGFP) chimeras expressed EGFP in non-hematopoietic cells, presumably lymphatic endothelial cells, on the SCS floor and roof. Upon footpad injection of fluorescent VSV into C57BL/6→Act (EGFP) chimeras, viral particles flooded the SCS. Three hours later, unbound lumenal VSV had disappeared, but the SCS floor displayed prominent patches of VSV that did not colocalize with $EGFP^+$ cells, suggesting that VSV was captured by hematopoietic cells (FIG. 11B). To characterize the putative VSV-capturing leukocytes, we performed electron microscopy on popliteal LNs that were harvested 5 min after VSV injection (FIG. 11C). Bullet-shaped, electron-dense VSV particles were selectively bound to discrete regions on the surface of scattered large cells that resided within the SCS or just below the SCS floor. VSV-binding cells that were located beneath the SCS floor were typically in contact with the lymph compartment via protrusions that extended into the SCS lumen.

Ultrastructural studies of LNs have shown that the SCS contains many macrophages (Clark, 1962, *Am. J. Anat.,* 110:217; and Farr et al., 1980, *Am. J. Anat.,* 157:265; both of which are incorporated herein by reference), so we hypothesized that the VSV-retaining cells belonged to this population. Indeed, confocal microscopy of frozen LN sections obtained thirty minutes after footpad injection showed that VSV co-localized in the SCS with a macrophage marker, CD169/sialoadhesin (FIG. 11D). Using flow cytometry, we detected CD169 on approximately 1%-2% of mononuclear cells (MNCs) in LNs, which uniformly co-expressed CD11b and MHC-II, indicating that the VSV-binding cells are indeed macrophages (FIG. 12). Most $CD169^+$ cells also expressed other macrophage markers, including CD68 and F4/80, while few expressed the granulocyte/monocyte marker Gr-1. $CD169^+$ cells also expressed CD11c, but at lower levels than $CD11c^{high}$ conventional dendritic cells (DCs). Intact virions enter the lymph within minutes after transcutaneous deposition and accumulate rapidly and selectively on macrophages in the medulla and SCS of draining LNs.

To explore mechanisms for virus fixation, live VSV (20 μg containing $2\times10^8$ pfu) was injected into hind footpads and viral titers in draining LNs were assessed 2 hours later. There was no defect in VSV retention in draining LNs of complement C3-deficient mice (FIG. 11E). DH-LMP2a mice, which lack secreted immunoglobulins, had reduced virus titers in spleen, but not in popliteal LNs (FIG. 11F). Therefore, VSV fixation in LNs occurs via a mechanism distinct from that used by splenic marginal zone macrophages, which require C3 and natural antibodies to capture blood-borne VSV (Ochsenbein et al., 1999, *J. Exp. Med.,* 190:1165; and Ochsenbein et al., 1999, *Science,* 286:2156; both of which are incorporated herein by reference). Conceivably, the VSV surface glycoprotein (VSV-G) may be recognized in LNs by macrophage-expressed carbohydrate-binding scavenger receptors (Taylor et al., 2005, *Ann. Rev. Immunol.,* 23:901; incorporated herein by reference), but the precise mechanism will require further investigation.

What are the consequences of viral capture by macrophages for virus dissemination and anti-viral immunity? To address this question, we depleted LN-resident macrophages by footpad injection of clodronate liposomes (CLL; Delemarre et al., 1990, *J. Leukoc. Biol.,* 47:251; incorporated herein by reference). At the dose used, sc injected CLL selectively eliminated macrophages in LNs draining the injection site, including the popliteal, inguinal and paraortic LNs (Delemarre et al., 1990, *J. Leukoc. Biol.,* 47:251; incorporated herein by reference), while macrophages in distal LNs and spleen were spared (FIGS. 13 A, B). Among the different LN-resident $CD11b^+MHCII^+$ phagocytes, CLL preferentially removed the $CD169^+$ subset, whereas $LYVE\text{-}1^+$ cells and conventional DCs remained unchanged. CLL-treated popliteal LNs had increased B cell numbers and enlarged follicles 7 days after treatment, but other morphological parameters, e.g. demarcation of the T/B border and SCS ultrastructure remained unaltered (FIGS. 13 C-E).

Compared to untreated LNs, we recovered approximately 10-fold lower viral titers from the draining LNs of CLL-treated mice (FIG. 11G), suggesting that macrophage depletion rendered lymph filtration inefficient. Indeed, VSV titers were dramatically increased in blood, spleen, and non-draining LNs of CLL-treated mice. Viral dissemination from the injection site to the blood depended strictly on lymph drainage, because circulating VSV was undetectable when virus was injected into footpads of mice that carried an occluding catheter in the thoracic duct (TD), even in CLL-treated mice. Viral titers were low, but detectable in TD lymph fluid of untreated mice, but increased significantly in CLL-treated animals (FIG. 11H). This indicates that the principal conduit for early viral dissemination from peripheral tissues is the lymph, which is monitored by LN-resident, CLL-sensitive macrophages that prevent the systemic spread of lymphborne VSV.

Figure 14A:
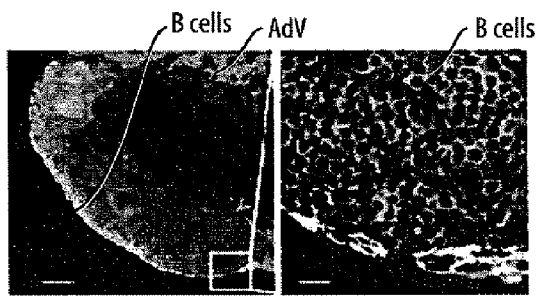
Figure 14C:
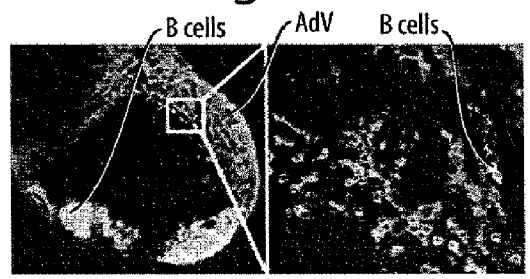
Figure 14D:
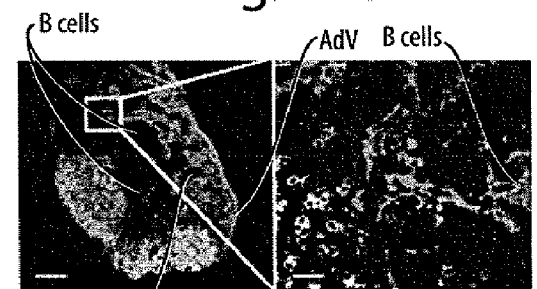
Figure 14B:
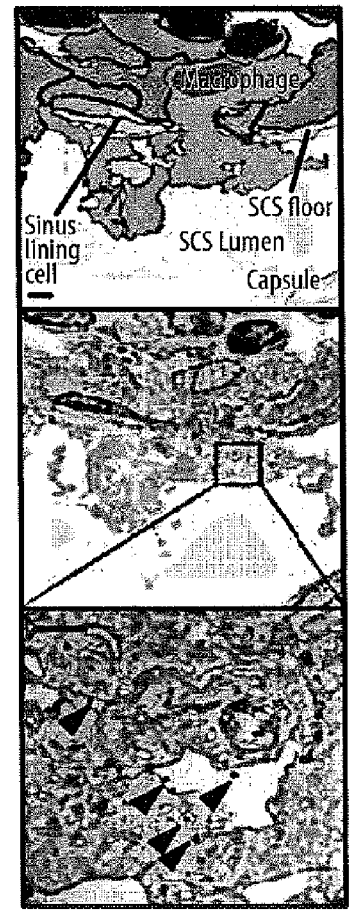
Figure 14E:
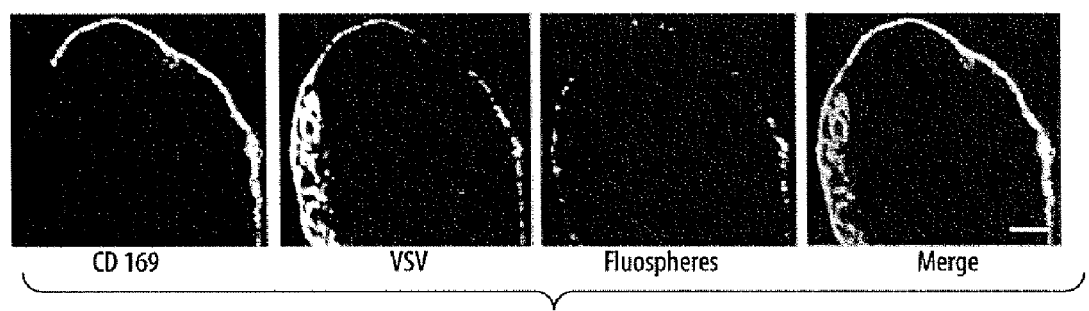
Figure 15A:
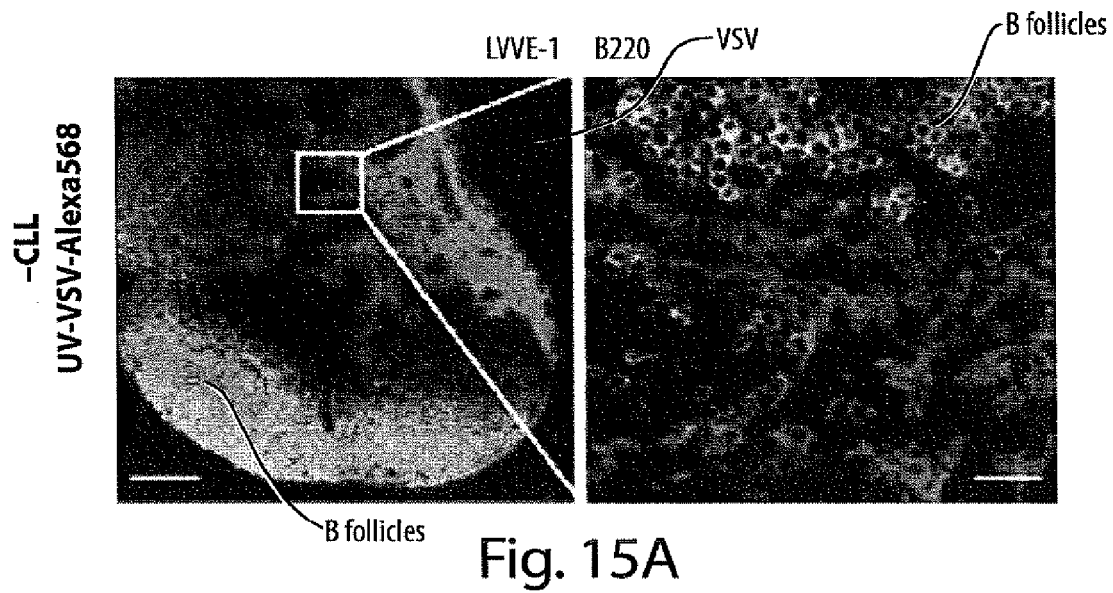
Figure 15B:
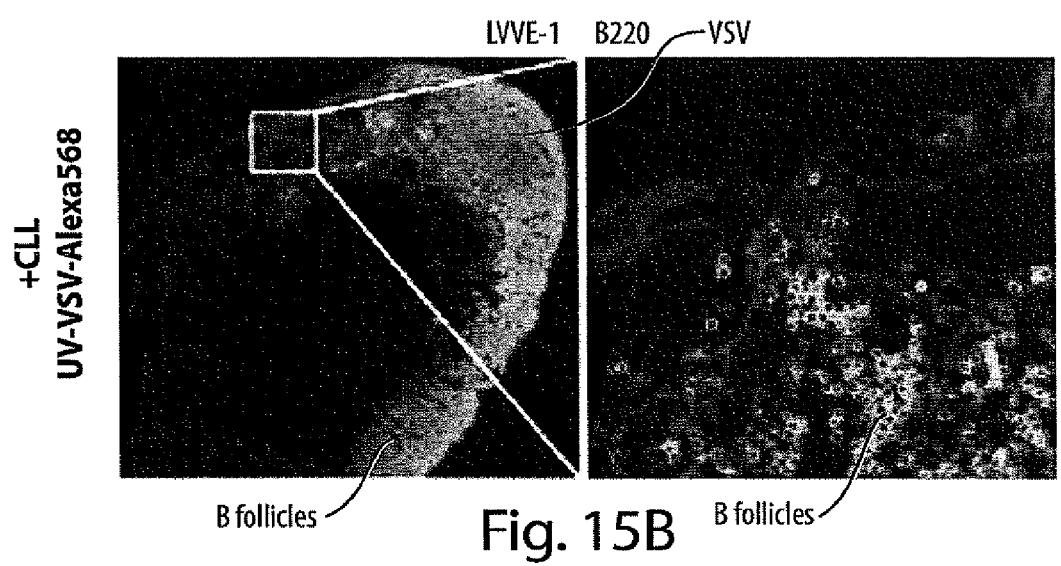

This capture mechanism was not unique to VSV; CD169$^+$ SCS macrophages also retained adenovirus (AdV; FIGS. 14 A-C) and vaccinia virus (VV, FIG. 14D), indicating that macrophages act as guardians against many structurally distinct pathogens. In contrast, virus-sized latex beads (200 nm) were poorly retained in the SCS after footpad injection (FIG. 14E). Thus, SCS macrophages discriminate between lymph-borne viruses and other particles of similar size. Fluorescent VSV, AdV and VV also accumulated in the medulla of draining LNs, where they were not only bound by CD169$^{low}$ cells (FIG. 11D) but also by CD169$^-$LYVE-1$^+$ lymphatic endothelial cells (FIGS. 14 C, D). This was corroborated in CLL-treated LNs, where VSV accumulated exclusively on medullary LYVE-1$^+$ cells (FIG. 15).

Figure 16A:
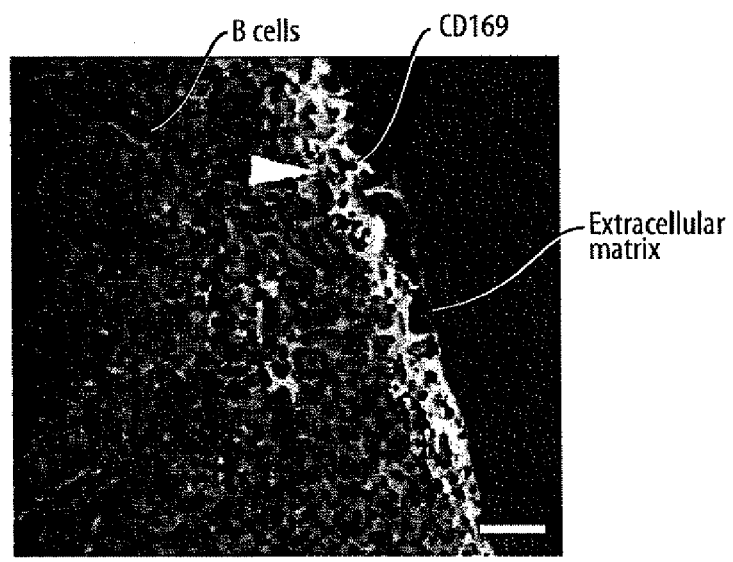
Figure 16B:
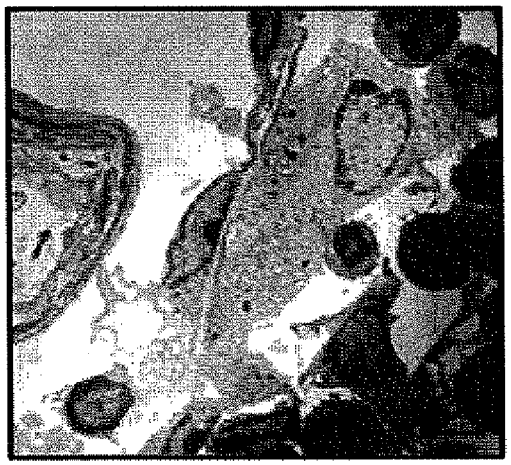
Figure 16C:
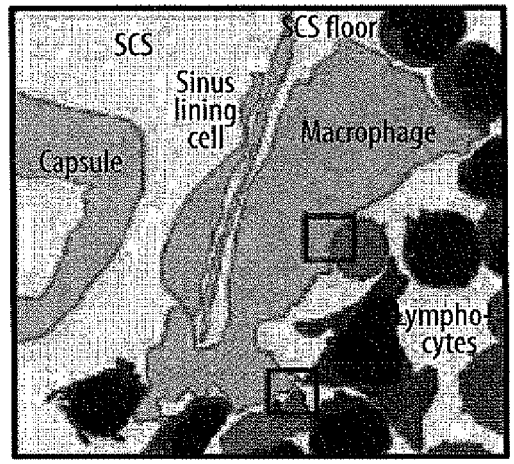
Figure 16D:
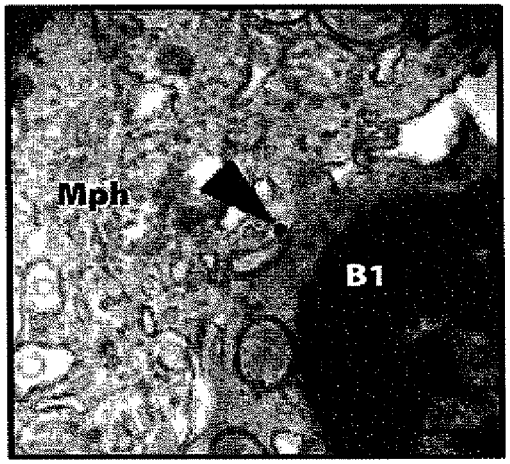
Figure 16E:
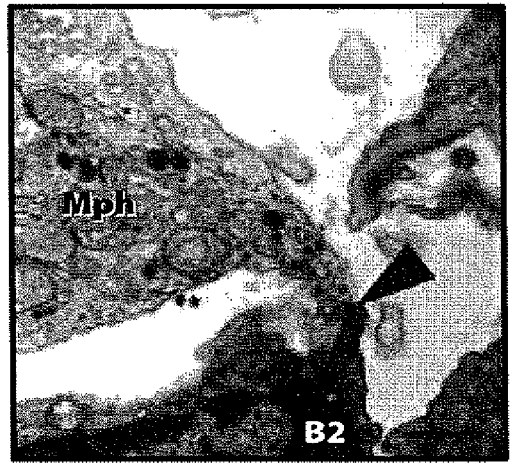

Next, we examined how captured VSV is recognized by B cells. Popliteal LNs contain rare B cells in the SCS lumen (FIG. 16A), but we found no evidence for virus-binding lymphocytes within the SCS on electron micrographs. Instead, viral particles were presented to B cells within superficial follicles by macrophages that extended across the SCS floor. Following injection of either VSV (FIG. 17A) or AdV (FIGS. 16 B-E), virions were readily detectable at B cell-macrophage interfaces for at least 4 hours. This suggested that SCS macrophages shuttle viral particles across the SCS floor for presentation to B cells. Transcytosis seemed unlikely, because the few vesicles containing VSV in SCS macrophages showed evidence of viral degradation. In addition, we did not detect substantial motility of virus-binding macrophages by MP-IVM, at least during the first 6 hours after challenge. Therefore, viral particles most likely reached the LN parenchyma by moving along the macrophage surface. Of note, VSV and other antigens are also presented to B cells by DCs immigrating from peripheral locations (Ludewig et al., 2000, Eur. J. Immunol., 30:185; and Qi et al., 2006, Science, 312: 1672; both of which are incorporated herein by reference), but footpad-derived DCs are not likely to play a role during these very early events, because their migration into popliteal LNs takes much longer. The SCS floor is not unsurmountable for lymph-borne viruses; CD169$^+$ macrophages appear to act as gatekeepers and facilitators of viral translocation and presentation to B cells.

Next, we explored how naive B cells respond to viral encounter using two VSV serotypes, Indiana (VSV-IND) and New Jersey (VSV-NJ) (FIG. 18; Roost et al., 1996, J. Immunol. Methods, 189:233; incorporated herein by reference). We compared wildtype B cells to B cells from VI10YEN mice, which express a VSV-IND-specific B cell receptor that does not bind VSV-NJ (Hangartner et al., 2003, Proc. Natl. Acad. Sci., USA, 100:12883; incorporated herein by reference). By contrast, a small fraction (2%-5%) of wildtype B cells bound both serotypes without being activated. This might reflect low-affinity reactivity with VSV-G or indirect interactions, e.g. via complement (Rossbacher and Shlomchik, 2003, J. Exp. Med., 198:591; incorporated herein by reference). To assess in vivo responses, differentially labeled wildtype and VI10YEN B cells were adoptively transferred and allowed to home to LN follicles. Fluorescent UV-inactivated virus was then injected into footpads and popliteal LNs were recorded by MP-IVM about 5-35 minutes later. In virus-free LNs or after injection of VSV-NJ, VI10YEN and control B cells displayed the same distribution (FIGS. 17 B-C). In contrast, upon VSV-IND injection VI10YEN cells rapidly accumulated below and at the SCS floor. There was no difference in baseline B cell motility and distribution between CLL-treated and untreated LNs, suggesting that VSV-specific B cells are equally likely to probe the SCS in both conditions. However, in CLL-treated LNs, fluorescent virus was not retained in the SCS and VI10YEN B cells failed to congregate in that region, indicating that SCS macrophages are essential for both events (FIG. 17B).

Figure 17E:
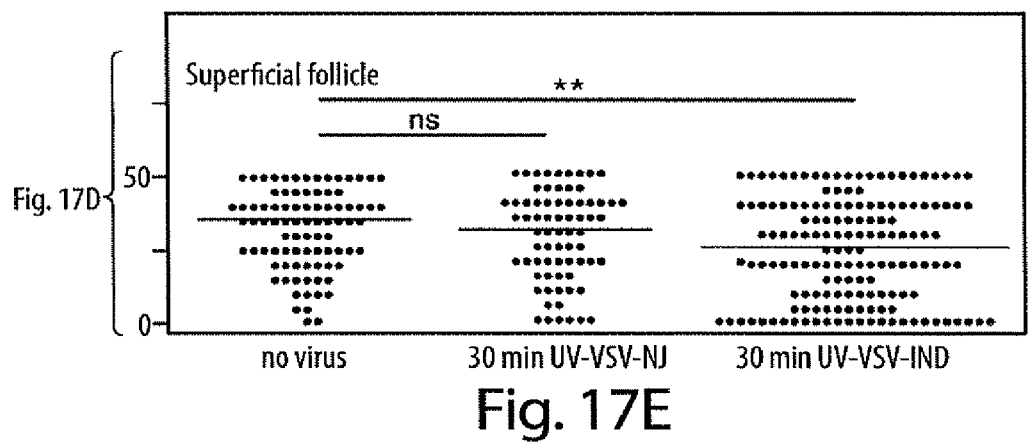

To rigorously quantify VI10YEN B cell distribution, LNs were harvested 30 minutes after VSV challenge and analyzed by confocal microscopy. While the entire follicular VI10YEN population retained its overall distribution (FIG. 17D), the subset of cells residing ≤50 µm below the SCS shifted toward the SCS in VSV-IND, but not VSV-NJ containing LNs (FIG. 17E). It seems unlikely that VI10YEN B cells redistributed to the SCS because of chemoattractant signals, since unresponsive polyclonal B cells express the same chemoattractant receptors. More likely, the random contacts of motile VI10YEN cells with macrophage-bound VSV-IND triggered a BCR-dependent "stop signal" (Okada et al., 2005, PLoS Biol., 3:e150; incorporated herein by reference): Short-term exposure to VSV-IND activates LFA-1 and/or α4 integrins (Dang and Rock, 1991, J. Immunol., 146:3273; incorporated herein by reference) on VI10YEN B cells, resulting in adhesion to the respective ligands, ICAM-1 and VCAM-1, which are both expressed in the SCS (FIG. 19). Additionally, VSV-IND bound to SCS macrophages may provide a substrate for VI10YEN B cell adhesion directly via the BCR.

To investigate how captured virions are processed upon detection by B cells, we tested B cells from VI10YEN× MHCII-EGFP mice, which allowed us to visualize endocytosed VSV co-localizing with endosomal MHC-II as an indicator of B cell priming (Vascotto et al., 2007, Curr., Opin., Immunol., 19:93; incorporated herein by reference). Within 30 minutes after injection, VI10YEN×MHCII-EGFP B cells in the superficial follicle had extensively internalized VSV-IND, but not VSV-NJ particles (FIGS. 20 A, B). Virus-carrying VSV-specific B cells were infrequent, but detectable in deep follicles. These cells may have acquired virions from rare polyclonal B cells that carried VSV on their surface, or may correspond to VI10YEN cells which failed to arrest at the SCS after acquiring VSV-IND.

Figure 18A:
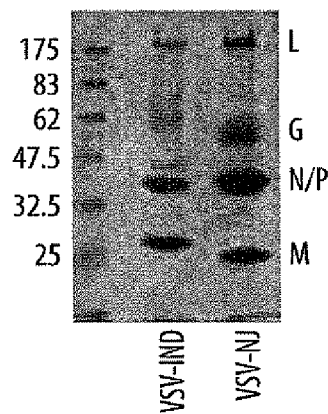
FIG. 18: Characteristics of VSV serotypes and VSV-IND-specific VI10YEN B cells. (A) SDS-PAGE gels (12%) of purified VSV lysates. Top: VSV-IND and VSV-NJ. The N and P proteins co-migrate in VSV-NJ, approximate molecular weights are shown in parentheses. (B) Binding of Alexa-488 labeled VSV-IND (middle row) or VSV-NJ (bottom row) to B cells from C57BL/6 mice (left column) or VI10YEN mice (right column). The upper row shows control staining with the anti-idiotypic antibody 35.61 to the VI10YEN BCR (Dang and Rock, 1991, *J. Immunol.*, 146:3273). (C) Intracellular calcium flux in CD43$^{neg}$ purified, Fluo-LOJO loaded B cells from VI10YEN mice (upper row) or C57BL/6 mice (lower row). Events were collected continuously over time, asterisks indicate the timepoint when antibodies or virus were added. Virus particles were used at 1000/B cell, anti-IgM-(Fab)$_2$ at 10 μg/10$^6$ B cells. (D) Neutralization assay for total Ig and IgG in serum of C57BL/6 mice 4 and 10 days after immunization by footpad injection of 10 μg UV-VSV or UV-VSV-AlexaFluor-488-IND. (E) Calcium flux in VI10YEN B cells exposed to supernatant from VSV stocks. Supernatant was generated by ultracentrifugation through a sucrose cushion resulting in approximately 10,000-fold reduction in viral titers and was used on B cells either undiluted (top right) or at 1:100 dilution (bottom right). As a control, VSV stock solution was diluted to equivalent viral titers (MOI; left panels). The results demonstrate the presence of antigenic VSV-G that is not associated with virus particles in our virus preparation.
Figure 18B:
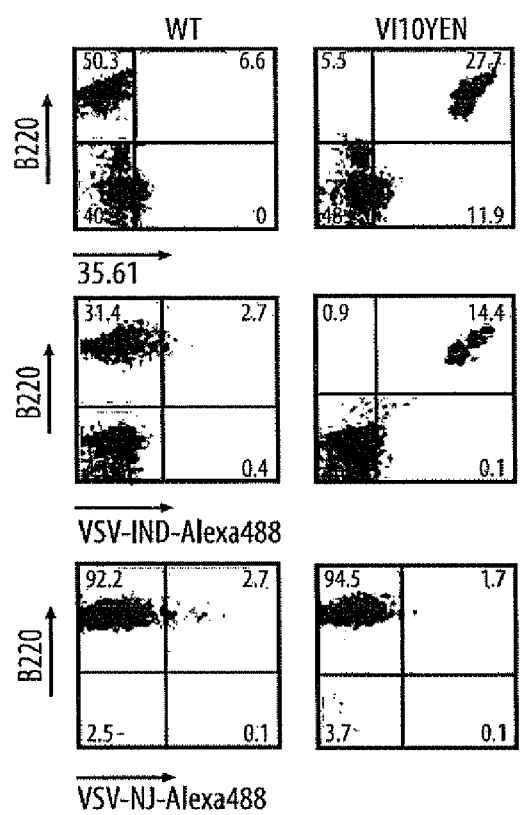
Figure 18C:
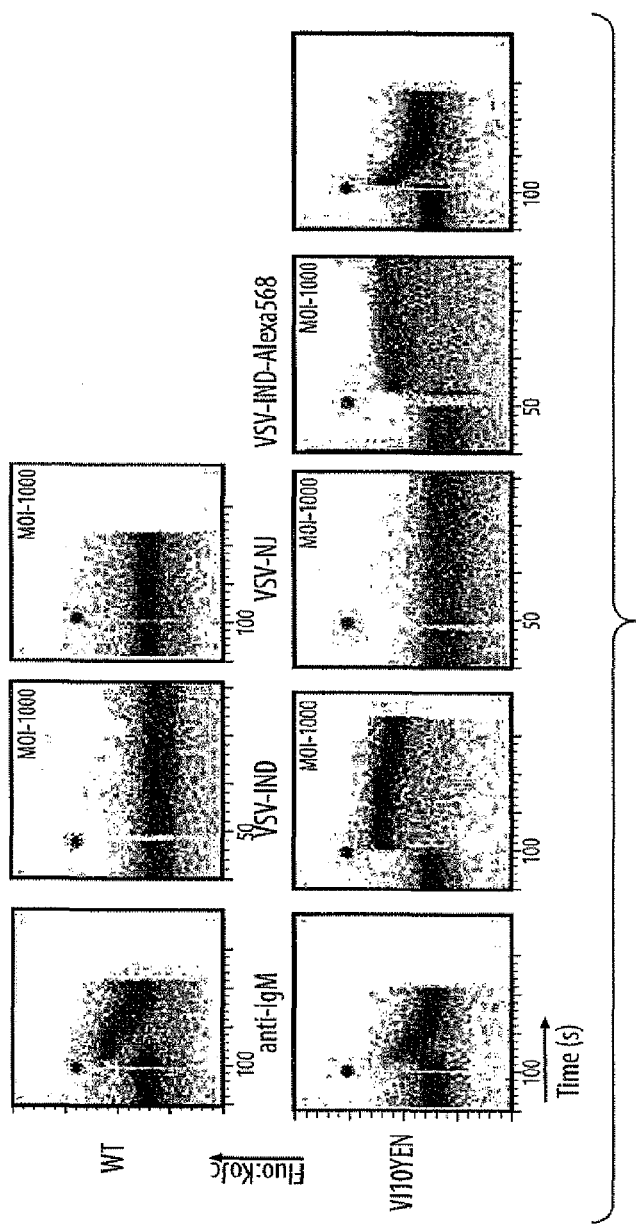
Figure 18D:
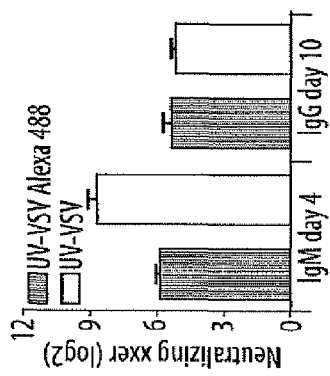
Figure 18E:
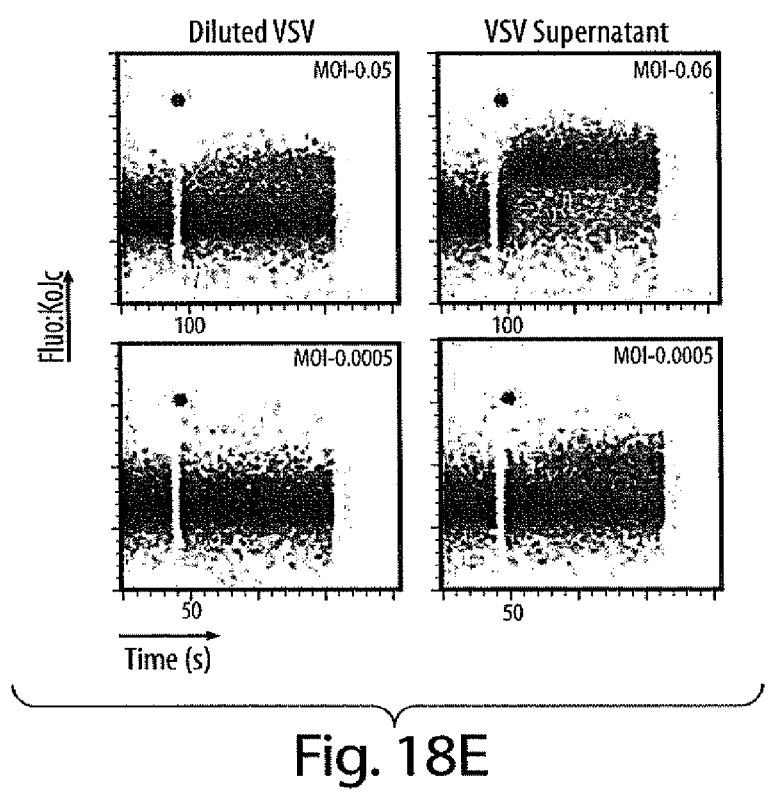
Figure 19A:
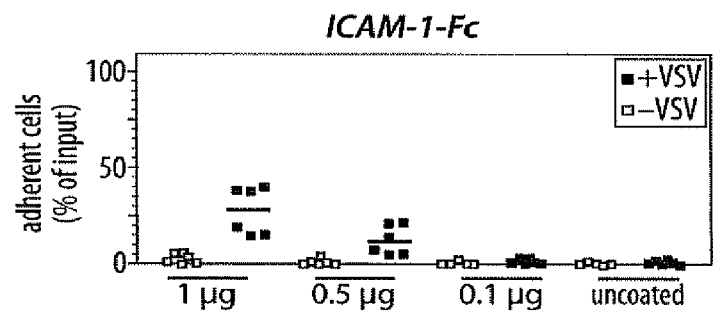
FIG. 19: VSV-induced adhesion of VI10YEN B cells to ICAM-1 and VCAM-1. (A,B) Adhesion of purified naïve and VSV-IND activated (30 minute exposure) VI10YEN B cells to plastic plates coated with the indicated concentrations of recombinant ICAM-1-Fc (A) or VCAM-1-Fc (B). Pooled data of two triplicate experiments are shown. Horizontal bars represent means. (C, D) Confocal micrographs of ICAM-1 and VCAM-1 expression in popliteal LNs of C57BL/6 mice. Scale bars: 50 μm. (E) Adhesion of purified naïve wildtype and VI10YEN B cells to plastic dishes coated with the indicated pfu-equivalent concentrations of UV-inactivated VSV-IND. Data represent means±SEM of triplicates.
Figure 19B:
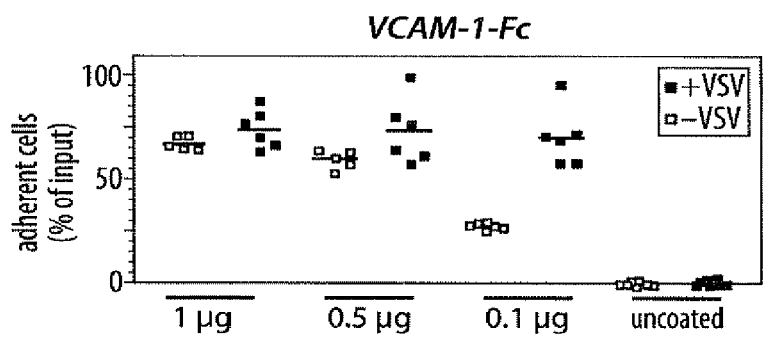
Figure 19C:
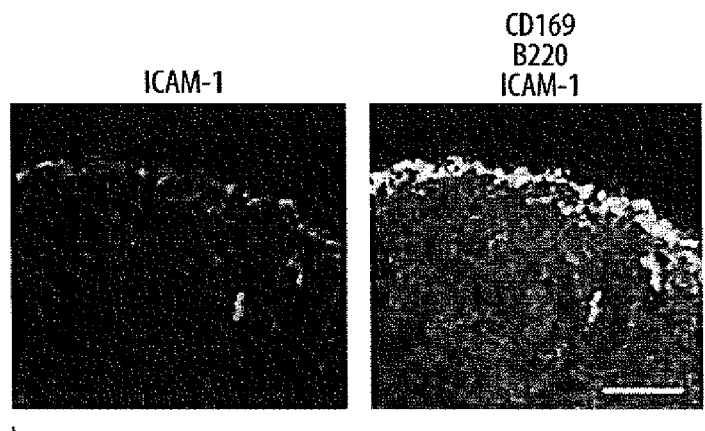
Figure 19D:
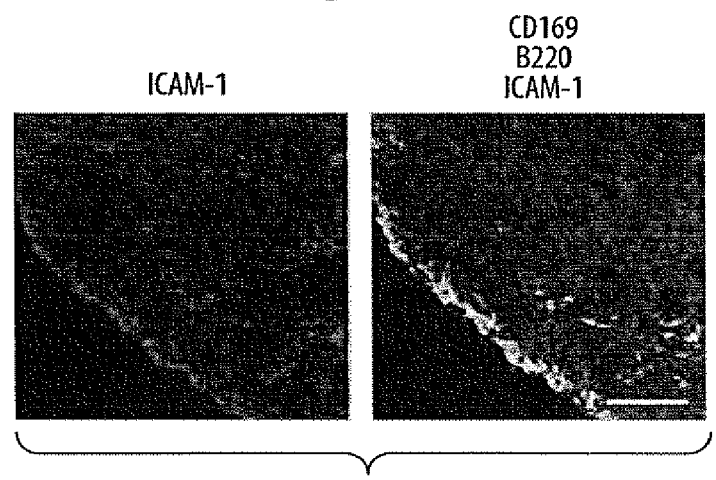
Figure 19E:
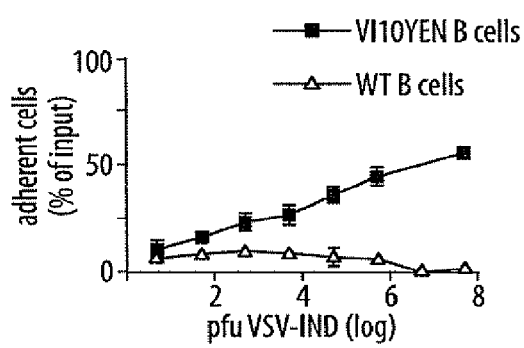
Figure 20A:
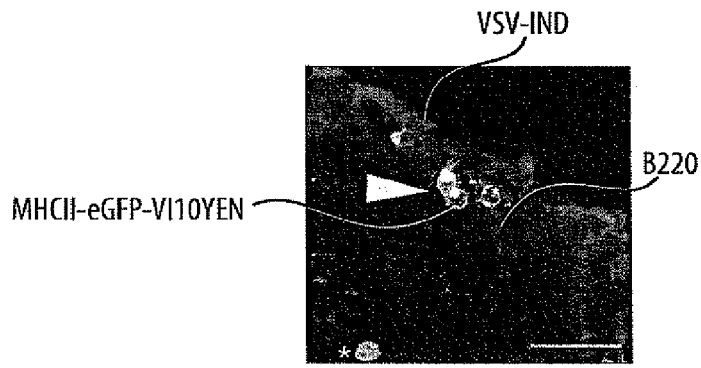
FIG. 20: SCS macrophages are required for early activation of VSV-specific B cells in LNs. (A) Confocal micrograph shows MHC-II colocalization with VSV-IND (30 minutes after injection) in VI10YEN×MHCII(EGFP) B cells at the SCS (arrowhead), not the deep follicle (asterisk). Scale bar: 25 μm. (B) Distance of VSV-associated and VSV-free VI10YEN×MHCII(EGFP) B cells to the SCS. Horizontal lines: medians. (C) BCR expression kinetics on VI10YEN and (D) polyclonal B cells after VSV-IND footpad injection. (E) BCR expression on VI10YEN cells in CLL-treated or untreated popliteal LNs after VSV-IND injection (20 μg). Mean fluorescence intensities were normalized to virus-free values (dashed line). Means±SEM (3-5 mice). (F) Confocal micrograph of VI10YEN B cells in control and (G) CLL-treated popliteal LNs 6 hours after VSV-IND injection (0.4 μg). Scale bar: 125 μm. (H) VI10YEN B cell frequency at T/B borders and in follicles 6 hours after VSV-IND injection at indicated doses. Means±SEM; n=3-4 follicles/2 mice; *: p<0.05; : p<0.01; *: p<0.001 (t-test).
Figure 20B:
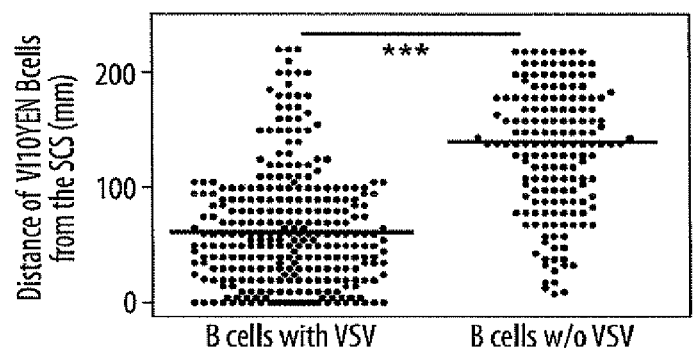
Figure 20C:
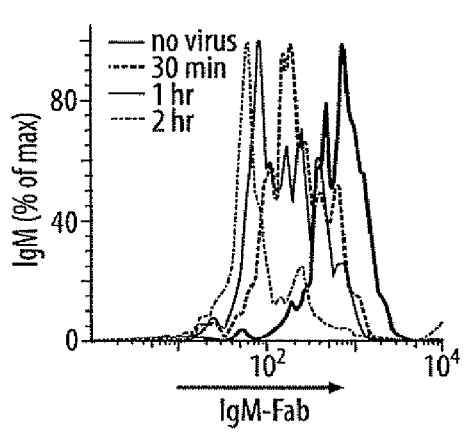
Figure 20D:
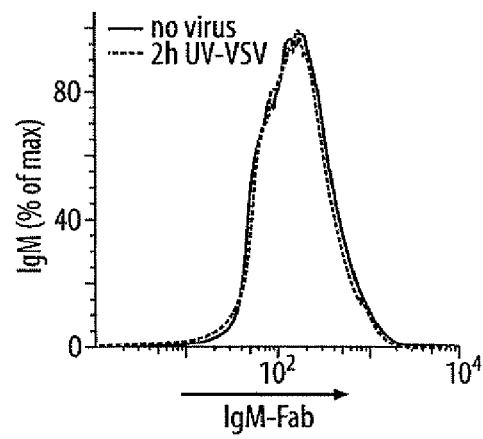
Figure 20E:
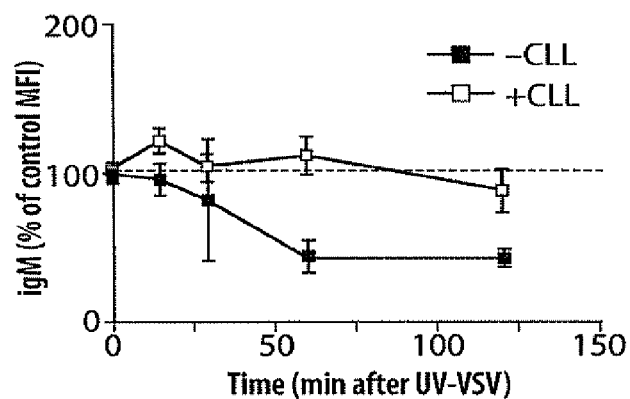
Figure 20F:
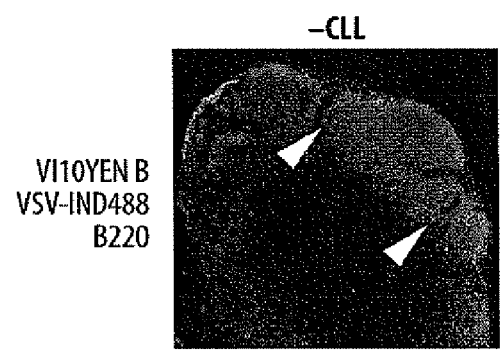
Figure 20G:
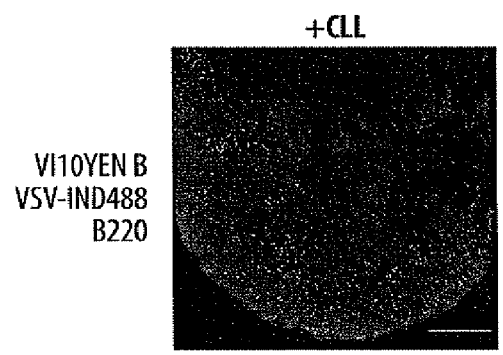
Figure 20H:
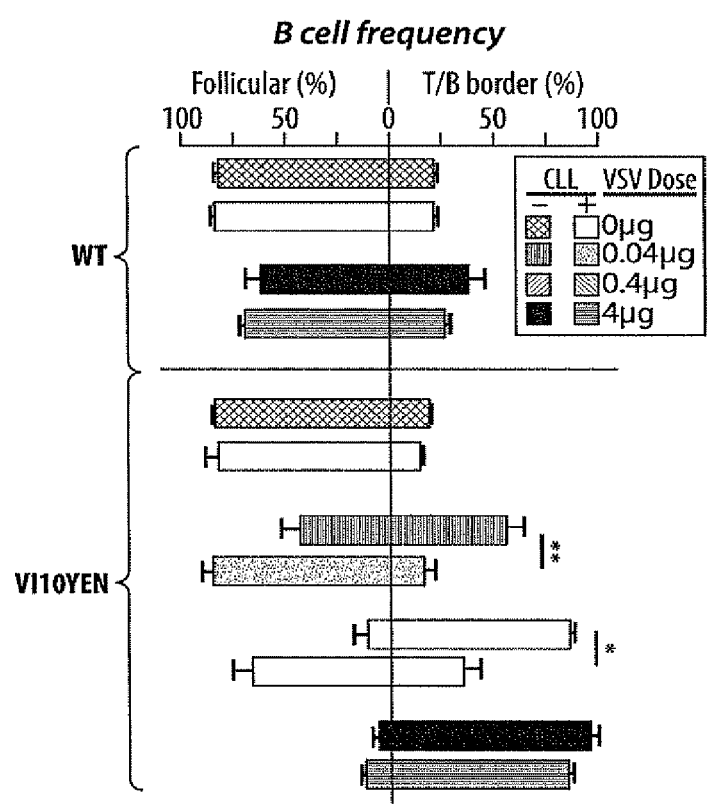
Figure 21:
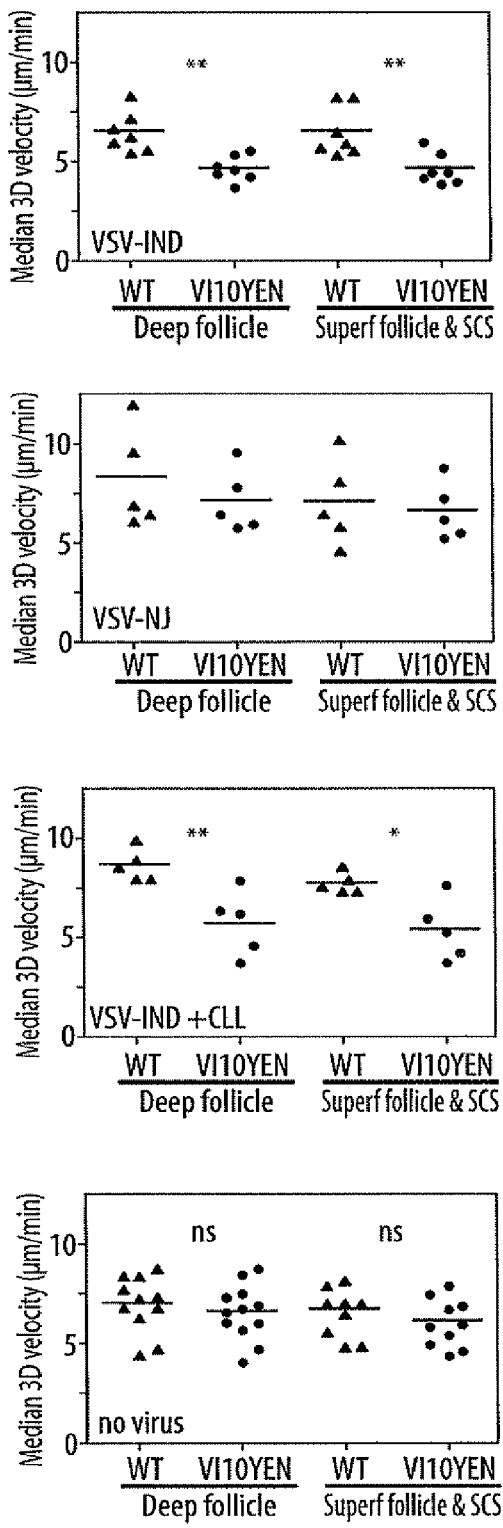
FIG. 21: VI10YEN B cell motility in draining LNs following virus injection. Median 3D instantaneous velocities of wildtype (triangles) and VI10YEN B cells (circles) in deep follicles and the SCS/superficial follicle about 5-35 min after VSV footpad injection. Horizontal bars represent means; *: p<0.05; **: p<0.01 (one-way ANOVA with Bonferroni's post test). Note that specific B cells slow down throughout the entire follicle, likely as a consequence of free VSV-G in our preparation (see FIG. 18). Control experiments showed similar B cell motility parameters in CLL-treated and nontreated popLNs.

While our histological findings demonstrate that intact virions are preferentially detected and acquired by B cells in the SCS and superficial follicle, MP-IVM measurements of B cell motility revealed broader antigen dissemination. After VSV-IND injection, VI10YEN cells exhibited a rapid drop in velocity throughout the entire B follicle, (FIG. 21). This was equally observed in CLL-treated and control LNs, indicating that viral antigen reached B cells independent of macrophages. This antigenic material was most likely composed of free viral protein, an inevitable by-product of natural infections. Indeed, purified supernatant of our VSV stocks induced a potent calcium flux in VI10YEN B cells (FIG. 18E). Small lymph-borne proteins are known to diffuse rapidly into follicles and activate cognate B cells (Pape et al., 2007, Immunity, 26:491; incorporated herein by reference). Accordingly, injection of viral supernatant suppressed the motility of follicular VI10YEN B cells without inducing their accumulation at the SCS, indicating that free VSV-G was contained and active within the viral inoculum. This can explain the macrophage-independent pan-follicular effect of VSV-IND injection.

Figure 22A:
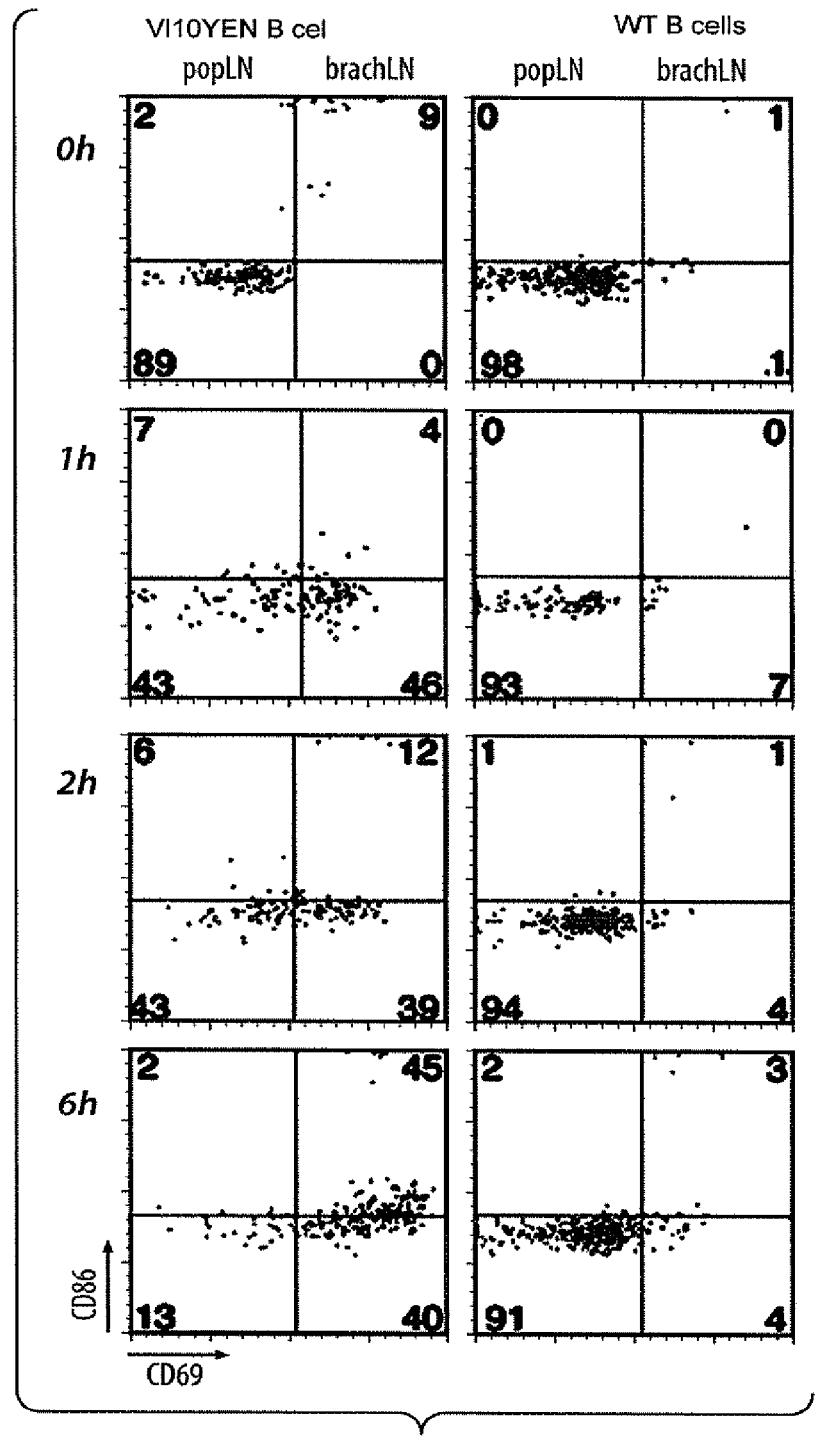
FIG. 22: Timecourse of activation marker induction on VI10YEN B cells in virus-draining and non-draining LNs following injection of VSV-IND. VI10YEN B cells were fluorescently tagged with CMTMR and transferred to naïve mice that were injected 18 hours later with 20 μg UV-inactivated VSV-IND (time 0 hours). The draining popliteal LN (popLN) and a distal brachial LN (brachLN) were harvested after the indicated time intervals to generate single-cell suspensions. CD69 and CD86 expression on B cells was assessed by flow cytometry after gating on (A) B220$^+$CMTMR$^+$VI10YEN cells or (B) B220$^+$CMTMR$^-$ endogenous control B cells.
Figure 22B:
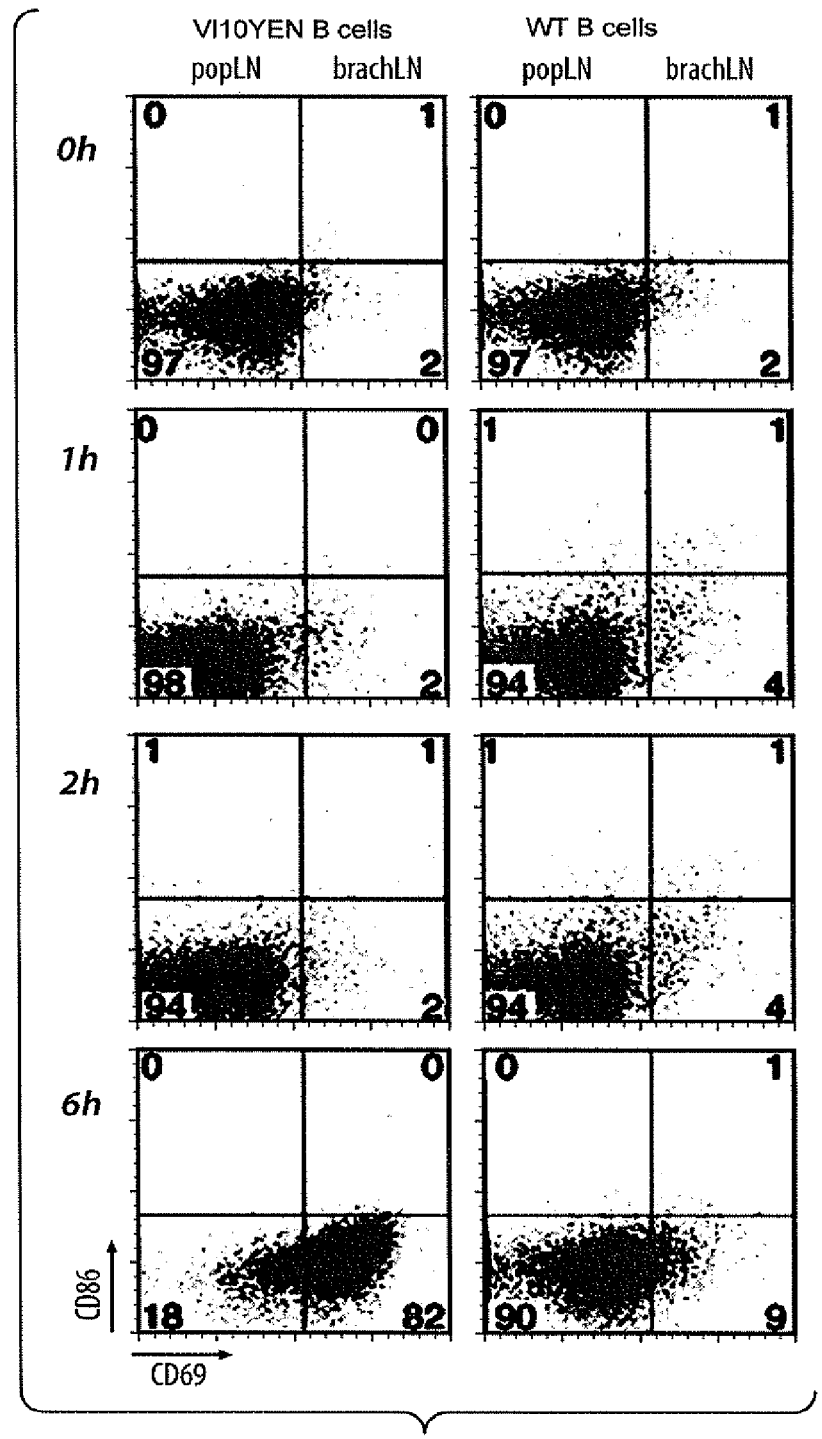
Figure 23:
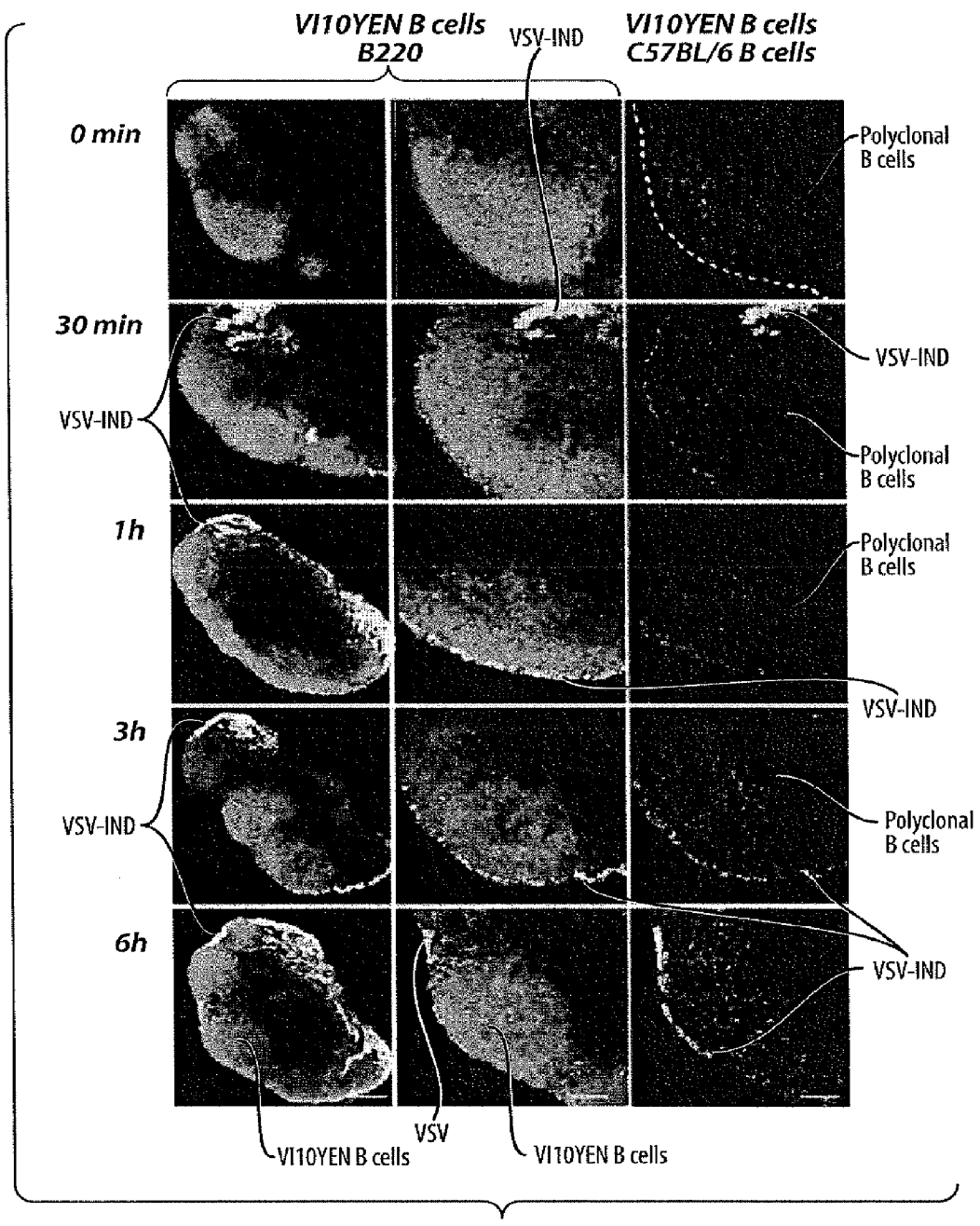
FIG. 23: Confocal (left and middle columns) and MP-IVM micrographs (right column) of popliteal LNs of mice that had received adoptive transfers of a mixture of CMTMR-labeled VI10YEN B cells and CMAC-labeled polyclonal B cells (in the right column). On the following day, 20 μg UV-inactivated VSV-IND was injected in a footpad and the draining popliteal LNs were either surgically prepared for MP-IVM or harvested for confocal analysis of frozen sections at the indicated time points. MP-IVM images show that VSV-specific, but not polyclonal B cells made contact with VSV in the SCS as early as 30 minutes after virus injection. VI10YEN B cells relocated to the T/B border at 6 hours following injection. Scale bars: 150 μm in the left column and 25 μm in the other columns.

To determine the kinetics of VI10YEN B cell activation upon viral encounter, we measured common activation markers (FIG. 22). The costimulatory molecule CD86 was first up-regulated 6 hours after VSV-IND challenge. CD69 was induced more rapidly, but also on polyclonal B cells, presumably by pleiotropic IFN-α signaling (Barchet et al., 2002, *J. Exp. Med.*, 195:507; and Shiow et al., 2006, *Nature,* 440:540; both of which are incorporated herein by reference). Surface IgM (FIGS. 20 C, D) was down-regulated as early as 30 minutes after challenge reaching a maximum within 2 h when >70% of VI10YEN cells were $BCR^{low/neg}$. Therefore, BCR internalization provided the earliest specific readout for virus-specific B cell activation. Remarkably, VI10YEN B cells in CLL-treated LNs failed to downregulate their BCR during the first 2 hours after subcutaneous injection of 20 µg VSV-IND (FIG. 20E), indicating that SCS macrophages are necessary for efficient early presentation of captured virions to B cells.

Primed B cells eventually solicit help from $CD4^+$ T cells (Vascotto et al., 2007, *Curr., Opin., Immunol.*, 19:93; incorporated herein by reference) for class switch recombination and germinal center formation. To contact T cells, newly activated B cells migrate toward the T/B border (Okada et al., 2005, *PLoS Biol.*, 3:e150; and Reif et al., *Nature,* 416:94; both of which are incorporated herein by reference). This mechanism operated efficiently in macrophage-sufficient mice; most VI10YEN B cells redistributed to the T/B border within 6 h after footpad injection of as little as 40 ng VSV-IND (FIGS. 20 F, H and 23). By contrast, a 100-fold higher viral dose was needed to elicit full redistribution of VI10YEN B cells in CLL-treated mice (FIGS. 20 G, H). By 12 hours after injection, most VSV-specific cells reached the T-B border, irrespective of the injected dose. Thus, even without SCS macrophages follicular B cells are eventually activated by VSV-derived antigen, albeit less efficiently.

In conclusion, we demonstrate a dual role for $CD169^+$ macrophages in LNs: they capture lymph-borne viruses preventing their systemic dissemination and they guide captured virions across the SCS floor for efficient presentation and activation of follicular B cells.

Example 2

Exemplary Lipid-Based Vaccine Nanotechnology Architectures

Liposome Nanocarriers

In some embodiments, small liposomes (10 nm-1000 nm) are manufactured and employed to deliver, in some embodiments, one or multiple immunomodulatory agents to cells of the immune system (FIG. 3). In general, liposomes are artificially-constructed spherical lipid vesicles, whose controllable diameter from tens to thousands of nm signifies that individual liposomes comprise biocompatible compartments with volume from zeptoliters ($10^{-21}$ L) to femtoliters ($10^{-15}$ L) that can be used to encapsulate and store various cargoes such as proteins, enzymes, DNA and drug molecules. Liposomes may comprise a lipid bilayer which has an amphiphilic property: both interior and exterior surfaces of the bilayer are hydrophilic, and the bilayer lumen is hydrophobic. Lipophilic molecules can spontaneously embed themselves into liposome membrane and retain their hydrophilic domains outside, and hydrophilic molecules can be chemically conjugated to the outer surface of liposome taking advantage of membrane biofunctionality.

In certain embodiments, lipids are mixed with a lipophilic immunomodulatory agent, and then formed into thin films on a solid surface. A hydrophilic immunomodulatory agent is dissolved in an aqueous solution, which is added to the lipid films to hydrolyze lipids under vortex. Liposomes with lipophilic immunomodulatory agents incorporated into the bilayer wall and hydrophilic immunomodulatory agents inside the liposome lumen are spontaneously assembled.

Nanoparticle-Stabilized Liposome Nanocarriers

In some embodiments, nanoparticle-stabilized liposomes are used to deliver one or a plurality of immunomodulatory agents to cells of the immune system (FIG. 4). When small charged nanoparticles approach the surface of liposomes carrying either opposite charge or no net charge, electrostatic or charge-dipole interaction between nanoparticles and membrane attracts the nanoparticles to stay on the membrane surface, being partially wrapped by lipid membrane. This induces local membrane bending and globule surface tension of liposomes, both of which enable tuning of membrane rigidity. This aspect is significant for vaccine delivery using liposomes to mimic viruses whose stiffness depends on the composition of other biological components within virus membrane. Moreover, adsorbed nanoparticles form a charged shell which protects liposomes against fusion, thereby enhancing liposome stability. In certain embodiments, small nanoparticles are mixed with liposomes under gentle vortex, and the nanoparticles stick to liposome surface spontaneously.

Liposome-Polymer Nanocarrier

In some embodiments, liposome-polymer nanocarriers are used to deliver one or a plurality of immunomodulatory agents to cells of the immune system (FIG. 5). Instead of keeping the liposome interior hollow, hydrophilic immunomodulatory agents may be encapsulated. FIG. 3 shows liposomes that are loaded with di-block copolymer nanoparticles to form liposome-coated polymeric nanocarriers, which have the merits of both liposomes and polymeric nanoparticles, while excluding some of their limitations. In some embodiments, the liposome shell can be used to carry lipophilic or conjugate hydrophilic immunomodulatory agents, and the polymeric core can be used to deliver hydrophobic immunomodulatory agents. In certain embodiments, pre-formulated polymeric nanoparticles (40 nm-1000 nm) are mixed with small liposomes (20 nm-100 nm) under gentle vortex to induce liposome fusion onto polymeric nanoparticle surface.

Nanoparticle-Stabilized Liposome-Polymer Nanocarriers

In some embodiments, nanoparticle-stabilized liposome-polymer nanocarriers are used to deliver one or a plurality of immunomodulatory agents (FIG. 6). By adsorbing small nanoparticles (1 nm-30 nm) to the liposome-polymer nanocarrier surface, the nanocarrier has not only the merit of both aforementioned nanoparticle-stabilized liposomes (FIG. 4) and aforementioned liposome-polymer nanoparticles (FIG. 5), but also tunable membrane rigidity and controllable liposome stability.

Liposome-Polymer Nanocarriers Comprising Reverse Micelles

In some embodiments, liposome-polymer nanocarriers containing reverse micelles are used to deliver one or a plurality of immunomodulatory agents (FIG. 7). Since the aforementioned liposome-polymer nanocarriers (FIGS. 5 and 6) are limited to carry hydrophobic immunomodulatory agents within polymeric nanoparticles, here small reverse micelles (1 nm-20 nm) are formulated to encapsulate hydrophilic immunomodulatory agents and then mixed with the di-block copolymers to formulate polymeric core of liposomes.

In certain embodiments, a hydrophilic immunomodulatory agent to be encapsulated is first incorporated into reverse micelles by mixing with naturally derived and non-toxic amphiphilic entities in a volatile, water-miscible organic solvent. The resulting biodegradable polymer-reverse micelle mixture is combined with a polymer-insoluble hydrophilic non-solvent to form nanoparticles by the rapid diffusion of the solvent into the non-solvent and evaporation of the organic solvent. Reverse micelle contained polymeric nanoparticles are mixed with lipid molecules to form the aforementioned liposome-polymer complex structure (FIG. 5).

Nanoparticle-Stabilized Liposome-Polymer Nanocarriers Comprising Reverse Micelles In some embodiments, nanoparticle-stabilized liposome-polymer nanocarriers containing reverse micelles are used to deliver one or a plurality of immunomodulatory agents (FIG. 8). By adsorbing small nanoparticles (1 nm-30 nm) to a liposome-polymer nanocarrier surface, the nanocarrier has not only the merit of both aforementioned nanoparticle-stabilized liposomes (FIG. 4) and aforementioned reverse micelle contained liposome-polymer nanoparticles (FIG. 7), but also tunable membrane rigidity and controllable liposome stability.

Lipid Monolayer-Stabilized Polymeric Nanocarrier

In some embodiments, lipid monolayer stabilized polymeric nanocarriers are used to deliver one or a plurality of immunomodulatory agents (FIG. 9). As compared to aforementioned liposome-polymer nanocarrier (FIGS. 5-8), this system has the merit of simplicity in terms to both agents and manufacturing. In some embodiments, a hydrophobic homopolymer can form the polymeric core in contrast to the di-block copolymer used in FIGS. 5-8, which has both hydrophobic and hydrophilic segments. Lipid-stabilized polymeric nanocarriers can be formed within one single step instead of formulating polymeric nanoparticle and liposome separately followed by fusing them together.

In certain embodiments, a hydrophilic immunomodulatory molecule is first chemically conjugated to a lipid headgroup. The conjugate is mixed with a certain ratio of unconjugated lipid molecules in an aqueous solution containing one or more water-miscible solvents. A biodegradable polymeric material is mixed with the hydrophobic immunomodulatory agents to be encapsulated in a water miscible or partially water miscible organic solvent. The resulting polymer solution is added to the aqueous solution of conjugated and unconjugated lipid to yield nanoparticles by the rapid diffusion of the organic solvent into the water and evaporation of the organic solvent.

Lipid Monolayer-Stabilized Polymeric Nanocarrier Comprising Reverse Micelles

In some embodiments, lipid monolayer stabilized polymeric nanoparticles comprising reverse micelles are used to deliver one or a plurality of immunomodulatory agents (FIG. 10). Since the aforementioned lipid-stabilized polymeric nanocarriers (FIG. 9) are limited to carry hydrophobic immunomodulatory agents, here, small reverse micelles (1 nm-20 nm) are formulated to encapsulate hydrophilic immunomodulatory agents and mixed with biodegradable polymers to form polymeric nanocarrier core.

Example 3

In Vivo Targeting of SCS-Mph Using Fc Fragments from Human IgG

Fluorescent unmodified control nanoparticles (top panel, FIG. 24A) or Fc surface-conjugated targeted nanoparticles (middle and lower panel, FIG. 24A) were injected into footpads of anesthetized mice, and the draining popliteal lymph node was excised 1 hour later and single-cell suspensions were prepared for flow cytometry. Targeted nanoparticles were also injected into mice one week after lymph node macrophages had been depleted by injection of clodronate-laden liposomes (lower panel, FIG. 24A). The cell populations in gates were identified as nanoparticle-associated macrophages based on high expression of CD11b. These results indicate that (i) nanoparticle binding depends on the presence of clodronate-sensitive macrophages and (ii) targeted nanoparticles are bound to twice as many macrophages as control nanoparticles.

Figure 24A:
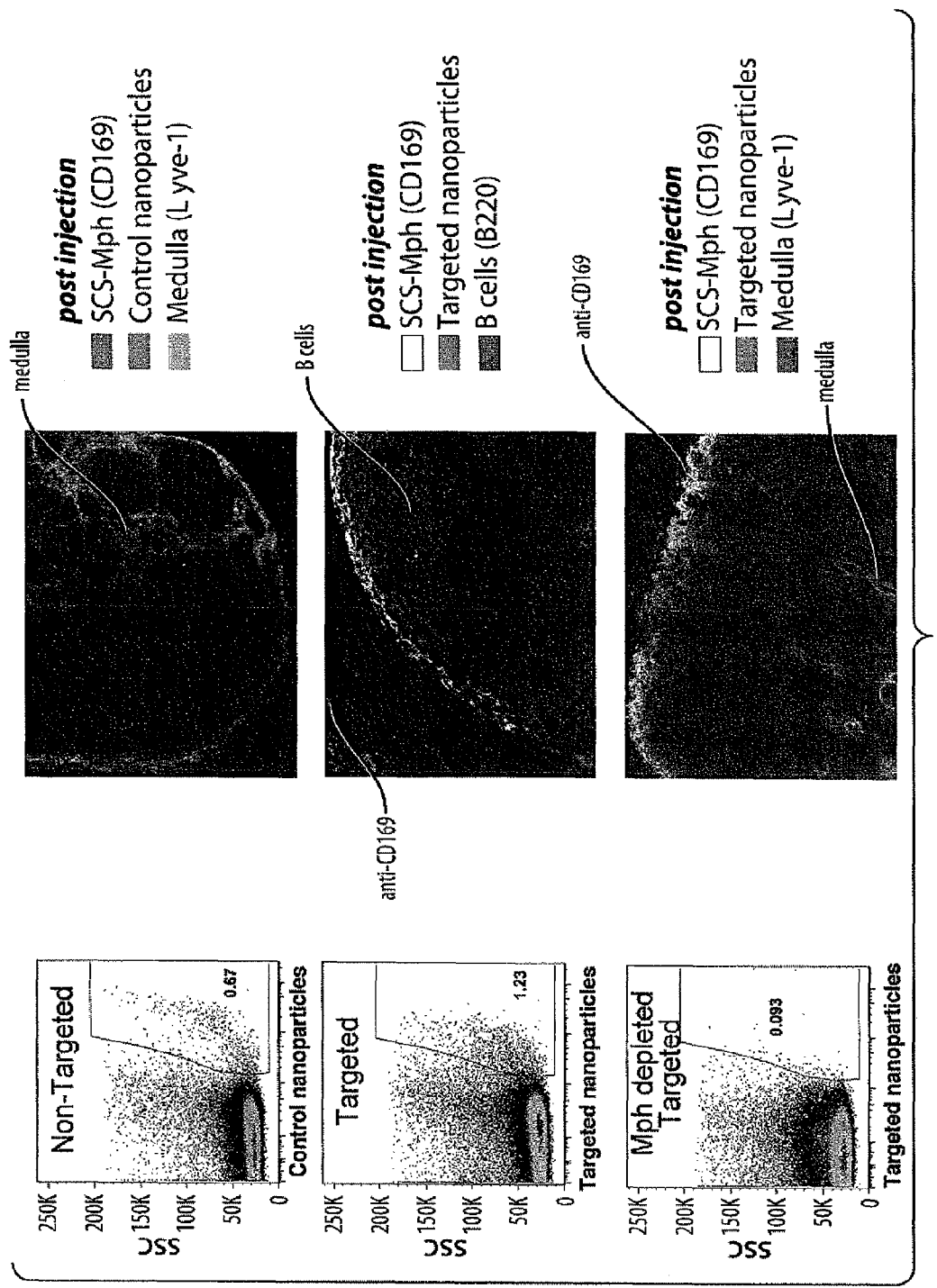
FIG. 24: In vivo targeting of SCS-Mph using Fc fragments from human IgG. (A) The FACS histograms on the left document the binding of fluorescent PEG-PLGA nanoparticles (~100 nm diameter) to lymph node macrophages. (B) Fc-nanoparticle (NP) targets SCS-Mph and follicular dendritic cells.
Figure 24B:
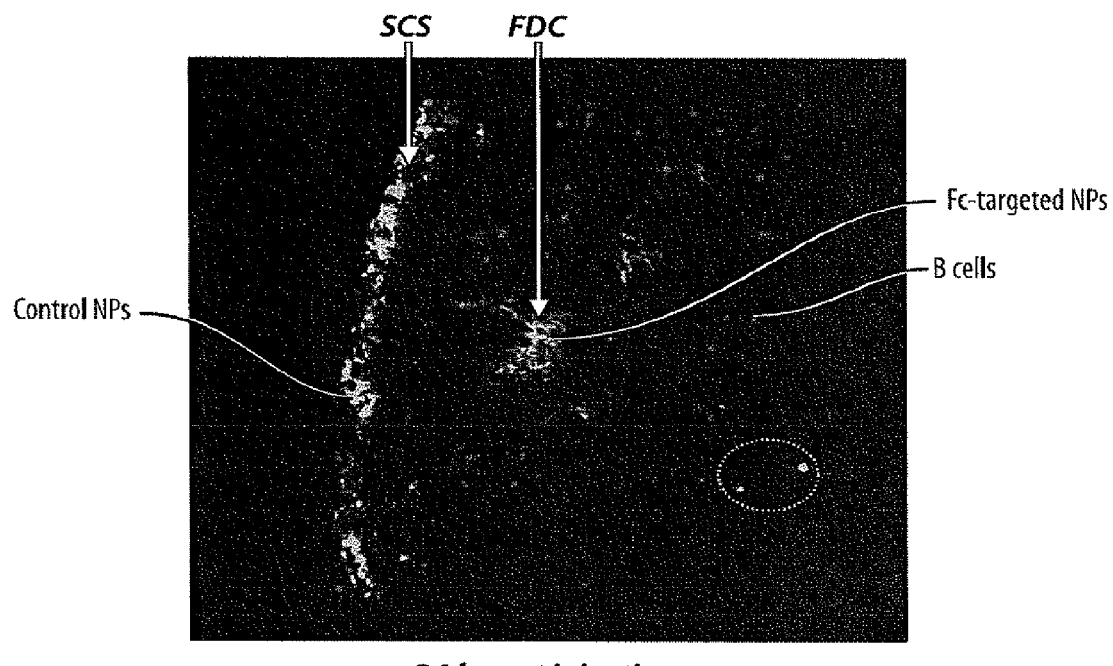
Figure 25:
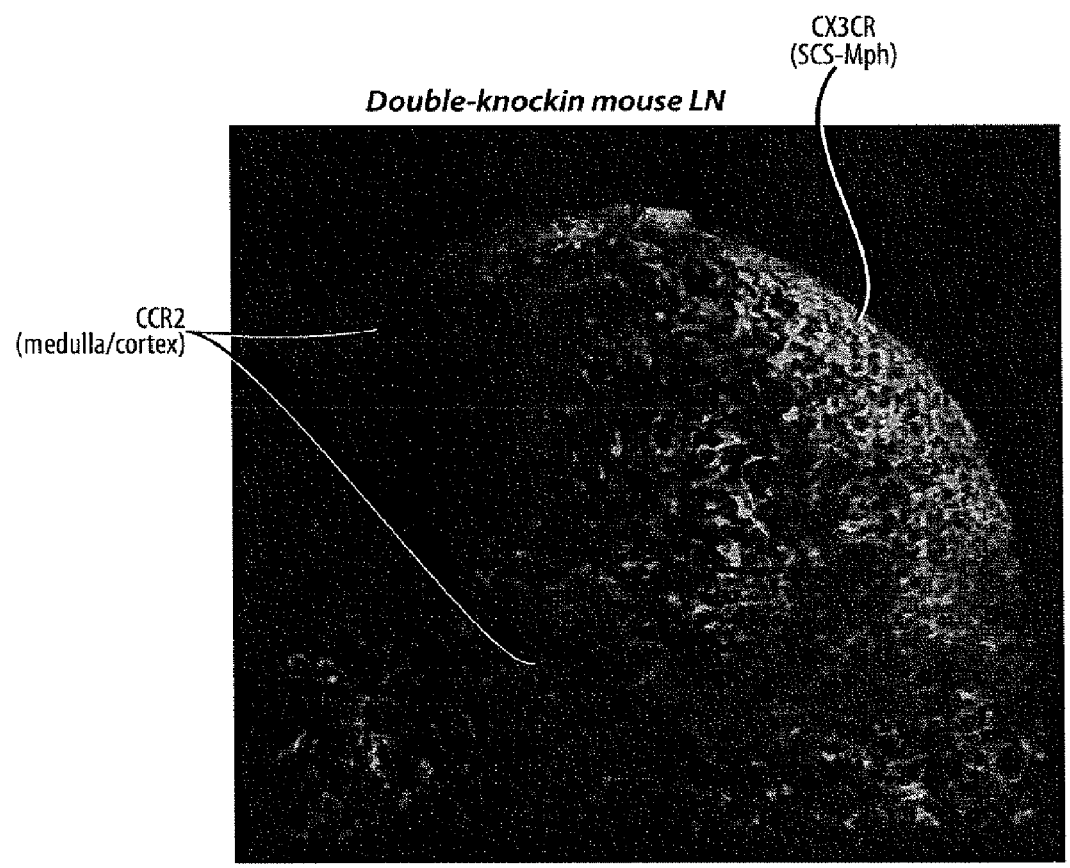
FIG. 25: Identification of the chemokine receptor CX3CR1 (fractalkine receptor) on macrophages in lymph node subcapsular sinus (SCS), but not in macrophages in the medulla. The micrograph on the right is a 3D projection of a lymph node from a double-knockin mouse where green fluorescent protein (GFP) is expressed in the CX3CR1 locus, while red fluorescent protein (RFP) reports the expression of another chemokine receptor, CCR2. SCS-Mph are readily identifiable by their prominent green fluorescence, while medullary macrophages express primarily RFP.
Figure 26:
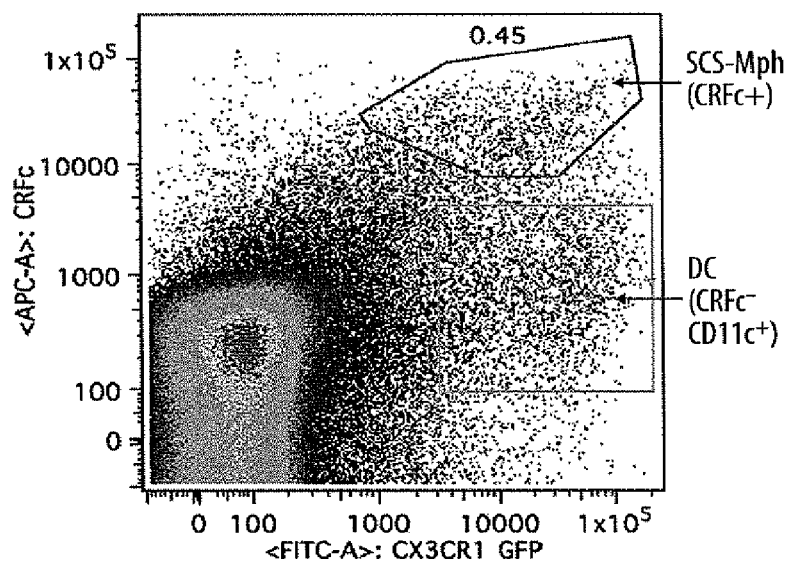
FIG. 26: SCS-Mph express the chemokine receptor CX3CR1. The graph shows a FACS plot of a single cell suspension from a lymph node of a knockin mouse that was genetically engineered to express GFP from the CX3CR1 locus. SCS-Mphs are identified by staining with a soluble receptor, CRFc, which binds macrophages in the SCS, but not the medulla. The CRFc negative CX3CR1-expressing (i.e., GFP-high) cells are conventional dendritic cells that express this chemokine receptor.

The Panels on the right of FIG. 24 show fluorescent micrographs of frozen lymph node sections after injection of blue fluorescent control (top panel, FIG. 24A) or targeted (middle and lower panels, FIG. 24A) nanoparticles. Sections were counter-stained with anti-CD169 and a marker that identifies either the medulla (in top and bottom panel, FIG. 24A) or B cells (in middle panel, FIG. 24A). At one hour after nanoparticle injection most control particles are found in the medulla (top, FIG. 24A), while targeted nanoparticles colocalise with CD169+ SCS-Mph adjacent to B cell follicles (middle, FIG. 24A). At 24 hours after injection, discrete cell-sized accumulations of targeted nanoparticles are seen in the cortical region between the SCS and the medulla, suggesting uptake and transport by migratory dendritic cells.

Mice were injected i.v. with red fluorescent B cells and in a footpad with a 1:1 mixture of control and Fc targeted nanoparticles. 24 hours later, when some of the transferred B cells had migrated into B cell follicles, the draining popliteal lymph node was excised and sectioned for confocal microscopy and quantitative image analysis of green:blue fluorescent ratios. The subcapsular sinus (SCS) region contained similar levels of blue and green nanoparticles (cells encircled on the right, FIG. 24B), while green fluorescence associated with Fc-targeted nanoparticles was about twice higher in the SCS. There were also prominent accumulations of green nanoparticles within B follicles delineated by scattered red B cells. These regions have the characteristic size, shape, and distribution of follicular dendritic cells (FDC), which like macrophages and dendritic cells are known to express abundant Fc receptors.

Example 4

Antigen-Bearing Targeted Nanoparticles are Highly Immunogenic and Induce High Antibody Titers Groups of mice (5/group) were immunized with: UV-inactivated vesicular stomatits virus (VSV, serotype Indiana) or with the purified immunogenic envelope glycoprotein (VSV-G) of VSV. VSV-G was either given in soluble form mixed with alum or conjugated to non-targeted or targeted (with surface immobilized human Fc) PLGA nanoparticles with or without alum as an adjuvant. The dose of free VSV-G was estimated to be ~10-fold higher than the dose of VSV-G delivered with nanoparticles. Mice received a booster injection at day 55 after the primary immunization, and serum was obtained after 10 weeks and tested for neutralization of VSV-mediated plaque formation on Vero cells. Results show titers as the highest serum dilution that blocked plaque formation by at least 50%. Each symbol reflects the neutralizing anti-VSV titer in one mouse. The group of mice immunized with VSV-G presented on Fc-targeted nanoparticles generated significantly higher neutralizing anti-VSV titers than any other group (the two animals with the highest titers in that group completely neutralized plaque formation at the highest dilution tested, so actual titers may have been even higher).

The induced immune response elicited by nanoparticle (NP) vaccines confers potent protection from a lethal dose of VSV. While all vaccinated groups showed some protection, only the group that received VSV-G conjugates to Fc-targeted NPs plus alum showed 100% protection from lethal infection. Recipients of free VSV-G (VSV-G+alum) received ~10-fold more antigen than animals that were given VSV-G conjugated to nanoparticles. As a negative control, one group of mice received Fc-targeted nanoparticles (NP-Fc) without VSV-G, which did not confer protection.

Example 5

In Vivo T Cell Activation by Immunomodulatory Nanoparticles

C57BL6J mice were injected i.v. with CFSE-labeled CD4 T cells from OT-II donor mice, which express a transgenic TCR specific for chicken ovalbumin (OVA) presented in MHC class II. Subsequently, immunization experiments were performed by injecting one footpad with free OVA or with nanoparticles composed of either PLA or PLGA that encapsulated an equivalent amount of OVA as a model antigen. All antigenic mixtures also contained CpG (a TLR9 agonist) as an adjuvant. The animals were injected, sacrificed three days after immunization, and OT-II T cell activation was assessed by flow cytometry in single-cell suspensions from different tissues.

Unstimulated 5,6-carboxy-succinimidyl-fluorescein-ester (CFSE)-labeled T cells do not divide and, therefore, carry an uniformly high concentration of CFSE resulting in a single narrow peak of brightly fluorescent cells. By contrast, activated T cells divide and in the process split the fluorescent dye evenly between the two daughter cells resulting in an incremental decrease in fluorescence intensity upon each successive division. Thus, the greater the left shift in CFSE, fluorescence the stronger T cells were activated. The results indicate that: (i) nanoparticle-encapsulated antigen generated a more potent CD4 T cell response than free antigen in the draining popliteal lymph node (popLN, top row); (ii) only nanoparticles, but not free OVA induced local T cell proliferation in distal lymphoid tissues, including the brachial lymph node (middle row) and the spleen (bottom row). In recipients of free OVA, the brachial LN and spleen contained only undivided cells or cells with very low CFSE content. The latter population does not indicate local T cell activation but migration of T cells that were activated elsewhere.

C57BL6J mice were injected i.v. with CFSE-labeled CD8 T cells from OT-I donor mice, which express a transgenic T cell receptor (TCR) specific for chicken ovalbumin (OVA) presented in MHC class I. The experimental protocol was otherwise identical as immediately described above.

C57BL6J mice were injected i.v. with CFSE-labeled CD8 T cells from OT-I donor mice as above. However, in this experiment CL097, an imidazoquinoline compound that activates TLR-7 and TLR-8, was used as adjuvant and different methods of adjuvant delivery were tested. T cell activation in this case was assessed by counting the total number of OT-I T cells in the draining popliteal lymph node three days after footpad injection of either free OVA (1 μg or 100 ng) mixed with free adjuvant (160 ng). All animals that received nanoparticles were given 100 ng OVA with or without 160 ng CL097. Material that was encapsulated within nanoparticles, but not covalently attached to the PLA polymer is shown in [ ]. Covalent linkage of CL097 to PLA is identified by hyphenation. Materials that were mixed in free form within the same compartment are separated by "+". These results revealed a marked increase in CD8 T cell proliferation in animals that received encapsulated OVA in nanoparticles in which the adjuvant was covalently linked to the excipient.

Example 6

Formation of Nanoparticles

PLA-PEG-COOH (3 mg/ml in DCM) was mixed with PLA-R848 (3 mg/ml in DCM) or R848 (15.7 mg/ml in DCM/DMSO (5%)). Added 500 μl of PLA-PEG-COOH solution to 500 μl PLA-R848, vortex, added 500 μl of OVA (5 mg/ml in water) or SIINFEKL (SEQ ID NO:1) peptide (2 mg/ml), sonicated (15sec, 50 Amplitude) using SINOMIX (sonicator S-4000), added 2 ml of PVA solution (1% w/v in water), sonicated (15sec, 50 Amplitude) and dropped the solution into 40 ml of water. Let stir for 2 hours, washed 3 times with water and 1 time with PBS. For encapsulated R848 formulation, added 500 μl of PLA-PEG-COOH solution to 400 μl free PLA (3.75 mg/ml) and 100 μl of R848, vortexed, added 500 μl of OVA (5 mg/ml in water) or SIINFEKL (SEQ ID NO:1) peptide (2 mg/ml), sonicated (15sec, 50 Amplitude) added 2 ml of PVA solution (1% w/v in water), sonicated (15see, 50 W) and dropped the solution into 40 ml of water. Let stir for 2 hours, washed 3 times with water and 1 time with PBS.

Example 7

Encapsulated R848 Formulation: Synthesis

Method 1, Tin Ethylhexanoate Catalysis.

To a two necked round bottom flask equipped with a stir bar and condenser was added the imidazoquinoline resiquimod (R-848, 100 mg, $3.18\times10^{-4}$ moles), D/L lactide (5.6 gm, $3.89\times10^{-2}$ moles) and anhydrous sodium sulfate (4.0 gm). The flask and contents were dried under vacuum at 50° C. for 8 hours. The flask was then flushed with argon and toluene (100 mL) was added. The reaction was stirred in an oil bath set at 120° C. until all of the lactide had dissolved and then tin ethylhexanoate (75 mg, 60 μL) was added via pipette. Heating was then continued under argon for 16 hours. After cooling, water (20 mL) was added and stirring was continued for 30 minutes. The reaction was diluted with additional toluene (200 mL) and was then washed with water (200 mL). The toluene solution was then washed in turn with 10% sodium chloride solution containing 5% conc. Hydrochloric acid (200 mL) followed by saturated sodium bicarbonate (200 mL). TLC (silica, 10% methanol in methylene chloride) showed that the solution contained no free R-848. The solution was dried over magnesium sulfate, filtered and evaporated under vacuum to give 3.59 grams of polylactic acid-R-848 conjugate. A portion of the polymer was hydrolyzed in base and examined by HPLC for R-848 content. By comparison to a standard curve of R-848 concentration vs HPLC response, it was determined that the polymer contained 4.51 mg of R-848 per gram of polymer. The molecular weight of the polymer was determined by GPC to be about 19,000.

Method 2, Lithium Diisopropylamide Catalysis.

The imidazoquinoline (R-848), D/L lactide and associated glassware were all dried under vacuum at 50° C. for 8 hours prior to use. To a round bottom flask equipped with a stir bar and condenser was added the R-848 (33 mg, $1.05\times10^{-4}$ moles), and dry toluene (5 mL). This was heated to reflux to dissolve all of the R-848. The solution was stirred under nitrogen and cooled to room temperature to provide a suspension of finely divided R-848. To this suspension was added a solution of lithium diisopropyl amide (2.0 M in THF, 50 μL, $1.0 \times 10^{-4}$ moles) after which stirring was continued at room temperature for 5 minutes. The pale yellow solution that had formed was added via syringe to a hot (120° C.) solution of D/L lactide (1.87 gm, $1.3 \times 10^{-2}$ moles) under nitrogen. The heat was removed and the pale yellow solution was stirred at room temperature for one hour. The solution was diluted with methylene chloride (200 mL) and this was then washed with 1% hydrochloric acid (2×50 mL) followed by saturated sodium bicarbonate solution (50 mL). The solution was dried over magnesium sulfate, filtered and evaporated under vacuum to give the polylactic acid-R-848 conjugate. TLC (silica, 10% methanol in methylene chloride) showed that the solution contained no free R-848. The polymer was dissolved in methylene chloride (10 mL) and the solution was dripped into stirred hexane (200 mL). The precipitated polymer was isolated by decantation and was dried under vacuum to give 1.47 grams of the polylactic acid—R-848 conjugate as a white solid. A portion of the polymer was hydrolyzed in base and examined by HPLC for R-848 content. By comparison to a standard curve of R-848 concentration vs HPLC response, it was determined that the polymer contained 10.96 mg of R-848 per gram of polymer R848 Derivative + D, L Di-Lactide PLA-R848 Conjugates Example 8

Encapsulated R848 Formulation: Encapsulation and Release

Added 500 ul of PLA-PEG-COOH solution (3 mg/ml in DCM) to 500 ul PLA-R848, vortex, added 500 ul of OVA or SIINFEKL (SEQ ID NO:1) peptide sonicate (15 sec, 50 Amplitude), add 2 ml of PVA solution (1% w/v in water), sonicated (15sec, 50 W) and dropped the solution into 40 ml of water. Let stirring for 2 hours, and wash 3 times with water and 1 time with PBS. The EE % of PLAR848 is assumed to be 100%, and the loading estimated to be ~5-10%. The loading is controlled by the amount of PLA-R848 mixed with PLA-PEG-COOH to form nanoparticles. HPLC experiment was conducted using reverse-phase C18 column (Supelco) with the mobile phase velocity of 1 mL/min. The mobile phase consists of 0.1% TFA/water and 0.1% TFA/ACN/water (60:40). The detection wavelength is 320 nm. Injection volume is 100 uL.

Free R848 1.57 mg (dissolved in 5% DMSO/DCM, 15.7 mg/ml) was mixed with PLA-PEGCOOH/PLA (1:1, total 3 mg/mL in DCM, 1 mL) and nano-precipitated by double emulsion technique. Final NP[R848] solution is 1.0 mL and average Np size ~250 nm. The EE % of free R848 encapsulation is 3.54%, and the loading is 1.85 wt %.

The R848 release experiment was conducted in 2 L PBS buffer at 37 degree C. 0.5 mL NP solution (1 mg/ml) was added in a mini-dialysis cassette (3500 Da), which was immersed in the PBS solution. Each time points, samples of 500 μl were redrawn (3 repeats) and 100 μl of the solution was mixed with 100 μl of acetonitrile prior injection to HPLC for analysis.

HPLC experiments to determine the concentration/amount of released R848 was conducted using reverse-phase C18 column (Supelco) with the mobile phase velocity of 1 mL/min. The mobile phase consists of 0.1% TFA/water and 0.1% TFA/ACN/water (60:40). The detection wavelength is 320 nm. Injection volume is 100 μL.

Figure 31:
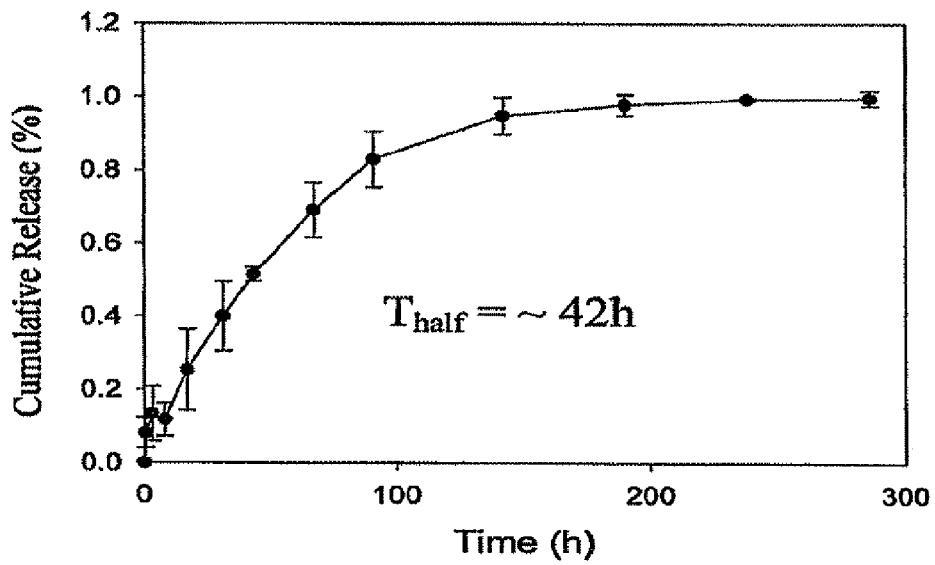
FIG. 31: Shows release profile data. Percent release of R848 over time from a formulation containing R848 encapsulated in nanoparticles.

Data are shown in FIG. 31.

Example 9

SIINFEKL Formulation: Encapsulation and Release

SIINFEKL(SEQ ID NO:1) is an immunogenic peptide derived from chicken ovalbumin (OVA) that binds to mouse MHC class I (H2k-b) and is recognized by transgenic OT-I T cells. SIINFEKL (SEQ ID NO:1) 2 mg/mL 500 uL was encapsulated inside 1 mL PLA-PEG-COOH/PLAR848 solution (1:1, total 3 mg/mL in DCM) by double emulsion technique. Final NPR848[SIINFEKL (SEQ ID NO:1)] solution is 1.5 mL. Average NP size is ~220 nm. The encapsulation efficiency (EE %) of SIINFEKL (SEQ ID NO:1) was 1.32%, and the loading is 0.44 wt %.

The SIINFEKL (SEQ ID NO:1) release experiment was conducted in 11 mL PBS buffer at 37° C. 0.5 mL NP solution was added in a mini-dialysis cassette (3500 Da), which was immersed in the PBS solution. Each time, 2 mL PBS was taken out and 2 mL fresh PBS was replaced. The samples were freeze-dried and dissolved in 150 uL DI water for HPLC analysis.

HPLC experiment to determine the amount of released SIINFEKL (SEQ ID NO:1) was conducted using reverse-phase C18 column (Supelco) with the velocity of 1 mL/min. The mobile phase includes 0.1% TFA/water and 0.1% TFA/ACN/water (60:40); with time gradient 0-16 min 100%→40% TFA/water and 16-38 min 40%→0% TFA/water. The detection wavelength is 215 nm. Injection volume is 100 uL. For each time point, the SIINFEKL (SEQ ID NO:1) release was quantified from 3 parallel samples and averaged.

Figure 32:
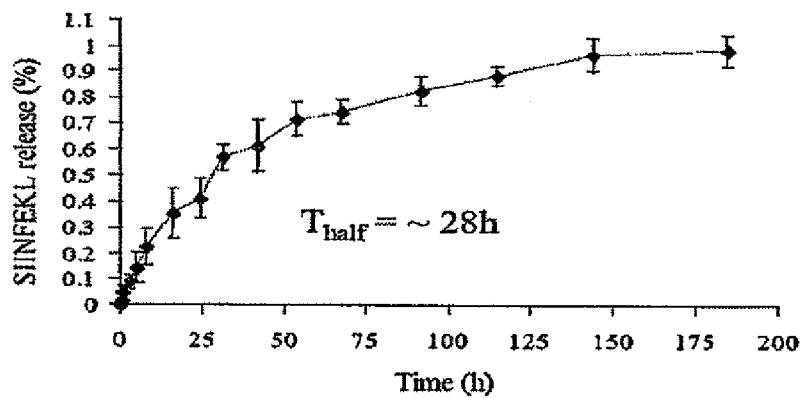
FIG. 32: Shows release profile data. Percent release of SIINFEKL (SEQ ID NO:1) over time from a formulation containing SIINFEKL (SEQ ID NO:1) encapsulated in nanoparticles.

Data for SIINFEKL (SEQ ID NO:1) release are shown in FIG. 32.

Example 10

Encapsulated OVA Formulation: Encapsulation and Release

The OVA release experiment was conducted in 10 mL PBS buffer at 37° C. 3 mg NP solution with encapsulated OVA (3 repeats), which was immersed in the PBS solution 10 ml. Each time points, 0.5 ml of solution is collected, centrifuged (8 min, 13 rpm), the supernatant is collected and the centrifuged nanoparticles for BCA quantification.

Method 1:

Using BCA assays for OVA quantification. Direct incubation of NP-OVA with BCA buffer solution @60° C. for 30 min.

Results:
1.0% PVA: 1.09 mg/mL; EE % 21.8%; Loading 36.3 wt %.
1.5% PVA: 1.18 mg/mL; EE % 23.6%; Loading 39.3 wt %.
2.0% PVA: 1.39 mg/mL; EE % 27.8%; Loading 46.3 wt %.

Method 2:

Using protein gel electrophoresis for OVA quantification. Direct Incubation of NP-OVA in loading buffer at 95° C. for 5 min. Bio-Rad ready gels (10% PAGE) were used, 200V for 30 min.

Results:
1.0% PVA: ~0.6 mg/mL; EE % 12%; Loading ~20 wt %.

Gel electrophoresis data indicated that, although there may have been some degradation/denaturation of OVA in the NP-OVA compositions, the OVA remained largely unchanged.

In Vivo Delivery and Processing of OVA.

DQ-OVA is comprised of OVA conjugated to a fluorophor that remains non-fluorescent until OVA is proteolytically processed by antigen-presenting cells (mostly DCs). Analysis of mouse LNs after administration of NP-encapsulated OVA demonstrated that NP-encapsulated OVA is processed, transported and presented by DCs in draining lymph nodes following sq injection.

Example 11

CD8 T Cell Activation In Vivo

Nanoparticles with OVA antigen and CL097 adjuvant were prepared and tested in vivo according to the procedures described herein. The following six compositions were prepared: (1) free OVA; (2) free OVA and free CL097; (3) NP[OVA] (i.e., nanoparticles containing encapsulated OVA); (4) NP[OVA+CL097] (i.e., nanoparticles containing encapsulated OVA and encapsulated CL097); (5) NP-CL097[OVA] (i.e., nanoparticles conjugated to CL097 and containing encapsulated OVA); and OVA+NP-CL097 (i.e., free OVA and nanoparticles conjugated to CL097). Lymph Node (LN) T cell number data are shown in FIG. 29C.

Figure 33:
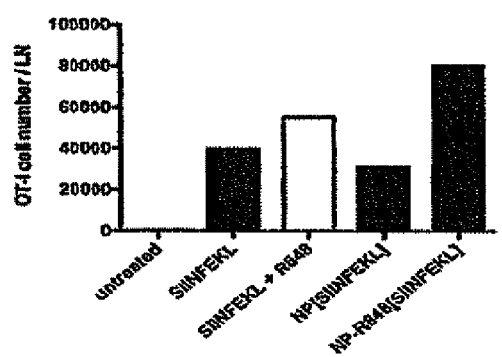
FIG. 33: Shows measured OT-I cell numbers in mouse lymph nodes (LN) after the mice have been administered one of several formulations.

FIG. 33 provides OT-I cell counts observed in mouse lymph nodes one day after administration of the following compositions: (1) free SIINFEKL (SEQ ID NO:1); (2) free SIINFEKL (SEQ ID NO:1) and free R848; (3) SIINFEKL (SEQ ID NO:1) encapsulated within nanoparticles; and (4) SIINFEKL (SEQ ID NO:1) encapsulated within nanoparticles conjugated to R848. The data shows that the SIINFEKL-encapsulating and R848conjugated nanoparticles obtained the highest OT-I cell count. The cell counts were measured after only one day; it is expected that the OT-I cell counts for compositions (1), (2), and (3) would be lower than the observed value if measured after more than one day, but that the OT-I cell count for composition (4) would be similar to the observed value if measured after more than one day.

Figure 29A:
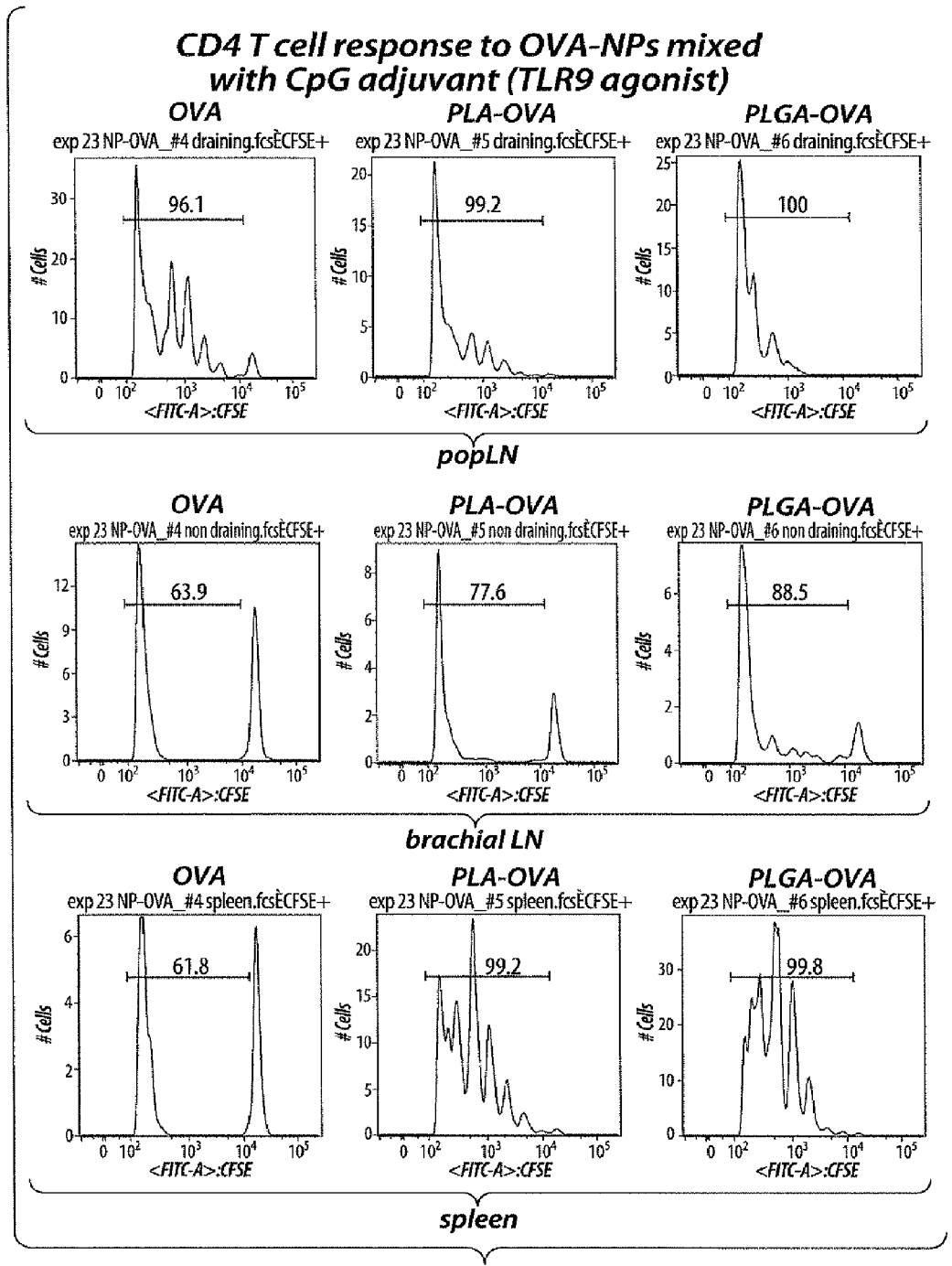
FIG. 29: In vivo T cell activation by immunomodulatory nanoparticles. (A) Effect of NPs on CD4 T cell activation. (B) Effect of NPs on CD8 T cell response mixed with CpG adjuvant (TLR9 agonist). (C) Effect of co-encapsulated adjuvant on CD8 T cell activation.
Figure 29B:
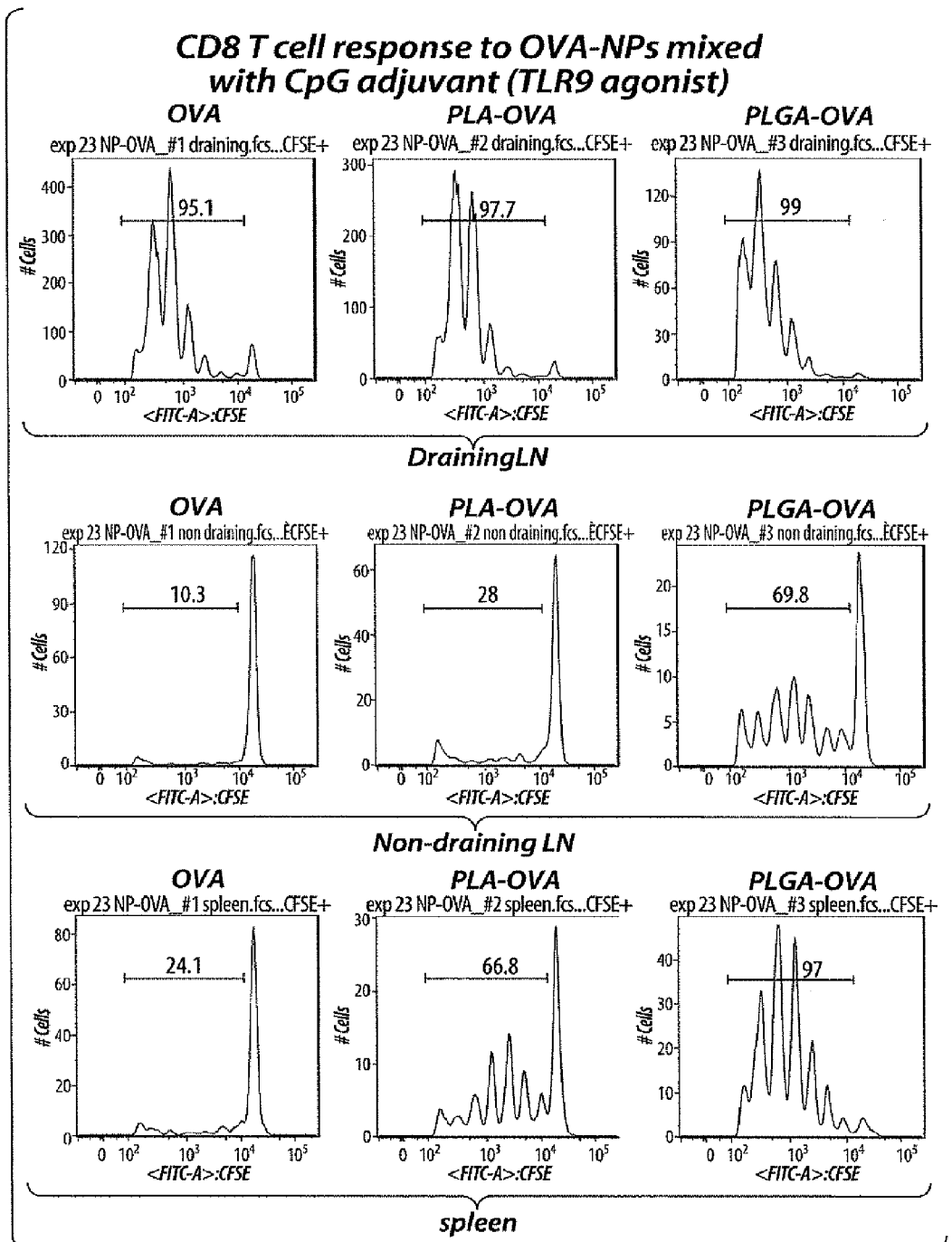
Figure 29C:
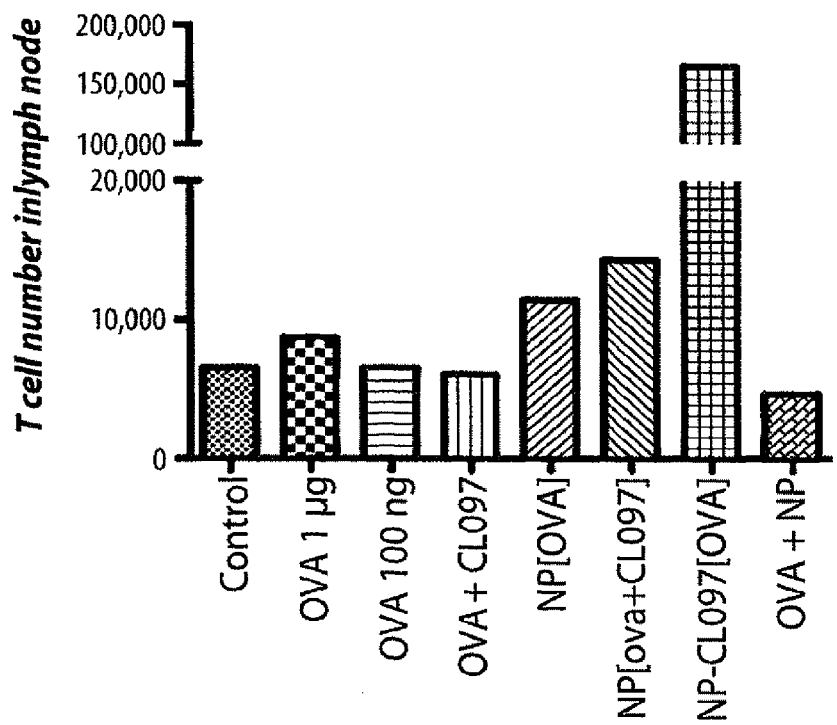
Figure 30:
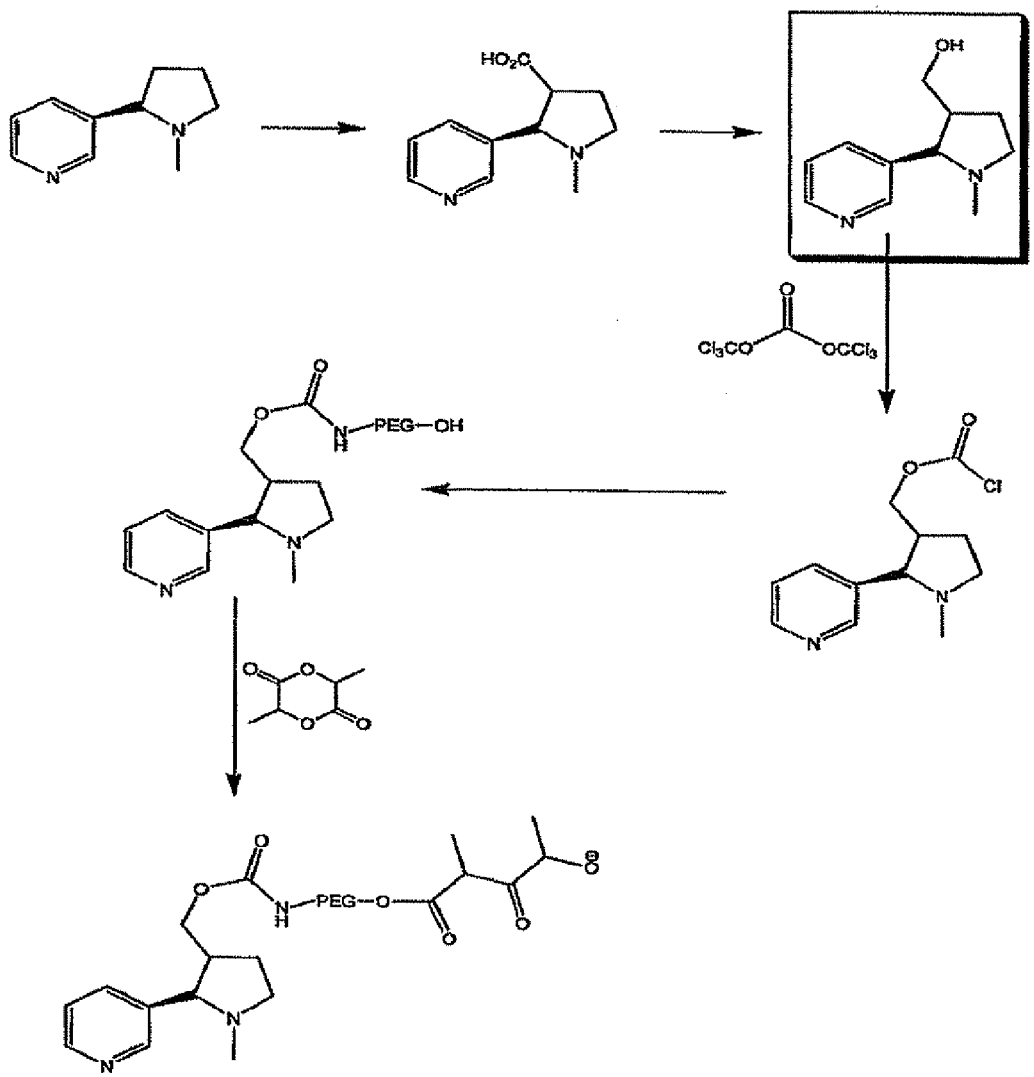
FIG. 30: Shows an exemplary R848 conjugation strategy.

Experiments in FIGS. 29B, 29C, and 33 demonstrate that synthetic nanocarriers that encapsulate a T cell antigen (OVA, ovalbumin protein) or an antigenic peptide (SIINFEKL (SEQ ID NO: 1), derived from ovalbumin) together with covalently bound adjuvant (CL097 or R848) induce potent proliferation of antigen-specific OT-I CD8+ T cells. This T cell subset (also called cytotoxic T cells) only responds to antigens that are presented in the MHC class-I pathway. Exogenous antigens, such as those provided by conventional vaccines, are preferentially presented by MHC class-II molecules that are not recognized by CD8+ T cells. Only certain subsets of dendritic cells (DC) are capable of shunting some of the exogenous antigen they acquire to the MHC class-I pathway, a process called 'cross-presentation'. Methods and compositions that result in enhanced cross-presentation of vaccine antigens are desirable because they are predicted to result in improved cytotoxic effector responses that would be useful for the prevention and therapy of cancer and infectious microbes. The data in FIGS. 29, and 33 clearly show that exogenous antigens delivered by inventive synthetic nanocarriers can be cross-presented in vivo resulting in CD8 T cell proliferation in lymph nodes, even when the synthetic nanocarriers do not present an immunofeature surface.

Example 12

T-Cell Expression

Figure 34A:
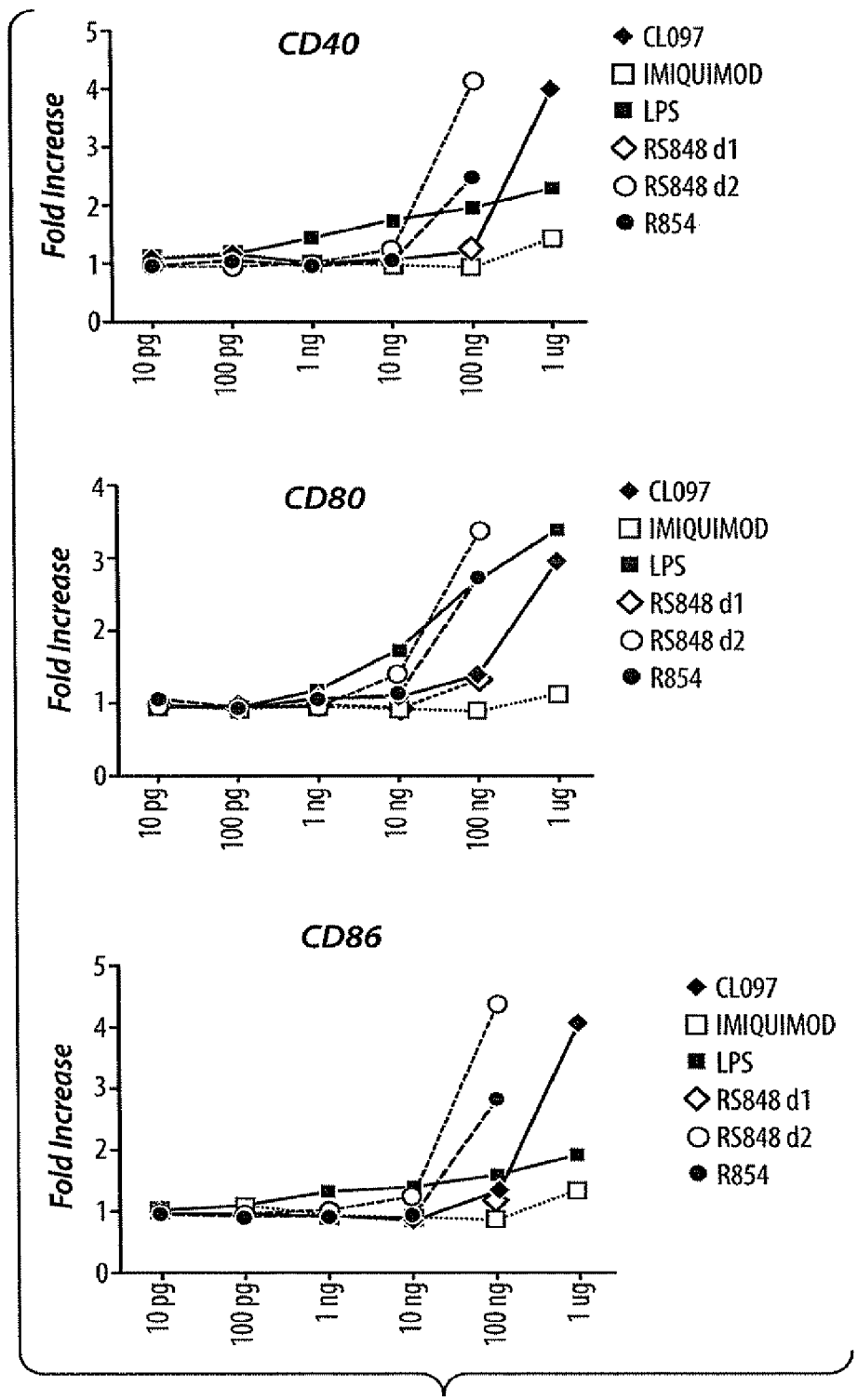
FIG. 34a: Shows increases in the expression of CD40, CD80, and CD86 proteins on the surface of dendritic cells having been incubated with various free adjuvants.
Figure 34B:
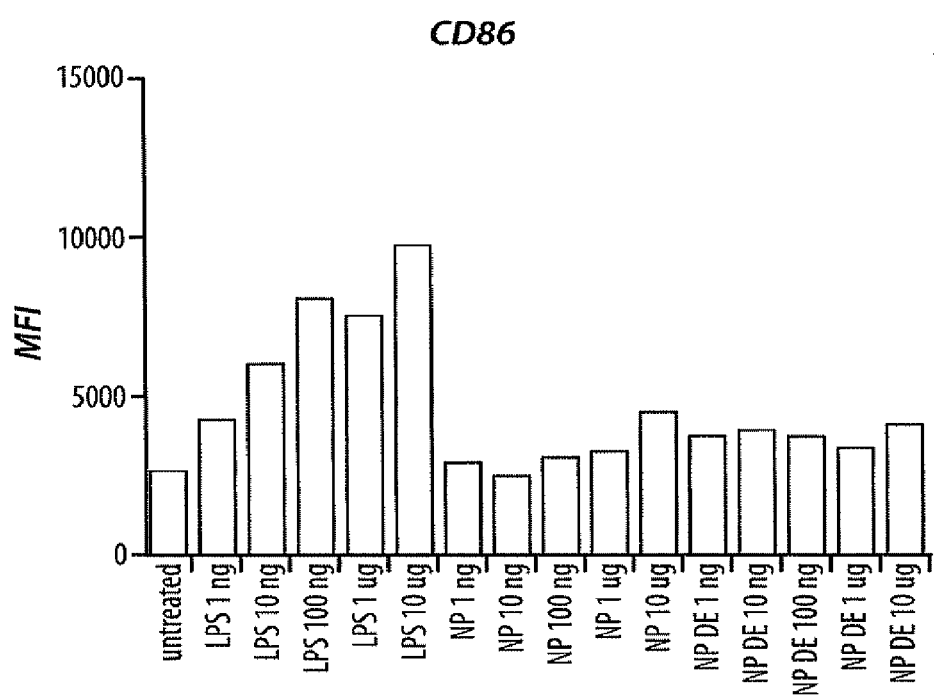
FIG. 34b: Shows mean fluorescence intensity (MFI) for CD86 in dendritic cells after such cells have been incubated with various compositions with or without nanoparticles.
Figure 34C:
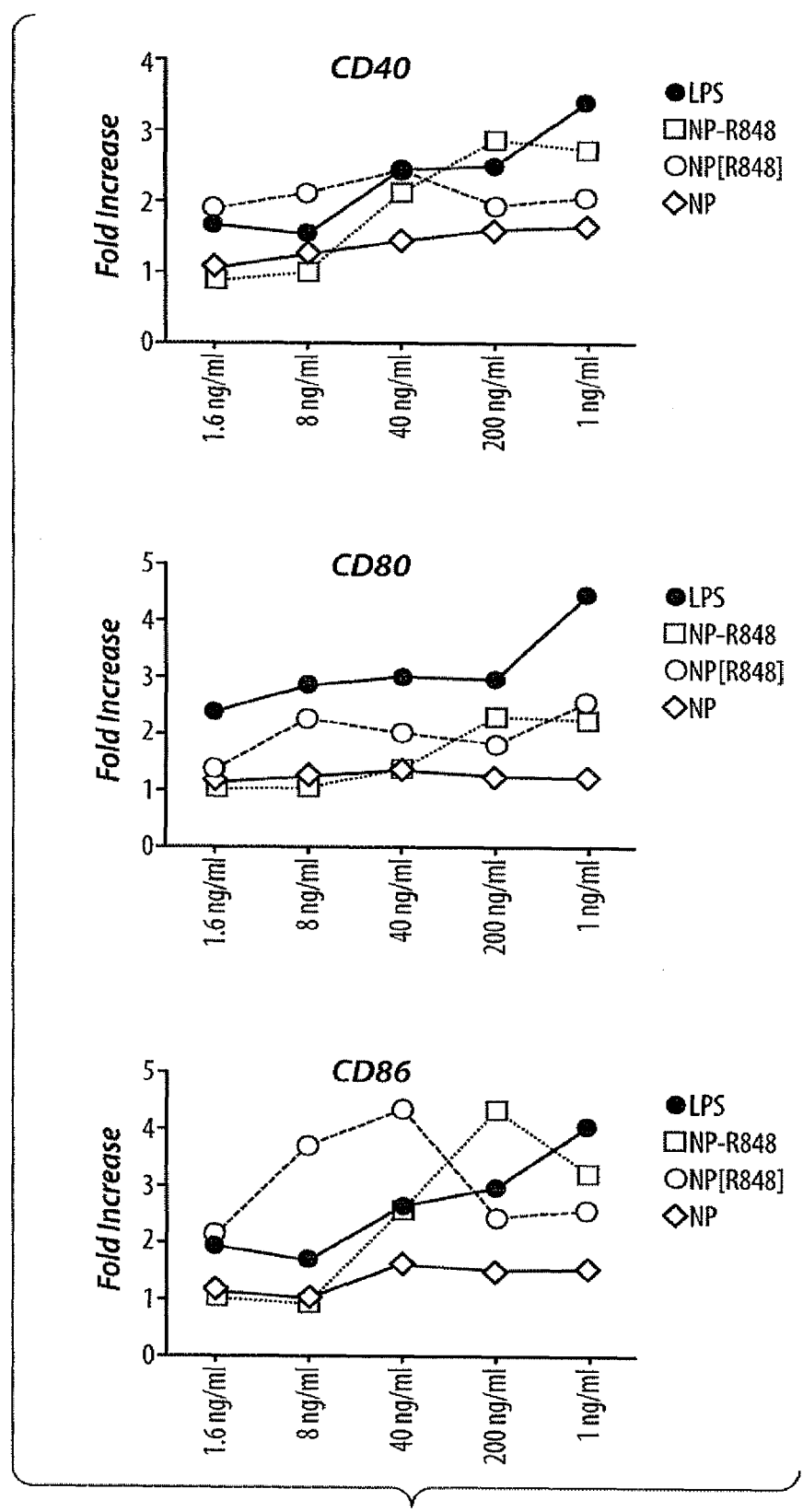
FIG. 34c: Shows increases in the expression of CD40, CD80, and CD86 proteins on the surface of dendritic cells having been incubated with various nanoparticle compositions, and comparison with DCs incubated with lipopolysaccharide (LPS).

A series of solutions containing various free adjuvants (i.e., not associated with nanoparticles) at various concentrations were prepared. The adjuvants were CL097, imiquimod, LPS, R848, and R854. To determine the ability of such adjuvants to induce the activation of dendritic cells, DCs were incubated overnight in the presence of the different adjuvant solutions. Surface expression of activation markers (CD40, CD80, and CD86) were measured. The data are shown in FIG. 34a, and results are expressed as fold induction relative to the untreated dendritic cells. Using the same experimental procedure, the activity of plain nanoparticles (i.e., non-functionalized or associated with immunostimulatory or immunomodulatory moieties) was tested and compared with LPS to show that NPs per se are not inducing DC acitation. The data are shown in FIG. 34b. Again, using the same experimental procedure, the activities of plain NPs, NPs with encapsulated R848 (NP[R848]), NP with conjugated R848 (NP-R848), and free LPS in inducing DC activity were compared. The data are shown in FIG. 34c.

Figure 35:
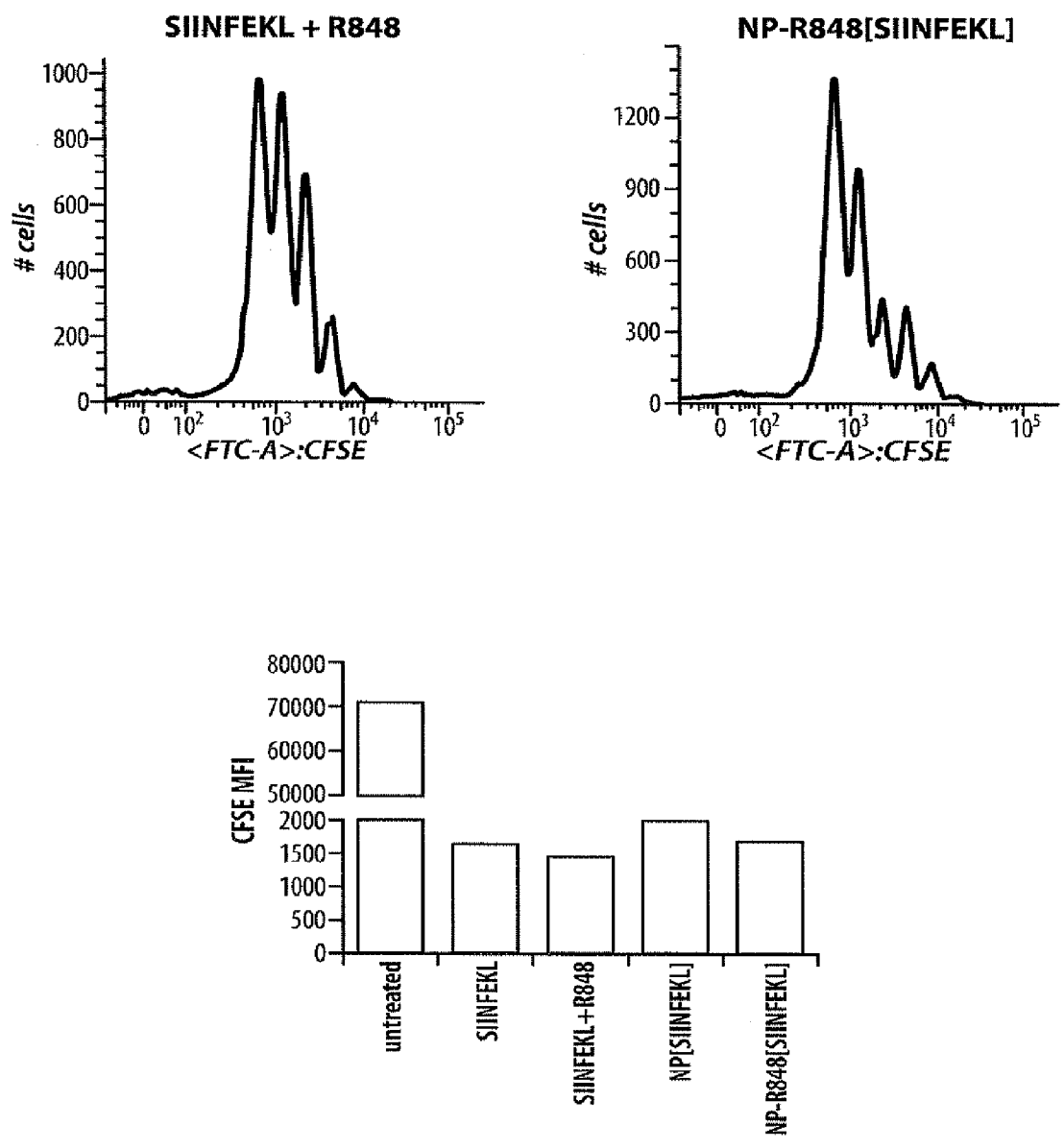
FIG. 35: shows FACS data showing T cells proliferation.

FIG. 35 provides FACS data showing T cells proliferation. Naive T cells are labelled with the cytoplasmic dye CFSE. When a cell divides, the dye gets divided among the daughter cells, so that they are half fluorescent. If these cells divide further they become a quarter fluorescent and so forth. In this way the peaks represent the number of cell divisions. The following formulations were tested: free SIINFEKL (SEQ ID NO:1); free SIINFEKL (SEQ ID NO:1) and free R848; NP with encapsulated SIINFEKL (SEQ ID NO:1) (NP[SIINFEKL]); and NP with conjugated R848 and encapsulated SIINFEKL (SEQ ID NO:1) (NP-R848[SIINFEKL]).

Example 13

PLA-PEG-COOH Synthesis

PLA-PEG-COOH was synthesized by ring opening polymerization method. To a two necked round bottom flask equipped with a stir bar and condenser was added the COOH-PEG3400-OH (0.085 mmol), D/L lactide (1.6 g, 11.1 mmol) and anhydrous sodium sulfate (200 mg). The flask and contents were dried under vacuum at 50° C. for 8 hours. The flask was then flushed with argon and toluene (10 mL) was added. The reaction was stirred in an oil bath set at 120° C. until all of the lactide had dissolved and then tin ethylhexanoate (30 mg) was added via pipette. Heating was then continued under argon for 16 hours. After cooling, transfer the resulting mixture to a separation funnel containing CHCl3 (50 mL) and water (30 mL). After layer separation, organic layer is collected (bottom layer), and dried using anhydrous MgSO4 (200 mg), filtered, and concentrated under reduced vacuum. The PLA-PEG-COOH polymer was then purified through precipitation.

Example 14

Conjugate Formation

Cotinine-PEG-cotinine conjugates were formed according to the following reaction equation, using doubly end-functionalized PEG:

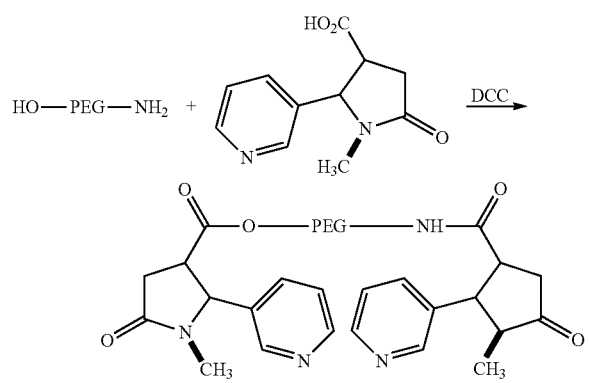

Reduction of cotinine-PEG-cotinine with lithium aluminum hydride allowed formation of HO-PEG-Nicotine:

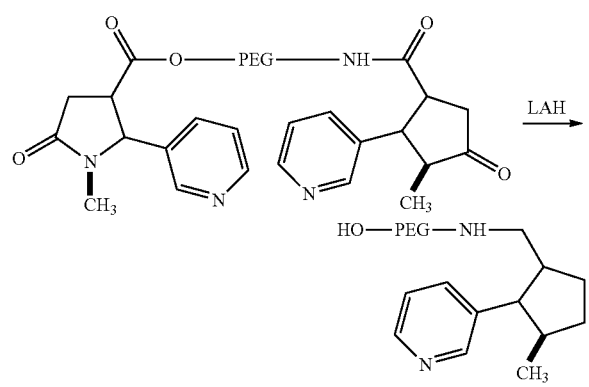

Similarly, copolymers of PLA and PEG, conjugated to nicotine, were prepared using HO-PEG-nicotine as an initiator in a ring-opening polymerization according to the following reaction:

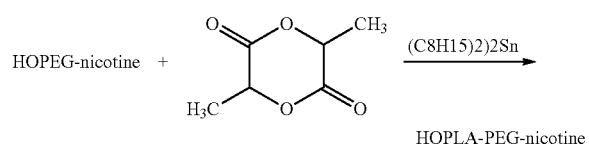

Nicotine-NP were prepared using 50% PLA-PEG-nicotine and 50% PLA and administered to mice via subcutaneous (sc) injection. The draining LNs were harvested 1 hour after sc injection and the sections were stained with APC-B220 to label B cells (in gray) and anti-nicotine Ab (clone HB-9123) followed by Alexa568-anti-mouse IgG (in red). Fluorescence data shows that nicotine-NP accumulate in the SCS of the draining LN 1 hour after sc injection.

Example 15

Anti-Nicotine IgG in Immunized Mice

Figure 36:
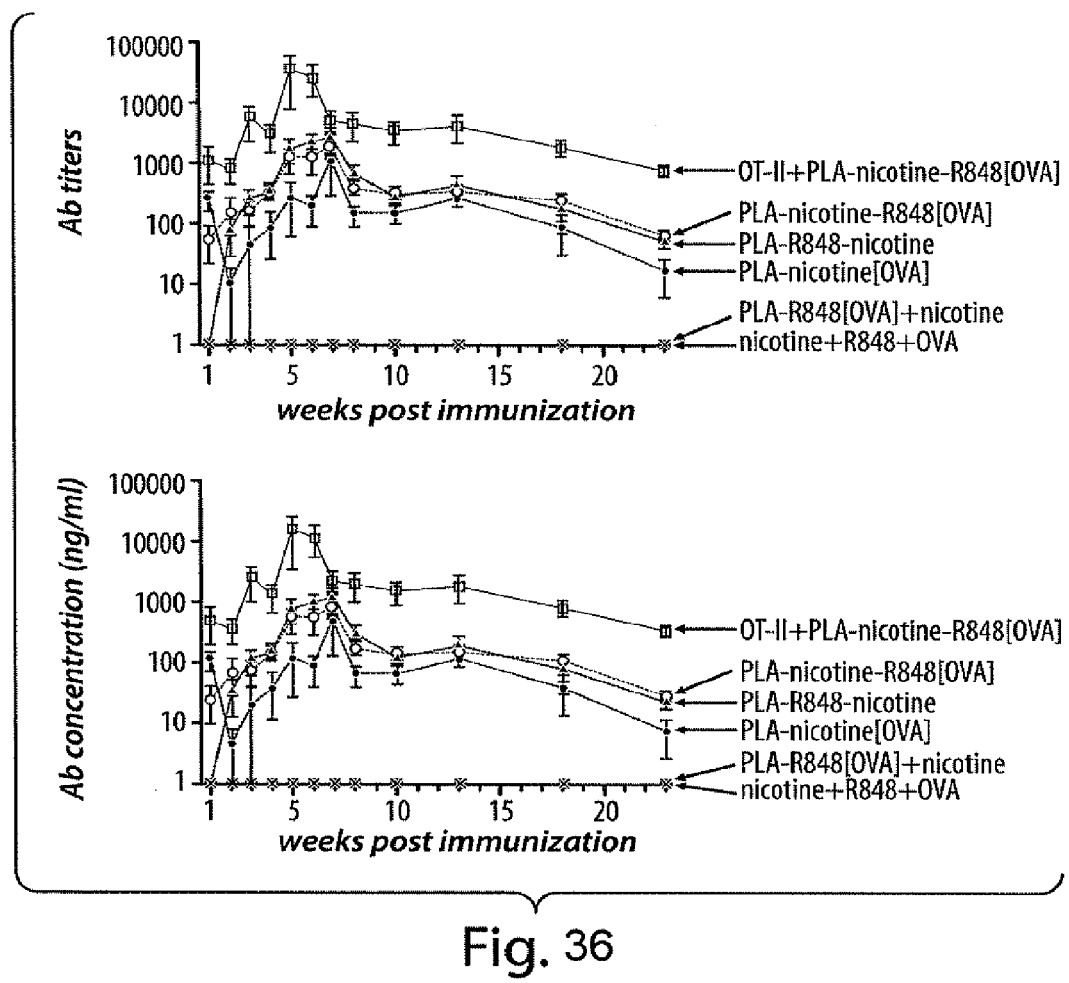
FIG. 36: Shows mouse anti-nicotine IgG titers and concentrations up to 23 weeks after the mice have been administered various compositions.

In a first series of experiments, groups of C57BL6 mice (4-5) were immunized with nicotine immunonanotherapeutic compositions on day 0 and boosted after 2, 4 and 8 weeks. Ab titers were measured by ELISA and compared to a standard curve from an anti-nicotine MAb to calculate concentrations. One group of mice received OVA-specific OT-II T cells ($5 \times 10^5$ IV) prior to vaccination to boost T cell help. Data are shown in FIG. 36. Curves are identified by the immunization formulation. For example, the data labeled "nicotine+R848+OVA" indicates mice that were immunized with a formulation containing free nicotine, free R848, and free OVA. The data labeled "PLA-nicotine[OVA]" indicates mice immunized with a formulation containing PLA-nicotine nanoparticles with encapsulated OVA.

Figure 37:
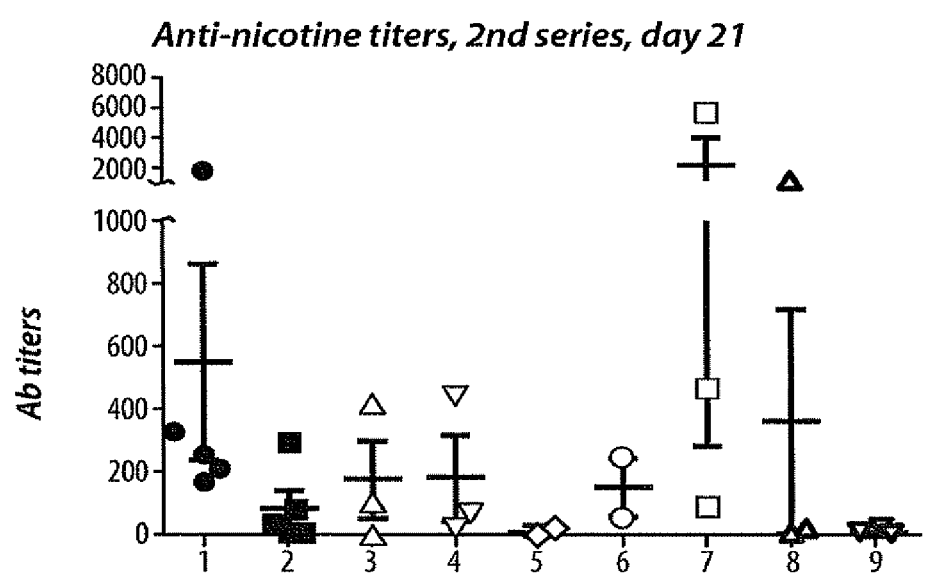
FIG. 37: Shows mouse anti-nicotine IgG titers and concentrations 21 days after the mice have been administered various compositions.

In a second series of experiments, additional nicotine titers were determined and are shown in FIG. 37. The additional data show initial (3 week) titers. The protocol in terms of dose and timing of injections was the same as for the first series. However, several new particle formulations were tested to assess: a) whether previously frozen nanoparticles (containing 50% nicotine-PEG-PLA) retain their immunogenicity; b) how the content of nicotine-PEG-PLA affects antibody titers; and c) whether the nanoparticles (50% nicotine-PEG-PLA) work in MHC class II deficient mice. The formulations are as follows: (1) NP having 50% nicotine-PEG-PLA and 50% PLA-R848, with encapsulated OVA, used as prepared (i.e., without freezing); (2) NP having 50% nicotine-PEG-PLA and 50% PLA-R848, with encapsulated OVA, used after overnight freezing and subsequent thawing; (3) NP having 5% nicotine-PEG-PLA, 45% PLA-PEG, and 50% PLA-R848; (4) NP having 25% nicotine-PEG-PLA, 25% PLA-PEG, and 50% PLA-R848; (5) NP having 75% nicotine-PEG-PLA and 25% PLA-R848, wherein the formulation was given at twice the regular dose to keep the R848 dose constant; (6) NP having 50% nicotine-PEG-PLA and 50% PLA, with encapsulated OVA, wherein free R848 was mixed into the formulation immediately prior to injection; (7) NP having 50% nicotine-PEG-PLA nanoparticles and 50% PLA-R848 with encapsulated OVA, wherein the mice received OVA-specific OT-II T cells prior to vaccination; (8) NP having 50% nicotine-PEG-PLA and 50% PLA-R848 with encapsulated OVA, MHC class II deficient mice; and (9) NP having 50% nicotine-PEG-PLA and 50% PLA with encapsulated OVA, MHC class II deficient mice. Due to differences in ELISA sensitivity, the absolute magnitude of titers in this series can't be compared directly to the first series of data. The following conclusions were reached: a) previously frozen and thawed NPs were still immunogenic; b) early antibody titers were similar in mice receiving NPs with nicotine-PEG-PLA content ranging from 5 to 50% (with always the same 50% amount of R848-PLA), but lower when NPs with 75% nicotine-PEG-PLA was used; c) a humoral response to nicotine-NPs was induced in MHC-II deficient mice, indicating the ability to induce a T-independent IgG response.

The data in FIGS. 36 and 37 show that free nicotine (i.e., not conjugated), even when administered along with PLA-R848, R848, and/or OVA, does not elicit the production of nicotine antibodies. However, nicotine nanoparticles do elicit such production. Even in the absence of T cell help, the nicotine nanoparticles described herein cause a substantial antibody production.

In summary, data shown in FIG. 36 and FIG. 37 further demonstrate that synthetic nanocarriers comprising an immunofeature surface, such as an immunofeature surface comprising nicotine, efficiently deliver adjuvants and protein-based antigens to APC resulting in potent T helper cell activation. This is evidenced by the fact that, upon immunization with PLA-PEG-nicotine synthetic nanocarriers that incorporated both R848 and OVA, anti-nicotine IgG titers were enhanced by ~10-fold in mice that had received naive OT-II (i.e. OVA-specific) T helper cells compared to mice that did not receive OT-II cells. This effect indicates that the adjuvant (R848) and T cell antigen (OVA) contained within the immunofeature-modified synthetic nanocarriers were efficiently targeted to DCs that presented OVA to T cells. The greater availability of OVA-specific T cells in animals that had received OT-II cells resulted in an enhanced helper response that, in turn, boosted the production of anti-nicotine antibodies by B cells. Thus, a moiety that can form an immunofeature surface according to the above criteria can boost synthetic nanocarrier immunogenicity even when its binding affinity to APC is too low to be detectable by in vitro capture assays.

Example 16

Prophetic Nanocarrier Formulation—HPV16 L2 17-36 Peptide

PLA-PEG-OCH3 (or PLA-PEG-COOH) polymer is prepared using HO-PEG-OCH3 (or HO-PEG-COOH, Aldrich Chemical, approximately MW of PEG=2 KD) which is used to initiate a ring opening polymerization of D,L-lactide (final polymer MW target=18-20 KD). The structure is confirmed by NMR. Polymer nanoparticles are synthesized by double emulsion technique as follows. 250 ul of PLA-PEG-COOH solution (3 mg/ml in DCM), 250 ul of PLA-PEG-methoxy solution (3 mg/ml in DCM) and 500 ul PLA-R848 (3 mg/mL in DCM) are mixed. 500 ul of Th epitope (P25) peptide (KLIPNASLIENCTKAEL, 1 mg/mL) solution is then added into the organic solvent. The whole solution is sonicated for 15 sec (50 Amplitude), mixed with 2 ml of PVA solution (1% w/v in water), and sonicated again (15 sec). The double emulsified solution is dropped the solution into 40 ml of water, stirred for 2 hours, and washed 3 times with water and 1 time with PBS. The final concentration of nanoparticle solution is about 1 mg/mL.

Next, HPV16 L2 17-36 peptide (QLYKTCKQAGTCPP-DIIPKV) is conjugated to PLA-PEG-COOH nanoparticles through EDC/NHS reaction. The carboxylic acid groups on the nanoparticle surface are activated by incubation with EDC/NHS (15 mg/mL) solution for 1 hour. Excess EDC and NHS are washed away with DI water and then PBS buffer. The NP solution is then mixed with HPV16 L2 17-36 peptide solution (the molar ratio of PLA-PEG-COOH polymer vs. peptide is 1:2) for 2 hours, and is washed with PBS buffer for three times to remove free peptides.

Example 17

Prophetic Nanocarrier Formulation—Cholera Toxin Subunit B Peptide 50-64

PLA-PEG-OCH3 (or PLA-PEG-COOH) polymer is prepared using HO-PEG-OCH3 (or HO-PEG-COOH, Aldrich Chemical, approximately MW of PEG=2 KD) which is used to initiate a ring opening polymerization of D,L-lactide (final polymer MW target=18-20 KD). The structure is confirmed by NMR. Polymer nanoparticles are synthesized by double emulsion technique as follows. 250 ul of PLA-PEG-COOH solution (3 mg/ml in DCM), 250 ul of PLA-PEG-methoxy solution (3 mg/ml in DCM) and 500 ul PLA-R848 (3 mg/mL in DCM) are mixed. 500 ul of ovalbumin (1 mg/mL) solution is then added into the organic solvent. The whole solution is sonicated for 15 sec (50 Amplitude), mixed with 2 ml of PVA solution (1% w/v in water), and sonicated again (15 sec). The double emulsified solution is dropped the solution into 40 ml of water, stirred for 2 hours, and washed 3 times with water and 1 time with PBS. The final concentration of nanoparticle solution is about 1 mg/mL.

Next, Cholera Toxin Subunit B peptide 50-64 (see C O Jacob et al., "Antibodies against synthetic peptides of the B Subunit of Cholera Toxin: Cross-reaction and neutralization of the toxin" Proc. Natl. Acad Sci. USA 80:7611-7615 (1983)) is conjugated to PLA-PEG-COOH nanoparticles through EDC/NHS reaction. The carboxylic acid groups on the nanoparticle surface are activated by incubation with EDC/NHS (15 mg/mL) solution for 1 hour. Excess EDC and NHS are washed away with DI water and then PBS buffer. The NP solution is then mixed with Cholera Toxin Subunit B peptide 50-64 solution (the molar ratio of PLA-PEG-COOH polymer vs. peptide is 1:2) for 2 hours, and is washed with PBS buffer for three times to remove free peptides.

Example 18

Nanoparticle Targeting to Lymph Node APC In Vivo

In vivo accumulation of nicotine-modified and control (PLA-PEG) nanoparticles on lymph node APC. Fluorescent nanoparticles (~100 nm) were generated using a double-emulsion procedure. Nicotine particles consisted of 50% PLA-PEG-Nic (~15 kD PLA), 15% PLGA-Dye-PLGA (~15 kD PLGA total), and 35% PLA (~15 kD), whereas control particles were generated using 50% PLA-PEG (~15 kD PLA, methoxy terminated PEG), 15% PLGA-Dye-PLGA (~15 kD PLGA total) and 35% PLA (~15 kD). To assess targeting to DC, two sets of control particles were generated, with and without encapsulated OVA protein (OVA). All sets of particles were produced to incorporate PLGA-Rhodamine-B (=PLGA-Dye) as a green (543 nm) fluorescent label. Additionally, control particles (without OVA) were also produced to incorporate Alexa 647, which has a spectrally distinct (red) fluorescence emission. All green particles were mixed with an equal amount of red control particles and the mixtures were injected into footpads of young adult C57/BL6 mice. The draining popliteal lymph node was harvested 4 h or 24 h later, fixed overnight at 4° C. with phosphate buffered L-lysine with 1% paraformaldehyde/periodate, cryoprotected by an ascending series of 10%, 20% and 30% sucrose in PBS, snap-frozen in tissue freezing medium (Triangle Biomedical Sciences, Durham, N.C.) and prepared for immunofluorescence analysis of frozen sections. Targeting to APC was determined by planimetry of digital confocal microscopy images using Adobe Photoshop CS3. Data are provided in FIGS. 38a and 38b.

Figure 38A:
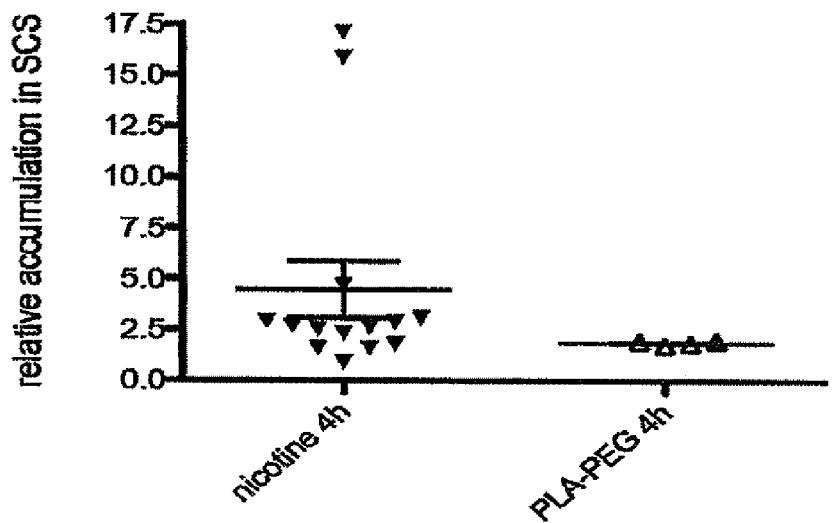
FIG. 38a: Shows relative accumulation of nicotine-modified nanoparticles in the SCS 4 hours after injection into mouse footpads, compared with control nanoparticles.

In FIG. 38a, the 4 h samples were used to assess accumulation on subcapsular sinus (SCS) macrophages by quantifying the total number of green (test) and red (control) fluorescent pixels in the entire lymph node section (F-total) and a region of interest (ROI) assigned to the SCS (F-scs). "Relative accumulation" is given F-scs/F-total×100%. As shown in the data, the nicotine-containing sample ("nicotine 4h") gave rise to significantly greater relative accumulation in the SCS compared with the control ("PLA-PEG 4h").

Figure 38B:
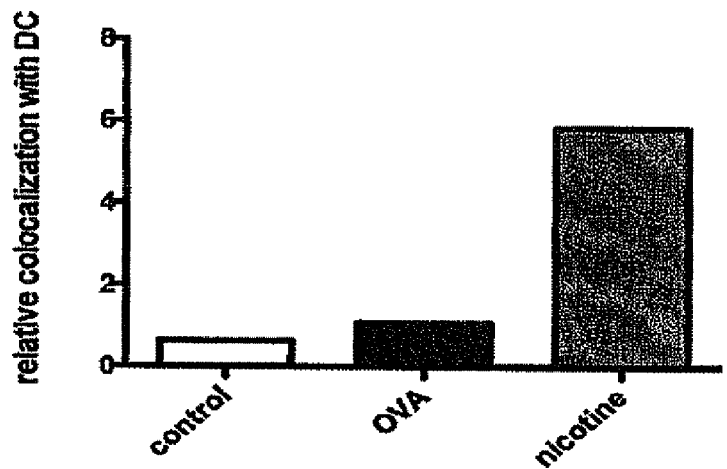
FIG. 38b: Shows relative colocalization with DC of nicotine-modified nanoparticles 24 hours after injection into mouse footpads, compared with control nanoparticles.

In FIG. 38b, CD11c colocalization analysis was performed in 24 h samples to assess targeting to dendritic cells (DC). DC in the T cell zone were identified by staining with blue fluorescent anti-CD11c and defined as ROI. The number of green and red pixels that colocalized to the ROI was measured and is expressed as ratio. Red and green fluorescent control particles as well as particles with encapsulated OVA showed similar accumulation on DC, whereas an immunofeature surface consisting of nicotine conferred statistically significant targeting to APC.

In summary, the data presented herein provide evidence that synthetic nanocarriers can be produced that incorporate immunofeature surfaces as defined elsewhere herein. Evidence for immunofeature surface-induced targeting of synthetic nanocarriers to subcapsular sinus macrophages (SCS-Mph) and dendritic cells (DC) was demonstrated by injecting fluorescent synthetic nanocarriers into footpads of mice followed by subsequent analysis of synthetic nanocarrier distribution and association with professional antigen presenting cells (APC) in the draining lymph node, as described above.

Furthermore, results shown in FIG. 38b show that synthetic nanocarrier targeting to lymph node DC can be substantially enhanced (at least 5-fold) when synthetic nanocarriers incorporate an immunofeature surface, such as an immunofeature surface comprising nicotine. Combining this result with the cross presentation data shown previously, the gain in targeting results in a proportional increase in the amount of antigen and adjuvant that is made available to the DC for cross-presentation to CD8+ T cells. Thus, immunofeature surface-mediated targeting of synthetic nanocarriers boosts the capacity of synthetic nanocarrier vaccines to elicit cytotoxic T cell responses above and beyond that of synthetic nanocarrier vaccines lacking an immunofeature surface.

Example 19

In Vitro Comparison of Dendritic Cell Binding

In vitro accumulation of mouse DC on microtiter plates coated with different densities of immobilized anti-CD11c or nicotine was used to provide further evidence of the properties of immunofeature surfaces. Data are shown in FIGS. 39a and 39b.

Figure 39A:
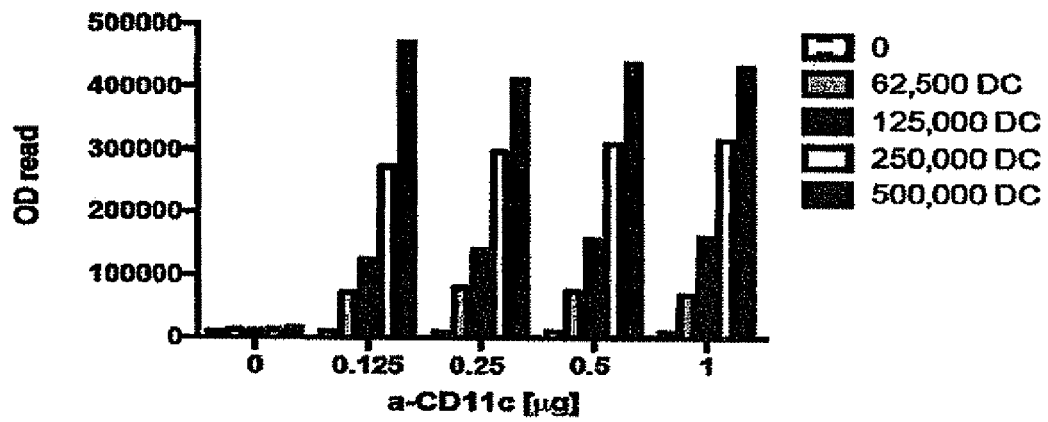
FIG. 39a: Shows the adhesion of DCs in vitro to a surface having immobilized anti-CD11c antibody.

In FIG. 39a MAXISORP™ NUNC-IMMUNO™ 96 MICROWELL™ Plates (Thermo Fisher Scientific, Waltham, Mass.) were coated with purified hamster anti-mouse CD11c antibody (Clone HL3, BD Biosciences, San Jose, Calif.) in phosphate buffered saline (PBS; Mediatech Inc., Manassas, Va.) at the indicated concentration for 1 hour at 37° C. The plates were then washed 3 times in PBS. Dendritic cells (DCs) were purified by positive immunomagnetic cell sorting (about 98% CD11c+; Miltenyi Biotec) from spleens of donor C57BL/6 mice (Charles River, Wilmington, Mass. DCs were incubated for 7 min at 25° C. with 5 mM CFSE (carboxyfluorescein diacetate succinimidyl ester; Invitrogen, Carlsbad, Calif.) in RPMI (Mediatech Inc., Manassas, Va.) with 10% (vol/vol) fetal calf serum (FCS; Invitrogen, Carlsbad, Calif.), washed and added to each well at the indicated concentration. The plates were then incubated at 37° C. for 15 minutes on a shaker at 60 rpm. The plates were washed twice by submerging in PBS, fixed with 4% paraformaldehyde and read using a Perkin Elmer Victor Fluorescence Plate Reader (485 nm/535 nm, 1.0 s). The data show that surface immobilized CD11c antibody provides significant binding to dendritic cells at all concentrations tested.

Figure 39B:
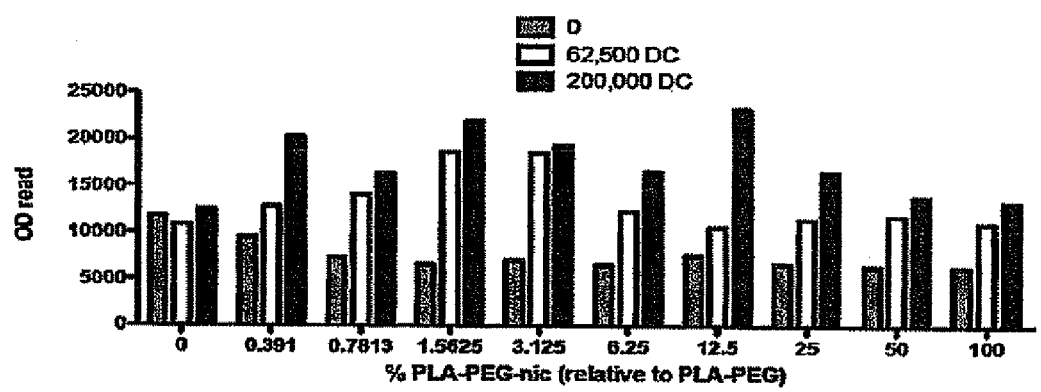
FIG. 39b: Shows the adhesion of DCs in vitro to a surface having immobilized nicotine.

In FIG. 39b, Microtiter plates were coated with PLA-PEG-nicotine that was either used undiluted (100%) or mixed at different ratios with methoxy terminated PEG-PLA. Nicotine immobilization was verified by measuring binding of a nicotine-specific MAb (clone 402C10; Bjercke et al. *J Immunol Methods*. 1986 Jun. 24, 90 (2):203-13). Plates coated with 100% PLA-PEG-nicotine are estimated to present $10^{15}$ nicotine molecules/cm$^2$, whereas maximal anti-CD11c MAb coating (1 µg) resulted in an approximate density of $10^{11}$ IgG molecules/cm$^2$. DCs were purified, stained and added to the plate as in (A). Plates were incubated, washed, fixed and read as in (A). Although nicotine conferred in vivo APC targeting properties when used as an immunofeature on nanocarriers (as demonstrated previously), the binding affinity to APC was too low to mediate detectable binding of APC, even at a coating density that was more then 4 orders of magnitude higher than the coating density of a high affinity antibody required to confer maximal APC binding. This is further evidence that nicotine-NP provide a low affinity, high avidity surface.

FIGS. 39a and 39b demonstrate that the nicotine immunofeature surface interacts with APC through low affinity/high avidity interactions. Microtiter plates were surface coated at a broad range of concentrations with either nicotine (using nicotine-PEG-PLA) or a high affinity MAb to CD11c, a glycoprotein that is specifically expressed on DC. Panel A shows that the high affinity MAb efficiently binds and immobilizes suspended DC that had been added to the microtiter plate. By contrast, nicotine immunofeature surface-coated plates did not efficiently capture DC when compared to uncoated control surfaces, even at the highest achievable nicotine density ($10^{15}$ molecules/cm$^2$), which was at least 3 orders of magnitude higher than MAb densities that mediated efficient DC binding under identical assay conditions. This demonstrates that at the assay conditions employed, the affinity of a nicotine immunofeature surface for mouse DC was too low to allow DC binding with sufficient mechanical strength to resist DC detachment upon gentle washing of the plate. Nonetheless, based on the in vivo targeting results presented herein it is reasonable to conclude that nicotine immunofeature surfaces can bind APC with sufficiently high avidity to resist detachment of synthetic nanocarriers with a nicotine immunofeature surface.

Example 20

In Vivo Testing of APC Targeting

Figure 27:
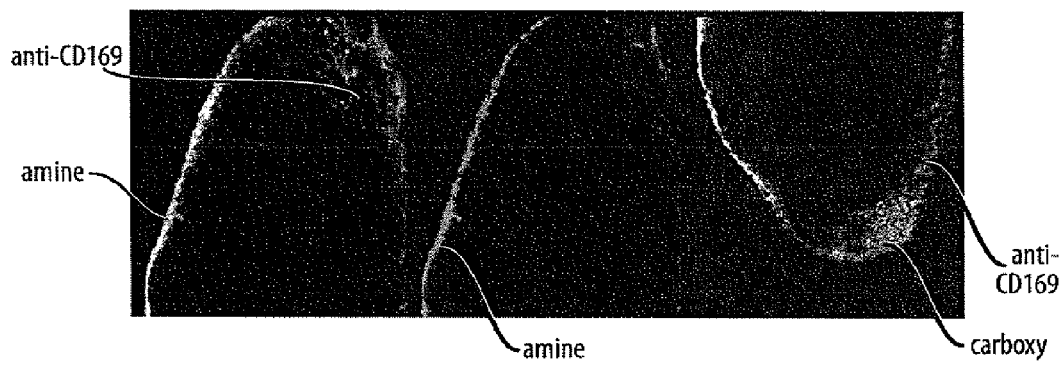
FIG. 27: Fluorescent micrographs of frozen sections from mouse popliteal lymph nodes 24 h after footpad injection of 0.2 μm diameter Latex beads surface modified with either amine (left and middle panel) or carboxy moieties (right panel). Both sets of beads were purchased from Invitrogen (Cat. no. F8763 and F8805). Sections on left and right were counterstained with anti-CD169. Images are oriented so that the medulla (weak, diffuse staining with anti-CD169) faces to the right and the subcapsular sinus (SCS) region (bright anti-CD169) faces to the left. Note that the red amine modified particles prominently localize to the SCS, while blue carboxy modified beads are primarily retained in the medulla.

The data in FIG. 27 (described previously) demonstrate that amine-modified synthetic nanocarriers are targeted to SCS-Mph more efficiently than carboxylate-modified synthetic nanocarriers. Thus, amine modification creates one embodiment of an immunofeature surface.

Figure 40:
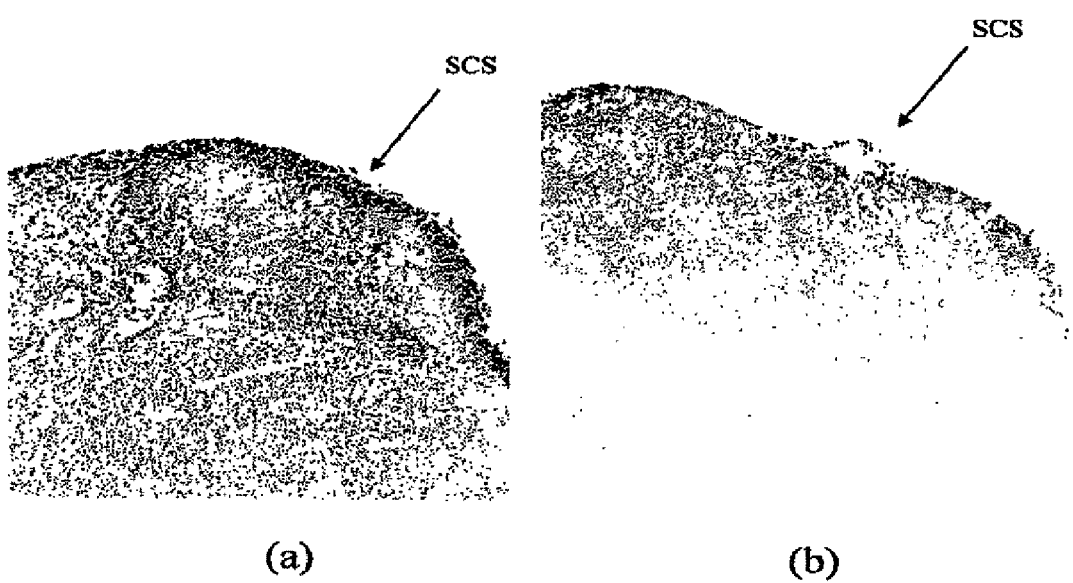
FIG. 40(a)-(b): Shows the accumulation of nicotine-modified nanoparticles compared with control nanoparticles in the SCS after injection into mouse footpads.
Figure 41:
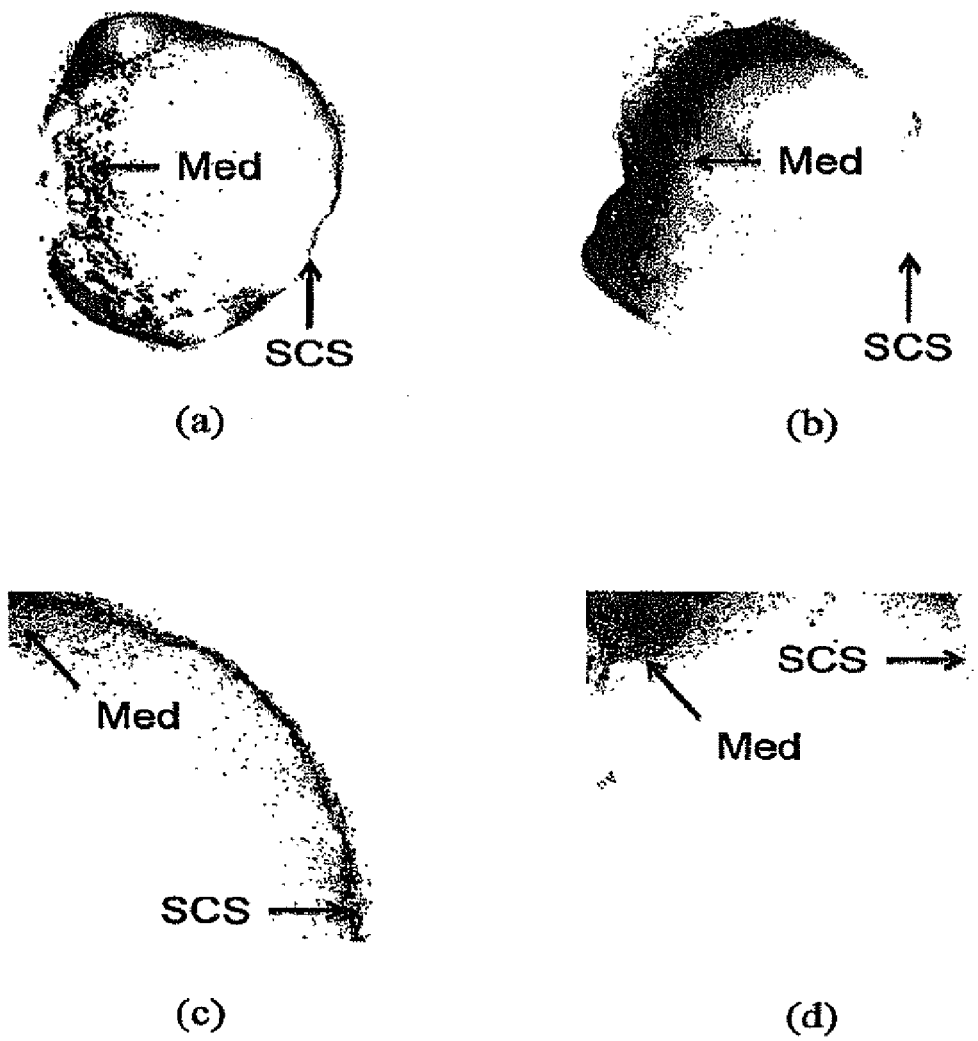
FIG. 41(a)-(d): Shows the accumulation of GM3-modified nanoparticles in the SCS and Medulla region of popliteal lymph nodes after injection of the nanoparticles into mouse footpads.

Furthermore, FIGS. 40a and 40b demonstrate that an immunofeature surface comprising nicotine confers targeting to SCS-Mph, whereas control particles do not confer such targeting. PLA-PEG-nicotine (left) or PLA-PEG control nanoparticles (right) were injected into footpads of young adult C57/BL6 mice. Particles were the same as in the immunization experiment described for FIG. 36. The draining popliteal lymph node was harvested 1 h later, fixed overnight at 4° C. with phosphate buffered L-lysine with 1% paraformaldehyde/periodate, cryoprotected by an ascending series of 10%, 20% and 30% sucrose in PBS, snap-frozen in tissue freezing medium (Triangle Biomedical Sciences, Durham, N.C.) and prepared for immunofluorescence analysis of frozen sections. Sections were stained with a nicotine-specific MAb (clone 402C10; Bjercke et al. *J Immunol Methods.* 1986 Jun. 24; 90 (2):203-13) followed by an Alexa568-conjugated anti-mouse IgG2a secondary Ab. Digital greyscale images of antibody staining were acquired and processed using identical settings. To improve visibility, images were digitally inverted using Adobe Photoshop CS3. In FIGS. 40*a* and 40*b*, the SCS regions are identified by arrows. In FIG. 40*a*, a significant amount of nanoparticles are observed in the SCS, whereas in FIG. 40*b*, no significant amount of nanoparticles are observed in the SCS.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a nanoparticle" includes a plurality of such nanoparticle, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any immunomodulatory agent, any targeting moiety, any immunostimulatory agent, any antigen presenting cell, any vaccine nanocarrier architecture, any microorganism, any method of administration, any prophylactic and/or therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

We claim:
1. A composition comprising:
   (1) polymeric synthetic nanocarriers comprising an immunofeature surface formed of an array of binding moieties, the array binding to dendritic or subcapsular sinus macrophages with high avidity and low affinity as compared to antibody binding; and
   (2) a pharmaceutically acceptable excipient.
2. The composition of claim 1, comprising an immunostimulatory agent.
3. The composition of claim 1, comprising MHC Class I, MHC Class II or CD-1 presentable polypeptide associated with the immunofeature surface; associated with a second surface of the nanocarrier; or encapsulated within the nanocarrier.
4. The composition of claim 1, wherein the immunofeature surface is formed of a plurality of moieties that are present in a density equal to or greater than the density required to obtain at least 10% of the maximal immobilization observed for a monoclonal antibody (MAb) in an antigen presenting cell (APC) binding assay.
5. The composition of claim 4, comprising an immunostimulatory agent, wherein the half maximal binding density for the immunostimulatory agent is at least twice the half maximal binding density for the MAb and the immunostimulatory agent is present in a density equal to or greater than the density required to obtain at least 20% of the maximal immobilization observed for a MAb in a APC binding assay.
6. The composition of claim 5, wherein the half maximal binding density for the immunostimulatory agent is at least four times the half maximal binding density for the MAb.
7. The composition of claim 4, wherein the APC binding assay comprises:
   (a) preparing a series of substrates having coatings of an functional moiety at a series of surface coating densities, wherein the functional moiety is capable of binding to dendritic cell (DC) or subcapsular sinus macrophage surface receptors;
   (b) exposing the series of substrates to single-cell suspensions of DCs or subcapsular sinus macrophage for a predetermined period of time;
   (c) removing non-adhered APCs from the series of substrates, and fixing the adhered APCs to the series of substrates;
   (d) quantifying the number of adhered APCs per unit surface area for each substrate in the series of substrates;
   (e) plotting the result from (d) against the coating density of the functional moiety;
   (f) obtaining a value for the maximal immobilization by determining the maximum number of adhered APCs per unit surface area for the series of substrates; and
   (g) obtaining a value for half maximal binding density by determining the surface coating density that provides 50% of the maximum.
8. The composition of claim 4, wherein the MAb is anti-CD1c (BDCA-1) Clone AD5-8E7 or rat anti-mouse CD169 clone 3D6.112.
9. The composition of claim 2, wherein immunostimulatory agent is a Toll-Like Receptor (TLR) agonist.
10. The composition of claim 9, wherein the TLR agonist is a TLR-1, TLR-2, TLR-3, TLR-4, TLR-5, TLR-6, TLR-7, TLR-8, TLR-9, or TLR-10 agonist.
11. The composition of claim 2, wherein the immunostimulatory agent is selected from an interleukin, an interferon, a cytokine, and an adjuvant.
12. The composition of claim 1, wherein the composition is capable of providing enhanced T-cell proliferation in a human subject.
13. The composition of claim 1, wherein the composition elicits dendritic cell maturation when administered to a human subject.
14. The composition of claim 1, wherein the nanocarriers comprises two or more different MHC Class I, MHC Class II or CD 1 presentable polypeptides.
15. The composition of claim 1, wherein the composition comprises two or more immunostimulatory agents.
16. The composition of claim 15, wherein the composition comprises two or more Toll-Like Receptor (TLR) agonists.
17. The composition of claim 15, wherein the composition comprises one Toll-Like Receptor (TLR) agonist and one non-TLR agonist.
18. The composition of claim 17, wherein the non-TLR agonist is a moiety that induces signaling through the inflammasome, CD40, or a cytokine receptor.
19. The composition of claim 3, wherein the MHC Class I presentable peptide is selected from the group consisting of SIINFEKL (SEQ ID NO:1), GP33, Core 18-27, and MAGE.
20. The composition of claim 3, wherein the MHC Class II presentable peptide is selected from the group consisting of GP61, MAGE-A4 280-299, tetanus toxoid, diphtheria toxoid, and PADRE peptide.
21. The composition of claim 3, wherein the CD1 presentable peptide is selected from the group consisting of mycolic acid, sulpholipids, lipophosphoglycan, diacylglycerols, glycoshpingolipids, alpha-galactosylceramide, isoglobotrihexosylceramide, and ganglioside GD3.
22. The composition of claim 1, further comprising an immunomodulatory agent selected from the group consisting of proteins, peptides, carbohydrates, glycoproteins, glycopeptides, proteoglycans, inactivated organisms and viruses, dead organisms and virus, genetically altered organisms or viruses, antigens of fungal organisms, protozoan organisms, parasitic organisms, and cell extracts.
23. A method comprising:
   administering to a subject an initial dose of a composition comprising:
   polymeric synthetic nanocarriers comprising an immunofeature surface formed of an array of binding moieties, the array binding to dendritic or subcapsular sinus macrophages with high avidity and low affinity as compared to antibody binding; and
   a pharmaceutically acceptable excipient; and
   administering to the subject a first subsequent dose of the composition at a time period after the administration of the initial dose.
24. The method of claim 23, wherein the time period is an interval ranging from 1 day to 1 year.
25. The method of claim 23, wherein the first dose of the composition elicits T-cell proliferation in the subject.
26. The method of claim 23, wherein one week after administration of the initial dose the blood concentration of antigen-specific T cells in the subject is at least 10-fold higher than the concentration of T cells recognizing an irrelevant antigen to which the subject has no immunological memory.
27. The method of claim 26, wherein the irrelevant anitigen is bovine serum albumin.
28. The method of claim 23, wherein one week after administration of the first subsequent dose the blood concentration of antigen-specific T cells in the subject is at least 10-fold higher than the concentration of T cells recognizing an irrelevant antigen to which the subject has no immunological memory.

29. The method of claim 28, wherein the irrelevant antigen is bovine serum albumin.

30. The composition of claim 1, wherein the moieties are present in an amount effective to provide avidity-based binding to binding to mammalian antigen presenting cells.

31. The composition of claim 1, wherein the diameter of the nanocarriers is greater than 100 nm.

32. The composition of claim 1, wherein the pharmaceutically acceptable excipient is selected from the group consisting of solvents, dispersion media, diluents, dispersion or suspension aids, surface active agents, isotonic agents, thickening or emulsifying agents, preservatives, solid binders, and lubricants.

33. The composition of claim 1, wherein the composition targets a dendritic cell.

34. The composition of claim 1, wherein the composition does not substantially activate complement.

\* \* \* \* \*

UNITED STATES PATENT AND TRADEMARK OFFICE
CERTIFICATE OF CORRECTION

PATENT NO. : 8,637,028 B2  Page 1 of 1
APPLICATION NO. : 13/123888
DATED : January 28, 2014
INVENTOR(S) : Alexis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 49 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
1               5
```